US008409809B2

(12) United States Patent
Meitinger et al.

(10) Patent No.: US 8,409,809 B2
(45) Date of Patent: Apr. 2, 2013

(54) KASPP (LRRK2) GENE, ITS PRODUCTION AND USE FOR THE DETECTION AND TREATMENT OF NEURODEGENERATIVE DISORDERS

(75) Inventors: Thomas Meitinger, Munich (DE); Tim Matthias Strom, Munich (DE); Saskia Biskup, Stuttgart (DE); Marius Ueffing, Munich (DE); Elisabeth Kremmer, Freising (DE); Christian Johannes Gloeckner, Rottenburg-Hailfingen (DE); Thomas Gasser, Tuebingen (DE); Petra Herzig, Basel (CH); Friedrich Asmus, Teubingen (DE); Nadja Patenge, Rostock (DE); Alexander Zimprich, Vienna (AT); Matthew J. Farrer, Jacksonville, FL (US); Jennifer M. Kachergus, Atlantic Beach, FL (US); Sara J. Lincoln, Jacksonville, FL (US); Mary M. Hulihan, Atlanta, GA (US); Zibigniew Wszolek, Jacksonville, FL (US); Ryan Uitti, Jacksonville, FL (US)

(73) Assignees: Helmholtz Zentrum München Deutsches Forschungszentrum für Gesundheit und Umwelt (GmbH), Neuheberg (DE); Eberhard-Karls-Universitaet Tuebingen, Tuebingen (DE); Mayo Foundation For Medical Education and Research, Jacksonville, FL (US)

( * ) Notice: Subject to any disclaimer, the term of this patent is extended or adjusted under 35 U.S.C. 154(b) by 0 days.

(21) Appl. No.: 13/219,131

(22) Filed: Aug. 26, 2011

(65) Prior Publication Data
US 2012/0035072 A1    Feb. 9, 2012

Related U.S. Application Data

(62) Division of application No. 11/665,875, filed as application No. PCT/EP2005/010428 on Sep. 27, 2005, now Pat. No. 8,029,986.

(60) Provisional application No. 60/620,893, filed on Oct. 21, 2004, provisional application No. 60/621,169, filed on Oct. 22, 2004.

(51) Int. Cl.
*C12Q 1/68* (2006.01)
(52) U.S. Cl. ................................. 435/6.16; 435/6.18
(58) Field of Classification Search .................... None
See application file for complete search history.

(56) References Cited

U.S. PATENT DOCUMENTS
5,744,305 A    4/1998  Fodor et al.
6,174,670 B1   1/2001  Wittwer et al.

FOREIGN PATENT DOCUMENTS
| WO | WO 92/02638    | 2/1992  |
| WO | WO 95/02051    | 1/1995  |
| WO | WO 03/012065   | 2/2003  |
| WO | WO 03/101283   | 12/2003 |
| WO | WO 2004/006838 | 1/2004  |
| WO | WO 2004/023973 | 3/2004  |

OTHER PUBLICATIONS

Hernandez et al., "Clinical and Positron Emission Tomography of Parkinson's Disease Caused by *LRRK2*," *Ann. Neurol.*, 57:453-456, 2005.
Polymeropoulos et al., "Mutation in the α-Synuclein Gene Identified in Families with Parkinson's Disease." *Science*,276:2045-2047, 1997.
Ausubel et al., *Current Protocols in Molecular Biology*, John Wily & Sons, Inc., New York, NY, unit 4.9, 1989.
Berg et al., "Iron Accumulation in the Substantia Nigra in Rats Visualized by Ultrasound," *Ultrasound Med. Biol*, 25: 901-904, 1999.
Berg et al., "Echogenicity of the Substantia Nigra in Parkinson's Disease and Its Relation to Clinical Findings," *J Neurol*, 248:684-689, 2001.
Bonifati et al., "Mutations in the DJ-1 Gene Associated with Autosomal Recessive Early-Onset Parkinsonism," *Science*, 299, 256-259, 2003.
Bosgraaf et al., "Roc, a Ras/GTPase Domain in Complex Proteins," *Biochim. Biophys. Acta.*, 1643, 5-10, 2003.
Chalandon & Schwaller, "Targeting Mutated Protein Tyrosine Kinases and their Signaling Pathways in Hematologic Malignancies," *The Hematology Journal* 90, 949-968, 2005.
Daum et al., "Riechprüfung mit "Sniffin' Sticks" zur Klinischen Diagnostik des Morbus Parkinson," *Nervenarzt*, 71:643-650, 2000 (No Translation).
Dibb et al., "Switching on Kinases: Oncogenic Activation of BRAF and the PDGFR Family," *Nature Reviews*, 4, 718-727, 2004.
Ghetti et al., "Frontotemporal Demitia and Parkinsonism Linked to Chromosome 17 Associated with Tau Gene Mutations (FTDP17T)" *Chap. 3 Tauoptathies: FTDP-017* pp. 86-102, 2003.
Di Fonzo et al., "A Frequent LRRK2 Gene Mutation Associated with Autosomal Dominant Parkinson's Disease," *Lancet*, 365:412-415, 2005.
Duda et al., "Concurrence of α-Synuclein and Tau Brain Pathology in the Contursi Kindred," *Acta. Neuropathol. Berl.*, 104, 7-11, 2002.
Elbaz et al., "Familial Aggregation of Parkinson's Disease: A Population-Based Case-Control Study in Europe," *Neurology*, 52:1876-1882, 1999.
Fahn et al., *Recent Developments in Parkinson's Disease*, New York, Macmillan, 153-163 (1987).
Fujiki et al., "Isolation of Intracellular Membranes by Means of Sodium Carbonate Treatment: Application to Endoplasmic Reticulum," *J. Cell Biol.*, 93, 97-102, 1982.
Funayama et al., "A New Locus for Parkinson's Disease (*PARK8*) Maps to Chromosome 12p11.2-q13.1," *Ann. Neurol.*, 51, 296-301, 2002.

(Continued)

*Primary Examiner* — John Ulm
(74) *Attorney, Agent, or Firm* — Clark & Elbing LLP

(57) ABSTRACT

The present invention refers to a newly discovered gene named KASPP for Kinase Associated with Parkinsonism with Pleiomorphic Pathology or alternatively named LRRK2 for Leucine-Rich Repeat Kinase 2, its production, biochemical characterization and use for the detection and treatment of neurodegenerative disorders, such as Parkinson disease (PD) including, without limitation, sporadic PD, Alzheimer disease (AD), amyotrophic lateral sclerosis (ALS), and other synucleinopathies and/or tauopathy as well as several polymorphisms and mutations in the KASPP/LRRK2 gene segregated with PD.

16 Claims, 55 Drawing Sheets

OTHER PUBLICATIONS

Funayama et al., "An *LRRK2* Mutation as a Cause for the Parkinsonism in the Original *PARK8* Family," *Ann. Neurol.*, 57:918-921, 2005.

Garini, Y. et al., "From Micro to Nano: Recent Advances in High-Resolution Microscopy," *Curr. Opin. Biotechnol.*, 16, 3-12, 2005.

Gasser et al., "A Susceptibility Locus for Parkinson's Disease Maps to Chromosome 2p13," *Nat. Genet.*, 18, 262-265, 1998.

Gilks et al., "A Common *LRRK2* Mutation in Idiopathic Parkinson's Disease," *Lancet*, 365:415-416, 2005.

Gotz. "Formation of Neurofibrillary Tangles in P301L Tau Transgenic Mice Induced by Aβ42 Fibrils," *Science*, 293, 1491-1495, 2001.

Hernandez et al., "Clinical and Positron Emission Tomography of Parkinson's Disease Caused by *LRRK2*," *Ann. Neurol.*, 57:453-456, 2005.

Hicks et al., "A Susceptibility Gene for Late-Onset Idiopathic Parkinson's Disease," *Ann. Neurol.*, 52, 549-555, 2002.

Hubbard et al., "Protein Tyrosine Kinase Structure and Function," *Annu. Rev. Biochem.*, 69, 373-398, 2000.

Hughes et al., " Accuracy of Clinical Diagnosis of Idiopathic Parkinson's Disease: a Clinico-Pathological Study of 100 Cases," *J. Neurol. Neurosurg. Psychiatry*, 55:181-184, 1992.

Kitada et al., "Mutations in the *Parkin* Gene Cause Autosomal Recessive Juvenile Parkinsonism," *Nature*, 392, 605-608, 1998.

Kobe and Kajava, "The Leucine-Rich Repeat as a Protein Recognition Motif," *Curr. Opin. Struct. Biol.*, 11, 725-732, 2001.

Kotzbauer et al., "Fibrillization of α-Synuclein and Tau in Familial Parkinson's Disease Caused by the A53T α-Synuclein Mutation," *Exp. Neurol.*, 187, 279-288, 2004.

Kumar et al., "Sleep Disorders in Parkinson's Disease," *Movement Disorders* 17: 775-781, 2002.

Lees et al., "The Nighttime Problems of Parkinson's Disease," *Clinical Neuro.*, 11: 512-519, 1988.

Ludwig, E. et al., "Diminished Rev-Mediated Stimulation of Human Immunodeficiency Virus Type 1 Protein Synthesis is a Hallmark of Human Astrocytes," *J. Virol.*, 73, 8279-8289, 1999.

Mata et al., "*LRRK2* R1441G in Spanish Patients with Parkinson's Disease," *Neuroscience Letters* 382:309-311, 2005.

Neuhoff, V. et al., "Improved Staining of Proteins in Polyacrylamide Gels Including Isoelectric Focusing Gels with Clear Background at Nanogram Sensitivity Using Coomassie Brilliant Blue G-250 and R-250," *Electrophoresis*, 9, 255-262, 1988.

Paisan-Ruiz et al., "Cloning of the Gene Containing Mutations that Cause PARK8-Linked Parkinson's Disease," *Neuron*, 44, 595-600, 2004.

Paisan-Ruiz et al., "Familial Parkinson's disease: Clinical and Genetic Analysis of Four Basque Families," *Ann. Neurol.*, 57:365-372, 2005.

Pankratz et al., "Significant Linkage of Parkinson Disease to Chromosome 2q36-37," *Am. J. Hum. Genet.*, 72, 1053-1057, 2003.

Polymeropoulos et al., "Mutation in the α-Synuclein Gene Identified in Families with Parkinson's Disease." *Science*, 276:2045-2047, 1997.

Ridley, "Rho Family Proteins: Coordinating Cell Responses," *Trends Cell. Biol.*, 11, 471-476, 2001.

Ross & Farrer, "Pathophysiology, Pleotrophy, and Paradigm Shifts: Genetic Lessons from Parkinson's Disease," *Biochem. Soc. Trans.*, 33, 586-590, 2005.

Scott et al., "Fine Mapping of the Chromosome 12 Late-Onset Alzheimer Disease Locus: Potenia Genetic and Phenotypic Heterogeneity," *Am. J. Hum. Genet.*, 66, 922-932, 2000.

Shevchenko, A. et al., "Mass Spectrometric Sequencing of Proteins from Silver-Stained Polyacrylamide Gels," *Anal. Chem.* 68,850-858, 1996.

Smith et al., "The WD Repeat: A Common Architecture for Diverse Functions," *TIBS*, 24, 181-185, 1999.

Tang et al., "Chip-Based Genotyping by Mass Spectrometry," *Proc. Natl. Acad. Sci USA* 96, 10016-10020, 1999.

Toft et al., "LRRK2 Mutations and Parkinsonism," *Lancet*, 365:1229-1230, 2005.

Valente et al., "Hereditary Early-Onset Parkinson's Disease Caused by Mutations in *PINK1*," *Science*, 304, 1158-1160, 2004.

Walter et al., "Substantia Nigra Echogenicity is Normal in Non-Extrapyramidal Cerebral Disorders but Increased in Parkinson's Disease," *J. Neural Transm.*, 109:191-196, 2002.

Wszolek et al., "Autosomal Dominant Parkinsonism Associated with Variable Synuclein and Tau Pathology," *Neurology*, 62, 1619-1622, 2004.

Zimprich et al., "The PARK8 Locus in Autosomal Dominant Parkinsonism: Confirmation of Linkage and Further Delineation of the Disease-Containing Interval," *Am. J. Hum. Genet.*,74, 11-19, 2004.

Zimprich et al., "Mutations in *LRRK2* Cause Autosomal-Dominant Parkinsonism with Pleomorphic Pathology," *Neuron*, 44, 601-607, 2004.

International Preliminary Report (PCT/EP2005/010428) mailed Jan. 22, 2007.

Written Opinion of the Preliminary Examining Authority (PCT/EP2005/010428) mailed Nov. 22, 2006.

International Search Report (PCT/EP2005/010428) mailed Jun. 16, 2006.

Invitation to Pay Additional Fees from the International Searching Authority (PCT/EP2005/010428) mailed Apr. 10, 2006.

Written Opinion of the International Searching Authority (PCT/EP2005/010428), dated Jun. 16, 2006.

Family A (German-Canadian)
(Y1699C)

Family D (Western Nebraska)
(R1441C)

|        | I1122V  | R1441C  | Y1699C  | I1122T  |
|--------|---------|---------|---------|---------|
| Human  | ISQFCSP | IKARASS | EMPYFPM | DYGIAQY |
| Mouse  | ISQFCSP | IKARASS | EMPYFPM | DYGIAQY |
| Fugu   | IAELCVP | IKAVAPL | EMPYFPM | .YGIAQH |
| Worm   | IQ....E | IHARAPN | ALAYIPS | DYGISRS |
| Fly    | IS..CWP | IQARAPN | LMTYFPS | DYGISRQ |
| Family | 21      | D/469   | A       | 32      |
| Exon   | 24      | 30      | 34      | 40      |

```
                                2005034094.TXT
          10        20        30        40        50        60
    ----:----|----:----|----:----|----:----|----:----|----:----|
    ATGGCTAGTGGCAGCTGTCAGGGGTGCGAAGAGGACGAGGAAACTCTGAAGAAGTTGATA
     M  A  S  G  S  C  Q  G  C  E  E  D  E  E  T  L  K  K  L  I 70        80        90       100       110       120
    ----:----|----:----|----:----|----:----|----:----|----:----|
    GTCAGGCTGAACAATGTCCAGGAAGGAAAACAGATAGAAACGCTGGTCCAAATCCTGGAG
     V  R  L  N  N  V  Q  E  G  K  Q  I  E  T  L  V  Q  I  L  E 130       140       150       160       170       180
    ----:----|----:----|----:----|----:----|----:----|----:----|
    GATCTGCTGGTGTTCACGTACTCCGAGCACGCCTCCAAGTTATTTCAAGGCAAAAATATC
     D  L  L  V  F  T  Y  S  E  H  A  S  K  L  F  Q  G  K  N  I
                                     ||
                                  exon1/exon2

190       200       210       220       230       240
    ----:----|----:----|----:----|----:----|----:----|----:----|
    CATGTGCCTCTGTTGATCGTCTTGGACTCCTATATGAGAGTCGCGAGTGTGCAGCAGGTG
     H  V  P  L  L  I  V  L  D  S  Y  M  R  V  A  S  V  Q  Q  V
                                                             ||
                                                         exon2/exon3

250       260       270       280       290       300
    ----:----|----:----|----:----|----:----|----:----|----:----|
    GGTTGGTCACTTCTGTGCAAATTAATAGAAGTCTGTCCAGGTACAATGCAAAGCTTAATG
     G  W  S  L  L  C  K  L  I  E  V  C  P  G  T  M  Q  S  L  M 310       320       330       340       350       360
    ----:----|----:----|----:----|----:----|----:----|----:----|
    GGACCCCAGGATGTTGGAAATGATTGGGAAGTCCTTGGTGTTCACCAATTGATTCTTAAA
     G  P  Q  D  V  G  N  D  W  E  V  L  G  V  H  Q  L  I  L  K
                                                       ||
                                                    exon3/exon4

370       380       390       400       410       420
    ----:----|----:----|----:----|----:----|----:----|----:----|
    ATGCTAACAGTTCATAATGCCAGTGTAAACTTGTCAGTGATTGGACTGAAGACCTTAGAT
     M  L  T  V  H  N  A  S  V  N  L  S  V  I  G  L  K  T  L  D 430       440       450       460       470       480
    ----:----|----:----|----:----|----:----|----:----|----:----|
    CTCCTCCTAACTTCAGGTAAAATCACCTTGCTGATACTGGATGAAGAAAGTGATATTTTC
     L  L  L  T  S  G  K  I  T  L  L  I  L  D  E  E  S  D  I  F
                       ||
                   exon4/exon5

490       500       510       520       530       540
    ----:----|----:----|----:----|----:----|----:----|----:----|
    ATGTTAATTTTTGATGCCATGCACTCATTTCCAGCCAATGATGAAGTCCAGAAACTTGGA
     M  L  I  F  D  A  M  H  S  F  P  A  N  D  E  V  Q  K  L  G 550       560       570       580       590       600
    ----:----|----:----|----:----|----:----|----:----|----:----|
    TGCAAAGCTTTACATGTGCTGTTTGAGAGAGTCTCAGAGGAGCAACTGACTGAATTTGTT
     C  K  A  L  H  V  L  F  E  R  V  S  E  E  Q  L  T  E  F  V
                                         ||
                                      exon5/exon6

610       620       630       640       650       660
    ----:----|----:----|----:----|----:----|----:----|----:----|
    GAGAACAAAGATTATATGATATTGTTAAGTGCGTCAACAAATTTTAAAGATGAAGAGGAA
     E  N  K  D  Y  M  I  L  L  S  A  S  T  N  F  K  D  E  E  E 670       680       690       700       710       720
                              Seite 1
```

2005034094.TXT

```
            10         20         30         40         50         60
   ----:----|----:----|----:----|----:----|----:----|----:----|
   ATGGCTAGTGGCAGCTGTCAGGGGTGCGAAGAGGACGAGGAAACTCTGAAGAAGTTGATA
    M  A  S  G  S  C  Q  G  C  E  E  D  E  E  T  L  K  K  L  I 70         80         90        100        110        120
   ----:----|----:----|----:----|----:----|----:----|----:----|
   GTCAGGCTGAACAATGTCCAGGAAGGAAAACAGATAGAAACGCTGGTCCAAATCCTGGAG
    V  R  L  N  N  V  Q  E  G  K  Q  I  E  T  L  V  Q  I  L  E 130        140        150        160        170        180
   ----:----|----:----|----:----|----:----|----:----|----:----|
   GATCTGCTGGTGTTCACGTACTCCGAGCACGCCTCCAAGTTATTTCAAGGCAAAAATATC
    D  L  L  V  F  T  Y  S  E  H  A  S  K  L  F  Q  G  K  N  I
                                      ||
                                  exon1/exon2

190        200        210        220        230        240
   ----:----|----:----|----:----|----:----|----:----|----:----|
   CATGTGCCTCTGTTGATCGTCTTGGACTCCTATATGAGAGTCGCGAGTGTGCAGCAGGTG
    H  V  P  L  L  I  V  L  D  S  Y  M  R  V  A  S  V  Q  Q  V
                                                             ||
                                                        exon2/exon3

250        260        270        280        290        300
   ----:----|----:----|----:----|----:----|----:----|----:----|
   GGTTGGTCACTTCTGTGCAAATTAATAGAAGTCTGTCCAGGTACAATGCAAAGCTTAATG
    G  W  S  L  L  C  K  L  I  E  V  C  P  G  T  M  Q  S  L  M 310        320        330        340        350        360
   ----:----|----:----|----:----|----:----|----:----|----:----|
   GGACCCCAGGATGTTGGAAATGATTGGGAAGTCCTTGGTGTTCACCAATTGATTCTTAAA
    G  P  Q  D  V  G  N  D  W  E  V  L  G  V  H  Q  L  I  L  K
                                                       ||
                                                  exon3/exon4

370        380        390        400        410        420
   ----:----|----:----|----:----|----:----|----:----|----:----|
   ATGCTAACAGTTCATAATGCCAGTGTAAACTTGTCAGTGATTGGACTGAAGACCTTAGAT
    M  L  T  V  H  N  A  S  V  N  L  S  V  I  G  L  K  T  L  D 430        440        450        460        470        480
   ----:----|----:----|----:----|----:----|----:----|----:----|
   CTCCTCCTAACTTCAGGTAAAATCACCCTTCTGATACTGGATGAAGAAAGTGATATTTTC
    L  L  L  T  S  G  K  I  T  L  L  I  L  D  E  E  S  D  I  F
              ||
         exon4/exon5

490        500        510        520        530        540
   ----:----|----:----|----:----|----:----|----:----|----:----|
   ATGTTAATTTTTGATGCCATGCACTCATTTCCAGCCAATGATGAAGTCCAGAAACTTGGA
    M  L  I  F  D  A  M  H  S  F  P  A  N  D  E  V  Q  K  L  G 550        560        570        580        590        600
   ----:----|----:----|----:----|----:----|----:----|----:----|
   TGCAAAGCTTTACATGTGCTGTTTGAGAGAGTCTCAGAGGAGCAACTGACTGAATTTGTT
    C  K  A  L  H  V  L  F  E  R  V  S  E  E  Q  L  T  E  F  V
                                              ||
                                         exon5/exon6

610        620        630        640        650        660
   ----:----|----:----|----:----|----:----|----:----|----:----|
   GAGAACAAAGATTATATGATATTGTTAAGTGCGTCAACAAATTTTAAAGATGAAGAGGAA
    E  N  K  D  Y  M  I  L  L  S  A  S  T  N  F  K  D  E  E  E 670        680        690        700        710        720
```

Fig. 4A

```
                                      2005034094.TXT
----:----|----:----|----:----|----:----|----:----|----:----|
ATTGTGCTTCATGTGCTGCATTGTTTACATTCCCTAGCGATTCCTTGCAATAATGTGGAA
 I  V  L  H  V  L  H  C  L  H  S  L  A  I  P  C  N  N  V  E
                                              ||
                                         exon6/exon7

730       740       750       760       770       780
----:----|----:----|----:----|----:----|----:----|----:----|
GTCCTCATGAGTGGCAATGTCAGGTGTTATAATATTGTGGTGGAAGCTATGAAAGCATTC
 V  L  M  S  G  N  V  R  C  Y  N  I  V  V  E  A  M  K  A  F 790       800       810       820       830       840
----:----|----:----|----:----|----:----|----:----|----:----|
CCTATGAGTGAAAGAATTCAAGAAGTGAGTTGCTGTTTGCTCCATAGGCTTACATTAGGT
 P  M  S  E  R  I  Q  E  V  S  C  C  L  L  H  R  L  T  L  G
                                                          ||
                                                     exon7/exon8

850       860       870       880       890       900
----:----|----:----|----:----|----:----|----:----|----:----|
AATTTTTTCAATATCCTGGTATTAAACGAAGTCCATGAGTTTGTGGTGAAAGCTGTGCAG
 N  F  F  N  I  L  V  L  N  E  V  H  E  F  V  V  K  A  V  Q 910       920       930       940       950       960
----:----|----:----|----:----|----:----|----:----|----:----|
CAGTACCCAGAGAATGCAGCATTGCAGATCTCAGCGCTCAGCTGTTTGGCCCTCCTCACT
 Q  Y  P  E  N  A  A  L  Q  I  S  A  L  S  C  L  A  L  L  T
                                                          ||
                                                     exon8/exon9

970       980       990      1000      1010      1020
----:----|----:----|----:----|----:----|----:----|----:----|
GAGACTATTTTCTTAAATCAAGATTTAGAGGAAAAGAATGAGAATCAAGAGAATGATGAT
 E  T  I  F  L  N  Q  D  L  E  E  K  N  E  N  Q  E  N  D  D 1030      1040      1050      1060      1070      1080
----:----|----:----|----:----|----:----|----:----|----:----|
GAGGGGGAAGAAGATAAATTGTTTTGGCTGGAAGCCTGTTACAAAGCATTAACGTGGCAT
 E  G  E  E  D  K  L  F  W  L  E  A  C  Y  K  A  L  T  W  H 1090      1100      1110      1120      1130      1140
----:----|----:----|----:----|----:----|----:----|----:----|
AGAAAGAACAAGCACGTGCAGGAGGCCGCATGCTGGGCACTAAATAATCTCCTTATGTAC
 R  K  N  K  H  V  Q  E  A  A  C  W  A  L  N  N  L  L  M  Y
                  ||
             exon9/exon10

1150      1160      1170      1180      1190      1200
----:----|----:----|----:----|----:----|----:----|----:----|
CAAAACAGTTTACATGAGAAGATTGGAGATGAAGATGGCCATTTCCCAGCTCATAGGGAA
 Q  N  S  L  H  E  K  I  G  D  E  D  G  H  F  P  A  H  R  E
                                          ||
                                     exon10/exon11

1210      1220      1230      1240      1250      1260
----:----|----:----|----:----|----:----|----:----|----:----|
GTGATGCTCTCCATGCTGATGCATTCTTCATCAAAGGAAGTTTTCCAGGCATCTGCGAAT
 V  M  L  S  M  L  M  H  S  S  S  K  E  V  F  Q  A  S  A  N 1270      1280      1290      1300      1310      1320
----:----|----:----|----:----|----:----|----:----|----:----|
GCATTGTCAACTCTCTTAGAACAAAATGTTAATTTCAGAAAAATACTGTTATCAAAGGA
 A  L  S  T  L  L  E  Q  N  V  N  F  R  K  I  L  L  S  K  G
                                ||
                           exon11/exon12

```
                                 2005034094.TXT
ATACACCTGAATGTTTTGGAGTTAATGCAGAAGCATATACATTCTCCTGAAGTGGCTGAA
 I  H  L  N  V  L  E  L  M  Q  K  H  I  H  S  P  E  V  A  E
          1390      1400      1410      1420      1430      1440
    ----:----|----:----|----:----|----:----|----:----|----:----|
AGTGGCTGTAAAATGCTAAATCATCTTTTTGAAGGAAGCAACACTTCCCTGGATATAATG
 S  G  C  K  M  L  N  H  L  F  E  G  S  N  T  S  L  D  I  M
                                          ||
                                      exon12/exon13

1450      1460      1470      1480      1490      1500
    ----:----|----:----|----:----|----:----|----:----|----:----|
GCAGCAGTGGTCCCCAAAATACTAACAGTTATGAAACGTCATGAGACATCATTACCAGTG
 A  A  V  V  P  K  I  L  T  V  M  K  R  H  E  T  S  L  P  V 1510      1520      1530      1540      1550      1560
    ----:----|----:----|----:----|----:----|----:----|----:----|
CAGCTGGAGGCGCTTCGAGCTATTTTACATTTTATAGTGCCTGGCATGCCAGAAGAATCC
 Q  L  E  A  L  R  A  I  L  H  F  I  V  P  G  M  P  E  E  S
                                                ||
                                            exon13/exon14

1570      1580      1590      1600      1610      1620
    ----:----|----:----|----:----|----:----|----:----|----:----|
AGGGAGGATACAGAATTTCATCATAAGCTAAATATGGTTAAAAAACAGTGTTTCAAGAAT
 R  E  D  T  E  F  H  H  K  L  N  M  V  K  K  Q  C  F  K  N 1630      1640      1650      1660      1670      1680
    ----:----|----:----|----:----|----:----|----:----|----:----|
GATATTCACAAACTGGTCCTAGCAGCTTTGAACAGGTTCATTGGAAATCCTGGGATTCAG
 D  I  H  K  L  V  L  A  A  L  N  R  F  I  G  N  P  G  I  Q
                                          ||
                                      exon14/exon15

1690      1700      1710      1720      1730      1740
    ----:----|----:----|----:----|----:----|----:----|----:----|
AAATGTGGATTAAAAGTAATTTCTTCTATTGTACATTTTCCTGATGCATTAGAGATGTTA
 K  C  G  L  K  V  I  S  S  I  V  H  F  P  D  A  L  E  M  L 1750      1760      1770      1780      1790      1800
    ----:----|----:----|----:----|----:----|----:----|----:----|
TCCCTGGAAGGTGCTATGGATTCAGTGCTTCACACACTGCAGATGTATCCAGATGACCAA
 S  L  E  G  A  M  D  S  V  L  H  T  L  Q  M  Y  P  D  D  Q 1810      1820      1830      1840      1850      1860
    ----:----|----:----|----:----|----:----|----:----|----:----|
GAAATTCAGTGTCTGGGTTTAAGTCTTATAGGATACTTGATTACAAAGAAGAATGTGTTC
 E  I  Q  C  L  G  L  S  L  I  G  Y  L  I  T  K  K  N  V  F
 ||
exon15/exon16

1870      1880      1890      1900      1910      1920
    ----:----|----:----|----:----|----:----|----:----|----:----|
ATAGGAACTGGACATCTGCTGGCAAAAATTCTGGTTTCCAGCTTATACCGATTTAAGGAT
 I  G  T  G  H  L  L  A  K  I  L  V  S  S  L  Y  R  F  K  D 1930      1940      1950      1960      1970      1980
    ----:----|----:----|----:----|----:----|----:----|----:----|
GTTGCTGAAATACAGACTAAAGGATTTCAGACAATCTTAGCAATCCTCAAATTGTCAGCA
 V  A  E  I  Q  T  K  G  F  Q  T  I  L  A  I  L  K  L  S  A
                                  ||
                              exon16/exon17

1990      2000      2010      2020      2030      2040
    ----:----|----:----|----:----|----:----|----:----|----:----|
TCTTTTTCTAAGCTGCTGGTGCATCATTCATTTGACTTAGTAATATTCCATCAAATGTCT
 S  F  S  K  L  L  V  H  H  S  F  D  L  V  I  F  H  Q  M  S
```

Fig. 4C

```
                                    2005034094.TXT
          2050      2060      2070      2080      2090      2100
    ----:----|----:----|----:----|----:----|----:----|----:----|
    TCCAATATCATGGAACAAAAGGATCAACAGTTTCTAAACCTCTGTTGCAAGTGTTTTGCA
     S  N  I  M  E  Q  K  D  Q  Q  F  L  N  L  C  C  K  C  F  A
                                    ||
                                    exon17/exon18

2110      2120      2130      2140      2150      2160
    ----:----|----:----|----:----|----:----|----:----|----:----|
    AAAGTAGCTATGGATGATTACTTAAAAAATGTGATGCTAGAGAGAGCGTGTGATCAGAAT
     K  V  A  M  D  D  Y  L  K  N  V  M  L  E  R  A  C  D  Q  N 2170      2180      2190      2200      2210      2220
    ----:----|----:----|----:----|----:----|----:----|----:----|
    AACAGCATCATGGTTGAATGCTTGCTTCTATTGGGAGCAGATGCCAATCAAGCAAAGGAG
     N  S  I  M  V  E  C  L  L  L  L  G  A  D  A  N  Q  A  K  E 2230      2240      2250      2260      2270      2280
    ----:----|----:----|----:----|----:----|----:----|----:----|
    GGATCTTCTTTAATTTGTCAGGTATGTGAGAAAGAGAGCAGTCCCAAATTGGTGGAACTC
     G  S  S  L  I  C  Q  V  C  E  K  E  S  S  P  K  L  V  E  L
                               ||
                               exon18/exon19

2290      2300      2310      2320      2330      2340
    ----:----|----:----|----:----|----:----|----:----|----:----|
    TTACTGAATAGTGGATCTCGTGAACAAGATGTACGAAAAGCGTTGACGATAAGCATTGGG
     L  L  N  S  G  S  R  E  Q  D  V  R  K  A  L  T  I  S  I  G 2350      2360      2370      2380      2390      2400
    ----:----|----:----|----:----|----:----|----:----|----:----|
    AAAGGTGACAGCCAGATCATCAGCTTGCTCTTAAGGAGGCTGGCCCTGGATGTGGCCAAC
     K  G  D  S  Q  I  I  S  L  L  L  R  R  L  A  L  D  V  A  N 2410      2420      2430      2440      2450      2460
    ----:----|----:----|----:----|----:----|----:----|----:----|
    AATAGCATTTGCCTTGGAGGATTTTGTATAGGAAAAGTTGAACCTTCTTGGCTTGGTCCT
     N  S  I  C  L  G  G  F  C  I  G  K  V  E  P  S  W  L  G  P 2470      2480      2490      2500      2510      2520
    ----:----|----:----|----:----|----:----|----:----|----:----|
    TTATTTCCAGATAAGACTTCTAATTTAAGGAAACAAACAAATATAGCATCTACACTAGCA
     L  F  P  D  K  T  S  N  L  R  K  Q  T  N  I  A  S  T  L  A
                                              ||
                                              exon19/exon20

2530      2540      2550      2560      2570      2580
    ----:----|----:----|----:----|----:----|----:----|----:----|
    AGAATGGTGATCAGATATCAGATGAAAAGTGCTGTGGAAGAAGGAACAGCCTCAGGCAGC
     R  M  V  I  R  Y  Q  M  K  S  A  V  E  E  G  T  A  S  G  S 2590      2600      2610      2620      2630      2640
    ----:----|----:----|----:----|----:----|----:----|----:----|
    GATGGAAATTTTTCTGAAGATGTGCTGTCTAAATTTGATGAATGGACCTTTATTCCTGAC
     D  G  N  F  S  E  D  V  L  S  K  F  D  E  W  T  F  I  P  D 2650      2660      2670      2680      2690      2700
    ----:----|----:----|----:----|----:----|----:----|----:----|
    TCTTCTATGGACAGTGTGTTTGCTCAAAGTGATGACCTGGATAGTGAAGGAAGTGAAGGC
     S  S  M  D  S  V  F  A  Q  S  D  D  L  D  S  E  G  S  E  G
                                                          ||
                                                          exon20/exon21

2710      2720      2730      2740      2750      2760
    ----:----|----:----|----:----|----:----|----:----|----:----|
    TCATTTCTTGTGAAAAAGAAATCTAATTCAATTAGTGTAGGAGAATTTTACCGAGATGCC
     S  F  L  V  K  K  K  S  N  S  I  S  V  G  E  F  Y  R  D  A
```

Fig. 4D

2005034094.TXT

```
           2770      2780      2790      2800      2810      2820
    ----:----|----:----|----:----|----:----|----:----|----:----|
    GTATTACAGCGTTGCTCACCAAATTTGCAAAGACATTCCAATTCCTTGGGGCCCATTTTT
     V  L  Q  R  C  S  P  N  L  Q  R  H  S  N  S  L  G  P  I  F
                                                       ||
                                                  exon21/exon22

2830      2840      2850      2860      2870      2880
    ----:----|----:----|----:----|----:----|----:----|----:----|
    GATCATGAAGATTTACTGAAGCGAAAAAGAAAAATACTATCTTCAGATGATTCACTCAGG
     D  H  E  D  L  L  K  R  K  R  K  I  L  S  S  D  D  S  L  R
                                                                ||
                                                         exon22/exon23

2890      2900      2910      2920      2930      2940
    ----:----|----:----|----:----|----:----|----:----|----:----|
    TCATCAAAACTTCAATCCCATATGAGGCATTCAGACAGCATTTCTTCTCTGGCTTCTGAG
     S  S  K  L  Q  S  H  M  R  H  S  D  S  I  S  S  L  A  S  E 2950      2960      2970      2980      2990      3000
    ----:----|----:----|----:----|----:----|----:----|----:----|
    AGAGAATATATTACATCACTAGACCTTTCAGCAAATGAACTAAGAGATATTGATGCCCTA
     R  E  Y  I  T  S  L  D  L  S  A  N  E  L  R  D  I  D  A  L 3010      3020      3030      3040      3050      3060
    ----:----|----:----|----:----|----:----|----:----|----:----|
    AGCCAGAAATGCTGTATAAGTGTTCATTTGGAGCATCTTGAAAAGCTGGAGCTTCACCAG
     S  Q  K  C  C  I  S  V  H  L  E  H  L  E  K  L  E  L  H  Q 3070      3080      3090      3100      3110      3120
    ----:----|----:----|----:----|----:----|----:----|----:----|
    AATGCACTCACGAGCTTTCCACAACAGCTATGTGAAACTCTGAAGAGTTTGACACATTTG
     N  A  L  T  S  F  P  Q  Q  L  C  E  T  L  K  S  L  T  H  L
                                         ||
                                    exon23/exon24

3130      3140      3150      3160      3170      3180
    ----:----|----:----|----:----|----:----|----:----|----:----|
    GACTTGCACAGTAATAAATTTACATCATTTCCTTCTTATTTGTTGAAAATGAGTTGTATT
     D  L  H  S  N  K  F  T  S  F  P  S  Y  L  L  K  M  S  C  I 3190      3200      3210      3220      3230      3240
    ----:----|----:----|----:----|----:----|----:----|----:----|
    GCTAATCTTGATGTCTCTCGAAATGACATTGGACCCTCAGTGGTTTTAGATCCTACAGTG
     A  N  L  D  V  S  R  N  D  I  G  P  S  V  V  L  D  P  T  V 3250      3260      3270      3280      3290      3300
    ----:----|----:----|----:----|----:----|----:----|----:----|
    AAATGTCCAACTCTGAAACAGTTTAACCTGTCATATAACCAGCTGTCTTTTGTACCTGAG
     K  C  P  T  L  K  Q  F  N  L  S  Y  N  Q  L  S  F  V  P  E 3310      3320      3330      3340      3350      3360
    ----:----|----:----|----:----|----:----|----:----|----:----|
    AACCTCACTGATGTGGTAGAGAAACTGGAGCAGCTCATTTTAGAAGGAAATAAAATATCA
     N  L  T  D  V  V  E  K  L  E  Q  L  I  L  E  G  N  K  I  S
                                                                ||
                                                         exon24/exon25

3370      3380      3390      3400      3410      3420
    ----:----|----:----|----:----|----:----|----:----|----:----|
    GGGATATGCTCCCCCTTGAGACTGAAGGAACTGAAGATTTTAAACCTTAGTAAGAACCAC
     G  I  C  S  P  L  R  L  K  E  L  K  I  L  N  L  S  K  N  H 3430      3440      3450      3460      3470      3480
    ----:----|----:----|----:----|----:----|----:----|----:----|
    ATTTCATCCCTATCAGAGAACTTTCTTGAGGCTTGTCCTAAAGTGGAGAGTTTCAGTGCC
     I  S  S  L  S  E  N  F  L  E  A  C  P  K  V  E  S  F  S  A
```

Fig. 4E

2005034094.TXT

```
            3490      3500      3510      3520      3530      3540
       ----:----|----:----|----:----|----:----|----:----|----:----|
       AGAATGAATTTTCTTGCTGCTATGCCTTTCTTGCCTCCTTCTATGACAATCCTAAAATTA
        R  M  N  F  L  A  A  M  P  F  L  P  P  S  M  T  I  L  K  L
                       ||
                   exon25/exon26

3550      3560      3570      3580      3590      3600
       ----:----|----:----|----:----|----:----|----:----|----:----|
       TCTCAGAACAAATTTTCCTGTATTCCAGAAGCAATTTTAAATCTTCCACACTTGCGGTCT
        S  Q  N  K  F  S  C  I  P  E  A  I  L  N  L  P  H  L  R  S
                                                            ||
                                                      exon26/exon27

3610      3620      3630      3640      3650      3660
       ----:----|----:----|----:----|----:----|----:----|----:----|
       TTAGATATGAGCAGCAATGATATTCAGTACCTACCAGGTCCCGCACACTGGAAATCTTTG
        L  D  M  S  S  N  D  I  Q  Y  L  P  G  P  A  H  W  K  S  L 3670      3680      3690      3700      3710      3720
       ----:----|----:----|----:----|----:----|----:----|----:----|
       AACTTAAGGGAACTCTTATTTAGCCATAATCAGATCAGCATCTTGGACTTGAGTGAAAAA
        N  L  R  E  L  L  F  S  H  N  Q  I  S  I  L  D  L  S  E  K 3730      3740      3750      3760      3770      3780
       ----:----|----:----|----:----|----:----|----:----|----:----|
       GCATATTTATGGTCTAGAGTAGAGAAACTGCATCTTTCTCACAATAAACTGAAAGAGATT
        A  Y  L  W  S  R  V  E  K  L  H  L  S  H  N  K  L  K  E  I
                                                                ||
                                                          exon27/exon28

3790      3800      3810      3820      3830      3840
       ----:----|----:----|----:----|----:----|----:----|----:----|
       CCTCCTGAGATTGGCTGTCTTGAAAATCTGACATCTCTGGATGTCAGTTACAACTTGGAA
        P  P  E  I  G  C  L  E  N  L  T  S  L  D  V  S  Y  N  L  E 3850      3860      3870      3880      3890      3900
       ----:----|----:----|----:----|----:----|----:----|----:----|
       CTAAGATCCTTTCCCAATGAAATGGGGAAATTAAGCAAAATATGGGATCTTCCTTTGGAT
        L  R  S  F  P  N  E  M  G  K  L  S  K  I  W  D  L  P  L  D 3910      3920      3930      3940      3950      3960
       ----:----|----:----|----:----|----:----|----:----|----:----|
       GAACTGCATCTTAACTTTGATTTTAAACATATAGGATGTAAAGCCAAAGACATCATAAGG
        E  L  H  L  N  F  D  F  K  H  I  G  C  K  A  K  D  I  I  R
                                                                ||
                                                          exon28/exon29

3970      3980      3990      4000      4010      4020
       ----:----|----:----|----:----|----:----|----:----|----:----|
       TTTCTTCAACAGCGATTAAAAAAAGGCTGTGCCTTATAACCGAATGAAACTTATGATTGTG
        F  L  Q  Q  R  L  K  K  A  V  P  Y  N  R  M  K  L  M  I  V 4030      4040      4050      4060      4070      4080
       ----:----|----:----|----:----|----:----|----:----|----:----|
       GGAAATACTGGGAGTGGTAAAACCACCTTATTGCAGCAATTAATGAAAACCAAGAAATCA
        G  N  T  G  S  G  K  T  T  L  L  Q  Q  L  M  K  T  K  K  S 4090      4100      4110      4120      4130      4140
       ----:----|----:----|----:----|----:----|----:----|----:----|
       GATCTTGGAATGCAAAGTGCCACAGTTGGCATAGATGTGAAAGACTGGCCTATCCAAATA
        D  L  G  M  Q  S  A  T  V  G  I  D  V  K  D  W  P  I  Q  I 4150      4160      4170      4180      4190      4200
       ----:----|----:----|----:----|----:----|----:----|----:----|
       AGAGACAAAAGAAAGAGAGATCTCGTCCTAAATGTGTGGGATTTTGCAGGTCGTGAGGAA
        R  D  K  R  K  R  D  L  V  L  N  V  W  D  F  A  G  R  E  E
                                                                ||
```

Fig. 4F

2005034094.TXT exon29/exon30

```
        4210      4220      4230      4240      4250      4260
----:----|----:----|----:----|----:----|----:----|----:----|
TTCTATAGTACTCATCCCCATTTTATGACGCAGCGAGCATTGTACCTTGCTGTCTATGAC
 F  Y  S  T  H  P  H  F  M  T  Q  R  A  L  Y  L  A  V  Y  D 4270      4280      4290      4300      4310      4320
----:----|----:----|----:----|----:----|----:----|----:----|
CTCAGCAAGGGACAGGCTGAAGTTGATGCCATGAAGCCTTGGCTCTTCAATATAAAGGCT
 L  S  K  G  Q  A  E  V  D  A  M  K  P  W  L  F  N  I  K  A
                                                          ||
                                                 exon30/exon31

4330      4340      4350      4360      4370      4380
----:----|----:----|----:----|----:----|----:----|----:----|
CGCGCTTCTTCTTCCCCTGTGATTCTCGTTGGCACACATTTGGATGTTTCTGATGAGAAG
 R  A  S  S  S  P  V  I  L  V  G  T  H  L  D  V  S  D  E  K 4390      4400      4410      4420      4430      4440
----:----|----:----|----:----|----:----|----:----|----:----|
CAACGCAAAGCCTGCATGAGTAAAATCACCAAGGAACTCCTGAATAAGCGAGGGTTCCCT
 Q  R  K  A  C  M  S  K  I  T  K  E  L  L  N  K  R  G  F  P 4450      4460      4470      4480      4490      4500
----:----|----:----|----:----|----:----|----:----|----:----|
GCCATACGAGATTACCACTTTGTGAATGCCACCGAGGAATCTGATGCTTTGGCAAAACTT
 A  I  R  D  Y  H  F  V  N  A  T  E  E  S  D  A  L  A  K  L 4510      4520      4530      4540      4550      4560
----:----|----:----|----:----|----:----|----:----|----:----|
CGGAAAACCATCATAAACGAGAGCCTTAATTTCAAGATCCGAGATCAGCTTGTTGTTGGA
 R  K  T  I  I  N  E  S  L  N  F  K  I  R  D  Q  L  V  V  G
                                       ||
                                exon31/exon32

4570      4580      4590      4600      4610      4620
----:----|----:----|----:----|----:----|----:----|----:----|
CAGCTGATTCCAGACTGCTATGTAGAACTTGAAAAAATCATTTTATCGGAGCGTAAAAAT
 Q  L  I  P  D  C  Y  V  E  L  E  K  I  I  L  S  E  R  K  N 4630      4640      4650      4660      4670      4680
----:----|----:----|----:----|----:----|----:----|----:----|
GTGCCAATTGAATTTCCCGTAATTGACCGGAAACGATTATTACAACTAGTGAGAGAAAAT
 V  P  I  E  F  P  V  I  D  R  K  R  L  L  Q  L  V  R  E  N 4690      4700      4710      4720      4730      4740
----:----|----:----|----:----|----:----|----:----|----:----|
CAGCTGCAGTTAGATGAAAATGAGCTTCCTCACGCAGTTCACTTTCTAAATGAATCAGGA
 Q  L  Q  L  D  E  N  E  L  P  H  A  V  H  F  L  N  E  S  G
                                                          ||
                                                 exon32/exon33

4750      4760      4770      4780      4790      4800
----:----|----:----|----:----|----:----|----:----|----:----|
GTCCTTCTTCATTTTCAAGACCCAGCACTGCAGTTAAGTGACTTGTACTTTGTGGAACCC
 V  L  L  H  F  Q  D  P  A  L  Q  L  S  D  L  Y  F  V  E  P 4810      4820      4830      4840      4850      4860
----:----|----:----|----:----|----:----|----:----|----:----|
AAGTGGCTTTGTAAAATCATGGCACAGATTTTGACAGTGAAAGTGGAAGGTTGTCCAAAA
 K  W  L  C  K  I  M  A  Q  I  L  T  V  K  V  E  G  C  P  K
                                ||
                         exon33/exon34

4870      4880      4890      4900      4910      4920
----:----|----:----|----:----|----:----|----:----|----:----|
CACCCTAAGGGCATTATTTCGCGTAGAGATGTGGAAAAATTTCTTTCAAAAAAAAGGAAA
```

Fig. 4G

2005034094.TXT

```
               H  P  K  G  I  I  S  R  R  D  V  E  K  F  L  S  K  K  R  K
                4930       4940       4950       4960       4970       4980
           ----:----|----:----|----:----|----:----|----:----|----:----|
           TTTCCAAAGAACTACATGTCACAGTATTTTAAGCTCCTAGAAAAATTCCAGATTGCTTTG
            F  P  K  N  Y  M  S  Q  Y  F  K  L  L  E  K  F  Q  I  A  L
                4990       5000       5010       5020       5030       5040
           ----:----|----:----|----:----|----:----|----:----|----:----|
           CCAATAGGAGAAGAATATTTGCTGGTTCCAAGCAGTTTGTCTGACCACAGGCCTGTGATA
            P  I  G  E  E  Y  L  L  V  P  S  S  L  S  D  H  R  P  V  I
                                              ||
                                       exon34/exon35

5050       5060       5070       5080       5090       5100
           ----:----|----:----|----:----|----:----|----:----|----:----|
           GAGCTTCCCCATTGTGAGAACTCTGAAATTATCATCCGACTATATGAAATGCCTTATTTT
            E  L  P  H  C  E  N  S  E  I  I  I  R  L  Y  E  M  P  Y  F 5110       5120       5130       5140       5150       5160
           ----:----|----:----|----:----|----:----|----:----|----:----|
           CCAATGGGATTTTGGTCAAGATTAATCAATCGATTACTTGAGATTTCACCTTACATGCTT
            P  M  G  F  W  S  R  L  I  N  R  L  L  E  I  S  P  Y  M  L 5170       5180       5190       5200       5210       5220
           ----:----|----:----|----:----|----:----|----:----|----:----|
           TCAGGGAGAGAACGAGCACTTCGCCCAAACAGAATGTATTGGCGACAAGGCATTTACTTA
            S  G  R  E  R  A  L  R  P  N  R  M  Y  W  R  Q  G  I  Y  L
                    ||
               exon35/exon36

5230       5240       5250       5260       5270       5280
           ----:----|----:----|----:----|----:----|----:----|----:----|
           AATTGGTCTCCTGAAGCTTATTGTCTGGTAGGATCTGAAGTCTTAGACAATCATCCAGAG
            N  W  S  P  E  A  Y  C  L  V  G  S  E  V  L  D  N  H  P  E 5290       5300       5310       5320       5330       5340
           ----:----|----:----|----:----|----:----|----:----|----:----|
           AGTTTCTTAAAAATTACAGTTCCTTCTTGTAGAAAAGGCTGTATTCTTTTGGGCCAAGTT
            S  F  L  K  I  T  V  P  S  C  R  K  G  C  I  L  L  G  Q  V
                                              ||
                                       exon36/exon37

5350       5360       5370       5380       5390       5400
           ----:----|----:----|----:----|----:----|----:----|----:----|
           GTGGACCACATTGATTCTCTCATGGAAGAATGGTTTCCTGGGTTGCTGGAGATTGATATT
            V  D  H  I  D  S  L  M  E  E  W  F  P  G  L  L  E  I  D  I 5410       5420       5430       5440       5450       5460
           ----:----|----:----|----:----|----:----|----:----|----:----|
           TGTGGTGAAGGAGAAACTCTGTTGAAGAAATGGGCATTATATAGTTTTAATGATGGCGAA
            C  G  E  G  E  T  L  L  K  K  W  A  L  Y  S  F  N  D  G  E 5470       5480       5490       5500       5510       5520
           ----:----|----:----|----:----|----:----|----:----|----:----|
           GAACATCAAAAAATCTTACTTGATGACTTGATGAAGAAAGCAGAGGAAGGAGATCTCTTA
            E  H  Q  K  I  L  L  D  D  L  M  K  K  A  E  E  G  D  L  L
                                                                ||
                                                         exon37/exon38

5530       5540       5550       5560       5570       5580
           ----:----|----:----|----:----|----:----|----:----|----:----|
           GTAAATCCAGATCAACCAAGGCTCACCATTCCAATATCTCAGATTGCCCCTGACTTGATT
            V  N  P  D  Q  P  R  L  T  I  P  I  S  Q  I  A  P  D  L  I 5590       5600       5610       5620       5630       5640
           ----:----|----:----|----:----|----:----|----:----|----:----|
           TTGGCTGACCTGCCTAGAAATATTATGTTGAATAATGATGAGTTGGAATTTGAACAAGCT
```

Fig. 4H

2005034094.TXT

```
       L  A  D  L  P  R  N  I  M  L  N  N  D  E  L  E  F  E  Q  A
            5650       5660       5670       5680       5690       5700
     ----:----|----:----|----:----|----:----|----:----|----:----|
     CCAGAGTTTCTCCTAGGTGATGGCAGTTTTGGATCAGTTTACCGAGCAGCCTATGAAGGA
      P  E  F  L  L  G  D  G  S  F  G  S  V  Y  R  A  A  Y  E  G
                       ||
                  exon38/exon39

5710       5720       5730       5740       5750       5760
     ----:----|----:----|----:----|----:----|----:----|----:----|
     GAAGAAGTGGCTGTGAAGATTTTTAATAAACATACATCACTCAGGCTGTTAAGACAAGAG
      E  E  V  A  V  K  I  F  N  K  H  T  S  L  R  L  L  R  Q  E
                                                              ||
                                                          exon39/exon40

5770       5780       5790       5800       5810       5820
     ----:----|----:----|----:----|----:----|----:----|----:----|
     CTTGTGGTGCTTTGCCACCTCCACCACCCCAGTTTGATATCTTTGCTGGCAGCTGGGATT
      L  V  V  L  C  H  L  H  H  P  S  L  I  S  L  L  A  A  G  I 5830       5840       5850       5860       5870       5880
     ----:----|----:----|----:----|----:----|----:----|----:----|
     CGTCCCCGGATGTTGGTGATGGAGTTAGCCTCCAAGGGTTCCTTGGATCGCCTGCTTCAG
      R  P  R  M  L  V  M  E  L  A  S  K  G  S  L  D  R  L  L  Q 5890       5900       5910       5920       5930       5940
     ----:----|----:----|----:----|----:----|----:----|----:----|
     CAGGACAAAGCCAGCCTCACTAGAACCCTACAGCACAGGATTGCACTCCACGTAGCTGAT
      Q  D  K  A  S  L  T  R  T  L  Q  H  R  I  A  L  H  V  A  D 5950       5960       5970       5980       5990       6000
     ----:----|----:----|----:----|----:----|----:----|----:----|
     GGTTTGAGATACCTCCACTCAGCCATGATTATATACCGAGACCTGAAACCCCACAATGTG
      G  L  R  Y  L  H  S  A  M  I  I  Y  R  D  L  K  P  H  N  V
                 ||
             exon40/exon41

6010       6020       6030       6040       6050       6060
     ----:----|----:----|----:----|----:----|----:----|----:----|
     CTGCTTTTCACACTGTATCCCAATGCTGCCATCATTGCAAAGATTGCTGACTACGGCATT
      L  L  F  T  L  Y  P  N  A  A  I  I  A  K  I  A  D  Y  G  I 6070       6080       6090       6100       6110       6120
     ----:----|----:----|----:----|----:----|----:----|----:----|
     GCTCAGTACTGCTGTAGAATGGGGATAAAAACATCAGAGGGCACACCAGGGTTTCGTGCA
      A  Q  Y  C  C  R  M  G  I  K  T  S  E  G  T  P  G  F  R  A
                                                           ||
                                                       exon41/exon42

6130       6140       6150       6160       6170       6180
     ----:----|----:----|----:----|----:----|----:----|----:----|
     CCTGAAGTTGCCAGAGGAAATGTCATTTATAACCAACAGGCTGATGTTTATTCATTTGGT
      P  E  V  A  R  G  N  V  I  Y  N  Q  Q  A  D  V  Y  S  F  G 6190       6200       6210       6220       6230       6240
     ----:----|----:----|----:----|----:----|----:----|----:----|
     TTACTACTCTATGACATTTTGACAACTGGAGGTAGAATAGTAGAGGGTTTGAAGTTTCCA
      L  L  L  Y  D  I  L  T  T  G  G  R  I  V  E  G  L  K  F  P 6250       6260       6270       6280       6290       6300
     ----:----|----:----|----:----|----:----|----:----|----:----|
     AATGAGTTTGATGAATTAGAAATACAAGGAAAATTACCTGATCCAGTTAAAGAATATGGT
      N  E  F  D  E  L  E  I  Q  G  K  L  P  D  P  V  K  E  Y  G
                                                  ||
                                              exon42/exon43

2005034094.TXT

```
    ----:----|----:----|----:----|----:----|----:----|----:----|
    TGTGCCCCATGGCCTATGGTTGAGAAATTAATTAAACAGTGTTTGAAAGAAAATCCTCAA
     C  A  P  W  P  M  V  E  K  L  I  K  Q  C  L  K  E  N  P  Q
             6370      6380      6390      6400      6410      6420
    ----:----|----:----|----:----|----:----|----:----|----:----|
    GAAAGGCCTACTTCTGCCCAGGTCTTTGACATTTTGAATTCAGCTGAATTAGTCTGTCTG
     E  R  P  T  S  A  Q  V  F  D  I  L  N  S  A  E  L  V  C  L
                            ||
                      exon43/exon44
             6430      6440      6450      6460      6470      6480
    ----:----|----:----|----:----|----:----|----:----|----:----|
    ACGAGACGCATTTTATTACCTAAAAACGTAATTGTTGAATGCATGGTTGCTACACATCAC
     T  R  R  I  L  L  P  K  N  V  I  V  E  C  M  V  A  T  H  H
             6490      6500      6510      6520      6530      6540
    ----:----|----:----|----:----|----:----|----:----|----:----|
    AACAGCAGGAATGCAAGCATTTGGCTGGGCTGTGGGCACACCGACAGAGGACAGCTCTCA
     N  S  R  N  A  S  I  W  L  G  C  G  H  T  D  R  G  Q  L  S
             6550      6560      6570      6580      6590      6600
    ----:----|----:----|----:----|----:----|----:----|----:----|
    TTTCTTGACTTAAATACTGAAGGATACACTTCTGAGGAAGTTGCTGATAGTAGAATATTG
     F  L  D  L  N  T  E  G  Y  T  S  E  E  V  A  D  S  R  I  L
                                           ||
                                     exon44/exon45
             6610      6620      6630      6640      6650      6660
    ----:----|----:----|----:----|----:----|----:----|----:----|
    TGCTTAGCCTTGGTGCATCTTCCTGTTGAAAAGGAAAGCTGGATTGTGTCTGGGACACAG
     C  L  A  L  V  H  L  P  V  E  K  E  S  W  I  V  S  G  T  Q
             6670      6680      6690      6700      6710      6720
    ----:----|----:----|----:----|----:----|----:----|----:----|
    TCTGGTACTCTCCTGGTCATCAATACCGAAGATGGGAAAAAGAGACATACCCTAGAAAAG
     S  G  T  L  L  V  I  N  T  E  D  G  K  K  R  H  T  L  E  K
             6730      6740      6750      6760      6770      6780
    ----:----|----:----|----:----|----:----|----:----|----:----|
    ATGACTGATTCTGTCACTTGTTTGTATTGCAATTCCTTTTCCAAGCAAAGCAAACAAAAA
     M  T  D  S  V  T  C  L  Y  C  N  S  F  S  K  Q  S  K  Q  K
                                                          ||
                                                    exon45/exon46
             6790      6800      6810      6820      6830      6840
    ----:----|----:----|----:----|----:----|----:----|----:----|
    AATTTTCTTTTGGTTGGAACCGCTGATGGCAAGTTAGCAATTTTTGAAGATAAGACTGTT
     N  F  L  L  V  G  T  A  D  G  K  L  A  I  F  E  D  K  T  V
             6850      6860      6870      6880      6890      6900
    ----:----|----:----|----:----|----:----|----:----|----:----|
    AAGCTTAAAGGAGCTGCTCCTTTGAAGATACTAAATATAGGAAATGTCAGTACTCCATTG
     K  L  K  G  A  A  P  L  K  I  L  N  I  G  N  V  S  T  P  L
     ||
exon46/exon47
             6910      6920      6930      6940      6950      6960
    ----:----|----:----|----:----|----:----|----:----|----:----|
    ATGTGTTTGAGTGAATCCACAAATTCAACGGAAAGAAATGTAATGTGGGGAGGATGTGGC
     M  C  L  S  E  S  T  N  S  T  E  R  N  V  M  W  G  G  C  G
             6970      6980      6990      7000      7010      7020
    ----:----|----:----|----:----|----:----|----:----|----:----|
    ACAAAGATTTTCTCCTTTTCTAATGATTTCACCATTCAGAAACTCATTGAGACAAGAACA
     T  K  I  F  S  F  S  N  D  F  T  I  Q  K  L  I  E  T  R  T
             7030      7040      7050      7060      7070      7080
```

Fig. 4J

2005034094.TXT

```
         ----:----|----:----|----:----|----:----|----:----|----:----|
         AGCCAACTGTTTTCTTATGCAGCTTTCAGTGATTCCAACATCATAACAGTGGTGGTAGAC
          S  Q  L  F  S  Y  A  A  F  S  D  S  N  I  I  T  V  V  V  D
                ||
                exon47/exon48

7090      7100      7110      7120      7130      7140
         ----:----|----:----|----:----|----:----|----:----|----:----|
         ACTGCTCTCTATATTGCTAAGCAAAATAGCCCTGTTGTGGAAGTGTGGGATAAGAAAACT
          T  A  L  Y  I  A  K  Q  N  S  P  V  V  E  V  W  D  K  K  T 7150      7160      7170      7180      7190      7200
         ----:----|----:----|----:----|----:----|----:----|----:----|
         GAAAAACTCTGTGGACTAATAGACTGCGTGCACTTTTTAAGGGAGGTAATGGTAAAAGAA
          E  K  L  C  G  L  I  D  C  V  H  F  L  R  E  V  M  V  K  E
                                              ||
                                              exon48/exon49

7210      7220      7230      7240      7250      7260
         ----:----|----:----|----:----|----:----|----:----|----:----|
         AACAAGGAATCAAAACACAAAATGTCTTATTCTGGGAGAGTGAAAACCCTCTGCCTTCAG
          N  K  E  S  K  H  K  M  S  Y  S  G  R  V  K  T  L  C  L  Q 7270      7280      7290      7300      7310      7320
         ----:----|----:----|----:----|----:----|----:----|----:----|
         AAGAACACTGCTCTTTGGATAGGAACTGGAGGAGGCCATATTTTACTCCTGGATCTTTCA
          K  N  T  A  L  W  I  G  T  G  G  G  H  I  L  L  L  D  L  S 7330      7340      7350      7360      7370      7380
         ----:----|----:----|----:----|----:----|----:----|----:----|
         ACTCGTCGACTTATACGTGTAATTTACAACTTTTGTAATTCGGTCAGAGTCATGATGACA
          T  R  R  L  I  R  V  I  Y  N  F  C  N  S  V  R  V  M  M  T 7390      7400      7410      7420      7430      7440
         ----:----|----:----|----:----|----:----|----:----|----:----|
         GCACAGCTAGGAAGCCTTAAAAATGTCATGCTGGTATTGGGCTACAACCGGAAAAATACT
          A  Q  L  G  S  L  K  N  V  M  L  V  L  G  Y  N  R  K  N  T
                ||
                exon49/exon50

7450      7460      7470      7480      7490      7500
         ----:----|----:----|----:----|----:----|----:----|----:----|
         GAAGGTACACAAAAGCAGAAAGAGATACAATCTTGCTTGACCGTTTGGGACATCAATCTT
          E  G  T  Q  K  Q  K  E  I  Q  S  C  L  T  V  W  D  I  N  L
                               ||
                               exon50/exon51

7510      7520      7530      7540      7550      7560
         ----:----|----:----|----:----|----:----|----:----|----:----|
         CCACATGAAGTGCAAAATTTAGAAAAACACATTGAAGTGAGAAAAGAATTAGCTGAAAAA
          P  H  E  V  Q  N  L  E  K  H  I  E  V  R  K  E  L  A  E  K 7570      7580      7590      7600      7610      7620
         ----:----|----:----|----:----|----:----|----:----|----:----|
         ATGAGACGAACATCTGTTGAGTAA
          M  R  R  T  S  V  E  *
```

Fig. 4K

SEQ ID NO:1 and SEQ ID NO:8

| | | | | | | | | | | | | | | | | | |
|---|---|---|---|---|---|---|---|---|---|---|---|---|---|---|---|---|---|
| M | A | S | G | S | C | Q | G | C | E | E | D | E | E | T | L | K | K | 18 |
| ATG | GCT | AGT | GGC | AGC | TGT | CAG | GGG | TGC | GAA | GAG | GAC | GAG | GAA | ACT | CTG | AAG | AAG | 54 |

| L | I | V | R | L | N | N | V | Q | E | G | K | Q | I | E | T | L | V | 36 |
|---|---|---|---|---|---|---|---|---|---|---|---|---|---|---|---|---|---|---|
| TTG | ATA | GTC | AGG | CTG | AAC | AAT | GTC | CAG | GAA | GGA | AAA | CAG | ATA | GAA | ACG | CTG | GTC | 108 |

| Q | I | L | E | D | L | L | V | F | T | Y | S | E | R | A | S | K | L | 54 |
|---|---|---|---|---|---|---|---|---|---|---|---|---|---|---|---|---|---|---|
| CAA | ATC | CTG | GAG | GAT | CTG | CTG | GTG | TTC | ACG | TAC | TCC | GAG | CGC | GCC | TCC | AAG | TTA | 162 |

| F | Q | G | K | N | I | H | V | P | L | L | I | V | L | D | S | Y | M | 72 |
|---|---|---|---|---|---|---|---|---|---|---|---|---|---|---|---|---|---|---|
| TTT | CAA | GGC | AAA | AAT | ATC | CAT | GTG | CCT | CTG | TTG | ATC | GTC | TTG | GAC | TCC | TAT | ATG | 216 |

| R | V | A | S | V | Q | Q | V | G | W | S | L | L | C | K | L | I | E | 90 |
|---|---|---|---|---|---|---|---|---|---|---|---|---|---|---|---|---|---|---|
| AGA | GTC | GCG | AGT | GTG | CAG | CAG | GTG | GGT | TGG | TCA | CTT | CTG | TGC | AAA | TTA | ATA | GAA | 270 |

| V | C | P | G | T | M | Q | S | L | M | G | P | Q | D | V | G | N | D | 108 |
|---|---|---|---|---|---|---|---|---|---|---|---|---|---|---|---|---|---|---|
| GTC | TGT | CCA | GGT | ACA | ATG | CAA | AGC | TTA | ATG | GGA | CCC | CAG | GAT | GTT | GGA | AAT | GAT | 324 |

| W | E | V | L | G | V | H | Q | L | I | L | K | M | L | T | V | H | N | 126 |
|---|---|---|---|---|---|---|---|---|---|---|---|---|---|---|---|---|---|---|
| TGG | GAA | GTC | CTT | GGT | GTT | CAC | CAA | TTG | ATT | CTT | AAA | ATG | CTA | ACA | GTT | CAT | AAT | 378 |

| A | S | V | N | L | S | V | I | G | L | K | T | L | D | L | L | L | T | 144 |
|---|---|---|---|---|---|---|---|---|---|---|---|---|---|---|---|---|---|---|
| GCC | AGT | GTA | AAC | TTG | TCA | GTG | ATT | GGA | CTG | AAG | ACC | TTA | GAT | CTC | CTC | CTA | ACT | 432 |

| S | G | K | I | T | L | L | I | L | D | E | E | S | D | I | F | M | L | 162 |
|---|---|---|---|---|---|---|---|---|---|---|---|---|---|---|---|---|---|---|
| TCA | GGT | AAA | ATC | ACC | TTG | CTG | ATA | TTG | GAT | GAA | GAA | AGT | GAT | ATT | TTC | ATG | TTA | 486 |

| I | F | D | A | M | H | S | F | P | A | N | D | E | V | Q | K | L | G | 180 |
|---|---|---|---|---|---|---|---|---|---|---|---|---|---|---|---|---|---|---|
| ATT | TTT | GAT | GCC | ATG | CAC | TCA | TTT | CCA | GCC | AAT | GAT | GAA | GTC | CAG | AAA | CTT | GGA | 540 |

| C | K | A | L | H | V | L | F | E | R | V | S | E | E | Q | L | T | E | 198 |
|---|---|---|---|---|---|---|---|---|---|---|---|---|---|---|---|---|---|---|
| TGC | AAA | GCT | TTA | CAT | GTG | CTG | TTT | GAG | AGA | GTC | TCA | GAG | GAG | CAA | CTG | ACT | GAA | 594 |

| F | V | E | N | K | D | Y | M | I | L | L | S | A | S | T | N | F | K | 216 |
|---|---|---|---|---|---|---|---|---|---|---|---|---|---|---|---|---|---|---|
| TTT | GTT | GAG | AAC | AAA | GAT | TAT | ATG | ATA | TTG | TTA | AGT | GCG | TCA | ACA | AAT | TTT | AAA | 648 |

| D | E | E | E | I | V | L | H | V | L | H | C | L | H | S | L | A | I | 234 |
|---|---|---|---|---|---|---|---|---|---|---|---|---|---|---|---|---|---|---|
| GAT | GAA | GAG | GAA | ATT | GTG | CTT | CAT | GTG | CTG | CAT | TGT | TTA | CAT | TCC | CTA | GCG | ATT | 702 |

| P | C | N | N | V | E | V | L | M | S | G | N | V | R | C | Y | N | I | 252 |
|---|---|---|---|---|---|---|---|---|---|---|---|---|---|---|---|---|---|---|
| CCT | TGC | AAT | AAT | GTG | GAA | GTC | CTC | ATG | AGT | GGC | AAT | GTC | AGG | TGT | TAT | AAT | ATT | 756 |

| V | V | E | A | M | K | A | F | P | M | S | E | R | I | Q | E | V | S | 270 |

Fig. 17A

```
              GTG GTG GAA GCT ATG AAA GCA TTC CCT ATG AGT GAA AGA ATT CAA GAA GTG AGT      810

C   C   L   L   H   R   L   T   L   G   N   F   F   N   I   L   V   L            288
TGC TGT TTG CTC CAT AGG CTT ACA TTA GGT AAT TTT TTC AAT ATC CTG GTA TTA             864

N   E   V   H   E   F   V   V   K   A   V   Q   Q   Y   P   E   N   A            306
AAC GAA GTC CAT GAG TTT GTG GTG AAA GCT GTG CAG CAG TAC CCA GAG AAT GCA             918

A   L   Q   I   S   A   L   S   C   L   A   L   L   T   E   T   I   F            324
GCA TTG CAG ATC TCA GCG CTC AGC TGT TTG GCC CTC CTC ACT GAG ACT ATT TTC             972

L   N   Q   D   L   E   E   K   N   E   N   Q   E   N   D   D   E   G            342
TTA AAT CAA GAT TTA GAG GAA AAG AAT GAG AAT CAA GAG AAT GAT GAT GAG GGG            1026

E   E   D   K   L   F   W   L   E   A   C   Y   K   A   L   T   W   H            360
GAA GAA GAT AAA TTG TTT TGG CTG GAA GCC TGT TAC AAA GCA TTA ACG TGG CAT            1080

R   K   N   K   H   V   Q   E   A   A   C   W   A   L   N   N   L   L            378
AGA AAG AAC AAG CAC GTG CAG GAG GCC GCA TGC TGG GCA CTA AAT AAT CTC CTT            1134

M   Y   Q   N   S   L   H   E   K   I   G   D   E   D   G   H   F   P            396
ATG TAC CAA AAC AGT TTA CAT GAG AAG ATT GGA GAT GAA GAT GGC CAT TTC CCA            1188

A   H   R   E   V   M   L   S   M   L   M   H   S   S   S   K   E   V            414
GCT CAT AGG GAA GTG ATG CTC TCC ATG CTG ATG CAT TCT TCA TCA AAG GAA GTT            1242

F   Q   A   S   A   N   A   L   S   T   L   L   E   Q   N   V   N   F            432
TTC CAG GCA TCT GCG AAT GCA TTG TCA ACT CTC TTA GAA CAA AAT GTT AAT TTC            1296

R   K   I   L   L   S   K   G   I   H   L   N   V   L   E   L   M   Q            450
AGA AAA ATA CTG TTA TCA AAA GGA ATA CAC CTG AAT GTT TTG GAG TTA ATG CAG            1350

K   H   I   H   S   P   E   V   A   E   S   G   C   K   M   L   N   H            468
AAG CAT ATA CAT TCT CCT GAA GTG GCT GAA AGT GGC TGT AAA ATG CTA AAT CAT            1404

L   F   E   G   S   N   T   S   L   D   I   M   A   A   V   V   P   K            486
CTT TTT GAA GGA AGC AAC ACT TCC CTG GAT ATA ATG GCA GCA GTG GTC CCC AAA            1458

I   L   T   V   M   K   R   H   E   T   S   L   P   V   Q   L   E   A            504
ATA CTA ACA GTT ATG AAA CGT CAT GAG ACA TCA TTA CCA GTG CAG CTG GAG GCG            1512

L   R   A   I   L   H   F   I   V   P   G   M   P   E   E   S   R   E            522
CTT CGA GCT ATT TTA CAT TTT ATA GTG CCT GGC ATG CCA GAA GAA TCC AGG GAG            1566

D   T   E   F   H   H   K   L   N   M   V   K   K   Q   C   F   K   N            540
GAT ACA GAA TTT CAT CAT AAG CTA AAT ATG GTT AAA AAA CAG TGT TTC AAG AAT            1620
```

Fig. 17B

```
      D   I   H   K   L   V   L   A   A   L   N   R   F   I   G   N   P   G      558
     GAT ATT CAC AAA CTG GTC CTA GCA GCT TTG AAC AGG TTC ATT GGA AAT CCT GGG     1674

I   Q   K   C   G   L   K   V   I   S   S   I   V   H   F   P   D   A      576
     ATT CAG AAA TGT GGA TTA AAA GTA ATT TCT TCT ATT GTA CAT TTT CCT GAT GCA     1728

L   E   M   L   S   L   E   G   A   M   D   S   V   L   H   T   L   Q      594
     TTA GAG ATG TTA TCC CTG GAA GGT GCT ATG GAT TCA GTG CTT CAC ACA CTG CAG     1782

M   Y   P   D   D   Q   E   I   Q   C   L   G   L   S   L   I   G   Y      612
     ATG TAT CCA GAT GAC CAA GAA ATT CAG TGT CTG GGT TTA AGT CTT ATA GGA TAC     1836

L   I   T   K   K   N   V   F   I   G   T   G   H   L   L   A   K   I      630
     TTG ATT ACA AAG AAG AAT GTG TTC ATA GGA ACT GGA CAT CTG CTG GCA AAA ATT     1890

L   V   S   S   L   Y   R   F   K   D   V   A   E   I   Q   T   K   G      648
     CTG GTT TCC AGC TTA TAC CGA TTT AAG GAT GTT GCT GAA ATA CAG ACT AAA GGA     1944

F   Q   T   I   L   A   I   L   K   L   S   A   S   F   S   K   L   L      666
     TTT CAG ACA ATC TTA GCA ATC CTC AAA TTG TCA GCA TCT TTT TCT AAG CTG CTG     1998

V   H   H   S   F   D   L   V   I   F   H   Q   M   S   S   N   I   M      684
     GTG CAT CAT TCA TTT GAC TTA GTA ATA TTC CAT CAA ATG TCT TCC AAT ATC ATG     2052

E   Q   K   D   Q   Q   F   L   N   L   C   C   K   C   F   A   K   V      702
     GAA CAA AAG GAT CAA CAG TTT CTA AAC CTC TGT TGC AAG TGT TTT GCA AAA GTA     2106

A   M   D   D   Y   L   K   N   V   M   L   E   R   A   C   D   Q   N      720
     GCT ATG GAT GAT TAC TTA AAA AAT GTG ATG CTA GAG AGA GCG TGT GAT CAG AAT     2160

N   S   I   M   V   E   C   L   L   L   G   A   D   A   N   Q   A          738
     AAC AGC ATC ATG GTT GAA TGC TTG CTT CTA TTG GGA GCA GAT GCC AAT CAA GCA     2214

K   E   G   S   S   L   I   C   Q   V   C   E   K   E   S   S   P   K      756
     AAG GAG GGA TCT TCT TTA ATT TGT CAG GTA TGT GAG AAA GAG AGC AGT CCC AAA     2268

L   V   E   L   L   N   S   G   S   R   E   Q   D   V   R   K   A          774
     TTG GTG GAA CTC TTA CTG AAT AGT GGA TCT CGT GAA CAA GAT GTA CGA AAA GCG     2322

L   T   I   S   I   G   K   G   D   S   Q   I   I   S   L   L   R          792
     TTG ACG ATA AGC ATT GGG AAA GGT GAC AGC CAG ATC ATC AGC TTG CTC TTA AGG     2376

R   L   A   L   D   V   A   N   N   S   I   C   L   G   G   F   C   I      810
     AGG CTG GCC CTG GAT GTG GCC AAC AAT AGC ATT TGC CTT GGA GGA TTT TGT ATA     2430
```

Fig. 17C

```
       G   K   V   E   P   S   W   L   G   P   L   F   P   D   K   T   S   N     828
      GGA AAA GTT GAA CCT TCT TGG CTT GGT CCT TTA TTT CCA GAT AAG ACT TCT AAT    2484

L   R   K   Q   T   N   I   A   S   T   L   A   R   M   V   I   R   Y     846
      TTA AGG AAA CAA ACA AAT ATA GCA TCT ACA CTA GCA AGA ATG GTG ATC AGA TAT    2538

Q   M   K   S   A   V   E   E   G   T   A   S   G   S   D   G   N   F     864
      CAG ATG AAA AGT GCT GTG GAA GAA GGA ACA GCC TCA GGC AGC GAT GGA AAT TTT    2592

S   E   D   V   L   S   K   F   D   E   W   T   F   I   P   D   S   S     882
      TCT GAA GAT GTG CTG TCT AAA TTT GAT GAA TGG ACC TTT ATT CCT GAC TCT TCT    2646

M   D   S   V   F   A   Q   S   D   D   L   D   S   E   G   S   E   G     900
      ATG GAC AGT GTG TTT GCT CAA AGT GAT GAC CTG GAT AGT GAA GGA AGT GAA GGC    2700

S   F   L   V   K   K   K   S   N   S   I   S   V   G   E   F   Y   R     918
      TCA TTT CTT GTG AAA AAG AAA TCT AAT TCA ATT AGT GTA GGA GAA TTT TAC CGA    2754

D   A   V   L   Q   R   C   S   P   N   L   Q   R   H   S   N   S   L     936
      GAT GCC GTA TTA CAG CGT TGC TCA CCA AAT TTG CAA AGA CAT TCC AAT TCC TTG    2808

G   P   I   F   D   H   E   D   L   L   K   R   K   R   K   I   L   S     954
      GGG CCC ATT TTT GAT CAT GAA GAT TTA CTG AAG CGA AAA AGA AAA ATA TTA TCT    2862

S   D   D   S   L   R   S   S   K   L   Q   S   H   M   R   H   S   D     972
      TCA GAT GAT TCA CTC AGG TCA TCA AAA CTT CAA TCC CAT ATG AGG CAT TCA GAC    2916

S   I   S   S   L   A   S   E   R   E   Y   I   T   S   L   D   L   S     990
      AGC ATT TCT TCT CTG GCT TCT GAG AGA GAA TAT ATT ACA TCA CTA GAC CTT TCA    2970

A   N   E   L   R   D   I   D   A   L   S   Q   K   C   C   I   S   V    1008
      GCA AAT GAA CTA AGA GAT ATT GAT GCC CTA AGC CAG AAA TGC TGT ATA AGT GTT    3024

H   L   E   H   L   E   K   L   E   L   H   Q   N   A   L   T   S   F    1026
      CAT TTG GAG CAT CTT GAA AAG CTG GAG CTT CAC CAG AAT GCA CTC ACG AGC TTT    3078

P   Q   Q   L   C   E   T   L   K   S   L   T   H   L   D   L   H   S    1044
      CCA CAA CAG CTA TGT GAA ACT CTG AAG AGT TTG ACA CAT TTG GAC TTG CAC AGT    3132

N   K   F   T   S   F   P   S   Y   L   L   K   M   S   C   I   A   N    1062
      AAT AAA TTT ACA TCA TTT CCT TCT TAT TTG TTG AAA ATG AGT TGT ATT GCT AAT    3186

L   D   V   S   R   N   D   I   G   P   S   V   V   L   D   P   T   V    1080
      CTT GAT GTC TCT CGA AAT GAC ATT GGA CCC TCA GTG GTT TTA GAT CCT ACA GTG    3240

```
AAA TGT CCA ACT CTG AAA CAG TTT AAC CTG TCA TAT AAC CAG CTG TCT TTT GTA    3294

P   E   N   L   T   D   V   V   E   K   L   E   Q   L   I   L   E   G    1116
CCT GAG AAC CTC ACT GAT GTG GTA GAG AAA CTG GAG CAG CTC ATT TTA GAA GGA    3348  /g
                                                                                 fam.38
 N   K   I   S   G   I   C   S   P   L   R   L   K   E   L   K   I   L    1134
AAT AAA ATA TCA GGG ATA TGC TCC CCC TTG AGA CTG AAG GAA CTG AAG ATT TTA    3402  Ex25/g
                                                                                 Fam.21
 N   L   S   K   N   H   I   S   S   L   S   E   N   F   L   E   A   C    1152
AAC CTT AGT AAG AAC CAC ATT TCA TCC CTA TCA GAG AAC TTT CTT GAG GCT TGT    3456

P   K   V   E   S   F   S   A   R   M   N   F   L   A   A   M   P   F    1170
CCT AAA GTG GAG AGT TTC AGT GCC AGA ATG AAT TTT CTT GCT GCT ATG CCT TTC    3510

L   P   P   S   M   T   I   L   K   L   S   Q   N   K   F   S   C   I    1188
TTG CCT CCT TCT ATG ACA ATC CTA AAA TTA TCT CAG AAC AAA TTT TCC TGT ATT    3564

P   E   A   I   L   N   L   P   H   L   R   S   L   D   M   S   S   N    1206
CCA GAA GCA ATT TTA AAT CTT CCA CAC TTG CGG TCT TTA GAT ATG AGC AGC AAT    3618

D   I   Q   Y   L   P   G   P   A   H   W   K   S   L   N   L   R   E    1224
GAT ATT CAG TAC CTA CCA GGT CCC GCA CAC TGG AAA TCT TTG AAC TTA AGG GAA    3672

L   L   F   S   H   N   Q   I   S   I   L   D   L   S   E   K   A   Y    1242
CTC TTA TTT AGC CAT AAT CAG ATC AGC ATC TTG GAC TTG AGT GAA AAA GCA TAT    3726

L   W   S   R   V   E   K   L   H   L   S   H   N   K   L   K   E   I    1260
TTA TGG TCT AGA GTA GAG AAA CTG CAT CTT TCT CAC AAT AAA CTG AAA GAG ATT    3780

P   P   E   I   G   C   L   E   N   L   T   S   L   D   V   S   Y   N    1278
CCT CCT GAG ATT GGC TGT CTT GAA AAT CTG ACA TCT CTG GAT GTC AGT TAC AAC    3834

L   E   L   R   S   F   P   N   E   M   G   K   L   S   K   I   W   D    1296
TTG GAA CTA AGA TCC TTT CCC AAT GAA ATG GGG AAA TTA AGC AAA ATA TGG GAT    3888

L   P   L   D   E   L   H   L   N   F   D   F   K   H   I   G   C   K    1314
CTT CCT TTG GAT GAA CTG CAT CTT AAC TTT GAT TTT AAA CAT ATA GGA TGT AAA    3942

A   K   D   I   I   R   F   L   Q   Q   R   L   K   K   A   V   P   Y    1332
GCC AAA GAC ATC ATA AGG TTT CTT CAA CAG CGA TTA AAA AAG GCT GTG CCT TAT    3996

N   R   M   K   L   M   I   V   G   N   T   G   S   G   K   T   T   L    1350
AAC CGA ATG AAA CTT ATG ATT GTG GGA AAT ACT GGG AGT GGT AAA ACC ACC TTA    4050

L   Q   Q   L   M   K   T   K   K   S   D   L   G   M   Q   S   A   T    1368
TTG CAG CAA TTA ATG AAA ACC AAG AAA TCA GAT CTT GGA ATG CAA AGT GCC ACA    4104
```

Fig. 17E

```
      V   G   I   D   V   K   D   W   P   I   Q   I   R   D   K   R   K   R     1386
     GTT GGC ATA GAT GTG AAA GAC TGG CCT ATC CAA ATA AGA GAC AAA AGA AAG AGA    4158

D   L   V   L   N   V   W   D   F   A   G   R   E   E   F   Y   S   T     1404
     GAT CTC GTC CTA AAT GTG TGG GAT TTT GCA GGT CGT GAG GAA TTC TAT AGT ACT    4212

H   P   H   F   M   T   Q   R   A   L   Y   L   A   V   Y   D   L   S     1422
     CAT CCC CAT TTT ATG ACG CAG CGA GCA TTG TAC CTT GCT GTC TAT GAC CTC AGC    4266

K   G   Q   A   E   V   D   A   M   K   P   W   L   F   N   I   K   A     1440
     AAG GGA CAG GCT GAA GTT GAT GCC ATG AAG CCT TGG CTC TTC AAT ATA AAG GCT    4320

R   A   S   S   S   P   V   I   L   V   G   T   H   L   D   V   S   D     1458
     CGC GCT TCT TCT TCC CCT GTG ATT CTC GTT GGC ACA CAT TTG GAT GTT TCT GAT    4374   Ex31/t
                                                                                        fam.D E   K   Q   R   K   A   C   M   S   K   I   T   K   E   L   L   N   K     1476
     GAG AAG CAA CGC AAA GCC TGC ATG AGT AAA ATC ACC AAG GAA CTC CTG AAT AAG    4428

R   G   F   P   A   I   R   D   Y   H   F   V   N   A   T   E   E   S     1494
     CGA GGG TTC CCT GCC ATA CGA GAT TAC CAC TTT GTG AAT GCC ACC GAG GAA TCT    4482

D   A   L   A   K   L   R   K   T   I   I   N   E   S   L   N   F   K     1512
     GAT GCT TTG GCA AAA CTT CGG AAA ACC ATC ATA AAC GAG AGC CTT AAT TTC AAG    4536

I   R   D   Q   L   V   V   G   Q   L   I   P   D   C   Y   V   E   L     1530
     ATC CGA GAT CAG CTT GTT GTT GGA CAG CTG ATT CCA GAC TGC TAT GTA GAA CTT    4590

E   K   I   I   L   S   E   R   K   N   V   P   I   E   F   P   V   I     1548
     GAA AAA ATC ATT TTA TCG GAG CGT AAA AAT GTG CCA ATT GAA TTT CCC GTA ATT    4644

D   R   K   R   L   L   Q   L   V   R   E   N   Q   L   Q   L   D   E     1566
     GAC CGG AAA CGA TTA TTA CAA CTA GTG AGA GAA AAT CAG CTG CAG TTA GAT GAA    4698

N   E   L   P   H   A   V   H   F   L   N   E   S   G   V   L   L   H     1584
     AAT GAG CTT CCT CAC GCA GTT CAC TTT CTA AAT GAA TCA GGA GTC CTT CTT CAT    4752

F   Q   D   P   A   L   Q   L   S   D   L   Y   F   V   E   P   K   W     1602
     TTT CAA GAC CCA GCA CTG CAG TTA AGT GAC TTG TAC TTT GTG GAA CCC AAG TGG    4806

L   C   K   I   M   A   Q   I   L   T   V   K   V   E   G   C   P   K     1620
     CTT TGT AAA ATC ATG GCA CAG ATT TTG ACA GTG AAA GTG GAA GGT TGT CCA AAA    4860

H   P   K   G   I   I   S   R   D   V   E   K   F   L   S   K   K         1638
     CAC CCT AAG GGC ATT ATT TCG CGT AGA GAT GTG GAA AAA TTT CTT TCA AAA AAA    4914
```

Fig. 17F

```
R   K   F   P   K   N   Y   M   S   Q   Y   F   K   L   L   E   K   F       1656
AGG AAA TTT CCA AAG AAC TAC ATG TCA CAG TAT TTT AAG CTC CTA GAA AAA TTC     4968

Q   I   A   L   P   I   G   E   E   Y   L   L   V   P   S   S   L   S       1674
CAG ATT GCT TTG CCA ATA GGA GAA GAA TAT TTG CTG GTT CCA AGC AGT TTG TCT     5022

D   H   R   P   V   I   E   L   P   H   C   E   N   S   E   I   I   I       1692
GAC CAC AGG CCT GTG ATA GAG CTT CCC CAT TGT GAG AAC TCT GAA ATT ATC ATC     5076

R   L   Y   E   M   P   Y   F   P   M   G   F   W   S   R   L   I   N       1710    Ex35
CGA CTA TAT GAA ATG CCT TAT TTT CCA ATG GGA TTT TGG TCA AGA TTA ATC AAT     5130    /g
                                                                                    Fam.A

R   L   L   E   I   S   P   Y   M   L   S   G   R   E   R   A   L   R       1728
CGA TTA CTT GAG ATT TCA CCT TAC ATG CTT TCA GGG AGA GAA CGA GCA CTT CGC     5184

P   N   R   M   Y   W   R   Q   G   I   Y   L   N   W   S   P   E   A       1746
CCA AAC AGA ATG TAT TGG CGA CAA GGC ATT TAC TTA AAT TGG TCT CCT GAA GCT     5238

Y   C   L   V   G   S   E   V   L   D   N   H   P   E   S   F   L   K       1764
TAT TGT CTG GTA GGA TCT GAA GTC TTA GAC AAT CAT CCA GAG AGT TTC TTA AAA     5292

I   T   V   P   S   C   R   K   G   C   I   L   L   G   Q   V   V   D       1782
ATT ACA GTT CCT TCT TGT AGA AAA GGC TGT ATT CTT TTG GGC CAA GTT GTG GAC     5346

H   I   D   S   L   M   E   E   W   F   P   G   L   L   E   I   D   I       1800
CAC ATT GAT TCT CTC ATG GAA GAA TGG TTT CCT GGG TTG CTG GAG ATT GAT ATT     5400

C   G   E   G   E   T   L   L   K   K   W   A   L   Y   S   F   N   D       1818
TGT GGT GAA GGA GAA ACT CTG TTG AAG AAA TGG GCA TTA TAT AGT TTT AAT GAT     5454

G   E   E   H   Q   K   I   L   L   D   D   L   M   K   K   A   E   E       1836
GGT GAA GAA CAT CAA AAA ATC TTA CTT GAT GAC TTG ATG AAG AAA GCA GAG GAA     5508

G   D   L   L   V   N   P   D   Q   P   R   L   T   I   P   I   S   Q       1854
GGA GAT CTC TTA GTA AAT CCA GAT CAA CCA AGG CTC ACC ATT CCA ATA TCT CAG     5562

I   A   P   D   L   I   L   A   D   L   P   R   N   I   M   L   N   N       1872
ATT GCC CCT GAC TTG ATT TTG GCT GAC CTG CCT AGA AAT ATT ATG TTG AAT AAT     5616

D   E   L   E   F   E   Q   A   P   E   F   L   L   G   D   G   S   F       1890
GAT GAG TTG GAA TTT GAA CAA GCT CCA GAG TTT CTC CTA GGT GAT GGC AGT TTT     5670

G   S   V   Y   R   A   A   Y   E   G   E   E   V   A   V   K   I   F       1908
GGA TCA GTT TAC CGA GCA GCC TAT GAA GGA GAA GAA GTG GCT GTG AAG ATT TTT     5724

```
AAT AAA CAT ACA TCA CTC AGG CTG TTA AGA CAA GAG CTT GTG GTG CTT TGC CAC   5778

L   H   H   P   S   L   I   S   L   L   A   A   G   I   R   P   R   M   1944
CTC CAC CAC CCC AGT TTG ATA TCT TTG CTG GCA GCT GGG ATT CGT CCC CGG ATG   5832

L   V   M   E   L   A   S   K   G   S   L   D   R   L   L   Q   Q   D   1962
TTG GTG ATG GAG TTA GCC TCC AAG GGT TCC TTG GAT CGC CTG CTT CAG CAG GAC   5886

K   A   S   L   T   R   T   L   Q   H   R   I   A   L   H   V   A   D   1980
AAA GCC AGC CTC ACT AGA ACC CTA CAG CAC AGG ATT GCA CTC CAC GTA GCT GAT   5940

G   L   R   Y   L   H   S   A   M   I   I   Y   R   D   L   K   P   H   1998
GGT TTG AGA TAC CTC CAC TCA GCC ATG ATT ATA TAC CGA GAC CTG AAA CCC CAC   5994

N   V   L   L   F   T   L   Y   P   N   A   A   I   I   A   K   I   A   2016
AAT GTG CTG CTT TTC ACA CTG TAT CCC AAT GCT GCC ATC ATT GCA AAG ATT GCT   6048

D   Y   G   I   A   Q   Y   C   C   R   M   G   I   K   T   S   E   G   2034 Ex41
GAC TAC GGC ATT GCT CAG TAC TGC TGT AGA ATG GGG ATA AAA ACA TCA GAG GGC   6102 /c
                                                                               fam.32

T   P   G   F   R   A   P   E   V   A   R   G   N   V   I   Y   N   Q   2052
ACA CCA GGG TTT CGT GCA CCT GAA GTT GCC AGA GGA AAT GTC ATT TAT AAC CAA   6156

Q   A   D   V   Y   S   F   G   L   L   Y   D   I   L   T   T   G       2070
CAG GCT GAT GTT TAT TCA TTT GGT TTA CTA CTC TAT GAC ATT TTG ACA ACT GGA   6210

G   R   I   V   E   G   L   K   F   P   N   E   F   D   E   L   E   I   2088
GGT AGA ATA GTA GAG GGT TTG AAG TTT CCA AAT GAG TTT GAT GAA TTA GAA ATA   6264

Q   G   K   L   P   D   P   V   K   E   Y   G   C   A   P   W   P   M   2106
CAA GGA AAA TTA CCT GAT CCA GTT AAA GAA TAT GGT TGT GCC CCA TGG CCT ATG   6318

V   E   K   L   I   K   Q   C   L   K   E   N   P   Q   E   R   P   T   2124
GTT GAG AAA TTA ATT AAA CAG TGT TTG AAA GAA AAT CCT CAA GAA AGG CCT ACT   6372

S   A   Q   V   F   D   I   L   N   S   A   E   L   V   C   L   T   R   2142
TCT GCC CAG GTC TTT GAC ATT TTG AAT TCA GCT GAA TTA GTC TGT CTG ACG AGA   6426

R   I   L   L   P   K   N   V   I   V   E   C   M   V   A   T   H   H   2160
CGC ATT TTA TTA CCT AAA AAC GTA ATT GTT GAA TGC ATG GTT GCT ACA CAT CAC   6480

N   S   R   N   A   S   I   W   L   G   C   G   H   T   D   R   G   Q   2178
AAC AGC AGG AAT GCA AGC ATT TGG CTG GGC TGT GGG CAC ACC GAC AGA GGA CAG   6534

L   S   F   L   D   L   N   T   E   G   Y   T   S   E   E   V   A   D   2196
CTC TCA TTT CTT GAC TTA AAT ACT GAA GGA TAC ACT TCT GAG GAA GTT GCT GAT   6588
```

Fig. 17H

```
  S   R   I   L   C   L   A   L   V   H   L   P   V   E   K   E   S   W    2214
AGT AGA ATA TTG TGC TTA GCC TTG GTG CAT CTT CCT GTT GAA AAG GAA AGC TGG    6642

I   V   S   G   T   Q   S   G   T   L   L   V   I   N   T   E   D   G    2232
ATT GTG TCT GGG ACA CAG TCT GGT ACT CTC CTG GTC ATC AAT ACC GAA GAT GGG    6696

K   K   R   H   T   L   E   K   M   T   D   S   V   T   C   L   Y   C    2250
AAA AAG AGA CAT ACC CTA GAA AAG ATG ACT GAT TCT GTC ACT TGT TTG TAT TGC    6750

N   S   F   S   K   Q   S   K   Q   K   N   F   L   L   V   G   T   A    2268
AAT TCC TTT TCC AAG CAA AGC AAA CAA AAA AAT TTT CTT TTG GTT GGA ACC GCT    6804

D   G   K   L   A   I   F   E   D   K   T   V   K   L   K   G   A   A    2286
GAT GGC AAG TTA GCA ATT TTT GAA GAT AAG ACT GTT AAG CTT AAA GGA GCT GCT    6858

P   L   K   I   L   N   I   G   N   V   S   T   P   L   M   C   L   S    2304
CCT TTG AAG ATA CTA AAT ATA GGA AAT GTC AGT ACT CCA TTG ATG TGT TTG AGT    6912

E   S   T   N   S   T   E   R   N   V   M   W   G   G   C   G   T   K    2322
GAA TCC ACA AAT TCA ACG GAA AGA AAT GTA ATG TGG GGA GGA TGT GGC ACA AAG    6966

I   F   S   F   S   N   D   F   T   I   Q   K   L   I   E   T   R   T    2340
ATT TTC TCC TTT TCT AAT GAT TTC ACC ATT CAG AAA CTC ATT GAG ACA AGA ACA    7020

S   Q   L   F   S   Y   A   A   F   S   D   S   N   I   I   T   V   V    2358
AGC CAA CTG TTT TCT TAT GCA GCT TTC AGT GAT TCC AAC ATC ATA ACA GTG GTG    7074

V   D   T   A   L   Y   I   A   K   Q   N   S   P   V   V   E   V   W    2376
GTA GAC ACT GCT CTC TAT ATT GCT AAG CAA AAT AGC CCT GTT GTG GAA GTG TGG    7128

D   K   K   T   E   K   L   C   G   L   I   D   C   V   H   F   L   R    2394
GAT AAG AAA ACT GAA AAA CTC TGT GGA CTA ATA GAC TGC GTG CAC TTT TTA AGG    7182

E   V   M   V   K   E   N   K   E   S   K   H   K   M   S   Y   S   G    2412
GAG GTA ATG GTA AAA GAA AAC AAG GAA TCA AAA CAC AAA ATG TCT TAT TCT GGG    7236

R   V   K   T   L   C   L   Q   K   N   T   A   L   W   I   G   T   G    2430
AGA GTG AAA ACC CTC TGC CTT CAG AAG AAC ACT GCT CTT TGG ATA GGA ACT GGA    7290

G   G   H   I   L   L   L   D   L   S   T   R   R   L   I   R   V   I    2448
GGA GGC CAT ATT TTA CTC CTG GAT CTT TCA ACT CGT CGA CTT ATA CGT GTA ATT    7344

Y   N   F   C   N   S   V   R   V   M   M   T   A   Q   L   G   S   L    2466
TAC AAC TTT TGT AAT TCG GTC AGA GTC ATG ATG ACA GCA CAG CTA GGA AGC CTT    7398
```

Fig. 17I

| | | | | | | | | | | | | | | | | |
|---|---|---|---|---|---|---|---|---|---|---|---|---|---|---|---|---|
| K | N | V | M | L | V | L | G | Y | N | R | K | N | T | E | G | T | Q | 2484 |
| AAA | AAT | GTC | ATG | CTG | GTA | TTG | GGC | TAC | AAC | CGG | AAA | AAT | ACT | GAA | GGT | ACA | CAA | 7452 |

| K | Q | K | E | I | Q | S | C | L | T | V | W | D | I | N | L | P | H | 2502 |
|---|---|---|---|---|---|---|---|---|---|---|---|---|---|---|---|---|---|---|
| AAG | CAG | AAA | GAG | ATA | CAA | TCT | TGC | TTG | ACC | GTT | TGG | GAC | ATC | AAT | CTT | CCA | CAT | 7506 |

| E | V | Q | N | L | E | K | H | I | E | V | R | K | E | L | A | E | K | 2520 |
|---|---|---|---|---|---|---|---|---|---|---|---|---|---|---|---|---|---|---|
| GAA | GTG | CAA | AAT | TTA | GAA | AAA | CAC | ATT | GAA | GTG | AGA | AAA | GAA | TTA | GCT | GAA | AAA | 7560 |

M   R   R   T   S   V   E   *                                                                                                              2528
ATG AGA CGA ACA TCT GTT GAG TAA gagagaaataggaattgtctttggataggaaaattattc 7623 tctcctcttgtaaatatttattttaaaaatgttcacatggaaagggtactcacattttttgaaatagctcgt 7695 gtgtatgaaggaatgttattattttttaatttaaatatatgtaaaaatacttaccagtaaatgtgtattttaa 7767 agaactatttaaaacacaatgttatatttcttataaataccagttactttcgttcattaattaatgaaaata 7839 aatctgtgaagtacctaatttaagtactcatactaaaatttataaggccgataatttttgttttcttgtct 7911 gtaatggaggtaaactttatttttaaattctgtgcttaagacaggactattgcttgtcgattttctagaaat 7983 ctgcacggtataatgaaaatattaagacagtttcccatgtaatgtattccttcttagattgcatcgaaatgc 8055 actatcatatatgcttgtaaatattcaaatgaatttgcactaataaagtcctttgttggtatgtgaattctc 8127 tttgttgctgttgcaaacagtgcatcttacacaacttcactcaattcaaaagaaaactccattaaaagtact 8199 aatgaaaaaacatgacatactgtcaaagtcctcatatctaggaaagacacagaaactctctttgtcacagaa 8271 actctctgtgtctttcctagacataatagagttgttttcaactctatgtttgaatgtggatacctgaatt 8343 ttgtataattagtgtaaatacagtgttcagtccttcaagtgatattttatttttttattcataccactagc 8415 tacttgttttctaatctgcttcattctaatgcttatattcatcttttccctaaatttgtgatgctgcagatc 8487 ctacatcattcagatagaaaccttttttttttttcagaattatagaattccacagctcctaccaagaccatga 8559 ggataaatatctaacacttttcagttgctgaaggagaaaggagctttagttatgatggataaaaatatctgc 8631 caccctaggcttccaaattatacttaaattgtttacatagcttaccacaataggagtatcagggccaaatac 8703 ctatgtaataatttgaggtcatttctgctttaggaaaagtactttcggtaaattctttggccctgaccagta 8775 ttcattatttcagataattccctgtgataggacaactagtacatttaatattctcagaacttatggcatttt 8847

Fig. 17J

```
actatgtgaaaactttaaatttatttatattaagggtaatcaaattcttaaagatgaaagattttctgtatt    8919 ttaaaggaagctatgctttaacttgttatgtaattaacaaaaaaatcatatataatagagctctttgttcca    8991 gtgttatctctttcattgttactttgtatttgcaattttttttaccaaagacaaattaaaaaaatgaatacc    9063 atatttaaatggaataataaaggttttttaaaaactttaaa                                   9104
```

Fig. 17K

SEQ ID NO:2 and SEQ ID NO:9

| | | | | | | | | | | | | | | | | | | |
|---|---|---|---|---|---|---|---|---|---|---|---|---|---|---|---|---|---|---|
| M | A | S | G | S | C | Q | G | C | E | E | D | E | E | T | L | K | K | 18 |
| ATG | GCT | AGT | GGC | AGC | TGT | CAG | GGG | TGC | GAA | GAG | GAC | GAG | GAA | ACT | CTG | AAG | AAG | 54 |
| L | I | V | R | L | N | N | V | Q | E | G | K | Q | I | E | T | L | V | 36 |
| TTG | ATA | GTC | AGG | CTG | AAC | AAT | GTC | CAG | GAA | GGA | AAA | CAG | ATA | GAA | ACG | CTG | GTC | 108 |
| Q | I | L | E | D | L | L | V | F | T | Y | S | E | H | A | S | K | L | 54 |
| CAA | ATC | CTG | GAG | GAT | CTG | CTG | GTG | TTC | ACG | TAC | TCC | GAG | CAC | GCC | TCC | AAG | TTA | 162 |
| F | Q | G | K | N | I | H | V | P | L | L | I | V | L | D | S | Y | M | 72 |
| TTT | CAA | GGC | AAA | AAT | ATC | CAT | GTG | CCT | CTG | TTG | ATC | GTC | TTG | GAC | TCC | TAT | ATG | 216 |
| R | V | A | S | V | Q | Q | V | G | W | S | L | L | C | K | L | I | E | 90 |
| AGA | GTC | GCG | AGT | GTG | CAG | CAG | GTG | GGT | TGG | TCA | CTT | CTG | TGC | AAA | TTA | ATA | GAA | 270 |
| V | C | P | G | T | M | Q | S | L | M | G | P | Q | D | V | G | N | D | 108 |
| GTC | TGT | CCA | GGT | ACA | ATG | CAA | AGC | TTA | ATG | GGA | CCC | CAG | GAT | GTT | GGA | AAT | GAT | 324 |
| W | E | V | L | G | V | H | Q | L | I | L | K | M | L | T | V | H | N | 126 |
| TGG | GAA | GTC | CTT | GGT | GTT | CAC | CAA | TTG | ATT | CTT | AAA | ATG | CTA | ACA | GTT | CAT | AAT | 378 |
| A | S | V | N | L | S | V | I | G | L | K | T | L | D | L | L | L | T | 144 |
| GCC | AGT | GTA | AAC | TTG | TCA | GTG | ATT | GGA | CTG | AAG | ACC | TTA | GAT | CTC | CTC | CTA | ACT | 432 |
| S | G | K | I | T | L | L | I | L | D | E | E | S | D | I | F | M | L | 162 |
| TCA | GGT | AAA | ATC | ACC | TTG | CTG | ATA | CTG | GAT | GAA | GAA | AGT | GAT | ATT | TTC | ATG | TTA | 486 |
| I | F | D | A | M | H | S | F | P | A | N | D | E | V | Q | K | L | G | 180 |
| ATT | TTT | GAT | GCC | ATG | CAC | TCA | TTT | CCA | GCC | AAT | GAT | GAA | GTC | CAG | AAA | CTT | GGA | 540 |
| C | K | A | L | H | V | L | F | E | R | V | S | E | E | Q | L | T | E | 198 |
| TGC | AAA | GCT | TTA | CAT | GTG | CTG | TTT | GAG | AGA | GTC | TCA | GAG | GAG | CAA | CTG | ACT | GAA | 594 |
| F | V | E | N | K | D | Y | M | I | L | L | S | A | S | T | N | F | K | 216 |
| TTT | GTT | GAG | AAC | AAA | GAT | TAT | ATG | ATA | TTG | TTA | AGT | GCG | TCA | ACA | AAT | TTT | AAA | 648 |
| D | E | E | E | I | V | L | H | V | L | H | C | L | H | S | L | A | I | 234 |
| GAT | GAA | GAG | GAA | ATT | GTG | CTT | CAT | GTG | CTG | CAT | TGT | TTA | CAT | TCC | CTA | GCG | ATT | 702 |
| P | C | N | N | V | E | V | L | M | S | G | N | V | R | C | Y | N | I | 252 |
| CCT | TGC | AAT | AAT | GTG | GAA | GTC | CTC | ATG | AGT | GGC | AAT | GTC | AGG | TGT | TAT | AAT | ATT | 756 |

Fig. 18A

```
  V   V   E   A   M   K   A   F   P   M   S   E   R   I   Q   E   V   S    270
GTG GTG GAA GCT ATG AAA GCA TTC CCT ATG AGT GAA AGA ATT CAA GAA GTG AGT     810

C   C   L   L   H   R   L   T   L   G   N   F   F   N   I   L   V   L    288
TGC TGT TTG CTC CAT AGG CTT ACA TTA GGT AAT TTT TTC AAT ATC CTG GTA TTA     864

N   E   V   H   E   F   V   V   K   A   V   Q   Q   Y   P   E   N   A    306
AAC GAA GTC CAT GAG TTT GTG GTG AAA GCT GTG CAG CAG TAC CCA GAG AAT GCA     918

A   L   Q   I   S   A   L   S   C   L   A   L   L   T   E   T   I   F    324
GCA TTG CAG ATC TCA GCG CTC AGC TGT TTG GCC CTC CTC ACT GAG ACT ATT TTC     972

L   N   Q   D   L   E   E   K   N   E   N   Q   E   N   D   D   E   G    342
TTA AAT CAA GAT TTA GAG GAA AAG AAT GAG AAT CAA GAG AAT GAT GAT GAG GGG    1026

E   E   D   K   L   F   W   L   E   A   C   Y   K   A   L   T   W   H    360
GAA GAA GAT AAA TTG TTT TGG CTG GAA GCC TGT TAC AAA GCA TTA ACG TGG CAT    1080

R   K   N   K   H   V   Q   E   A   A   C   W   A   L   N   N   L   L    378
AGA AAG AAC AAG CAC GTG CAG GAG GCC GCA TGC TGG GCA CTA AAT AAT CTC CTT    1134

M   Y   Q   N   S   L   H   E   K   I   G   D   E   D   G   H   F   P    396
ATG TAC CAA AAC AGT TTA CAT GAG AAG ATT GGA GAT GAA GAT GGC CAT TTC CCA    1188

A   H   R   E   V   M   L   S   M   L   H   S   S   K   E   V    414
GCT CAT AGG GAA GTG ATG CTC TCC ATG CTG ATG CAT TCT TCA TCA AAG GAA GTT    1242

F   Q   A   S   A   N   A   L   S   T   L   L   E   Q   N   V   N   F    432
TTC CAG GCA TCT GCG AAT GCA TTG TCA ACT CTC TTA GAA CAA AAT GTT AAT TTC    1296

R   K   I   L   L   S   K   G   I   H   L   N   V   L   E   L   M   Q    450
AGA AAA ATA CTG TTA TCA AAA GGA ATA CAC CTG AAT GTT TTG GAG TTA ATG CAG    1350

K   H   I   H   S   P   E   V   A   E   S   G   C   K   M   L   N   H    468
AAG CAT ATA CAT TCT CCT GAA GTG GCT GAA AGT GGC TGT AAA ATG CTA AAT CAT    1404

L   F   E   G   S   N   T   S   L   D   I   M   A   A   V   P   K    486
CTT TTT GAA GGA AGC AAC ACT TCC CTG GAT ATA ATG GCA GCA GTG GTC CCC AAA    1458

I   L   T   V   M   K   R   H   E   T   S   L   P   V   Q   L   E   A    504
ATA CTA ACA GTT ATG AAA CGT CAT GAG ACA TCA TTA CCA GTG CAG CTG GAG GCG    1512

L   R   A   I   L   H   F   I   V   P   G   M   P   E   E   S   R   E    522
CTT CGA GCT ATT TTA CAT TTT ATA GTG CCT GGC ATG CCA GAA GAA TCC AGG GAG    1566
```

Fig. 18B

```
      D   T   E   F   H   H   K   L   N   M   V   K   K   Q   C   F   K   N    540
      GAT ACA GAA TTT CAT CAT AAG CTA AAT ATG GTT AAA AAA CAG TGT TTC AAG AAT  1620

D   I   H   K   L   V   L   A   A   L   N   R   F   I   G   N   P   G    558
      GAT ATT CAC AAA CTG GTC CTA GCA GCT TTG AAC AGG TTC ATT GGA AAT CCT GGG  1674

I   Q   K   C   G   L   K   V   I   S   S   I   V   H   F   P   D   A    576
      ATT CAG AAA TGT GGA TTA AAA GTA ATT TCT TCT ATT GTA CAT TTT CCT GAT GCA  1728

L   E   M   L   S   L   E   G   A   M   D   S   V   L   H   T   L   Q    594
      TTA GAG ATG TTA TCC CTG GAA GGT GCT ATG GAT TCA GTG CTT CAC ACA CTG CAG  1782

M   Y   P   D   D   Q   E   I   Q   C   L   G   L   S   L   I   G   Y    612
      ATG TAT CCA GAT GAC CAA GAA ATT CAG TGT CTG GGT TTA AGT CTT ATA GGA TAC  1836

L   I   T   K   K   N   V   F   I   G   T   G   H   L   L   A   K   I    630
      TTG ATT ACA AAG AAG AAT GTG TTC ATA GGA ACT GGA CAT CTG CTG GCA AAA ATT  1890

L   V   S   S   L   Y   R   F   K   D   V   A   E   I   Q   T   K   G    648
      CTG GTT TCC AGC TTA TAC CGA TTT AAG GAT GTT GCT GAA ATA CAG ACT AAA GGA  1944

F   Q   T   I   L   A   I   L   K   L   S   A   S   F   S   K   L   L    666
      TTT CAG ACA ATC TTA GCA ATC CTC AAA TTG TCA GCA TCT TTT TCT AAG CTG CTG  1998

V   H   H   S   F   D   L   V   I   F   H   Q   M   S   S   N   I   M    684
      GTG CAT CAT TCA TTT GAC TTA GTA ATA TTC CAT CAA ATG TCT TCC AAT ATC ATG  2052

E   Q   K   D   Q   Q   F   L   N   L   C   C   K   C   F   A   K   V    702
      GAA CAA AAG GAT CAA CAG TTT CTA AAC CTC TGT TGC AAG TGT TTT GCA AAA GTA  2106

A   M   D   D   Y   L   K   N   V   M   L   E   R   A   C   D   Q   N    720
      GCT ATG GAT GAT TAC TTA AAA AAT GTG ATG CTA GAG AGA GCG TGT GAT CAG AAT  2160

N   S   I   M   V   E   C   L   L   L   G   A   D   A   N   Q   A        738
      AAC AGC ATC ATG GTT GAA TGC TTG CTT CTA TTG GGA GCA GAT GCC AAT CAA GCA  2214

K   E   G   S   S   L   I   C   Q   V   C   E   K   E   S   S   P   K    756
      AAG GAG GGA TCT TCT TTA ATT TGT CAG GTA TGT GAG AAA GAG AGC AGT CCC AAA  2268

L   V   E   L   L   N   S   G   S   R   E   Q   D   V   R   K   A        774
      TTG GTG GAA CTC TTA CTG AAT AGT GGA TCT CGT GAA CAA GAT GTA CGA AAA GCG  2322

L   T   I   S   I   G   K   G   D   S   Q   I   I   S   L   L   L   R    792
      TTG ACG ATA AGC ATT GGG AAA GGT GAC AGC CAG ATC ATC AGC TTG CTC TTA AGG  2376

```
AGG CTG GCC CTG GAT GTG GCC AAC AAT AGC ATT TGC CTT GGA GGA TTT TGT ATA   2430  T11239

G   K   V   E   P   S   W   L   G   P   L   F   P   D   K   T   S   N    828
GGA AAA GTT GAA CCT TCT TGG CTT GGT CCT TTA TTT CCA GAT AAG ACT TCT AAT   2484

L   R   K   Q   T   N   I   A   S   T   L   A   R   M   V   I   R   Y    846
TTA AGG AAA CAA ACA AAT ATA GCA TCT ACA CTA GCA AGA ATG GTG ATC AGA TAT   2538

Q   M   K   S   A   V   E   E   G   T   A   S   G   S   D   G   N   F    864
CAG ATG AAA AGT GCT GTG GAA GAA GGA ACA GCC TCA GGC AGC GAT GGA AAT TTT   2592

S   E   D   V   L   S   K   F   D   E   W   T   F   I   P   D   S   S    882
TCT GAA GAT GTG CTG TCT AAA TTT GAT GAA TGG ACC TTT ATT CCT GAC TCT TCT   2646

M   D   S   V   F   A   Q   S   D   D   L   D   S   E   G   S   E   G    900
ATG GAC AGT GTG TTT GCT CAA AGT GAT GAC CTG GAT AGT GAA GGA AGT GAA GGC   2700

S   F   L   V   K   K   K   S   N   S   I   S   V   G   E   F   Y   R    918
TCA TTT CTT GTG AAA AAG AAA TCT AAT TCA ATT AGT GTA GGA GAA TTT TAC CGA   2754

D   A   V   L   Q   R   C   S   P   N   L   Q   R   H   S   N   S   L    936  DE022
GAT GCC GTA TTA CAG CGT TGC TCA CCA AAT TTG CAA AGA CAT TCC AAT TCC TTG   2808

G   P   I   F   D   H   E   D   L   L   K   R   K   R   K   I   L   S    954
GGG CCC ATT TTT GAT CAT GAA GAT TTA CTG AAG CGA AAA AGA AAA ATA CTA TCT   2862

S   D   D   S   L   R   S   S   K   L   Q   S   H   M   R   H   S   D    972
TCA GAT GAT TCA CTC AGG TCA TCA AAA CTT CAA TCC CAT ATG AGG CAT TCA GAC   2916

S   I   S   S   L   A   S   E   R   E   Y   I   T   S   L   D   L   S    990
AGC ATT TCT TCT CTG GCT TCT GAG AGA GAA TAT ATT ACA TCA CTA GAC CTT TCA   2970

A   N   E   L   R   D   I   D   A   L   S   Q   K   C   C   I   S   V   1008
GCA AAT GAA CTA AGA GAT ATT GAT GCC CTA AGC CAG AAA TGC TGT ATA AGT GTT   3024

H   L   E   H   L   E   K   L   E   L   H   Q   N   A   L   T   S   F   1026
CAT TTG GAG CAT CTT GAA AAG CTG GAG CTT CAC CAG AAT GCA CTC ACG AGC TTT   3078

P   Q   Q   L   C   E   T   L   K   S   L   T   H   L   D   L   H   S   1044
CCA CAA CAG CTA TGT GAA ACT CTG AAG AGT TTG ACA CAT TTG GAC TTG CAC AGT   3132

N   K   F   T   S   F   P   S   Y   L   L   K   M   S   C   I   A   N   1062
AAT AAA TTT ACA TCA TTT CCT TCT TAT TTG TTG AAA ATG AGT TGT ATT GCT AAT   3186

L   D   V   S   R   N   D   I   G   P   S   V   V   L   D   P   T   V   1080
CTT GAT GTC TCT CGA AAT GAC ATT GGA CCC TCA GTG GTT TTA GAT CCT ACA GTG   3240
```

Fig. 18D

```
  K   C   P   T   L   K   Q   F   N   L   S   Y   N   Q   L   S   F   V    1098 famE
AAA TGT CCA ACT CTG AAA CAG TTT AAC CTG TCA TAT AAC CAG CTG TCT TTT GTA    3294
                                                                                DE038
  P   E   N   L   T   D   V   V   E   K   L   E   Q   L   I   L   E   G    1116 T11288
CCT GAG AAC CTC ACT GAT GTG GTA GAG AAA CTG GAG CAG CTC ATT TTA GAA GGA    3348 /g
                                                                                Fam38
  N   K   I   S   G   I   C   S   P   L   R   L   K   E   L   K   I   L    1134
AAT AAA ATA TCA GGG ATA TGC TCC CCC TTG AGA CTG AAG GAA CTG AAG ATT TTA    3402 Ex25/g
                                                                                Fam21
  N   L   S   K   N   H   I   S   S   L   S   E   N   F   L   E   A   C    1152
AAC CTT AGT AAG AAC CAC ATT TCA TCC CTA TCA GAG AAC TTT CTT GAG GCT TGT    3456

P   K   V   E   S   F   S   A   R   M   N   F   L   A   A   M   P   F    1170
CCT AAA GTG GAG AGT TTC AGT GCC AGA ATG AAT TTT CTT GCT GCT ATG CCT TTC    3510

L   P   P   S   M   T   I   L   K   L   S   Q   N   K   F   S   C   I    1188
TTG CCT CCT TCT ATG ACA ATC CTA AAA TTA TCT CAG AAC AAA TTT TCC TGT ATT    3564

P   E   A   I   L   N   L   P   H   L   R   S   L   D   M   S   S   N    1206
CCA GAA GCA ATT TTA AAT CTT CCA CAC TTG CGG TCT TTA GAT ATG AGC AGC AAT    3618

D   I   Q   Y   L   P   G   P   A   H   W   K   S   L   N   L   R   E    1224
GAT ATT CAG TAC CTA CCA GGT CCC GCA CAC TGG AAA TCT TTG AAC TTA AGG GAA    3672

L   L   F   S   H   N   Q   I   S   I   L   D   L   S   E   K   A   Y    1242 DE031
CTC TTA TTT AGC CAT AAT CAG ATC AGC ATC TTG GAC TTG AGT GAA AAA GCA TAT    3726

L   W   S   R   V   E   K   L   H   L   S   H   N   K   L   K   E   I    1260
TTA TGG TCT AGA GTA GAG AAA CTG CAT CTT TCT CAC AAT AAA CTG AAA GAG ATT    3780

P   P   E   I   G   C   L   E   N   L   T   S   L   D   V   S   Y   N    1278
CCT CCT GAG ATT GGC TGT CTT GAA AAT CTG ACA TCT CTG GAT GTC AGT TAC AAC    3834

L   E   L   R   S   F   P   N   E   M   G   K   L   S   K   I   W   D    1296
TTG GAA CTA AGA TCC TTT CCC AAT GAA ATG GGG AAA TTA AGC AAA ATA TGG GAT    3888

L   P   L   D   E   L   H   L   N   F   D   F   K   H   I   G   C   K    1314
CTT CCT TTG GAT GAA CTG CAT CTT AAC TTT GAT TTT AAA CAT ATA GGA TGT AAA    3942

A   K   D   I   I   R   F   L   Q   Q   R   L   K   K   A   V   P   Y    1332
GCC AAA GAC ATC ATA AGG TTT CTT CAA CAG CGA TTA AAA AAG GCT GTG CCT TAT    3996

N   R   M   K   L   M   I   V   G   N   T   G   S   G   K   T   T   L    1350
AAC CGA ATG AAA CTT ATG ATT GTG GGA AAT ACT GGG AGT GGT AAA ACC ACC TTA    4050
```

Fig. 18E

```
L   Q   L   M   K   T   K   K   S   D   L   G   M   Q   S   A   T        1368
TTG CAG CAA TTA ATG AAA ACC AAG AAA TCA GAT CTT GGA ATG CAA AGT GCC ACA  4104

V   G   I   D   V   K   D   W   P   I   Q   I   R   D   K   R   K   R    1386
GTT GGC ATA GAT GTG AAA GAC TGG CCT ATC CAA ATA AGA GAC AAA AGA AAG AGA  4158

D   L   V   L   N   V   W   D   F   A   G   R   E   E   F   Y   S   T    1404
GAT CTC GTC CTA AAT GTG TGG GAT TTT GCA GGT CGT GAG GAA TTC TAT AGT ACT  4212

H   P   H   F   M   T   Q   R   A   L   Y   L   A   V   Y   D   L   S    1422
CAT CCC CAT TTT ATG ACG CAG CGA GCA TTG TAC CTT GCT GTC TAT GAC CTC AGC  4266

K   G   Q   A   E   V   D   A   M   K   P   W   L   F   N   I   K   A    1440
AAG GGA CAG GCT GAA GTT GAT GCC ATG AAG CCT TGG CTC TTC AAT ATA AAG GCT  4320

R   A   S   S   S   P   V   I   L   V   G   T   H   L   D   V   S   D    1458
CGC GCT TCT TCT TCC CCT GTG ATT CTC GTT GGC ACA CAT TTG GAT GTT TCT GAT  4374  Ex31/t
                                                                                famD E   K   Q   R   K   A   C   M   S   K   I   T   K   E   L   L   N   K    1476
GAG AAG CAA CGC AAA GCC TGC ATG AGT AAA ATC ACC AAG GAA CTC CTG AAT AAG  4428

R   G   F   P   A   I   R   D   Y   H   F   V   N   A   T   E   E   S    1494
CGA GGG TTC CCT GCC ATA CGA GAT TAC CAC TTT GTG AAT GCC ACC GAG GAA TCT  4482

D   A   L   A   K   L   R   K   T   I   I   N   E   S   L   N   F   K    1512
GAT GCT TTG GCA AAA CTT CGG AAA ACC ATC ATA AAC GAG AGC CTT AAT TTC AAG  4536

I   R   D   Q   L   V   V   G   Q   L   I   P   D   C   Y   V   E   L    1530
ATC CGA GAT CAG CTT GTT GTT GGA CAG CTG ATT CCA GAC TGC TAT GTA GAA CTT  4590

E   K   I   I   L   S   E   R   K   N   V   P   I   E   F   P   V   I    1548
GAA AAA ATC ATT TTA TCG GAG CGT AAA AAT GTG CCA ATT GAA TTT CCC GTA ATT  4644

D   R   K   R   L   L   Q   L   V   R   E   N   Q   L   Q   L   D   E    1566
GAC CGG AAA CGA TTA TTA CAA CTA GTG AGA GAA AAT CAG CTG CAG TTA GAT GAA  4698

N   E   L   P   H   A   V   H   F   L   N   E   S   G   V   L   L   H    1584
AAT GAG CTT CCT CAC GCA GTT CAC TTT CTA AAT GAA TCA GGA GTC CTT CTT CAT  4752

F   Q   D   P   A   L   Q   L   S   D   L   Y   F   V   E   P   K   W    1602
TTT CAA GAC CCA GCA CTG CAG TTA AGT GAC TTG TAC TTT GTG GAA CCC AAG TGG  4806

L   C   K   I   M   A   Q   I   L   T   V   K   V   E   G   C   P   K    1620
CTT TGT AAA ATC ATG GCA CAG ATT TTG ACA GTG AAA GTG GAA GGT TGT CCA AAA  4860

```
                CAC CCT AAG GGC ATT ATT TCG CGT AGA GAT GTG GAA AAA TTT CTT TCA AAA AAA   4914

R   K   F   P   K   N   Y   M   S   Q   Y   F   K   L   L   E   K   F   1656
AGG AAA TTT CCA AAG AAC TAC ATG TCA CAG TAT TTT AAG CTC CTA GAA AAA TTC   4968

Q   I   A   L   P   I   G   E   E   Y   L   L   V   P   S   S   L   S   1674
CAG ATT GCT TTG CCA ATA GGA GAA GAA TAT TTG CTG GTT CCA AGC AGT TTG TCT   5022

D   H   R   P   V   I   E   L   P   H   C   E   N   S   E   I   I   I   1692
GAC CAC AGG CCT GTG ATA GAG CTT CCC CAT TGT GAG AAC TCT GAA ATT ATC ATC   5076

R   L   Y   E   M   P   Y   F   P   M   G   F   W   S   R   L   I   N   1710  Ex35/g
CGA CTA TAT GAA ATG CCT TAT TTT CCA ATG GGA TTT TGG TCA AGA TTA ATC AAT   5130  famA R   L   L   E   I   S   P   Y   M   L   S   G   R   E   R   A   L   R   1728
CGA TTA CTT GAG ATT TCA CCT TAC ATG CTT TCA GGG AGA GAA CGA GCA CTT CGC   5184

P   N   R   M   Y   W   R   Q   G   I   Y   L   N   W   S   P   E   A   1746
CCA AAC AGA ATG TAT TGG CGA CAA GGC ATT TAC TTA AAT TGG TCT CCT GAA GCT   5238

Y   C   L   V   G   S   E   V   L   D   N   H   P   E   S   F   L   K   1764
TAT TGT CTG GTA GGA TCT GAA GTC TTA GAC AAT CAT CCA GAG AGT TTC TTA AAA   5292

I   T   V   P   S   C   R   K   G   C   I   L   L   G   Q   V   V   D   1782
ATT ACA GTT CCT TCT TGT AGA AAA GGC TGT ATT CTT TTG GGC CAA GTT GTG GAC   5346

H   I   D   S   L   M   E   E   W   F   P   G   L   L   E   I   D   I   1800
CAC ATT GAT TCT CTC ATG GAA GAA TGG TTT CCT GGG TTG CTG GAG ATT GAT ATT   5400

C   G   E   G   E   T   L   L   K   K   W   A   L   Y   S   F   N   D   1818
TGT GGT GAA GGA GAA ACT CTG TTG AAG AAA TGG GCA TTA TAT AGT TTT AAT GAT   5454

G   E   E   H   Q   K   I   L   L   D   D   L   M   K   K   A   E   E   1836
GGC GAA GAA CAT CAA AAA ATC TTA CTT GAT GAC TTG ATG AAG AAA GCA GAG GAA   5508

G   D   L   L   V   N   P   D   Q   P   R   L   T   I   P   I   S   Q   1854
GGA GAT CTC TTA GTA AAT CCA GAT CAA CCA AGG CTC ACC ATT CCA ATA TCT CAG   5562

I   A   P   D   L   I   L   A   D   L   P   R   N   I   M   L   N   N   1872
ATT GCC CCT GAC TTG ATT TTG GCT GAC CTG CCT AGA AAT ATT ATG TTG AAT AAT   5616

D   E   L   E   F   E   Q   A   P   E   F   L   L   G   D   G   S   F   1890
GAT GAG TTG GAA TTT GAA CAA GCT CCA GAG TTT CTC CTA GGT GAT GGC AGT TTT   5670

G   S   V   Y   R   A   A   Y   E   G   E   E   V   A   V   K   I   F   1908
GGA TCA GTT TAC CGA GCA GCC TAT GAA GGA GAA GAA GTG GCT GTG AAG ATT TTT   5724
```

Fig. 18G

```
  N   K   H   T   S   L   R   L   L   R   Q   E   L   V   V   L   C   H    1926
AAT AAA CAT ACA TCA CTC AGG CTG TTA AGA CAA GAG CTT GTG GTG CTT TGC CAC    5778

L   H   H   P   S   L   I   S   L   L   A   A   G   I   R   P   R   M    1944
CTC CAC CAC CCC AGT TTG ATA TCT TTG CTG GCA GCT GGG ATT CGT CCC CGG ATG    5832

L   V   M   E   L   A   S   K   G   S   L   D   R   L   L   Q   Q   D    1962
TTG GTG ATG GAG TTA GCC TCC AAG GGT TCC TTG GAT CGC CTG CTT CAG CAG GAC    5886

K   A   S   L   T   R   T   L   Q   H   R   I   A   L   H   V   A   D    1980
AAA GCC AGC CTC ACT AGA ACC CTA CAG CAC AGG ATT GCA CTC CAC GTA GCT GAT    5940

G   L   R   Y   L   H   S   A   M   I   I   Y   R   D   L   K   P   H    1998
GGT TTG AGA TAC CTC CAC TCA GCC ATG ATT ATA TAC CGA GAC CTG AAA CCC CAC    5994

N   V   L   L   F   T   L   Y   P   N   A   A   I   I   A   K   I   A    2016
AAT GTG CTG CTT TTC ACA CTG TAT CCC AAT GCT GCC ATC ATT GCA AAG ATT GCT    6048
                                                                           DE032
  D   Y   G   I   A   Q   Y   C   C   R   M   G   I   K   T   S   E   G    2034 T10738
GAC TAC GGC ATT GCT CAG TAC TGC TGT AGA ATG GGA ATA AAA ACA TCA GAG GGC    6102 Ex41/c
                                                                           fam32
  T   P   G   F   R   A   P   E   V   A   R   G   N   V   I   Y   N   Q    2052
ACA CCA GGG TTT CGT GCA CCT GAA GTT GCC AGA GGA AAT GTC ATT TAT AAC CAA    6156

Q   A   D   V   Y   S   F   G   L   L   L   Y   D   I   L   T   T   G    2070
CAG GCT GAT GTT TAT TCA TTT GGT TTA CTA CTC TAT GAC ATT TTG ACA ACT GGA    6210

G   R   I   V   E   G   L   K   F   P   N   E   F   D   E   L   E   I    2088
GGT AGA ATA GTA GAG GGT TTG AAG TTT CCA AAT GAG TTT GAT GAA TTA GAA ATA    6264

Q   G   K   L   P   D   P   V   K   E   Y   G   C   A   P   W   P   M    2106
CAA GGA AAA TTA CCT GAT CCA GTT AAA GAA TAT GGT TGT GCC CCA TGG CCT ATG    6318

V   E   K   L   I   K   Q   C   L   K   E   N   P   Q   E   R   P   T    2124
GTT GAG AAA TTA ATT AAA CAG TGT TTG AAA GAA AAT CCT CAA GAA AGG CCT ACT    6372

S   A   Q   V   F   D   I   L   N   S   A   E   L   V   C   L   T   R    2142
TCT GCC CAG GTC TTT GAC ATT TTG AAT TCA GCT GAA TTA GTC TGT CTG ACG AGA    6426

R   I   L   L   P   K   N   V   I   V   E   C   M   V   A   T   H   H    2160
CGC ATT TTA TTA CCT AAA AAC GTA ATT GTT GAA TGC ATG GTT GCT ACA CAT CAC    6480

N   S   R   N   A   S   I   W   L   G   C   G   H   T   D   R   G   Q    2178
AAC AGC AGG AAT GCA AGC ATT TGG CTG GGC TGT GGG CAC ACC GAC AGA GGA CAG    6534
```

Fig. 18H

```
L   S   F   L   D   L   N   T   E   G   Y   T   S   E   E   V   A   D      2196
CTC TCA TTT CTT GAC TTA AAT ACT GAA GGA TAC ACT TCT GAG GAA GTT GCT GAT    6588

S   R   I   L   C   L   A   V   H   L   P   V   E   K   E   S   W          2214
AGT AGA ATA TTG TGC TTA GCC TTG GTG CAT CTT CCT GTT GAA AAG GAA AGC TGG    6642

I   V   S   G   T   Q   S   G   T   L   L   V   I   N   T   E   D   G      2232
ATT GTG TCT GGG ACA CAG TCT GGT ACT CTC CTG GTC ATC AAT ACC GAA GAT GGG    6696

K   K   R   H   T   L   E   K   M   T   D   S   V   T   C   L   Y   C      2250
AAA AAG AGA CAT ACC CTA GAA AAG ATG ACT GAT TCT GTC ACT TGT TTG TAT TGC    6750

N   S   F   S   K   Q   S   K   Q   K   N   F   L   L   V   G   T   A      2268
AAT TCC TTT TCC AAG CAA AGC AAA CAA AAA AAT TTT CTT TTG GTT GGA ACC GCT    6804

D   G   K   L   A   I   F   E   D   K   T   V   K   L   K   G   A   A      2286
GAT GGC AAG TTA GCA ATT TTT GAA GAT AAG ACT GTT AAG CTT AAA GGA GCT GCT    6858

P   L   K   I   L   N   I   G   N   V   S   T   P   L   M   C   L   S      2304
CCT TTG AAG ATA CTA AAT ATA GGA AAT GTC AGT ACT CCA TTG ATG TGT TTG AGT    6912

E   S   T   N   S   T   E   R   N   V   M   W   G   G   C   G   T   K      2322
GAA TCC ACA AAT TCA ACG GAA AGA AAT GTA ATG TGG GGA GGA TGT GGC ACA AAG    6966

I   F   S   F   S   N   D   F   T   I   Q   K   L   I   E   T   R   T      2340
ATT TTC TCC TTT TCT AAT GAT TTC ACC ATT CAG AAA CTC ATT GAG ACA AGA ACA    7020

S   Q   L   F   S   Y   A   A   F   S   D   S   N   I   I   T   V   V      2358
AGC CAA CTG TTT TCT TAT GCA GCT TTC AGT GAT TCC AAC ATC ATA ACA GTG GTG    7074

V   D   T   A   L   Y   I   A   K   Q   N   S   P   V   V   E   V   W      2376
GTA GAC ACT GCT CTC TAT ATT GCT AAG CAA AAT AGC CCT GTT GTG GAA GTG TGG    7128

D   K   K   T   E   K   L   C   G   L   I   D   C   V   H   F   L   R      2394
GAT AAG AAA ACT GAA AAA CTC TGT GGA CTA ATA GAC TGC GTG CAC TTT TTA AGG    7182

E   V   M   V   K   E   N   K   E   S   K   H   K   M   S   Y   S   G      2412
GAG GTA ATG GTA AAA GAA AAC AAG GAA TCA AAA CAC AAA ATG TCT TAT TCT GGG    7236

R   V   K   T   L   C   L   Q   K   N   T   A   L   W   I   G   T   G      2430
AGA GTG AAA ACC CTC TGC CTT CAG AAG AAC ACT GCT CTT TGG ATA GGA ACT GGA    7290

G   G   H   I   L   L   D   L   S   T   R   R   L   I   R   V   I          2448
GGA GGC CAT ATT TTA CTC CTG GAT CTT TCA ACT CGT CGA CTT ATA CGT GTA ATT    7344

```
                TAC AAC TTT TGT AAT TCG GTC AGA GTC ATG ATG ACA GCA CAG CTA GGA AGC CTT    7398

K   N   V   M   L   V   L   G   Y   N   R   K   N   T   E   G   T   Q              2484
AAA AAT GTC ATG CTG GTA TTG GGC TAC AAC CGG AAA AAT ACT GAA GGT ACA CAA              7452

K   Q   K   E   I   Q   S   C   L   T   V   W   D   I   N   L   P   H              2502
AAG CAG AAA GAG ATA CAA TCT TGC TTG ACC GTT TGG GAC ATC AAT CTT CCA CAT              7506

E   V   Q   N   L   E   K   H   I   E   V   R   K   E   L   A   E   K              2520
GAA GTG CAA AAT TTA GAA AAA CAC ATT GAA GTG AGA AAA GAA TTA GCT GAA AAA              7560

M   R   R   T   S   V   E   *                                                        2528
ATG AGA CGA ACA TCT GTT GAG TAA gagagaaataggaattgtctttggataggaaaattattc              7623 tctcctcttgtaaatatttattttaaaaatgttcacatggaaagggtactcacattttttgaaatagctcgt            7695 gtgtatgaaggaatgttattattttaatttaaatatatgtaaaaatacttaccagtaaatgtgtattttaa             7767 agaactatttaaaacacaatgttatatttcttataaataccagttactttcgttcattaattaatgaaaata            7839 aatctgtgaagtacctaatttaagtactcatactaaaatttataaggccgataatttttgttttcttgtct             7911 gtaatggaggtaaactttatttttaaattctgtgcttaagacaggactattgcttgtcgatttttctagaaat           7983 ctgcacggtataatgaaaatattaagacagtttcccatgtaatgtattccttcttagattgcatcgaaatgc            8055 actatcatatatgcttgtaaatattcaaatgaatttgcactaataaagtcctttgttggtatgtgaattctc            8127 tttgttgctgttgcaaacagtgcatcttacacaacttcactcaattcaaaagaaaactccattaaaagtact            8199 aatgaaaaaacatgacatactgtcaaagtcctcatatctaggaaagacacagaaactctctttgtcacagaa            8271 actctctgtgtctttcctagacataatagagttgtttttcaactctatgtttgaatgtggatacctgaatt             8343 ttgtataattagtgtaaatacagtgttcagtccttcaagtgatatttttatttttttattcataccactagc            8415 tacttgttttctaatctgcttcattctaatgcttatattcatcttttccctaaatttgtgatgctgcagatc            8487 ctacatcattcagatagaaaccttttttttttttcagaattatagaattccacagctcctaccaagaccatga           8559 ggataaatatctaacacttttcagttgctgaaggagaaaggagctttagttatgatggataaaaatatctgc            8631 caccctaggcttccaaattatacttaaattgtttacatagcttaccacaataggagtatcagggccaaatac            8703 ctatgtaataatttgaggtcatttctgctttaggaaaagtactttcggtaaattctttggccctgaccagta            8775
```

Fig. 18J

```
ttcattatttcagataattccctgtgataggacaactagtacatttaatattctcagaacttatggcattttt    8847 actatgtgaaaactttaaatttatttatattaagggtaatcaaattcttaaagatgaaagattttctgtatt    8919 ttaaaggaagctatgctttaacttgttatgtaattaacaaaaaaatcatatataatagagctctttgttcca    8991 gtgttatctctttcattgttactttgtatttgcaattttttttaccaaagacaaattaaaaaaatgaatacc    9063 atatttaaatggaataataaaggttttttaaaaactttaaa    9104
```

Fig. 18K

SEQ ID NO: 3

CRMGIKTSEG TPGFRAPEVA RGNVIYNQQA D

SEQ ID NO: 4

LSALTN

SEQ ID NO: 5 ttaagtgcgt taacaaat

SEQ ID NO: 6

REVTVK

SEQ ID NO: 7 agggaggtaa cggtaaaa

Fig. 19

KASPP (LRRK2) GENE, ITS PRODUCTION AND USE FOR THE DETECTION AND TREATMENT OF NEURODEGENERATIVE DISORDERS

CROSS REFERENCE TO RELATED APPLICATIONS

This application is a divisional of U.S. patent application Ser. No. 11/665,875, filed Apr. 19, 2007, which is the U.S. National Stage of International Application No. PCT/EP2005/010428, filed Sep. 27, 2005, which claims benefit of U.S. Provisional Patent Application Nos. 60/620,893, filed Oct. 21, 2004, and 60/621,169, filed Oct. 22, 2004, each of which is hereby incorporated by reference.

STATEMENT AS TO FEDERALLY FUNDED RESEARCH

This invention was made with government support under NS040256 awarded by National Institute of Neurological Disorders and Stroke. The government has certain rights in the invention.

The present invention refers to a newly discovered gene named KASPP for Kinase Associated with Parkinsonism with Pleiomorphic Pathology or alternatively named LRRK2 for Leucine-Rich Repeat Kinase 2, its production, biochemical characterization and use for the detection and treatment of neurodegenerative disorders, such as Parkinson disease (PD) including, without limitation, sporadic PD, Alzheimer disease (AD), amyotrophic lateral sclerosis (ALS), and other synucleinopathies and/or tauopathy as well as several polymorphisms and mutations in the KASPP/LRRK2 gene segregated with PD.

Parkinson's disease (PD) is the second most neurodegenerative disorder affecting 1-2% of the population aged 65 and older characterized by a progressive loss of dopaminergic neurons of the substantia nigra, associated with the formation of fibrillar aggregates composed of α-synuclein and other proteins (Lewy bodies and Lewy neurites). In most cases, PD occurs as a sporadic disease of unknown etiology, but in rare instances, point mutations or multiplications of the α-synuclein gene can cause autosomal-dominant parkinsonism which resembles the sporadic disease in many aspects. Recessive forms of parkinsonism have been recognized, which are caused by mutations in the genes for parkin (Kitada T. et al., Nature, 392, 605-608, 1998), DJ-1 (Bonifati V. et al., Science, 299, 256-259, 2002) and PINK1 (Valente E. M. et al., Science, 304 (5674), 1158-1160, 2004). Additional loci have been mapped on chromosomes 2p (Gasser T. et al., Nat. Genet., 18, 262-265, 1998), 12cen (Funayama M. et al., Ann. Neurol., 51(3), 296-301, 2002), 1q (Hicks A. A. et al., Ann. Neurol., 52(5), 549-555, 2002), and 2q (Pankratz N. et al., Am. J. Hum. Genet., 72(4), 1053-1057, 2003). In more than 10% of patients with PD one or more relatives are also affected by this disorder (Elbaz et al., Neurology, 52:1876-82, 1999). However, genetic causes are only very rarely found.

As α-synuclein aggregation is a pathologic feature both in the common sporadic and a dominantly inherited form of PD, and also in other neurodegenerative diseases, such as dementia with Lewy bodies (DLB) and multiple systems atrophy (MSA), those diseases have collectively been called "synucleinopathies". Other forms of parkinsonism are associated with the accumulation of filaments composed of the microtubule associated protein tau (MAPT). Mutations in this gene explain at least a subgroup of families with frontotemporal dementia with parkinsonism (FTDP-17; Ghetti B. et al., "Frontotemporal dementia and parkinsonism linked to chromosome 17 associated with tau gene mutations (FTDP-17)". In: Dickson D. W., "Neurodegeneration: the molecular pathology of dementia and movement disorders" ISN Neuropath Press, Basal, 86-102, 2003), while sporadic cases with tau pathology most commonly present as progressive supranuclear palsy (PSP) or corticobasal degeneration (CBD). Based on the putative central role of the tau protein in these diseases, they have been called "tauopathies".

Recently it has been shown that two large families with autosomal-dominant late-onset parkinsonism (families A and D) are linked to the PARK8-locus on chromosome 12p11.2-q13.1 (OMIM# 607060), originally mapped in a Japanese family by Funayama et al. (Funayama et al., Ann. Neurol., 51(3), 296-301, 2002; Zimprich A. et al., Am. J. Hum. Genet., 74(1), 11-19, 2004).

Now, a haplotype analysis refined the candidate region to a 13 Mb interval between flanking markers D12S1692 and D12S85. A total of 29 genes have been sequenced in that region in two patients from each family (see Table 1).

A whole gene, part of that had previously been deposited under DKFZp434H211 (Accession: XM_058513), has been amplified from human brain cDNA using overlapping primers corresponding to published sequences of various ESTs and mRNAs. Nevertheless, it became clear from cross-species sequence alignments that the DKFZp434H211 clone was incomplete towards the 5'-end.

Surprisingly, several mutations, including missense mutations and a splice site mutation, have been found in newly discovered large gene coding for a multifunctional protein, which is referred to as Kinase ASsociated with Parkinsonism with Pleiomorphic Pathology, KASPP. KASPP spans a genomic region of 144 Kb and comprises 51 exons and encodes 2527 amino acids (see SEQ ID NOS: 1 and 2 and FIG. 4). The gene can also be named Leucine-Rich Repeat Kinase 2, LRRK2, because it is the only gene in the human genome encoding a kinase containing leucine rich repeats which was very surprising. KASPP/LRRK2 is a 285 kD protein.

Therefore, the present invention is directed to an isolated nucleic acid molecule comprising a polynucleotide sequence selected from:
(a) nucleotides 1 to 9104 of SEQ ID NO: 1 or 2;
(b) nucleotides 1 to 7584 of SEQ ID NO: 1 or 2;
(c) nucleotides 1 to 7581 of SEQ ID NO: 1 or 2;
(d) a nucleotide sequence coding for the protein sequence of SEQ ID NO: 1 or 2 or for the protein sequence of SEQ ID NO: 1 or 2 containing at least one of the mutations depicted in SEQ ID NO: 1 or 2, respectively;
(e) a nucleotide sequence complementary to either of the nucleotide sequences in (a), (b), (c) or (d); and/or
(f) a nucleotide sequence which hybridizes under high stringency conditions to any of the nucleotide sequences in (a), (b), (c), (d) or (e).

SEQ ID NO: 2 is particularly preferred because it reflects the amino acid sequence of human KASPP/LRRK2 and the human nucleotide sequence coding for the human KASPP/LRRK2.

Examples of polynucleotides selected from paragraph (f), above are the specific mutations, variants and polymorphisms described herein.

A polymorphism generally is the occurrence of different forms of nucleic acids or proteins in individual organisms or in organisms of the same species, independent of sexual variations. According to the present invention two different polymorphisms have been found for the human KASPP/LRRK2. One shows a variation from cytosine to thymidine at position 635 (c635t) causing a change in the amino acid sequence from serine to leucine (S212L) (see SEQ ID NOS: 4 and 5). The other shows a variation from thymidine to cytosine at position 7190 causing a change in the amino acid sequence from methionine to threonine (M2397T) (see SEQ ID NOS: 6 and 7).

Examples of high stringency hybridization conditions can be found e.g. in Ausubel, F. M. et al., *Current protocols in Molecular Biology*, John Wily & Sons, Inc., New York, N.Y. (1989). In a particular example, a filter, e.g. a nitrocellulose filter, is incubated overnight at 68° C. with a probe in a hybridization solution e.g. containing 50% formamide, high salt (either 5×SSC [20×: 3M NaCl/0.3M trisodium citrate] or 5×SSPE [20×: 3.6M NaCl/0.2M NaH$_2$PO$_4$/0.02M EDTA, pH 7.7]), 5× Denhardt's solution, 1% SDS, and 100 µg/ml denatured salmon sperm DNA. This is followed by several washes with buffer, e.g. in 0.2×SSC/0.1% SDS at a temperature selected based on the desired stringency and the melting temperature (Tm) of the DNA hybrid. For example, 68° C. are appropriate for high stringency hybridization.

The present invention is also directed to a fragment of the inventive nucleic acid molecule specified above containing at least one of the 51 exons and/or coding for at least one of the five domains as specified in FIGS. 4A-4K, FIGS. 5A-5C, and/or FIGS. 11A or 11B of the present specification. The boundaries of the exons as specified in FIGS. 4A-4K are applicable for the nucleotide sequences of SEQ ID NO:1 and SEQ ID NO:2.

In addition, the nucleic acid molecule as specified under (f) above may consist of 10 to 50 nucleotides, preferably from 10 to 35 nucleotides, in particular from 20 to 35 nucleotides. Such nucleic acid molecule can be used as a probe or primer for the detection of the polynucleotide of the present invention, in particular for the detection of a mutation thereof as explained in more details below.

Another example of a fragment is a nucleic acid coding for the immunogenic peptide of SEQ ID NO: 3 and the peptide itself.

Such fragments may be produced synthetically e.g. by nucleic acid synthesis or by a PCR or TR-PCR reaction.

Therefore, another embodiment of the present invention is directed to a nucleic acid molecule containing at least one of the mutations depicted in FIGS. 17A-17K or FIGS. 18A-18K, preferably only one of the mutations depicted in FIGS. 17A-17K or FIGS. 18A-18K, e.g., the mutation/s at position 2378, 2789, 3287, 3342, 3364, 3683, 4321, 5096 and/or 6059. In addition, the polymorphisms c635t and t7190c are also a specific embodiment of the present invention.

Surprisingly, is has been discovered that in family A (Y1699C; 5096A>G) and in family D (R1441C; 4321C>T) both mutations segregated with disease in the families (for pedigree structures see FIG. 1) and were not found in more than 1000 control individuals, nor in 300 sporadic PD-patients.

In Family A, 16 individuals were typed (8 unaffecteds, 8 affecteds). All affecteds were heterozygous for the mutation and all unaffecteds aged over 60 were wild-type. Individuals IV:1 and IV:2 (family A) were not included in our initial linkage analysis (Zimprich A. et al., 2004, supra), both individuals have now been genotyped. Recalculation of the two-point LOD scores using the mutation as a marker gives maximum LOD scores of 3.78 at θ=0.

In Family D, 34 individuals were typed (10 affecteds and 24 unaffecteds), all affecteds were heterozygous for the 4321C>T (2.1441C) mutation; out of the 24 clinically unaffected, genotyped individuals, only two were aged over 60 years and were mutation carriers. These individuals are at risk and likely to be presymptomatic given that the average age of onset in this family is 65 years according to Wszolek Z. K. et al., Neurology, 62(9), 1619-1622, 2004.

To estimate the prevalence of KASPP/LRRK2-mutations among PD-families, one index patient from 44 additional families with PD, 32 consistent with autosomal dominant parkinsonism and 12 affected sib-pairs, were subsequently sequenced.

Surprisingly, two further miss-sense and one putative splice site mutation have been identified, all in families with typical late onset PD, compatible with a dominant transmission: (I1122V; 3364A>G) in family 21; (I2020T; 6059T>C) in family 32, and (L1114L; 3342A>G) in family 38, which is 6 by away from the exon/intron border. Affected individuals in a further family (469) were found to carry the same mutation as family D (R1441C; 4321C>T). Those two families are not known to be related, nor did they share haplotypes for the closest flanking microsatellite repeat markers D12S2194, D12S1048 or three newly developed intragenic repeat markers, indicating that the mutations are extremely ancient or arose independently (for pedigree structures see FIG. 2).

Again, the mutations segregated with the disease in all families and none of them were found in controls. Three of the amino acid substitutions (R1441C, Y1699C and I1122T) are additionally highly conserved across species (see FIG. 3).

Screening the entire coding region of the KASPP/LRRK2 gene in a cohort of 53 apparently unrelated families with apparently autosomal mode of inheritance, seven more families with amino acid substitutions or one splice site mutation have been identified. Mutations in the KASPP/LRRK2 gene, therefore, account for 13% of familiar PD in our total cohort.

In the second study four novel mutations (R793M, Q930R, S1096C and S1228T) have been identified. Therefore, together with the published mutation, until now, 10 missense mutations and one splice site mutation have been described.

The KASPP/LRRK2 gene consists of 51 exons comprising five conserved domains (see FIGS. 5 and 7) indicating that it belongs to a recently defined ROCO protein family (Bosgraaf L. et al. Biochim. Biophys. Acta., 1643 (1-3), 5-10, 2003).

The five conserved domains are in detail:

(1) N-terminal leucine-rich repeat (LRR) consisting of 12 strands of a 22-28 amino acid motif, present in a tandem array; (2) ROC (Ras of complex) domain indicating the affiliation of the protein to the Ras/GTPase superfamily; (3) COR (C-terminal of Roc) domain; (4) tyrosine kinase catalytic domain (MAPKKK) and (5) C-terminal WD-40 domain.

Proteins containing LRRs are associated with diverse functions, such as hormone receptor interactions, enzyme inhibition, cell adhesion, cellular trafficking, splicing and substrate binding for ubquitination, a common property involves protein-protein interaction (Kobe B. et al., Curr. Opin. Struct. Biol., 11(6), 725-723, 2001). In particular, the N-terminal LRR and the C-terminal WD-40 propeller structure are assembly points for larger protein complexes. Ras/GTPase domains are involved in the reorganization of the actin cytoskeleton in response to external stimuli. They also have roles in cell transformation by Ras, in cytokinesis, in focal adhesion formation and in the stimulation of stress-activated kinase (Ridley A. J. Trends Cell. Biol, 2001). In particular, the fusion of a Ras-like domain with a MAPKKK domain indicates the function of KASPP/LRRK2 in intramolecular signal transduction. Furthermore, KASPP/LRRK2 should also function as a scaffolding protein like Ksr (Kinase suppressor of Ras). The KASPP/LRRK2 kinase domain shows also similarity to the RIR and Mixed lineage kinases which are part of the TKL-(thyrosine kinase like) branch of the human kinome indicating an involvement in stress-induced cell signalling and mediation of apoptosis. The COR domain is characteristic for this protein family and shows no significant sequence homology to any domain or protein today. Enzymes with a tyrosine kinase catalytic domain belong to an extensive family of proteins which share a conserved catalytic core common to both serine/threonine and tyrosine protein kinases. They exert their function by catalyzing the transfer of the gamma-phosphate of ATP to tyrosine residues on protein substrates (Hubbard S. R. et al. Annu. Rev. Biochem., 69, 373-398, 2000). The WD40 domain is implicated in signal transduction, pre-mRNA processing and cytoskeleton assembly (Smith T. F. et al., Trends Biochem. Sci., 24(5), 181-185, 1999).

In view of the present invention three Roco proteins of the Roco-protein family exist now in mammals: LRRK1, DAP-kinase (death associated protein kinase) and KASPP/LRRK2 of the present invention. The mammalian DAP-kinase, for example, should be involved in cytosceletal rearrangements and/or induction of apoptosis dependent on its activity.

The biochemical analysis of KASPP/LRRK2 and its Parkinson disease-associated variant, I2020T, bearing a mutation located next to the DFG motif (DYG in KASPP/LRRK2) at the beginning of the activation loop of the kinase domain which is highly conserved in almost all MAPKKK, indicates according to the present invention that KASPP/LRRK2 acts as a true protein kinase at cytoskeletal and membraneous structure within the cell. In addition, the found increase (approximately 30-50%) in the kinase activity of the I2020T mutant is consistent with mutations in homologous positions of other kinases like B-Raf associated with cancer (Dibb, N. J. et al. (2004), Nat. Rev. Cancer, 4, 718-727). It is also worth to be noted that this mutation is a dominant feature. In addition to an overall gain in kinase activity, the mutation could also alter substrate specificity. As with oncogenic kinase variants, kinase inhibitors could then be considered as a treatment option. The effectiveness of such therapeutic strategy has been proven with respect to specifically inhibiting the bcr-abl protein kinase within chronic myeloic leukemia (CML) through the kinase inhibitor 2-phenylaminopyrimidine STI571 (Gleevec), a small-molecule tyrosine kinase inhibitor for the treatment of CML (Chalandon, Y. & Schwaller, J., Haematologica, 90, 949-968, 2005).

In summary, the biochemical analysis of KASPP/LRRK2 and its I2020T mutant according to the present inventions shows that KASPP/LRRK2 shares common features with other MAPKKK, such as autophosphorylation, dimerisation or interaction with kinase specific chaperones. The autokinase activity of the mutant I2020T, localised within the activation loop of the KASPP/LRRK2 kinase domain is increased when compared to wild-type KASPP/LRRK2 according to the present invention. In view of its multimodular structure, KASPP/LRRK2 should be involved in functions as diverse as maintenance of microtubular ultrastructure and dynamics, vesicular trafficking (ER, Golgi compartment) and/or cytoskeletal rearrangements.

Interestingly, all ten mutations are within these conserved domains (FIG. 7). The R793M mutation, however, is located in exon 19 which is part of the ancyrin repeat region (amino acid 678-806), that seems to take part in protein-protein interactions.

In contrast to previous reports the so far most common mutation (G2019S; 6055G>A, Hernandez D G et al., Ann Neurol, 57: 453-6, 2005) was not detected in any of the families investigated but only in one patient with sporadic PD. Moreover, this mutation was found in only one out of 340 patients with sporadic PD. Therefore, the predominance of this mutation (Gilks et al., Lancet, 365: 415-6, 2005; Toft et al., Lancet, 365: 1229-30, 2005) can not be established for all populations. The screening in familial and sporadic PD patients showed frequencies of the G2019S mutation up to 7% in familial and almost 1% in sporadic PD cases, however, no association could be demonstrated of this mutant with the non-mendelian sporadic form of PD in a recent study of the inventors. In the present cohort comprising 340 patients with sporadic PD the novel R793M was additionally found in one sporadic patient. Therefore, KASPP/LRRK2 mutations account for only 0.6% of sporadic PD cases in the present population.

In three families the specific variation did not cosegregate with one family member each: In family DE022, the Q930R only three of the four family members affected by the disease were mutation carriers (FIG. 6b), in family E in fact only one of the two family members with PD phenotype was carrier of the S1096C mutation (FIG. 6f), and the splice site mutation cosegregating with PD in one previously investigated family (DE038) was only found in one of the clinically affected sisters (T112888) (FIG. 6c). As none of these variations was found in any of the 1200 controls investigated and the splice site variation affected two distinct PD families it is likely that they are causative for the disease, although incomplete penetrance at least in family DE022 could indicate that additional factors may contribute to manifestation of the disease in affected subjects. This may be due to phenocopies in these three families, as the high prevalence of PD in the population makes it well possible that other causes of PD occur in a family affected by KASPP/LRRK2 mutations. Disease phenocopy is not uncommon in PD. It has been described in the original α-synuclein A53T kindred (Polymeropoulos et al., Science, 276: 2045-7, 1997), in a family with the KASPP/LRRK2 G2019S mutation (Hernandez et al., 2005, supra), but also in family D with the KASPP/LRRK2 R1441C mutation.

Three of the present mutations affect at least two families. For two of these (R793M and I2020T) haplotype analysis revealed a common haplotype indicating a common founder. None of the families was aware of a possible relation to the respective family although the two families harbouring the I2020T mutation lived in the same geographic region. The same mutation has also been described in the Japanese family, who served as the basis for the original defining of the PARK8 locus (Funayama et al., Ann Neurol., 57: 918-21, 2005).

The R793M mutation, detected in two distinct families with the same haplotype, was also found in one patient with sporadic PD and one control person. Because of technical problems in assessing this CG rich exon call rate of the population screened was low (about 50% in three different tries). Therefore, it may well be, that this mutation is more frequent in apparently sporadic PD patients. Also, the possibility of a polymorphism needs to be taken into account, if this variation was detected in more controls. However, finding of a possible common founder in the two families with the mutation is an indication for a disease related amino-acid substitution. Common founders are also suggested for other families affected by mutations in the KASPP/LRRK2 gene (Mata et al., Neurosci Lett, 382: 309-311, 2005).

Mode of inheritance of KASPP/LRRK2 mutations is autosomal dominant. It has been suggested that penetrance of KASPP/LRRK2 mutations is age dependent (DiFonzo et al., Lancet, 365: 412-5, 2005; Toft et al., 2005, supra) accounting for the reduced penetrance in some families. In the present families reduced penetrance was only observed in mutations of exons 19 and 21 located before the highly conserved LRR domain. This indicates that mutations in this region are less severe and have to be associated with other so far unknown factors for disease manifestation. From the splice site mutation of exon 24 onwards, penetrance was complete, although one splice mutation carrier (DE038, III-1) had only slight resting tremor for several years, while his sister (III-3), mother and uncle were affected by severe PD.

In all families with definite documentation of age of onset an earlier recognitions of first Parkinsonian signs was observed in the younger generations. So far, there are no known pathomechanism that allow the hypothesis of anticipation. Rather, a greater awareness of a possible affliction and a more thorough investigation in families in whom PD has already been diagnosed could account for the earlier diagnoses.

The clinical presentation of KASPP/LRRK2 mutation carriers varies within families and between families affected by the same mutation. In general the typical phenotype of PD with resting tremor, bradykinesia, rigidity and olfactory dysfunction can be observed. Interestingly, tremor, the main and naming feature of some of the initially described to families (Paisan-Ruiz et al., Neuron, 44: 595-600, 2004) was neither the main initial nor the leading symptom in many of our PD patients. Two patients did not report any resting tremor in their medical history. Rather, the typical pattern of different subtypes known from idiopathic PD could be observed. All patients reported a substantial relief of symptoms after application of dopaminergic treatment, which was hampered by halluzinations in only the one patient with DLBD-phenotype (Diffuse Lewy Body Disease-phenotype).

In patients with KASPP/LRRK2 mutations a frequent, the patient strongly afflicting symptom seems to be sleeping abnormality. Eight out of 10 patients (80%) reported to suffer from difficulties of either falling a sleep, staying a sleep or both. According to several studies, sleeping disturbancies occur in about 40-75% of PD patients (Lees et al., Clin Neuropharmacol., 11:512-519, 1988; Kumar et al., Mov Disord, 17: 775-781, 2002), but only the minority (about 20%) reports sleeping abnormalities as a problem (Lees et al., 1988, supra). In the present study 80% stated that sleeping disturbances were indeed a problem. More detailed assessment on sleeping behaviour and pattern are to be decided, whether this symptom is more pronounced in KASPP/LRRK2 mutations carriers, possibly indicating an earlier involvement of the respective systems. Postural instability occurs late in the course of the disease. As also described by others (Paisan-Ruiz et al., Ann Neurol., 57:365-72, 2005) dementia is not a common finding in KASPP/LRRK2 associated PD and seems to occur rather late in the disease process. The same holds true for hallucinations in our patient cohort, occurring either late in the disease process or in combination with dementia. In the present cohort, one patient presented with the typical clinical picture of DLBD. Autopsy of one subject with dementia in our first cohort revealed diffuse Lewy Body pathology in one family affected by the Y1699C mutation. Description of the same phenotype in an other patient in this study affected by a different mutation favours the hypothesis that the clinical presentation of DLBD may be caused by the same pathophysiological alterations as the clinical picture of PD. Obviously specific pathophysiological changes (in this case caused by mutations in the KASPP/LRRK2 gene) may lead to the clinical and histopathological entity of both: PD and DLBD.

In our first study one patient showed mild signs of motor neuron disease. In the second study, however, motor neuron symptoms were neither clinically nor electrophysiologically disclosed in any patient investigated.

Structural neuroimaging revealed slight to marked atrophy in all 4 patients investigated, although disease duration was only 3-12 years in these and only one was classified as demented (Table 4). This contrasts findings of idiopathic PD, where structural MRI is usually normal and atrophy only occurs with disease progression, usually associated with dementia. The patient with the clinical presentation of DLBD had marked signs of microangiopathy, which may also be causative for an atypical Parkinsonian syndrome. The clinical presentation with fluctuation of vigilance, good response to L-dopa hampered by hypersensitivity and dementia developing over a short period of time, however, makes the diagnosis of DLBD more likely.

TCS revealed SN hyperechogenicity—the typical sign for idiopathic PD, found in more than 90% of PD patients (Berg et al., 2001, supra; Walter et al., J Neural Transm, 109:191-196, 2002)—on at least one side of KASPP/LRRK2 mutation carriers. Interestingly, SN hyperechogenicity was only moderate in all patients investigated, as opposed to idiopathic PD, where it is marked in 73-79% of the patients. This highly characteristic finding is supposed to be associated with an increase in tissue iron content and possible alterations in iron binding, antedating the manifestation of disease onset (Berg et al., 1999, supra: Berg et al., Neural Transm, 109:191-196, 2002). An only moderate hyperechogenicity of the SN in KASPP/LRRK2 associated PD may argue for a different course of underlying pathomechanisms, which may finally lead to less iron accumulation in KASPP/LRRK2 associated than in idiopathic PD. Similarly, the slower disease progress, documented by less although typically located reduction of F-Dopa uptake in PET examinations (Hernandez et al., 2005, supra) favours the hypothesis of a different course of the disease.

In conclusion, in two consecutive studies it has been shown that KASPP/LRRK2 mutations account for about 13% of apparently autosomal dominantly inherited PD and sib pairs in the population investigated. Although the phenotype varies within and between families affected by the same mutations it is very similar to the clinical presentation of idiopathic PD. The causal relation between disease manifestation and variation is not equally clear for all variations described. In three families the specific variations did not co-segregate with one family member each affected by the disease. As none of these mutations was found in 1200 control persons, and one variation was found in two distinct PD families phenocopies is indicative.

Moreover, two patients with the clinical presentation of DLBD should lead to the consideration of KASPP/LRRK2 mutations in families with the simultaneous occurrence of DLBD and PD.

As already pointed out above mutations have been found in different functional domains but it is unclear which of them are related to neurodegeneration. However, KASPP/LRRK2 may be central to a range of neurodegenerative processes because our findings show that (i) KASPP/LRRK2-mutations appear to be a numerically important cause of autosomal-dominant parkinsonism (6 independent mutations in 34 families with dominant inheritance) and (ii) affected individuals with KASPP/LRRK2 mutations exhibit strikingly variable pathologic changes, representing aspects of several of the major neurodegenerative diseases.

Using cell fractionation and carbonate extraction the present invention discloses that KASPP/LRRK2 is associated partially with mitochondria, the cytoskeleton and microsomal membranes, which is an indication that KASPP/LRRK2 is involved in cytoskeletal rearrangements. No KASPP/LRRK2 was found in the cytoplasm. Further, the autokinase activity of KASPP/LRRK2 is not significantly changed in the disease-associated I2020T mutant compared with wild-type, indicating that the autosomal dominant effect is caused by a toxic gain of function rather than loss of function. The I2020T mutation is located next to the conserved motif DFG (DYG in LRRK2) at the beginning of the activation segment of the kinase domain (Ross O. A. & Farrer M. J. Biochem. Soc. Trans., 33, 586-590, 2005) and in the mutation a hydrophobic leucine residue is exchanged by a polar threonine residue. This is also an indication that associated Parkinson's disease is caused by altered substrate specificity or higher KASPP/LRRK2 activity. Homodimerization and association with the HSP90/p50$^{cdc37}$ chaperone-system further indicate that the KASPP/LRRK2 function and activation mechanisms are similar to other MAPKKK. These effects serve as a basis for the development of a suitable screening assay and/or the development of a pharmaceutical or a diagnostic agent as described below in detail.

Autopsies performed on affected individuals uniformly demonstrated neuronal loss and gliosis in the substantia nigra as the pathological substrate of parkinsonism. However, α-synuclein pathology (Lewy-bodies, LBs) typical for PD was seen only in one case from family D. In another case from this family widespread LB's was more consistent with diffuse Lewy Body disease (DLB). Even more intriguingly, senile plaques and neurofibrillary tangles (NFTs) as well as prominent tau deposits were demonstrated in 3 other brains from both large kindreds. Spinal cord pathology consistent with a diagnosis of amyotrophic lateral sclerosis (ALS) was found in affected members of family A.

Hence, KASPP/LRRK2 is likely to be central to the aetiology of all neurodegenerative diseases such as PD, Alzheimer disease (AD) and amyotrophic lateral sclerosis (ALS) and pathologies, including synucleinopathy and tauopathy, associated with a clinical phenotype of parkinsonism.

It has previously been shown that tau and α-synuclein pathologies may be closely linked. Tau-aggregations have been found in the brains of patients carrying pathogenic A53T α-synuclein mutations (Kotzbauer P. T. et al., Exp. Neurol., 187(2), 279-288, 2004; Duda J. E. et al., Acta Neuropathol. Berl., 104, 7-11, 2002) Similarly, the major pathogenic protein aggregating in AD has been shown to promote fibrillization of tau and formation of neurofibrillary tangles in an animal model (Gotz J., Science, 293, 1491-1495, 2001). Interestingly, a genomic region overlapping the PARK8 locus has been identified in a linkage study of familial Alzheimer disease (Scott W. K. et al. Am. J. Hum. Genet., 66(3), 922-932, 2000). Evidence for linkage was derived in a large part from families with at least one member with autopsy proven diffuse Lewy body disease. Whether this linkage result reflects variants in the KASPP/LRRK2 gene remains to be determined.

The expression pattern of KASPP/LRRK2 was subsequently examined in brain and other tissues. Human brain and multiple tissue Northern blots were hybridized with a 1078 by 3' cDNA probe and found expression in most brain regions, albeit at a very low levels. Two transcripts of about 9 kb and 8 kb, respectively, and multiple bands at lower sizes were found. The two transcript sizes might be explained by alternative splicing and/or the alternative use of polyadenylation sites.

As low overall expression levels in brain precluded a detailed analysis of its regional distribution by Northern blotting, real-time RT-PCR was done using RNA isolated from adult and fetal whole brain as well as from different brain regions in order to assess quantitative gene expression and alternative splicing. Primers have been designed to generate specific PCR products for exon1-8, exon13-19 and exon 31-39, respectively. Within the same tissue or brain region transcript levels of all three assays showed no significant differences. Consistent expression in most brain regions have been found, slightly higher in putamen, substantia nigra and heart. The highest expression levels were observed in lung. The cDNA analysis, within in multiple tissues, confirms in silico prediction that at least 11 exons may be alternatively spliced. In adult human brain tissue, exon 6 was constitutively expressed within the full length mRNA.

In view of the above, the present invention is also directed to a vector, preferable an expression vector, containing the nucleic acid molecule of the present invention, to a cell containing the nucleic acid or the vector of the present invention and to a transgenic animal containing the nucleic acid or the vector of the present invention.

A vector can be a plasmid or phage DNA or any other DNA sequence into which DNA can be inserted to be cloned. The vector can replicate autonomously in a host cell, and can be further characterized by one or a small number of endonuclease recognition sites at which such DNA sequences can be cut in a determinable fashion and into which DNA can be inserted. The vector can further contain a marker suitable for use in the identification of cells transformed with the vector. Markers, for example, are tetracycline resistance genes or ampicillin resistance genes.

In a further embodiment the vector can be in the form of an expression vector containing an expression cassette which comprises the nucleic acid molecule of the present invention, but preferably also further comprising expression control sequences which are operatively linked to the nucleic acid molecule. The expression control sequences are chosen so that they allow expression of the encoded polypeptide in a host. For example a nucleic acid sequence encoding a polypeptide of the present invention can be isolated and cloned into an expression vector and the vector can then be transformed into a suitable host cell for expression of the polypeptide of the invention. Such a vector can be a plasmid, a phagemid or a cosmid. For example, a nucleic acid molecule of the invention can be cloned in a suitable fashion into prokaryotic or eukaryotic expression vectors, preferably into eukaryotic expression vectors and more preferably into expression vectors allowing expression in a mammalian and in particular in a human cell which is known to a person skilled in the art. Such expression vectors typically comprise at least one promoter and can also comprise a signal for translation initiation of the reading frame encoding the polypeptide and—in the case of prokaryotic expression vectors—a signal for translation termination, while in the case of eukaryotic expression vectors the expression cassette preferably comprises expression signals for transcriptional termination and polyadenylation. Examples of suitable eukaryotic expression vectors are well known for the person skilled in the art, e.g. for the expression in insect cells via baculovirus vectors, and for expression in mammalian cells, e.g. the SV40 or CMV vectors, the sindbisvirus expression system, or an adenovirus expression system, a Semliki Forest Virus-based expression system, or a lentivirus-based expression system. The molecular biological methods for the production of these expression vectors are also well known to the skilled person, as well as the methods for transfecting host cells and culturing such transfected host cells. In a preferred embodiment the above-mentioned expression control sequences specify induced expression of the polypeptide of the invention, that is induced transcription of the messenger RNA encoding the polypeptide of the invention upon addition or withdrawal of an external signal, such as a small chemical like tetracycline or a hormone like Ecdysone, but the extracellular signal can also be an increase or decrease in temperature or ionizing radiation. Also, inducible expression can be brought about by inducible translation initiation of the messenger RNA or a system in which mRNA stability is controlled in an inducible fashion. Examples of expression control sequences allowing induction of polypeptide production are reviewed in the following publications: the TET-off/TET-on system, suitable for both cell cultures and transgenic animals, but also the expression control system based on Cre-recombinase based methods, predominantly for use in transgenic animals. A further inducible expression system, for use in both cell culture and transgenic animals is based on the insect hormone Ecdysone. Another inducible expression system is the GAL4 system, which has been successfully applied with mice, zebrafish and *Drosophila*, and allows conditional expression at 26-29 degrees, or also a Rapamycin based conditionals expression system. A temperature-sensitive expression system is based on a Sindbis virus expression cassette and predominantly suitable for controlled expression in cell culture systems.

Another aspect of this invention relates to a cell comprising a nucleic acid or a vector of the present invention. Such a cell can be a mammalian, non-human cell inside or outside of the animal body or a human cell outside of the human body. But it can also be an insect cell, like a drosophila cell, in culture or in the context of a transgenic insect, like a transgenic *Drosophila*. It can also be a nematode cell, like, for example, present in transgenic *C. elegans*. Preferred host cells are mammalian, and particularly human, neuronal cells, microglia cells, astrocytes, oligodendrocytes, fibroblasts, monocytes, and macrophages and other non-neuronal primary cells, which can be kept in primary tissue culture and can be made capable of expressing the polypeptide of the invention by introducing the nucleic acid/or the expression cassette of the invention, for example by transfection with such a nucleic acid or expression cassette. Other means of introducing the nucleic acid and/or the expression cassette of the invention to the above-mentioned primary cells are "gene gun" approaches, mRNA transfer, viral infection, microinjection or liposomal nucleic acid transfer, to name but a few. Other suitable host cells are mammalian cells like HEK cells, HELA cells, PC12 cells, CHO cells, JURKAT cells, mouse 3T3 fibroblasts, mouse hepatoma cells, human neuroblastoma cells, but also established cancer cell lines, particularly neuronal cell lines, of mammalian and particularly of human origin.

The nucleic acid and/or the expression cassette of the invention can also be introduced into those cells by the above-mentioned nucleic acid transfer methods. Particularly preferred are stably transformed cell lines wherein the expression of the polypeptide of the invention is inducible. Since expression of the polypeptide of the invention may show increased neuropathology, it may be preferred that in such host cells the expression of the polypeptide of the invention is usually very low or off, for example during the generation of a stably transformed cell line, and only for experimental purposes and after establishment of such a stably transformed cell line the expression of the polypeptide of the invention is turned on by addition of a suitable stimulus, like e.g. a hormone like Ecdysone or a small chemical like the antibiotic tetracycline. Again, the above described examples of expression control sequences allowing induction of polypeptide production are suitable for this purpose, like the TET-off/TET-on system, the Cre-recombinase based methods, the Ecdysone system, the GAL4 system, Rapamycin-based systems, or the above described temperature-sensitive expression system based on a Sindbis virus expression cassette.

Another aspect of the invention relates to transgenic animals which comprise a host cell of the invention. Particularly preferred are transgenic flies, like transgenic *Drosophila*, transgenic nematodes, like transgenic *C elegans*, transgenic fish, like transgenic zebra fish, and transgenic non-human mammals, like transgenic rodents (mice, rats).

Meanwhile, the generation of transgenic animals are within the general skill of a person skilled in the art. In addition, it is pointed out that under the control of tissue-specific promoters expression could be targeted to the CNS in mice and others. Most tissue-specific to promoters could be used, for example, also in the context of viral vectors. In the following, tissue-specific promoters of rodents are listed. Expression in astrocytes: GFAP-promoter, macrophage colony-stimulating factor (c-fms). Expression in neurons: synapsin promoter, thy-1 promoter, neuron-specific rat enolase promotor (NSE), L7 promoter (Purkinje cells), dopamine beta-hydroxylase (DBH) promoter (predominantly in the peripheral nervous is system), brain dystrophin promoter, calmodulin gene II and III promoter (CaMII, CaMIII), human and murine neurofilament light gene promoter (NF-L), human hypoxanthine phosphoribosyltransferase (hHPRT) promoter, corticotropin-releasing hormone (CRH), T alpha 1 alpha-tubulin promoter, murine low-affinity NGF receptor promoter, hippocalcin gene promoter, olfactory marker protein (OMP) promoter (olfactory neurons), GABA(A) receptor alpha 6 subunit promoter, GABA(A) receptor delta subunit promoter, tyrosine hydroxylase (TH) promoter, mouse vesicular acetylcholine transporter (VAChT), mouse glutamate decarboxylase 65 and mouse glutamate decarboxylase 67 genes promoters, brain-specific promoter of the human FGF1, gonadotropin-releasing hormone (GnRH) promoter, N-methyl-D-aspartate receptor 2A subunit gene promoter; mouse metabotropic glutamate receptor subtype 6 (mGluR6) upstream sequence, Rod photoreceptor cGMP phosphodiesterase (PDE6), human blue opsin promoter and rhodopsin promoter (retina). Neuron-restrictive silencer elements: Neuron-restrictive silencer elements (NRSEs). Expression in oligodendrocytes: MBP (myelin basic protein), proteolipid protein (PLP) promoter.

Furthermore, the present invention is directed to a protein encoded by a nucleotide sequence of the present invention, in particular a protein containing the amino acid sequence of SEQ ID NO: 1 or 2 or at least one of the mutations depicted in SEQ ID NO: 1 or 2, such as the mutation R793M, Q930R, S1096C, L1114L, I1122V, S1228T, R1441C, Y1699C and/or I2020T.

It is particularly pointed out that the present invention encompasses also proteins which contain one or more amino acid substitutions in the KASPP/LRRK2 protein but still retains essentially its function. Such amino acid substitutions may be semi-conservative or conservative and more preferably a conservative amino acid residue exchange. In the following table such amino acid substitutions are exemplified.

| Amino acid | Conservative substitution | Semi-conservative substitution |
| --- | --- | --- |
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |

-continued

| Amino acid | Conservative substitution | Semi-conservative substitution |
| --- | --- | --- |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

For example, changing from A, F, H, I, L, M, P, V, W or Y to C is semi-conservative if the new cysteine remains as a free thiol. Furthermore, the skilled person knows that glycines at sterically demanding positions should not be substituted and that P should not be introduced into parts of the protein which have an alpha-helical or a beta-sheet structure.

The present invention is also directed to the manufacturing of the proteins by methods already explained above. In short such method comprises
(a) culturing a cell of the present invention under suitable conditions; and
(b) isolating the protein produced by the cultured cell.

Another preferred embodiment of the present invention is directed to a method of detecting a mutation at position 2378, 2789, 3287, 3342, 3364, 3683, 4321, 5096 and/or 6059 in the nucleic acid molecule of SEQ ID NO: 1 or 2 in a sample, the method comprising:
(a) contacting said sample with the nucleic acid molecule according to the present invention, and
(b) detecting the presence of the mutation.

Preferably, the sample is selected from
(a) a sample, in particular a biopsy, from human tissue or cells, in particular from the brain, in particular putamen or substantia nigra; heart, lung and/or blood lymphocytes; Or
(b) RNA and/or DNA from a sample, in particular a biopsy, from human tissue or cells, in particular from the brain, in particular putamen or substantia nigra; heart, lung and/or blood lymphocytes;

In general, the detection can be carried out by Southern blot hybridization, Northern blot hybridization, PCR or RT-PCR including real-time RT-PCR, techniques which are well known to a person skilled in the art. The mutation can also be detected by radiography, fluorescence, chemiluminescence, or any combination thereof. Preferably automated sequencing can be carried out, an electrophoresis method run basically in a capillary (column) combined with fluorescence.

Other methods for detection and/or quantification of the amount of polynucleotides, i.e. for the methods according to the invention allowing e.g. the determination of the level of expression of a polynucleotide containing a mutation, are real time methods known in the art as the TaqMan® method disclosed in WO92/02638. This method exploits the exonuclease activity of a polymerase to generate a signal. In detail, the (at least one) target nucleic acid component is detected by a process comprising contacting the sample with an oligonucleotide containing a sequence complementary to a region of the target nucleic acid component and a labeled oligonucleotide containing a sequence complementary to a second region of the same target nucleic acid component sequence strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments. The signal generated by the hydrolysis of the labeled oligonucleotide is detected and/or measured. TaqMan® technology eliminates the need for a solid phase bound reaction complex to be formed and made detectable. Other methods include e.g. fluorescence resonance energy transfer (FRET) between two adjacently hybridized probes as used in the LightCycler® format described in U.S. Pat. No. 6,174,670.

A preferred protocol if the polynucleotide is in form of a transcribed nucleotide is a method where total RNA is isolated, cDNA and, subsequently, cRNA is synthesized and biotin is incorporated during the transcription reaction. The purified cRNA is applied to commercially available arrays which can be obtained e.g. from Affymetrix. The hybridized cRNA is then detected. The arrays are produced by photolithography or other methods known to experts skilled in the art.

Consequently, the method can be carried out on an array, e.g. in a robotics system or using microfluidics.

The present invention is also directed to a diagnostic kit containing at least one nucleic acid molecule of the present invention for diagnosing a neuronal disease, in particular a neurodegenerative disorder, especially Parkinson Disease (PD) including, without limitation, sporadic PD, Alzheimer Disease (AD), amyotrophic lateral sclerosis (ALS), synucleinopathy and/or tauopathy, in combination with suitable auxiliaries. Suitable auxiliaries, as used herein, include buffers, enzymes, labelling compounds, and the like. In a preferred embodiment, the nucleic acid molecule contained in the kit is a nucleic acid molecule which is capable of hybridizing to the mRNA corresponding to at least one nucleic acid molecule of the present invention. Preferably, the nucleic acid molecule is attached to a solid support, e.g. a polystyrene microtiter dish, nitrocellulose membrane, glass surface or to non-immobilized particles in solution. Alternatively, the diagnostic kit contains one or more means necessary for automated sequencing.

The present invention refers also to a pharmaceutical containing at least one nucleic acid molecule or a protein of the present invention which can be used for the prevention or treatment of a neurodegenerative disorder, especially Parkinson disease including, without limitation, sporadic PD, AD, amyotrophic lateral sclerosis (ALS), synucleinopathy and/or tauopathy. Therefore, the nucleic acid molecule or protein of the present invention can also be used for the preparation of a medicament for treating a neurodegenerative disorder as e.g. exemplified above.

Another embodiment of the present invention is directed to a method for screening a pharmaceutical or diagnostic agent, the method comprising:
(a) providing at least one nucleic acid molecule or a protein of the present invention,
(b) providing a test compound, and
(c) measuring or detecting the influence of the test compound on the expression activity of the nucleic acid molecule or the protein.

For example, the test compound is provided in the form of a chemical compound library. According to the present invention the term "chemical compound library" refers to a plurality of chemical compounds that have been assembled from any of multiple sources, including chemically synthesized molecules and natural products, or that have been generated by combinatorial chemistry techniques.

The influence of the test compound can be measured or detected in a heterogeneous or homogeneous assay. As used herein, a heterogeneous assay is an assay which includes one or more washing steps, whereas in a homogeneous assay such washing steps are not necessary. The reagents and compounds are only mixed and measured. Heterogeneous assays are, for example, ELISA, DELFIA, SPA and flashplate assays. Alternative homogeneous assays are, for example, TR-FRET, FP, ALPHA and gene assays.

The method can also be carried out on an array or using whole cells, e. g. in a robotics system or using microfluidics.

Methods for preparing such arrays using solid phase chemistry and photolabile protecting groups are disclosed, for example, in U.S. Pat. No. 5,744,305. These arrays can also be brought into contact with test compound or compound libraries and tested for interaction, for example binding or changing conformation.

Whole cells usually grow at the bottom of multiwell plates and are fixed and permeabilized, blocked and incubated with e.g. a primary (P)-specific antibody against the substrate of interest. Then, e.g. Europium labelled or HRP conjugated secondary antibodies in conjunction with specific chemiluminescent or colorimetric substances, e.g. as described above, are utilized to generate the signal. In combination with the use of a microscope not only the amount of (P)-specific antibodies can be quantified on the single cell level, but also phosphorylation-induced translocations of a substrate or morphological changes of the cells.

The method can also be carried out in form of a high-through put screening system. In such a system advantageously the screening method is automated and miniaturized, in particular it uses miniaturized wells and microfluidics controlled by a roboter.

An example for a pharmaceutical or diagnostic agent which can be found by the screening assay of the present invention is an antibody or antibody derivative specifically binding a protein of the present invention.

Therefore, the present invention is also directed to an antibody or antibody derivative which specifically binds a protein of the present invention.

The antibody is either polyclonal or monoclonal, preferably it is a monoclonal antibody. The term antibody derivative is understood to also meaning antigen-binding parts of the inventive antibody, prepared by genetic engineering and optionally modified antibodies, such as, for example, chimeric antibodies, humanized antibodies, multifunctional antibodies, bi- or oligospecific antibodies, single-stranded antibodies, F(ab) or F(ab)$_2$ fragments, which are all well known for a person skilled in the art.

The antibodies of the present invention can also be produced by immunization of a mammal with an immunogenic peptide and/or recombinantly using standard protocols. A particularly preferred immunogenic peptide is the peptide with the amino acid sequence "CRMGIKTSEG TPGFRAPEVA RGNVIYNQQA D" (SEQ ID NO:3) because it represents the kinase domain of KASPP/LRRK2 (amino acids Nos. 2025-2055) and shows homology between mouse and human of 100%.

The antibodies and antibody derivatives of the present invention can be used e.g. for the diagnosis and/or prevention and/or treatment of a neuronal disease, in particular a neurodegenerative disorder, especially Parkinson disease (PD) including, without limitation, sporadic PD, Alzheimer disease (AD), amyotrophic lateral sclerosis (ALS), synucleinopathy and/or tauopathy, but also for the identification of other pharmacologically active substances. Particular uses of the antibodies and/or antibody derivatives of the present invention are e.g. in Western blots, immuno precipitation, immuno fluorescence or ELISA.

The invention will now be further illustrated below with the aid of the Figures, Tables, Sequence Listings and Examples, without being restricted hereto.

DESCRIPTION OF THE TABLES, THE SEQUENCES AND THE FIGURES

Table 1 shows the 29 genes and its sources which have been sequenced in the candidate region D12S1692-D12S85. "KASPP/LRRK2" is the abbreviation of the new gene of the present invention.

Table 2 shows primer sequences for haplotype analysis of the second study consisting of two flanking and three intragenic markers.

Table 3 shows the frequency of the mutations of the second study. Mutational screening was performed in 53 PD families additional to the 34 families of the first study, 337 patients with sporadic PD and 1200 matched controls.

Table 4 shows the clinical and neuroimaging features of affected members of the families of the second study. Not all subjects could be investigated with the same methods, which is indicated with nd (not done). No change in comparison with normal is indicated with na (no alteration). y year, ~ongoing at the time of examination, B bradykinesia, R rigidity, RT resting tremor. For brief evaluation of olfaction a sniffing test consisting of 8 different odours (/8) was used.

Table 5 shows the neuropsychological assessment of the second study. Tests applied for intelligence (LPS-K), executive function (Tower of London), interference (CWIT), dementia CERAD 1-8; concentration (D2) as well as mood (BDI) and quality of life (PDQ-39. ↓ performance below, ~average and I above average of matched healthy controls.

SEQ ID NO: 1 shows the nucleotide sequence and the amino acid sequence of a KASPP/LRRK2 including the sites of the particular mutations found in the specified families (bold face).

SEQ ID NO: 2 shows the nucleotide sequence and the amino acid sequence of human KASSP/LRRK2 including the sites of the particular mutations found in the specified families (bold face).

SEQ ID NO: 3 shows the amino acid sequence of the peptide used for the production of monoclonal antibodies against KASSP/LRRK2.

SEQ ID NO: 4 shows the relevant section of the amino acid sequence of the S212L polymorphism of human KASSP/LRRK2. The variation is shown in bold face.

SEQ ID NO: 5 shows the relevant section of the nucleic acid sequence of the c634t polymorphism of human KASSP/LRRK2. The variation is shown in bold face.

SEQ ID NO: 6 shows the relevant section of the amino acid sequence of the M2397T polymorphism of human KASSP/LRRK2. The variation is shown in bold face.

SEQ ID NO: 7 shows the relevant section of the amino acid sequence of the t7190c polymorphism of human KASSP/LRRK2. The variation is shown in bold face.

mutation carrier and wt: wildtype. To protect the confidentiality of these results, the genotypes of some unaffected individuals of families A and D are not shown.

Figure 1:
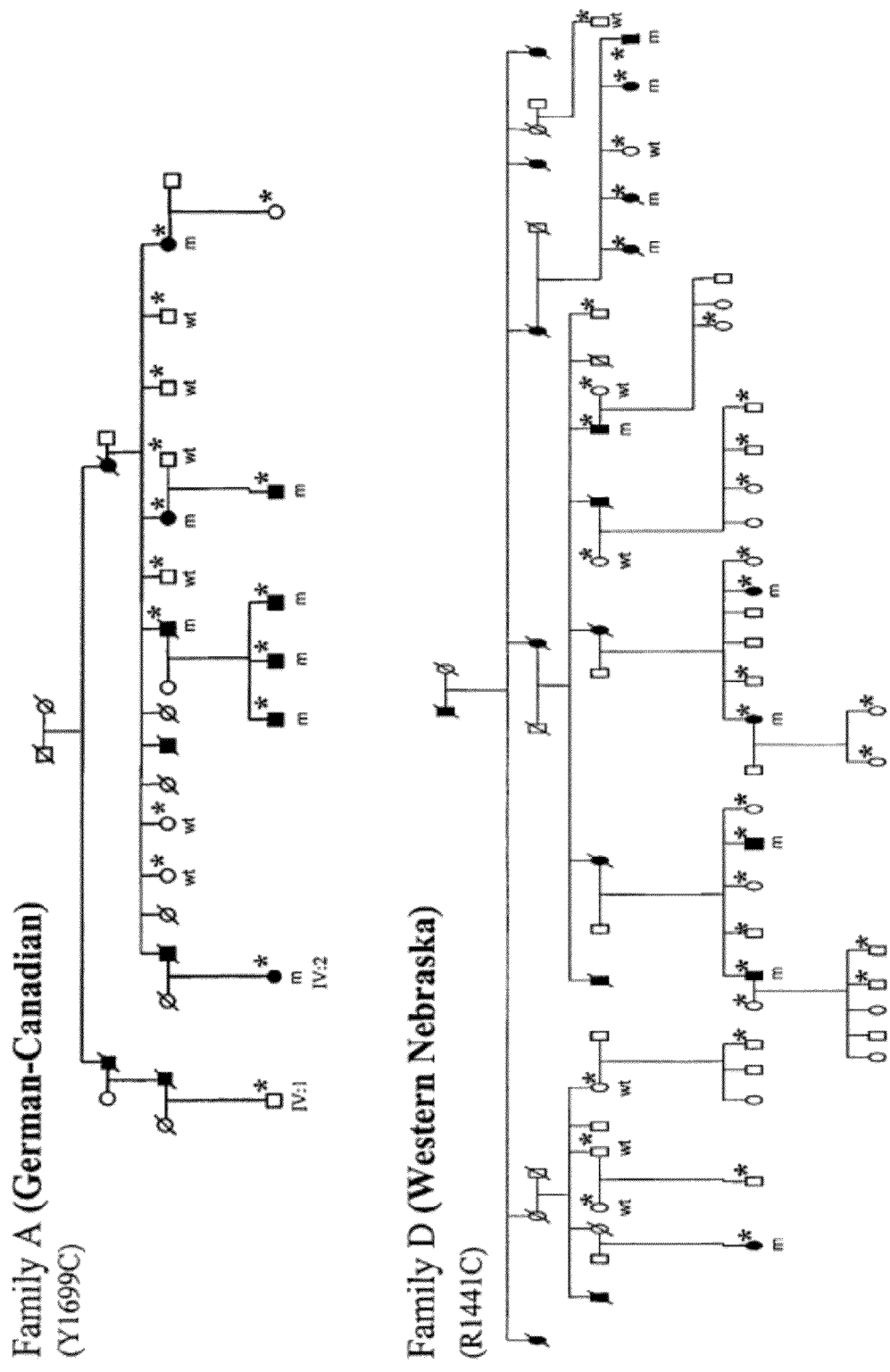
FIG. 1 shows the pedigree structure of the two largest families: A (German-Canadian), D (Western Nebraska) and with mutations. Blackened symbols denote affected family members; asterisks (*): individuals typed for the mutation, m.
Figure 2:
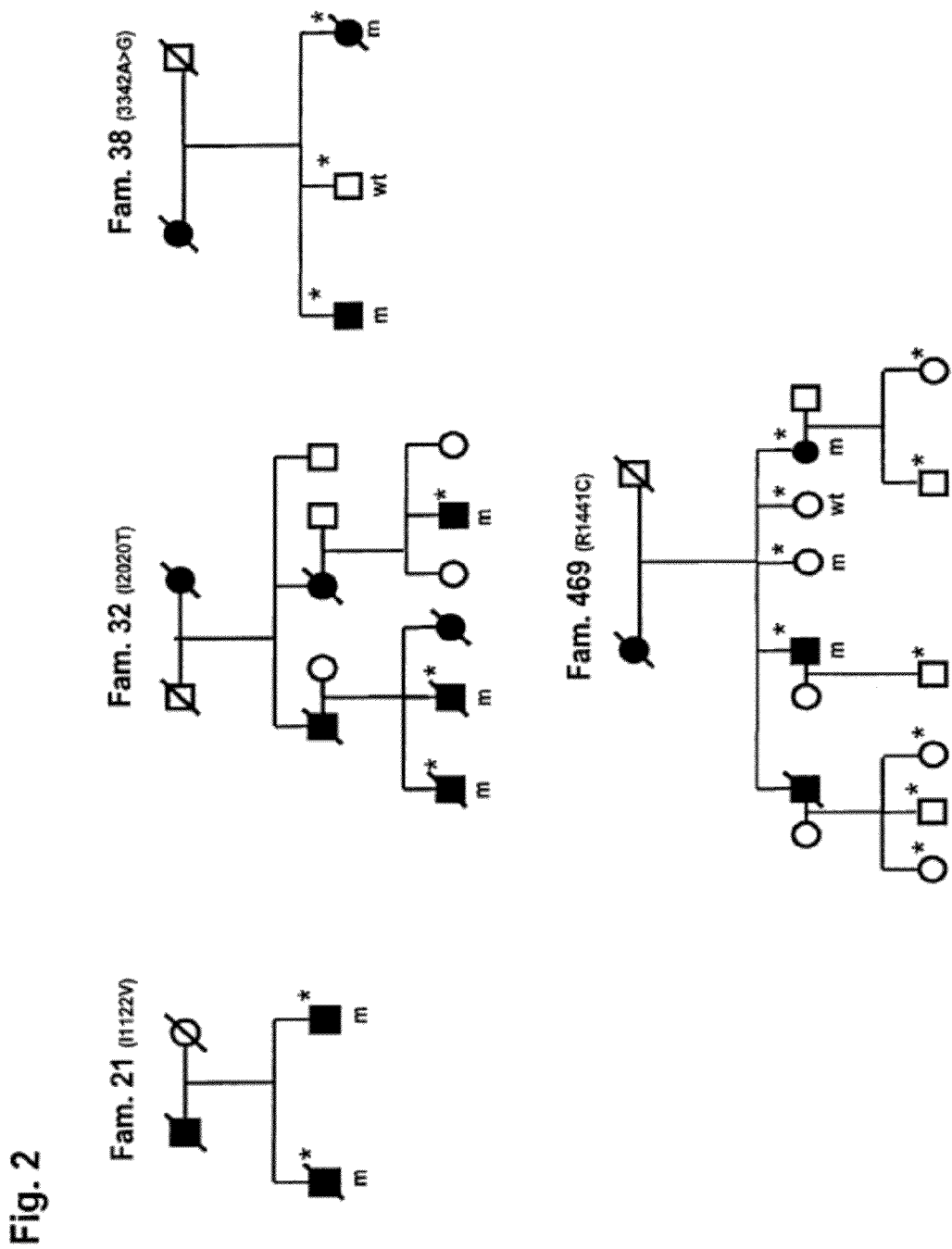

FIG. 2 shows pedigree structure of smaller families with mutations. Blackened symbols denote affected family members; asterisks (*): individuals typed for the mutation, m: mutation carrier and wt: wildtype. To protect the confidentiality of these results, the genotypes of some unaffected individuals of family 469 are not shown.

FIG. 3 shows the three across species highly conserved amino acid substitutions R1441C, Y1699C and I1122T (SEQ ID NOs:21-39).

FIGS. 4A-4K show the nucleotide (SEQ ID NO:20) and amino acid sequence (SEQ ID NO:8) of KASPP/LRRK2 as well as the location of the exons 1-51. The vertical lines mark the last and the first nucleotides of the exon, respectively.

Figure 5:
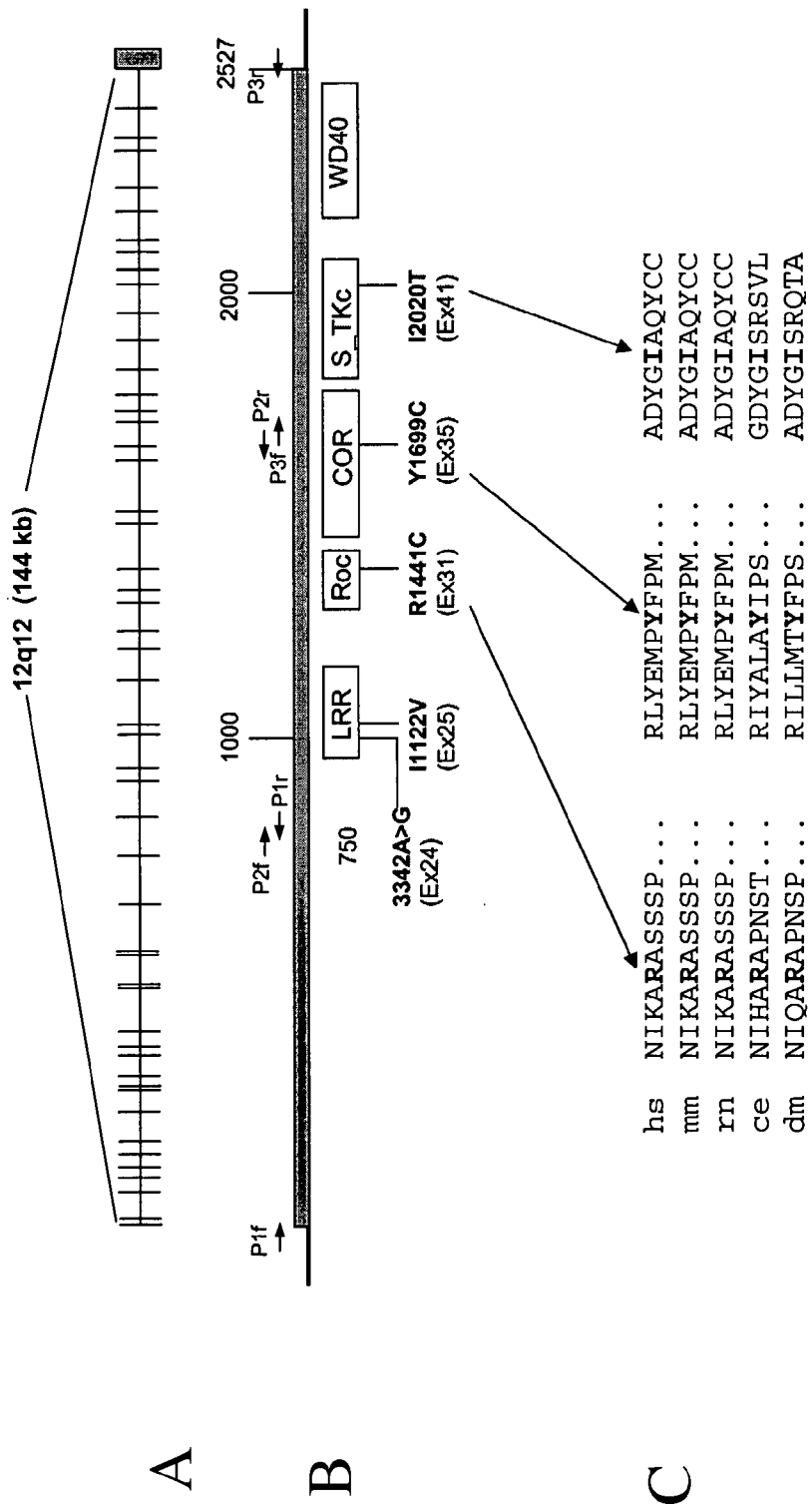

FIGS. 5A-5C show A: exon positions; B: schematic drawing of KASPP/LRRK2 with domains, primer positions for cDNA amplification and positions of mutations; and C: Protein alignment of three mutations conserved among hs: *Homo sapiens* (SEQ ID NOs:40, 45, and 50), mm: *Mus musculus* (SEQ ID NOs:41, 46, and 51), rn: *Rattus norvegicus* (SEQ ID NOs:42, 47, and 52), ce: *C. elegans* (SEQ ID NOs:43, 48, and 53) and dm: *Drosophila melanogaster* (SEQ ID NOs:44, 49, and 54).

FIGS. 6A-6F show pedigree structures of families with KASPP/LRRK2 mutation. Except for family DE038 which is shown to demonstrate cosegregation in the first family investigated and DE032 (FIG. 6E), which is displayed to demonstrate the same haplotypes in the two families affected by the I2020T mutation, all pedigrees display novel families. Blackend symbols denote family members with the clinical presentation of PD; "+" denotes a genotyped individual, with "M" for mutation carriers and "wt" for wild-type KASPP/LRRK2. The dotted symbols in FIG. 6F denote family members with the clinical presentation of tremor. To protect confidentiality the genotype of some unaffected family members are not shown. Moreover, the gender of individuals in the youngest generation of family E is disguised.

Figure 7:
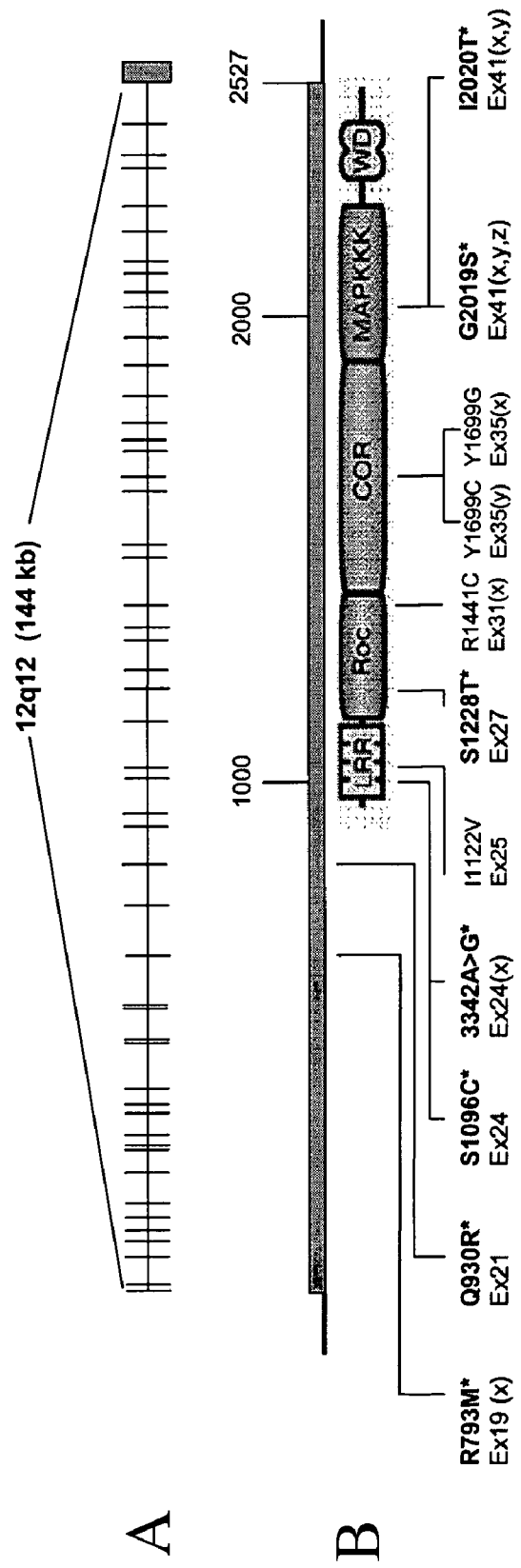

FIGS. 7A and 7B show A: exon positions; and B: schematic drawing of KASPP/LRRK2 with domains and positions of mutations.

Figure 8:
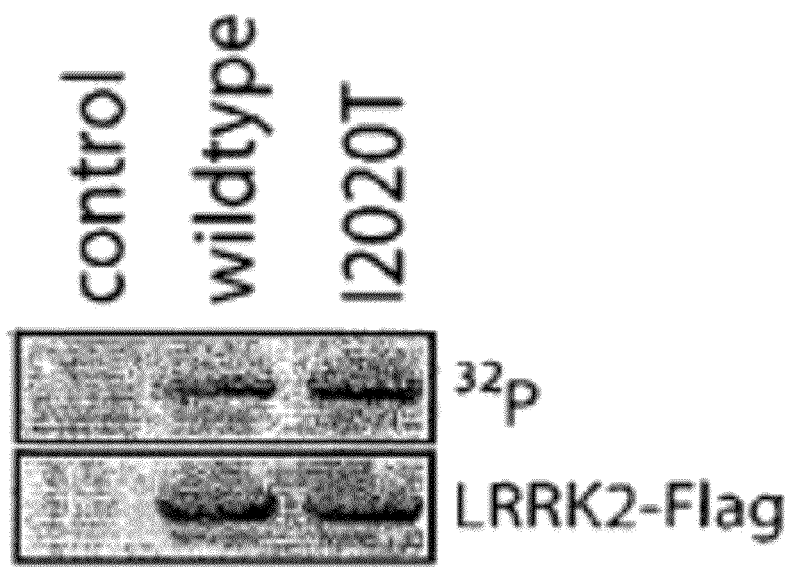

FIG. 8 shows the autophosphorylation of wild type and mutated KASPP/LRRK2. In the upper panel an autoradiogram of an SDS-PAGE blotted onto PVDF membranes is shown. $\gamma$-$^{32}$P-ATP incorporation (1 h) into KASPP/LRRK2 wildtype and I2020T mutant is visualized using a phospho-imaging system. A loading control by immunoblotting with anti FLAG M2 is shown in the lower panel. All samples shown are form the same experiment and were separated on the same gel.

Figure 9:
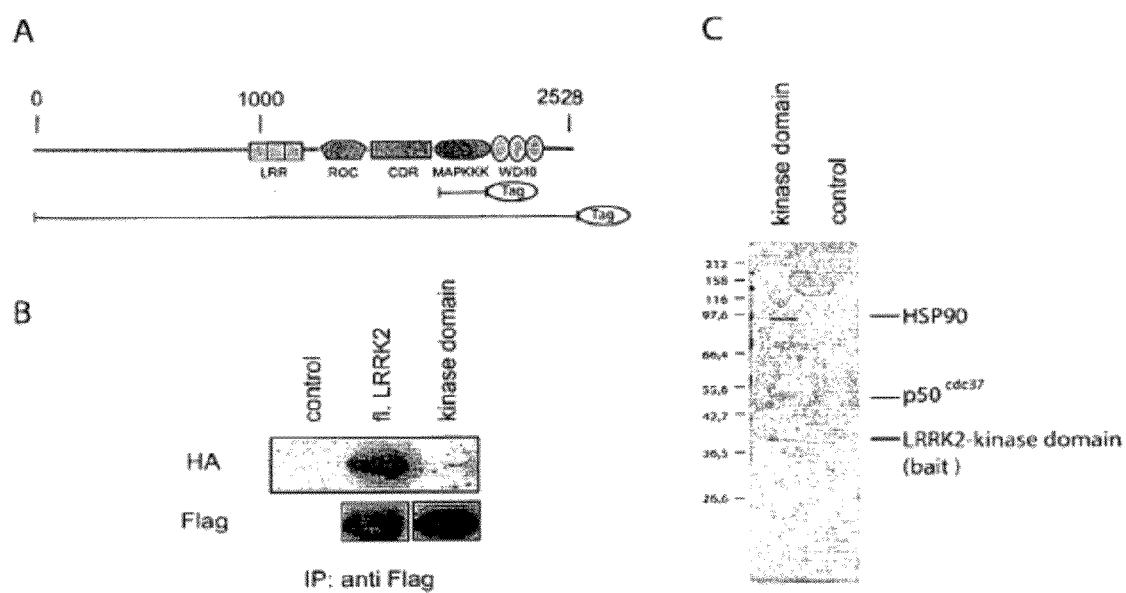

FIGS. 9 (A) shows a scheme of the KASPP/LRRK2-domain structure and the used Tag-fusion constructs of LRRK2.

(B) shows SDS gel separation of associated proteins co-isolated by tandem affinity purification of KASPP/LRRK2-kinase domain (lane 1) and a vector control (lane 2). The proteins were visualized by colloidal coomassie staining.

Figure 15:
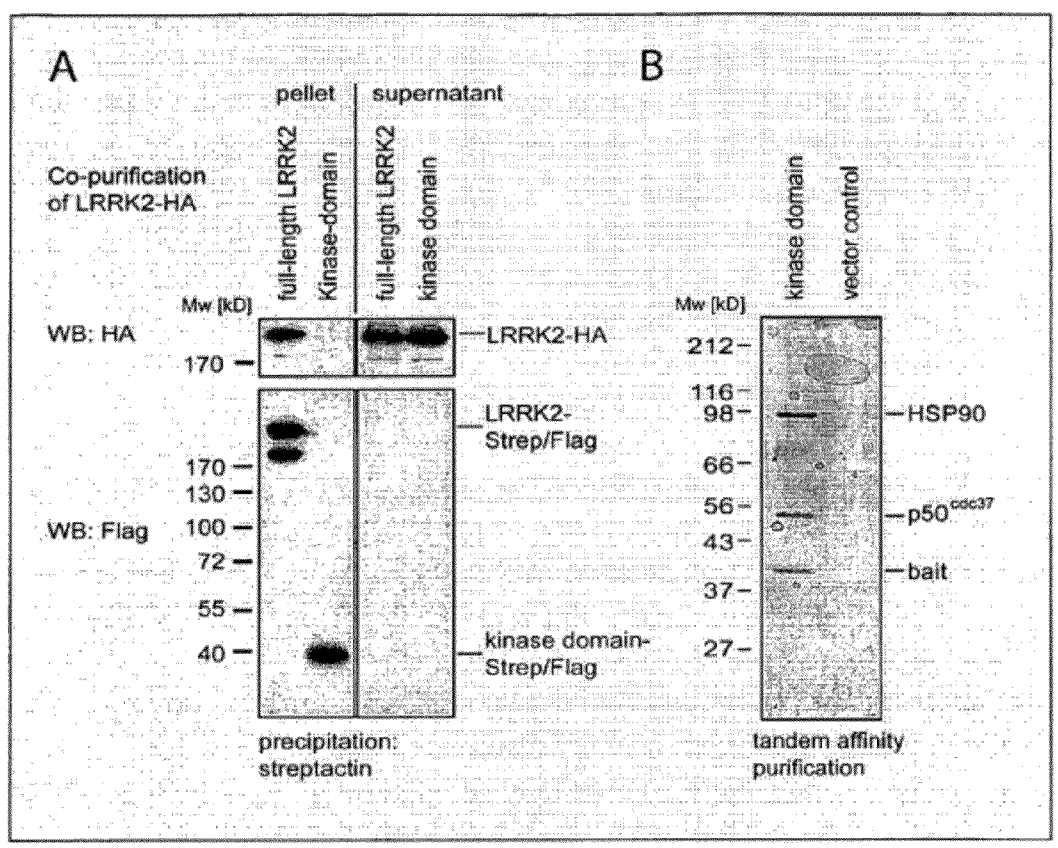

(C) shows coimmuno-precipitation. Two FLAG tagged LRRK2-baits (full-length and kinase domain) were tested for interaction with HA tagged full length KASPP/LRRK2. The co-precipitated HA-tagged KASPP/LRRK2 was visualized by immuno-blotting (3F10 anti HA, upper panel). A loading control for the bait-constructs is shown in the lower panel (immuno-blot: anti Flag M2). FIG. 15 (B) is the same figure as FIG. 9 (C) in a better shape.

Figure 10:
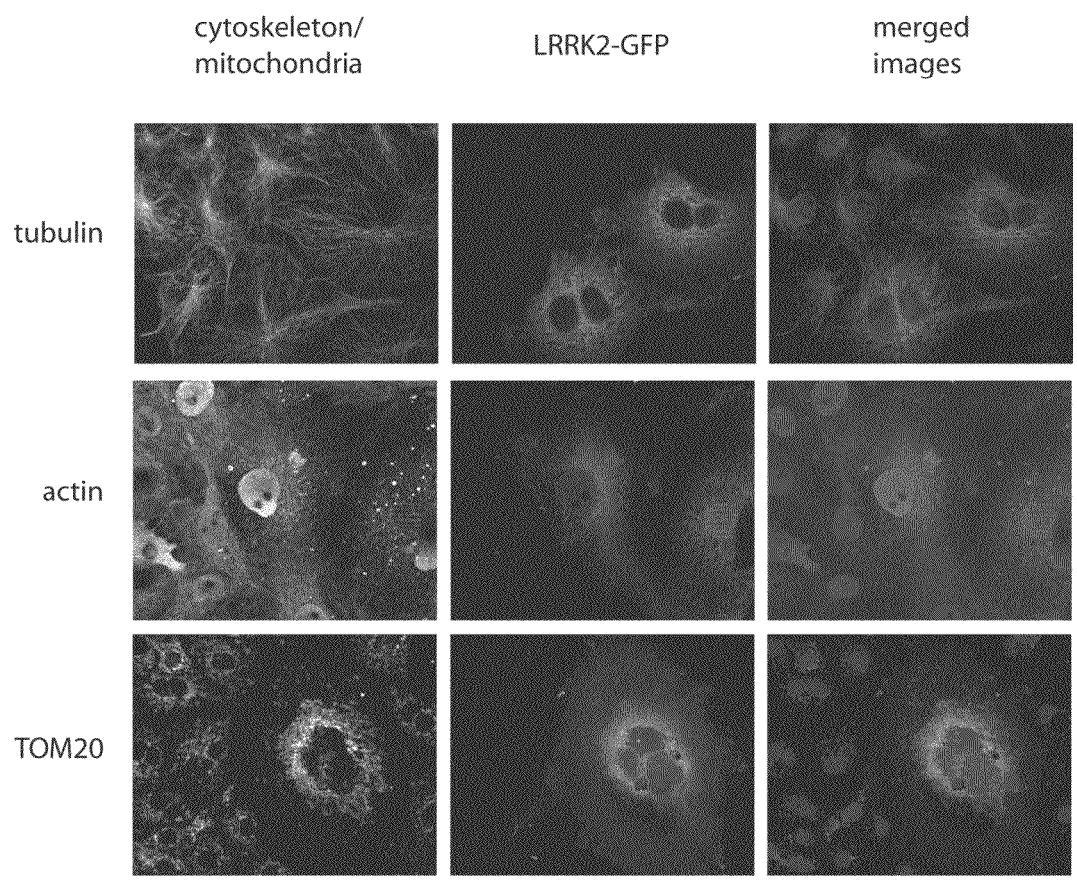

FIG. 10 shows the immunofluorescence of different cell structures.

Figure 11:
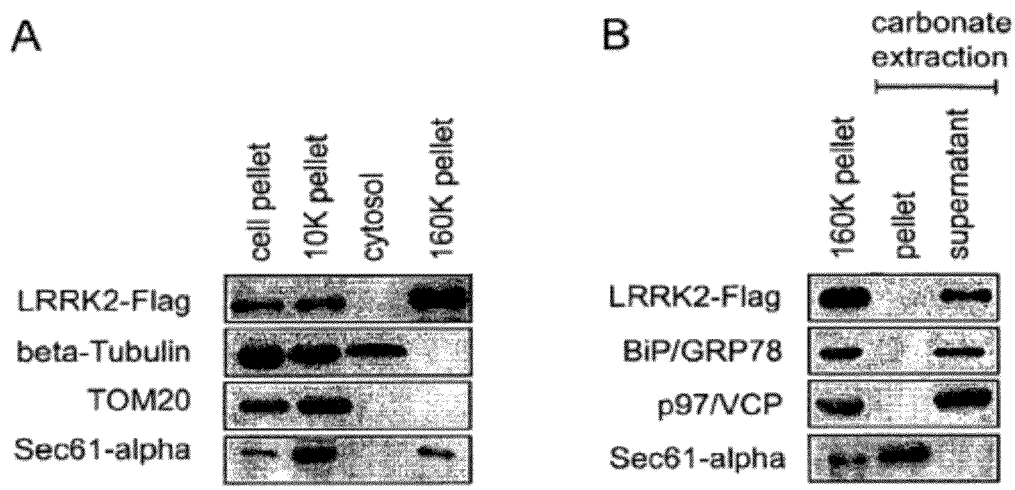

FIG. 11 (A) shows cell fractionation of HEK293 cells over expressing KASPP/LRRK2-Flag. The different pellet fractions 700×g pellet (cell pellet), the 10.000×g pellet (10K pellet), 160.000×g pellet (160K pellet) and the cytosolic fraction (160K supernatant) are shown. The localization of LRRK2-Flag is shown in the first lane. The localization of specific markers for the cytoskeleton (beta-tubulin), mitochondrial membranes (Tom20) and the endoplasmic reticulum membrane (Sec61-alpha) are shown below.

(B) shows carbonate extraction of the 160K pellet fraction. The starting material is shown in column 1, the pellet fraction in column 2 and the supernatant fraction in column 3. LRRK2-flag is shown in the first lane. For quality control of the extraction, immuno-blots for several ER-marker proteins have been provided: a luminal ER marker (BiP/GRP78, a 78 kD glucose regulated protein), a peripheral cytosolic ER-associated marker (p97, VCP) and an integral ER membrane marker (Sec61-alpha).

Figure 12:
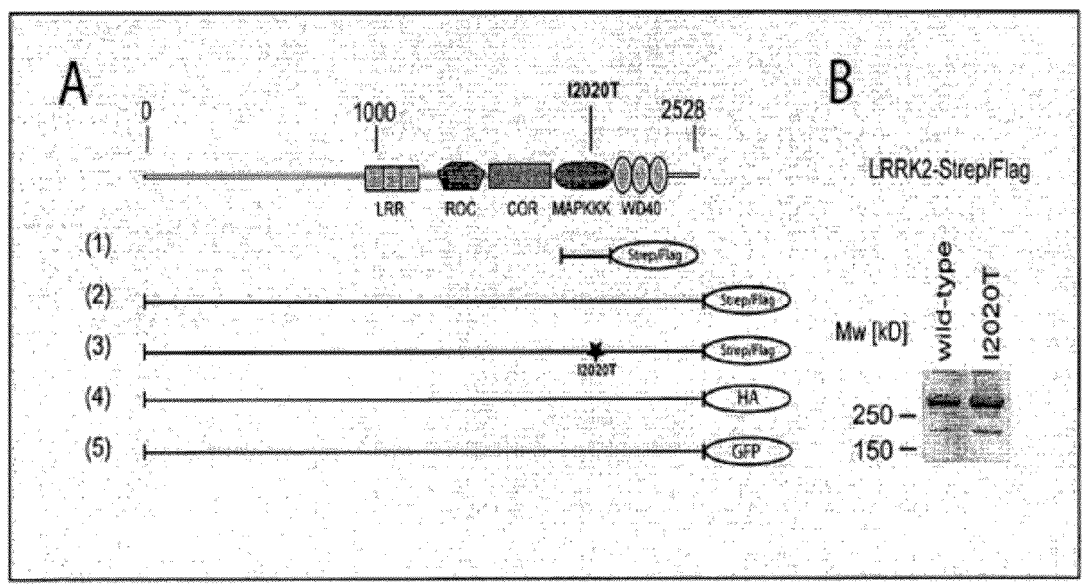

FIG. 12 (A) shows a further overview of KASPP/LRRK2-domain structure and constructs. The kinase domain of human KASPP/LRRK2 (1), the full-length LRRK2 (2) and a disease associated LRRK2 mutant I2020T (3) were cloned in frame into a modified pcDNA3.0, containing a C-terminal affinity tag. The I2020T mutation is localised, as marked, in the kinase domain of KASPP/LRRK2. Additionally, wild-type KASPP/LRRK2 was C-terminally tagged with a Hemagglutinin (HA) epitope (4) and a GFP (green fluorescent protein)-tag (5).

(B) shows LRRK2-tag and LRRK2 I2020T-tag constructs expressing an approximately 280 kD protein in HEK293 cells, visualised by Western-blotting after SDS-PAGE.

Figure 13:
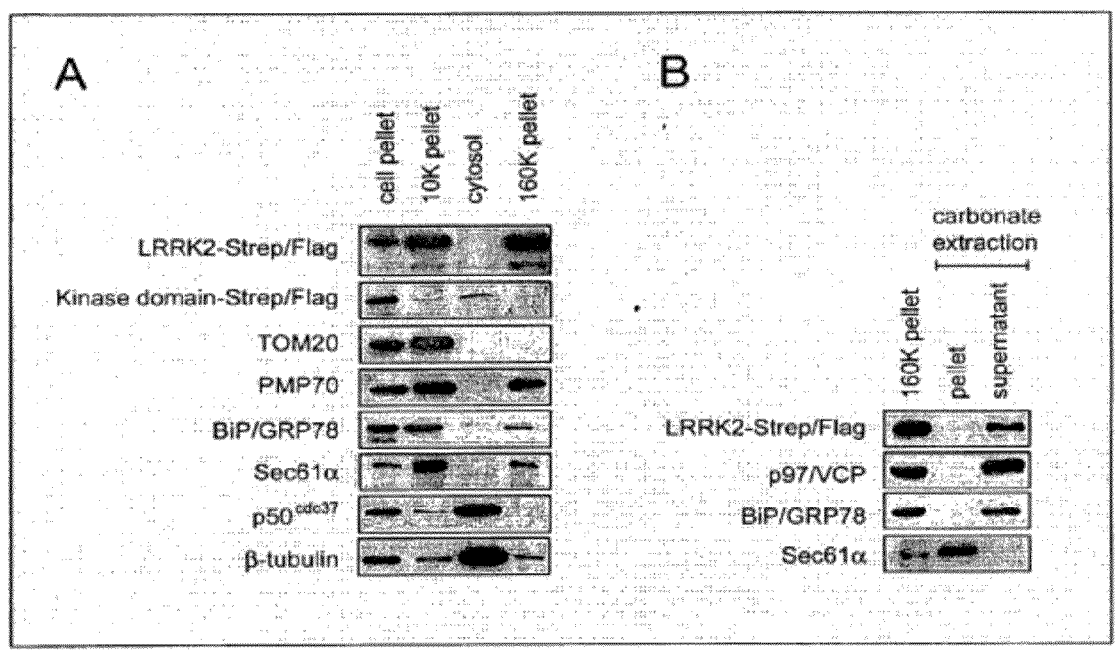

FIG. 13 shows KASPP/LRRK2 appearing in the particulate fractions upon subcellular fractionation and is associated with membranes.

(A) shows KASPP/LRRK2 co-sediments with membranes. HEK293 cells were fractionated into a cell pellet (700×g) an organelle pellet (10K pellet), a soluble cytosolic fraction (cytosol) and a microsomal fraction (160k pellet). The fractions were analysed by SDS-PAGE and Western blotting with antibodies against the Flag-tag, TOM20 (mitochondria), PMP70, (peroxisomes), BiP/GRP78, (ER lumen), Sec61α (ER membrane), p50$^{cdc37}$ (cytosol) and β-tubulin (microtubules).

(B) shows an alkaline extraction of KASPP/LRRK2. The 160K pellet was treated with 100 mM sodium carbonate. Membrane and soluble fraction (pellet and supernatant, respectively) were separated by centrifugation and analysed as in (A) using antibodies against the integral ER membrane protein Sec61α, the cytosolic ER-associated protein p97/VCP and the luminal ER protein BiP/GRP78.

Figure 14:
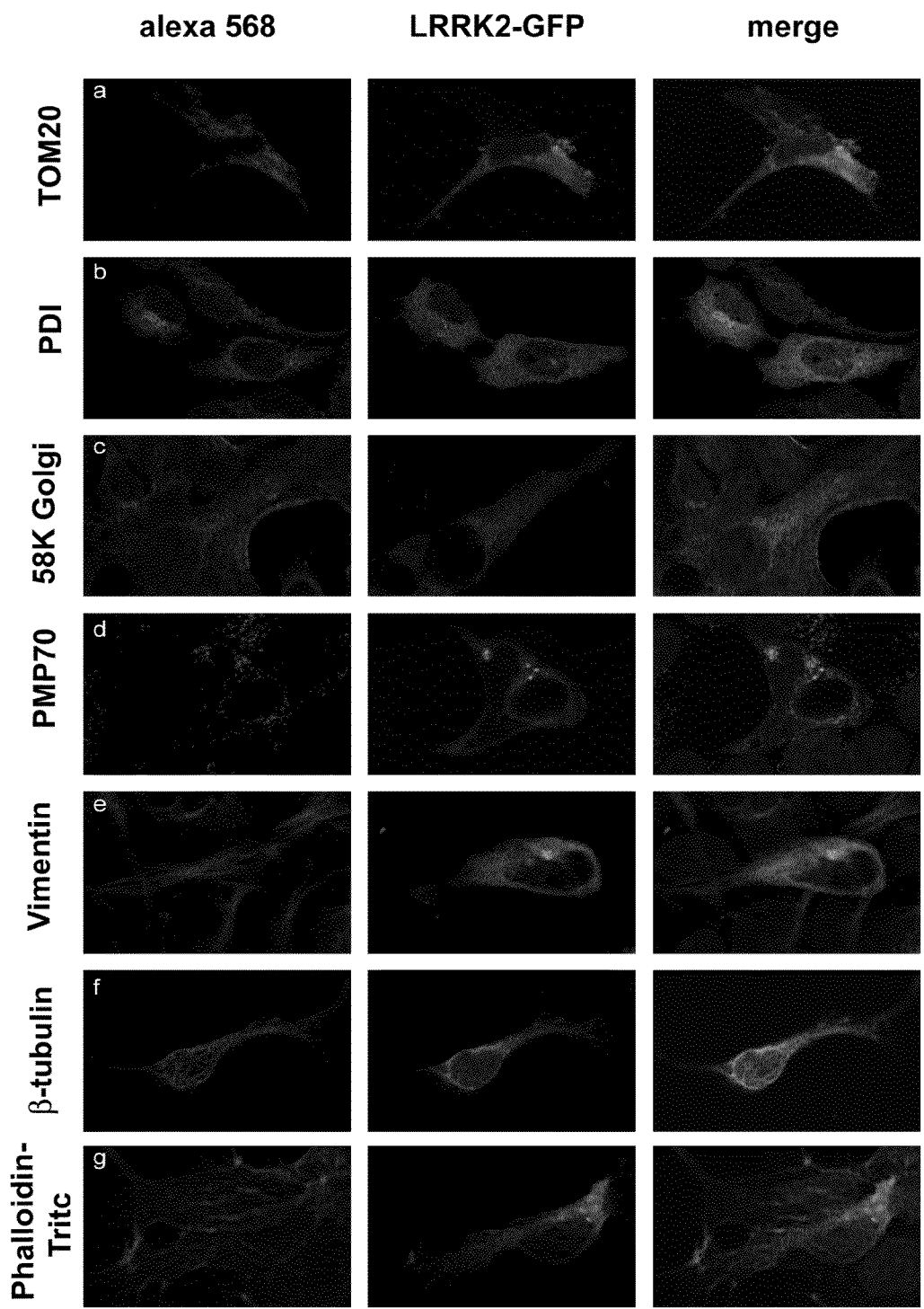

FIG. 14 shows that KASPP/LRRK2-GFP localises to mitochondria, endoplasmic KASPP/LRRK2-GFP (GFP fluorescence shown in the middle panel) were immunostained for a) mitochondria (TOM20), b) endoplasmic reticulum (PDI), c) Golgi (58K Golgi) d) peroxisomes (PMP70), e) intermediate filaments (vimentin), f) microtubular cytoskeleton (β-tubulin) and g) Phalloidin-Tritc (actin cytoskeleton). The right panel depicts digitally merged images taken from the same micrograph section and merges green fluorescence (GFP), red alexa 568 staining (specific markers) and nuclear staining with DAPI.

FIG. 15 shows that KASPP/LRRK2 dimerises and interacts with HSP90 and p50$^{cdc37}$.

(A) shows co-purification of differently tagged KASPP/ LRRK2-constructs: HA-tagged full-length KASPP/ LRRK2 was tested for its ability to interact with two different tagged KASPP/LRRK2 baits (a full-length and a kinase domain only construct). The constructs were co-expressed transiently in HEK293 cells prior to cell-lysis and purification. The result of the co-purification of HA-tagged KASPP/LRRK2 with the Step/Flag-tagged baits is shown in the upper left panel (pellet). The co-precipitated HA-tagged KASPP/LRRK2 was visualised by Western blotting (3F10 anti-HA).

(B) is the same figure as as FIG. 9 (C) in a better shape.

Controls: In order to demonstrate equal expression of KASPP/LRRK2-HA a Western blot (anti-HA) of the supernatants is shown (upper right panel). An equal loading of purified bait-proteins was ensured by Western blotting (anti-tag, lower left panel). Purification efficiency of Strep/Flag-tagged baits was determined by Western blotting of the depleted supernatants: after their affinity binding to the beads, no detectable bait protein remains in the supernatants (lower right panel).

Figure 16:
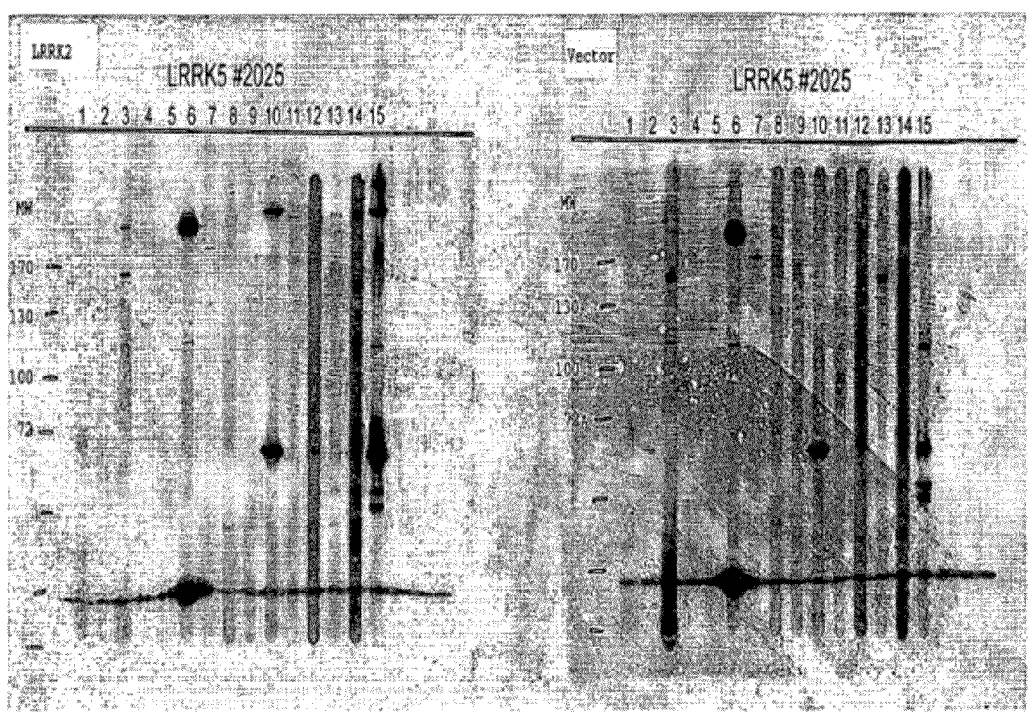

FIG. 16 shows western blots of HEK293 cells with different hybridoma supernatants. The first western blot shows the result of a lysate of HEK293 cells which overexpress KASPP/LRRK2 (named "LRRK2"). The other western blot shows the result of a lysate of HEK293 cells transfected with an empty vector (named "vector").

FIGS. 17A-17K show the nucleotide sequence (SEQ ID NO:1) and the amino acid sequence (SEQ ID NO:8) of a KASPP/LRRK2 including the sites of the particular mutations found in the specified families (bold face).

FIGS. 18A-18K show the nucleotide sequence (SEQ ID NO:2) and the amino acid sequence (SEQ ID NO:9) of a KASPP/LRRK2 including the sites of the particular mutations found in the specified families (bold face).

FIG. 19 shows the amino acid sequence of the peptide used for the production of monoclonal antibodies against KASSP/LRRK2 (SEQ ID NO:3), the relevant section of the amino acid sequence of the S212L polymorphism of human KASSP/LRRK2 (variation shown in bold; SEQ ID NO:4), the relevant section of the nucleic acid sequence of the c634t polymorphism of human KASSP/LRRK2 (variation shown in bold; SEQ ID NO:5), the relevant section of the amino acid sequence of the M2397T polymorphism of human KASSP/LRRK2 (variation shown in bold;

SEQ ID NO:6), and the relevant section of the amino acid sequence of the t7190c polymorphism of human KASSP/LRRK2 (variation shown in bold; SEQ ID NO:7).

Clones:

| 1) 4E1  | 2) 4A11  | 3) 3G3   | 4) 7F1   | 5) 2H8  |
| 6) 2D7  | 7) 4A8   | 8) 2B5   | 9) 4G11  | 10) 3G6 |
| 11) 4G11| 12) 3D9  | 13) 4H11 | 14) 4F12 | 15) 4B7.|

EXAMPLES OF THE FIRST STUDY

Example 1

Genetic Analysis

DNA Extraction

Genomic DNA from peripheral blood lymphocytes was extracted using standard protocols and after obtaining informant's consent from all participating family members.

Sequence Analysis

Genomic sequences and annotations were obtained from the National center for Biotechnology Information (NCBI) and University of California Santa Cruz (UCSC). Primers for mutation screening were designed using Primer3 software integrated into script to allow for automated primer design. Exon sequences and exon-intron boundaries were amplified with intronic primers and sequenced them directly by BigDye Terminator Cycle sequencing kit (Applied Biosystems). Between Markers D12S1692 and D12S85 a total of 29 genes or RNAs were sequenced (see Table 1).

Haplotype analysis

Haplotypes were constructed by hand using the repeat markers previously used for linkage analysis (Zimprich, A. et al., 2004, supra). Intragenic markers for haplotype analysis for fam 469 and fam D were established by searching the whole gene for repeat polymorphisms by use of a "tandem repeat finding program" (http://c3.biomath.mssm.edu/trf-.html). Polymorphic repeats were found in intron 5 (caa), intron 20 (atct) and intron 29 (ac).

Linkage analysis

Twopoint LOD scores were calculated using the MLINK program (V 5.10) in its FASTLINK implementation (V4.1P). Phenocopy rate was set at 0.01, penetrance for the heterozygous state and homozygous mutation carriers at 0.90. The allele frequency of the disease causing allele was set at 0.001, as was the frequency of the mutation used as the marker.

Screening of Mutations and Polymorphisms

For mutations 2000, for polymorphisms at least 1200 control chromosomes from a mixed European descent were screened as controls. In addition 300 patients were screened with sporadic parkinson's disease. Genotyping was performed on a MALDI-TOF mass-spectrometer (Sequenom MassArray system) using the homogeneous mass-extension (hME) process for producing primer extension products (Tang K. et al., Proc. Natl. Acad. Sci USA, 96, 10016-10020, 1999).

Amplifikation of KASPP/LRRK2

The complete coding sequence of KASPP/LRRK2 was amplified from human brain cDNA by using Marathon-Ready cDNA (BD Biosciences Clontech). Primers were set to amplify three overlapping fragments from exon1-21 (P1f, P1r), from exon 20-35 (p2f, p2r) and exon 34-51 (p3f, p3r) (see FIG. 5). Sequence information were derived from published the mRNA of DKFZp434H211. PCR products were run on agarose gel to check its length and integrity.

Example 2

Northern blot Analysis

Northern blot analysis was performed according to the manufacturers protocols (BD Biosciences). For hybridization a KASPP/LRRK2 cDNA fragment was used (bp 6577-7655; corresponding to exon 45-3'UTR.

Example 3

LightCycler Experiments mRNAs from different human tissues were purchased from BD Biosciences, (Clontech BD Sciences, Palo Alto, USA) and were reverse transcribed with the Transcriptor First Strand cDNA Synthesis Kit (Roche Applied Sciences, Mannheim, Germany) according to the manufacturers protocol. For real-time amplification of KASPP/LRRK2 three specific PCR products spanning exon1 to 8, exon13 to 19 and exon 31 to 39 were quantified using the LightCycler Instrument (Roche Applied Sciences, Mannheim, Germany). Fluorescence-labeled hybridization probes providing maximum specificity were used for product detection. Calculation of sample concentrations were performed using the fit-point algorithm. The Phorphobilinogen deaminase (h-PBGD) gene, a low-copy housekeeping to gene, was used as an external standard and absolutely quantified using the (h-PBGD Housekeeping Gene Set, Roche-Applied Science). Relative transcript levels were calculated as ratios of Park8/PBGD normalized to adult whole brain adult expression as 100%

EXAMPLES OF THE SECOND STUDY

Subjects and Methods

Subjects

DNA of 51 index patients from PD families compatible with an autosomal dominant mode of inheritance of PD or with a mode of inheritance that could not be assigned to a typical Mendelian trait, as well as two affected sib pairs were analyzed for mutations in the KASPP/LRRK2 gene. Clinical diagnosis was based on published criteria (Hughes et al., J Neurol Neurosurg Psychiatry; 55:181-4, 1992) and severity of the disease was rated according to the Unified Parkinson's Disease Rating Scale (UPDRS) (Fahn et al., Recent Developments in Parkinson's Disease. New York: Macmillan,153-163, 1987) and Hoehn and Yahr staging. In one family (family E) typical Parkinsonian features were only found in one member (III-11), while all other affected family members presented primarily with postural tremor. Moreover, all novel and known mutations were investigated in a cohort of 337 patients with apparently sporadic PD (204 male, 133 female, mean age 53±13 years) and a cohort of 1200 subjects without any extrapyramidal disorders matched for age±5 years and sex. Allele frequency of the polymorphism N551K; 1653C>G was investigated in 888 of these control subjects.

DNA of patients with familial and sporadic PD was obtained from our gene bank, while DNA of control subjects comprised the Kora cohort obtained form the National Research Center of Environment and Health/Munich, Germany. All patients and controls had given informed consent to mutational screenings, which was approved by the local ethical committee.

Mutational Screening

Genomic DNA was isolated from peripheral blood using standard protocols. Mutational screening in patients of families with autosomal dominant PD was performed for all exons and exon-intron boundaries of the KASPP/LRRK2 gene by direct sequencing of both strands using the BigDye Terminator Cycle sequencing kit (Applied Biosystems) with the same primers and under the same condition as described above.

Mutational screening in patients with sporadic PD and control subjects was performed using an ABI 7900 Allelic Detection system. As described above genotyping was performed on a MALDI-TOF mass-spectrometer (Sequenom Mass Array system) using the homogeneous mass-extension (hME) process for producing primer extension products.

In families with identical mutations haplotype analysis of the KASPP/LRRK2 region was performed. Haplotypes were constructed using 5 fluorescent-labeled microsatellite markers, two flanking and three intragenic (Table 2). DNA fragments containing the polymorphic marker sequences were amplified by PCR. Fluorescently labelled PCR products were analyzed on an ABI 3100 automated sequencer with a fluorescence detection system.

DNA extraction from Brain Tissue

In the large family with only one patient with the clinical picture of PD and many others affected by symptoms resembling essential tremor (family E), blood for DNA extraction was only available of the PD patient. To disclose a possible association of a KASPP/LRRK2 mutation and clinical features of essential tremor DNA was extracted from a microscope slide with paraffin-embedded brain tissue (cerebellum) of one family member with this phenotype (III-7).

Deparaffinisation was performed using xylene and ethanol followed by a proteinase K digestion. The probe was then purified using phenol/chloroform extraction and finally precipitated with LiCl and Ethanol.

Clinical Investigations

The index patients of families with mutations in the KASPP/LRRK2 gene were invited for a genetic consultation and clinical and neuroimaging investigations under an approved protocol. After informed consent was given a thorough neurological examination was performed and olfactory function was tested using sniffing sticks (Daum et al., Nervenarzt, 71:643-50, 2000). A neuropsychological test battery sensitive for dementia, concentration, planning, as well as intelligence was chosen (Table 5). To evaluate mood and sensitivity patients were asked to complete the Becks Depressions Inventar (BDI) and the PDQ-39 Parkinson's Disease Quality of Life Questionaire.

Electrophysiological investigations comprised neurography of the right tibial and sural nerve, and elektromyography of the quadriceps to discern subclinical changes in motor unit potentials and possible abnormal spontaneous activity. Moreover, magnet evoked potentials were performed in all patients without contraindications.

Neuroimaging

Structural neuroimaging comprised transcranial ultrasound (TCS) and magnet resonance imaging (MRI).

For TCS a phased-array ultrasound system equipped with a 2.5-MHz transducer with an axial resolution of approximately 0.7 mm and a lateral resolution of about 3 mm (Elegra, Siemens, Erlangen, Germany) was used. The examination was performed through a preauricular acoustic bone window with a penetration depth of 16 cm and a dynamic range of 45 dB as described previously (Berg et al., Ultrasound Med Biol, 25: 901-904, 1999). The SN was identified within the butterfly-shaped structure of the mesencephalic brainstem as clearly as possible, scanning from both temporal bone windows, then the area of hyperechogenic signals in the SN-region was encircled and measured (Berg et al., 1999, supra, Berg et al., J Neurol, 248:684-689, 2001). An area of SN hyperechogenicity $\leq 0.19$ cm$^2$ was classified as normal, an area >0.19 and $\leq 0.24$ cm$^2$ as moderately and an are of >0.24 cm$^2$ as markedly hyperechogenic (Berg et al., 1999, supra).

MRI was performed on a Magnetom Avanto 1.5 Tesla, Siemens AG, Germany.

Results

Mutational Screening

Screening the entire coding region of the KASPP/LRRK2 gene of one index patient each from 55 families identified 7 novel families with amino acid substitutions (FIG. 6a-f). Four of these are novel missense mutations: R793M; 2378G>T in family DE041 and to family T11239, Q930R; 2789A>G in family DE022; S1096C; 3287C>G in family E and S1228T;

3683G>C in family DE031. The missense mutation R793M was also found in one patient with sporadic PD and one control person.

The so far most common amino acid substitution G2019S; 6055G>A was only found in one sporadic PD patient, who showed typical levodopa responsive Parkinson's disease with an age of onset of XX and no additional clinical features. Moreover one additional patient was detected with the already above described splice site mutation 3342A>G (family T11288) and one more family with the above described I2020T mutation (family T10738).

Except for the R793M mutation, which was found in one control person none of the mutations were found in the control group (Table 3). There was no significant difference in the minor allele frequency of the known N551K; 1653C>G polymorphism between patients with sporadic PD (6.5%) and control subjects (7.3%).

Haplotype Analysis

Figure 6A:
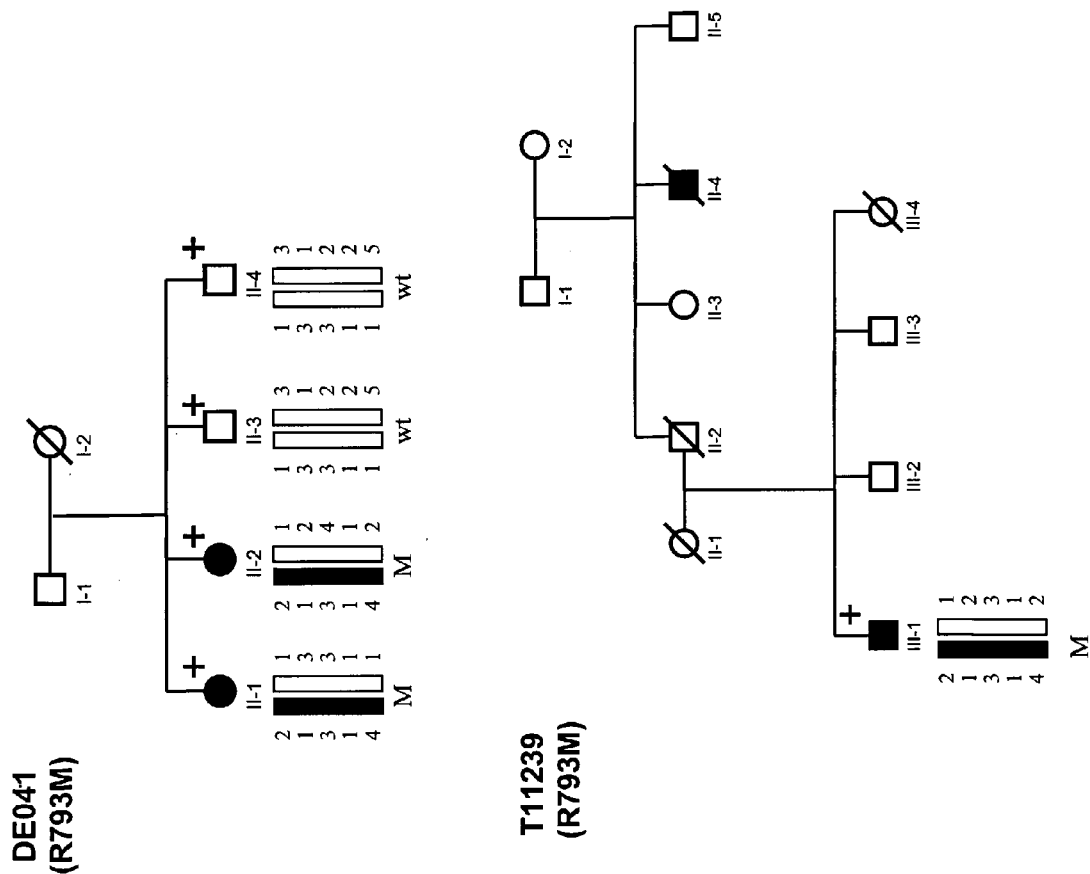
Figure 6B:
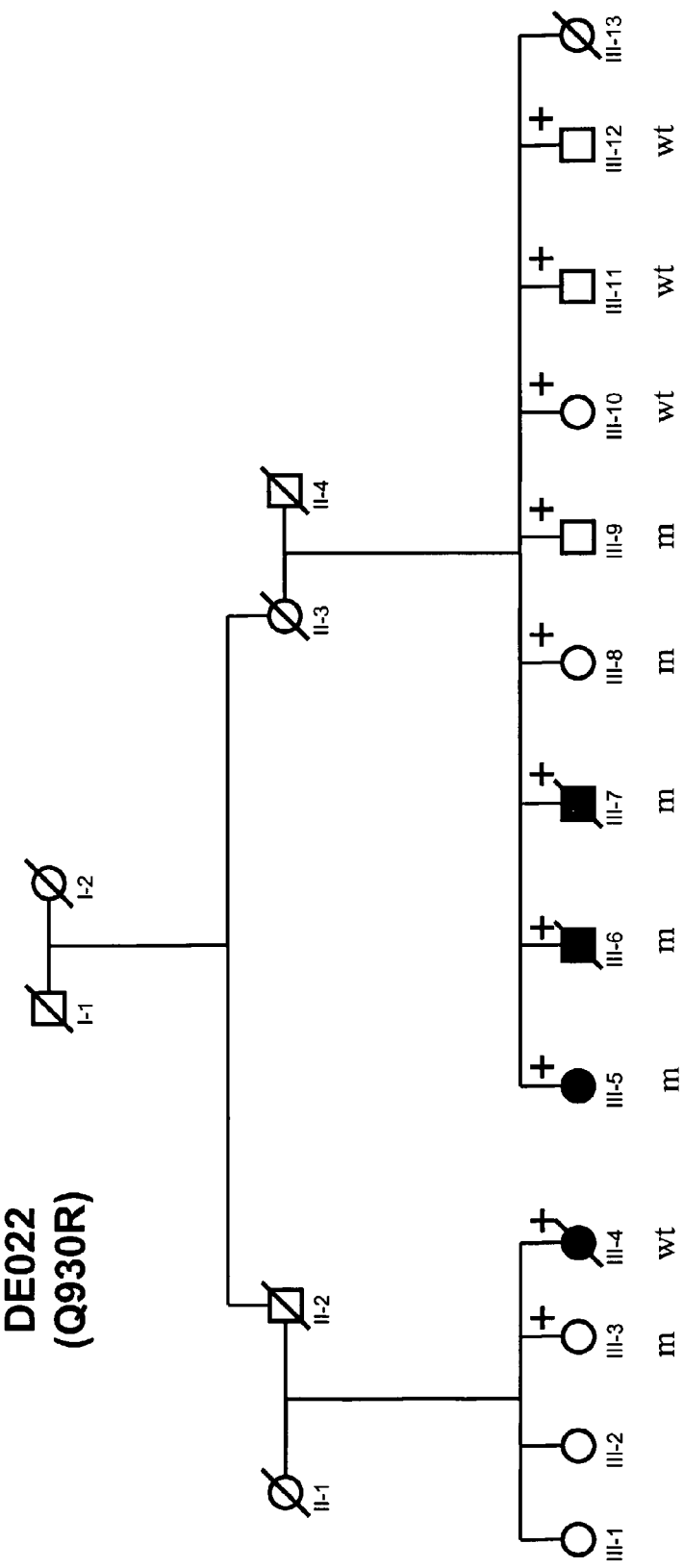
Figure 6C:
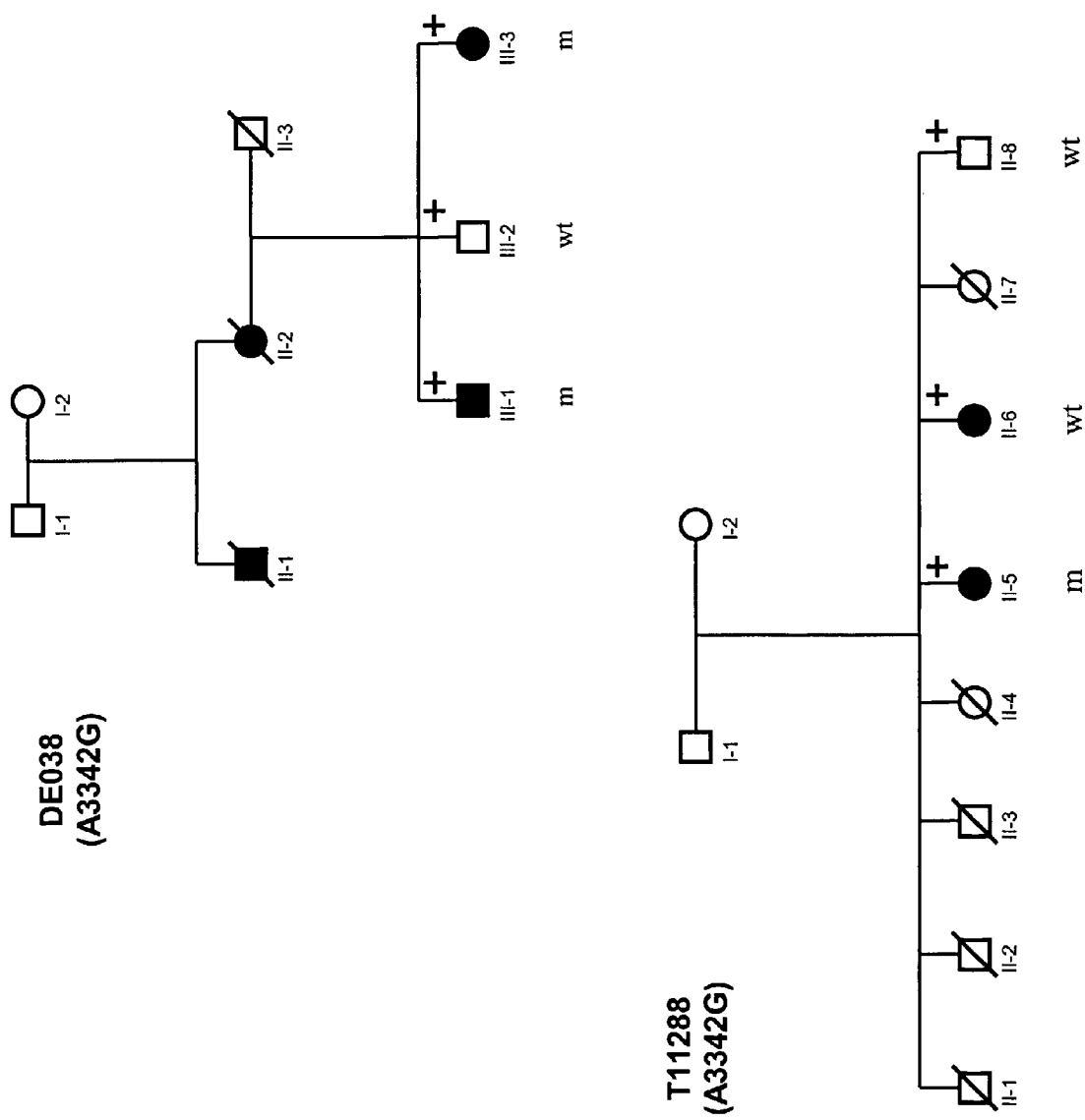
Figure 6D:
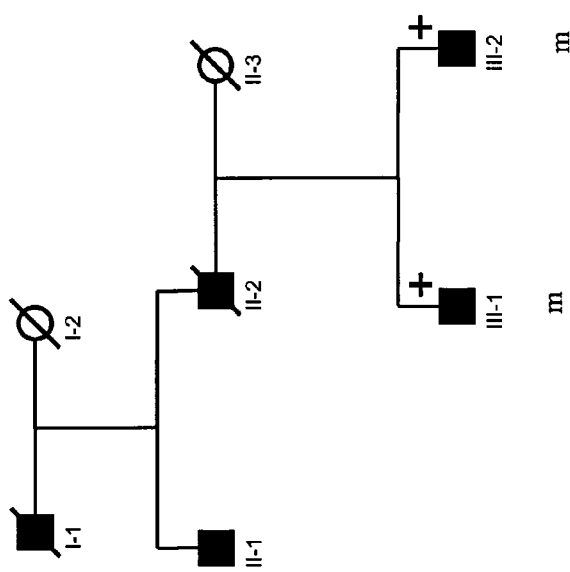
Figure 6E:
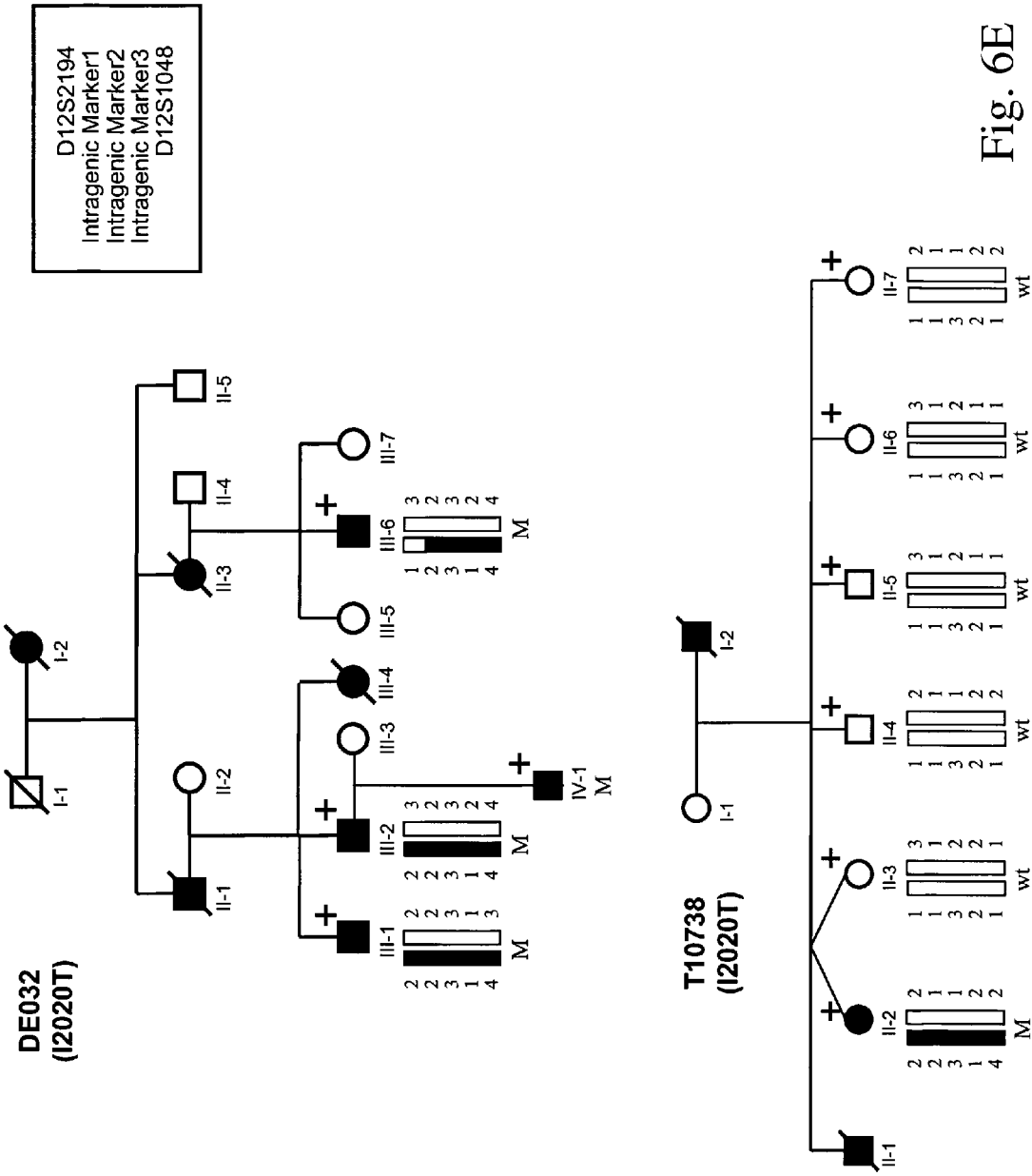

Haplotype analysis revealed common haplotypes for the two novel families affected by the R793M mutation as well as for family T10758 and family DE032 affected by the I2020T mutation, indicating common founders for these mutations (FIGS. 6a and 6e). Although members of family DE032 and T10758 were not aware of common ancestors, they originate from the same geographical area (Baden Wurttemberg, Southern Germany).

Family T11239 and DE041 were recruited from more distinct geographical areas (Baden Württemberg family T11239 and Hesse family DE041). Members of these families were also not aware of common ancestors. For the A3342G splice site mutation no common haplotype was found in the affected families (DE038 and T11288).

Clinical Findings

Extensive clinical a neuroimaging examination revealed the features listed in Table 4.

All patients investigated had typical signs of Parkinson's disease. However, features differed between members within the same family affected by the same mutation as well as between different families with the same mutation. Moreover, penetrance was found to vary for different mutations.

Common Findings in Patients with KASPP/LRRK2 Mutations

All mutation carriers with clinically apparent PD had the typical Parkinsonian features including bradykinesia, tremor and rigidity. Moreover, all patients experienced substantial relief of symptoms after application of L-dopa, although therapy was complicated in one patient (T11288 II-5) by hallucinations. Estimation of olfactory function by application of 8 sniffing sticks revealed a moderate to severe loss of identification capacity in three of 5 subjects. Postural instability was only found late in the disease course. Hallucinations were reported seldom and only occurred after long disease duration or associated with dementia, whereas sleep disturbances were reported by 80% (Table 4).

Intrafamily Differences in Clinical Presentation

R793M: Two sisters are affected with a difference of age of onset of 15 years. While at disease onset II-1 had only slight postural tremor on the right side, the initial symptom of II-2 was resting tremor on the left side. An equivalent type of PD developed in II-2 while II-1 showed no resting tremor at all but an akinetic-rigid type of PD (FIG. 6a).

Q930R: Span of age of onset was 21 years among the three members of the same generation affected. Only brother III-7 developed severe dementia and hallucinations after more than 20 years of disease duration (FIG. 6b).

3342A>G: While sister II-7 of family T11288 presented with typical Parkinsonian features, the clinical picture of early severe dementia, hypersensitivity to dopaminergic hallucinations and daytime sleepiness with fluctuation of vigilance resembled DLBD in II-5. However, mutational analysis revealed the wt allele in II-7. A phenocopy for the more typical PD presentation must therefore be postulated, while the atypical DLBD-type was indeed associated with the 3342A>G splice site mutation. However, the fact that this variation co-segregated with the mutation in the above described family DE038 is an indication for a mutation rather than a benign polymorphism.

Interfamily Differences in Clinical Presentation for the Same Mutation

R793M: While in III-3 of family T11239 speaking was impossible because of severe tongue dyskinesia, the affected sisters of family 41 did not show any atypical signs except of postural tremor in II-1 (FIG. 6a).

3342A>G: In family T11288 both sisters and in the reported family DE038 father and III-1 were severely affected by the disease. III-3, however, did not show any Parkinsonian symptoms except of minimal resting tremor of the right thumb for more than 15 years (FIG. 6c).

Age of Onset

Mean age of onset in the novel families was 58±14 years. However, age of onset differed between members of the same family. In offsprings of mutation carriers of the three novel families, in whom clear data of ancestors was available (Table 4) the diagnosis if PD was established earlier and also investigation of an additional family member in family DE032 revealed and earlier diagnosis (41 years), while mean age of onset was 54 (48-59 years) in generation I-III (FIG. 6e).

Penetrance

Combining findings of the second study and the first study a clear autosomal dominant mode of inheritance was found in at least one affected family for the splice site mutation of exon 24, and for the missense mutations of exon 25, exon 27, exon 31, and exon 41. No strong genetic pattern was found in families affected by missense mutations in exon 19, 21 and 24.

Exon 19; R793M: In family T11239 only the uncle of the index patient was affected, while the father who died at the age of 68 did no show any extrapyramidal sign during life time. In family DE041 two sisters showed typical signs of PD during life time, while none of the parents who died both at the age of 74 showed any Parkinsonian signs (FIG. 6a).

Exon 21, Q930R: Of nine sisters and brothers in family DE022 three were affected by the mutation and had clinical signs of PD, while one other sister and brother, also mutation carrier are not affected by PD at an age of more than 70 years. Neither the mother (II-3), who died at the age of 90 years nor her brother (II-2), who died at 75 years of age showed any Parkinsonian features during life time. The cousin of the affected members of the to family (III-4) displayed signs for typical PD but was not carrier for the Q930R mutation, indicating sporadic PD in this family member. However, her sister (III-3), was found to have the mutation. Having already reached the age of 77, she has no clinical signs allowing the diagnosis of PD. Both II-3 and II-2 must have been mutation carriers. The fact that none of them and also III-3 have not shown any Parkinsonian features during life time argues for incomplete penetrance of this mutation.

Exon 24, S1096C: In this large family with an additional tremor phenotype (1f) only III-12 was mutation carrier, affected by PD. One child of his brother, who showed only features of essential tremor but no Parkinsonian symptoms until death at the age of 66 years, is also mutation carrier, indicating incomplete penetrance for this mutation as well.

Phenocopies and Simultaneous Occurrence of Tremor

One family member with typical PD of DE022, associated with the Q930R mutation and one of the sisters of family T11288, (A3342G splice site mutation of the other sister), again with typical Parkinsonian features had wt alleles, arguing for idiopathic PD in these cases.

Figure 6F:
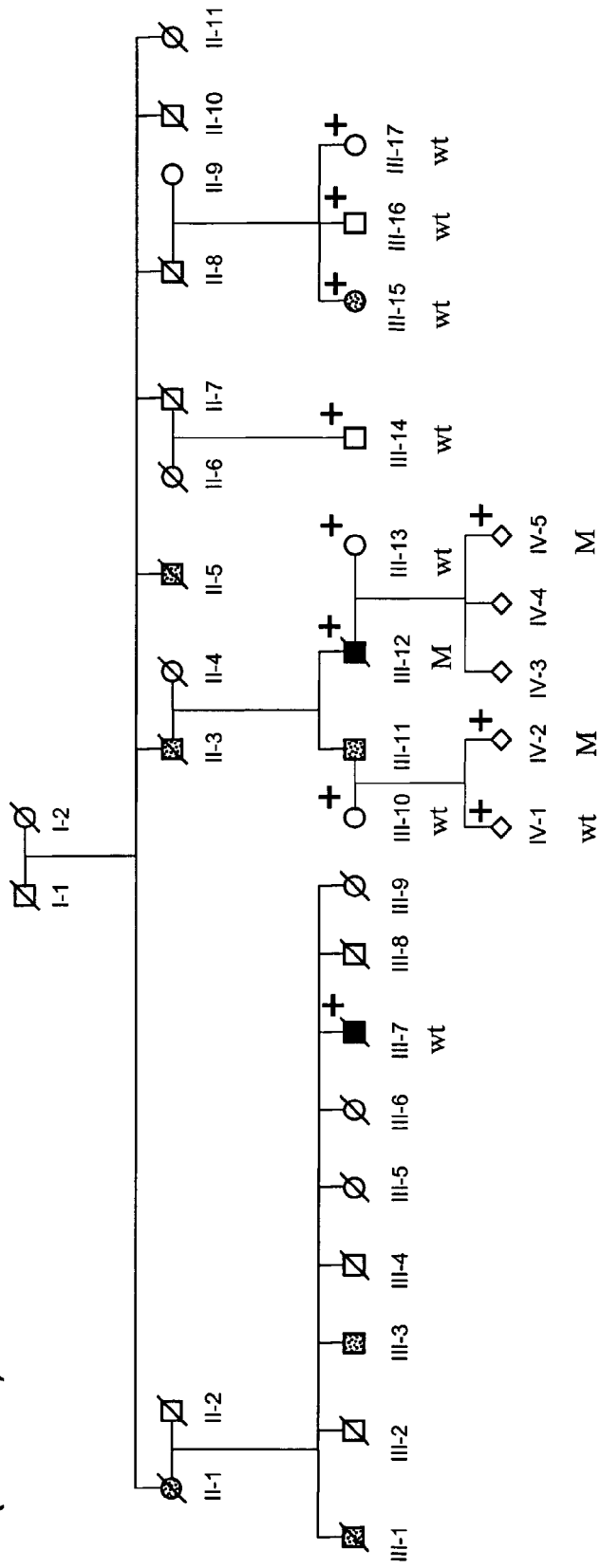

In family E an autosomal dominant inheritance of tremor is evident (FIG. 6f). Two family members (III-7 and III-11) showed typical Parkinsonian features during life time, in III-11 the S1096C mutation was detected. As there was no blood available of III-7, DNA extracted from brain tissue was investigated. However, in this patient the C3287G mutation could not be detected, indicating a different cause for Parkinson's disease. Of one of the siblings with a tremor phenotype (III-19, presenting with postural and vocal tremor) also only wild type alleles could be identified. The only family member with a tremor phenotype carrying the S1096C mutation must have been the brother of III-12, as one of his children is also mutation carrier. However, as the mutation could not be detected in III-19 incomplete penetrance of Parkinsonian symptoms in a subject also affected by tremor is more likely than an association of tremor with the mutation in this family.

Neuropsychological Findings

Of the 5 patients examined in a thorough neuropsychological investigation, three were able to complete the whole test battery. In all three intelligence was above average of a matched control group (LPS-K), suggesting that subtle neuropsychological deficits may well be compensated. Still, all three showed deficits in executive functions (Tower of London) and had high interference scores (CWIT) indicating incapacity to blind overstimulation (Table 5). This pattern is in accordance with neuropsychological deficits in idiopathic PD. The two others investigated were graded as demented. In patient III-3 of family T11239 MMSE was 22. Additionally, severe tongue dystonia prevented accomplishing the CERAD. In patient II-5 of family T11288 with 3342A>G splice site mutation exhaustability and dementia thwarted completing of neuropsychological testing.

TCS and MRI Findings

TCS: Moderate hyperechogenicity, at least on one side, was found in all but one patient with LRRK2 mutations. Interestingly, none of the patients displayed marked SN hyperechogenicity. MRI showed mild to marked atrophy in the 4 patients investigated (Table 4). The patient with the DLBD phenotype had additionally some evidence for microangiopathy.

BIOCHEMICAL CHARACTERIZATION OF KASPP/LRRK2

Material and Methods

Plasmid and Cloning

Human KASPP/LRRK2 was cloned via PCR from cDNA which has been generated from lymphoblast mRNA. KASPP/LRRK2 was cloned domain-wise in six fragments. Each fragment was cloned into pcDNA3.0 (Invitrogen) and verified by sequencing. The full length sequence was generated by subsequent fusion of the sub-constructs. The HA and FLAG tag were introduced at the 3' end (c-terminus) of the constructs. The I2020T mutation was introduced into KASPP/LRRK2 by site-directed mutagenesis using the QuikChange® II mutagenesis kit (Stratagene). For fluorescence microscopy, humanised GFP cDNA, derived from pFRED143 (Ludwig, E. et al., J. Virol., 73, 8279-8289, 1999)), was cloned in frame at the 3' end (c-terminus) of KASPP/LRRK2.

Cell Culture

HEK293 cells were cultured in DMEM supplemented with 10% FBS at 37° C. and 5% $CO_2$. For immuno precipitation (IP), tandem affinity purification or cell fractionation experiments cells were transfected with Effectene® (Qiagen) and kept under full medium for additional 48 h.

Electrophoresis and Immunoblotting

For immunoblotting analyses protein samples were separated by SDS-PAGE and transferred onto Hybond-P PVDF membranes (GE Healthcare). After blocking non-specific binding sites with 5% dry milk in TBST (1 h, RT) (25 mM Tris pH 7.4, 150 mM NaCl, 0.1% Tween-20) membranes were incubated overnight at 4° C. with primary antibodies in blocking buffer (mouse anti-Bip/GRP78 (BD), 1:1000; mouse anti-$p50^{cdc37}$ (BD), 1:1000; rat anti-HA 5F10, 1.3 µg/ml; mouse anti-p97/VCP (Progen), 1:1000; rabbit anti-PMP70 (Prof. Dr. A. Völkl, University of Heidelberg, Germany), 1:1000; rabbit anti-Sec61α (Acris), 1:1000; mouse anti-TOM20 (BD), 1:1000; mouse anti β-tubulin (Sigma), 1:2000), washed with TBST and incubated for 1 h with horseradish peroxidase (HRP)-coupled secondary antibodies. Membranes were washed and antibody-antigen complexes were visualized using the ECL+chemiluminescence detection system (GE Healthcare) on Hyperfilms (GE Healthcare). For the HA epitope the monoclonal anti HA 5F10 (Roche) was used in a concentration of 1.3 µg/ml (5% dry milk). For the FLAG epitope, the HRP-coupled monoclonal anti-FLAG M2 antibody (Sigma) was used in a dilution of 1:1000 (5% dry milk) Further antibodies are used with the following dilutions: mouse anti β-Tubulin (Sigma) 1:2000; rabbit anti Sec61-α (Acris) 1:1000; mouse anti TOM20 (BD) 1:1000; mouse anti Bip/GRP78 (BD) 1:1000; mouse anti p97/VCP (ProGen) 1:1000).

Cell Fractionation

Cells were harvested via trypsinisation, washed once with cold PBS, resuspended in cold homogenisation buffer (20 mM HEPES pH 7.4, 10 mM KCl, 1.5 mM $MgCl_2$, 1 mM EDTA, 1 mM EGTA, 1 mM DTT, 250 mM sucrose, protease inhibitor cocktail (Roche)) and homogenized. Homogenates were centrifuged at 700×g for 10 min to pellet nuclei, debris, and non-disrupted cells (cell pellet). The supernatant was centrifuged at 10,000×g for 20 min to obtain the 10K pellet. Cytosol and 160K pellet were prepared by ultracentrifugation of the 10K supernatant (160,000×g for 1 h).

Carbonate Extraction 160K fractions were diluted with 100 mM (final concentration) sodium carbonate pH 11.5 and for 30 min on ice. The suspensions were centrifuged for 1 h at 160,000×g at 4° C. The supernatants were recovered and proteins precipitated with 10% trichloracetic acid. Membrane pellets and precipitated proteins were subjected to SDS-PAGE and Western blotting analyses.

Immuno Precipitation (IP)

For interaction assays FLAG-tagged KASPP/LRRK2 was lysed for 1 h in lysis buffer (50 mM Tris-HCl pH 7.4, 150 mM NaCl, 0.5% Nonidet-P40, protease inhibitors (Roche), 1 mM orthovanadate) for 1 h at 4° C. After sedimentation of nuclei (10 min, 10.000 g, 4° C.), the supernatant was incubated with anti FLAG M2 agarose beads (Sigma) for 2 h at 4° C. After incubation, beads were washed 4× in lysis buffer and eluted with SDS-gel sample buffer.

Tandem Affinity Purification

The tandem affinity purification was done with a c-terminal tandem affinity purification tag consisting of a tandem StrepII tag and a Flag epitope (Strep/Flag-tag). HEK293 cells transiently expressing the Strep/Flag-tagged constructs were lysed in 50 mM Tris-HCl pH 7.4, 150 mM NaCl, 0.5% Nonidet-P40, protease inhibitors and 1 mM orthovanadate for 1 h at 4° C. Following sedimentation of nuclei, the cleared supernatant was incubated for 2 h at 4° C. with streptactin superflow (IBA). Prior to washing, the lysates with suspended resin were transferred to microspin columns (GE Healthcare). Washing (1× with lysis buffer and 2× with TBS) was done in the microspin columns. Washing solution was removed from the columns by centrifugation (10 s, 2,000×g) after each washing step. Protein baits were eluted with desthiobiotin (2 mM in TBS). The eluates were used for LRRK2 co-precipitation experiments of LRRK2-Strep/Flag constructs vs. LRRK2-HA.

For MS analysis, a second purification step was added. For this step, the eluates were transferred to anti-Flag M2 agarose (Sigma) and incubated for 2 h at 4° C. The beads were washed 3× with TBS in microspin columns. Proteins were eluted with Flag peptide (Sigma) in PBS at 200 µg/ml peptide. After purification samples were separated by SDS-PAGE and stained with colloidal coomassie according to standard protocols prior to MS identification (Neuhoff, V. et al., Electrophoresis, 9, 255-262, 1988).

Mass Spectrometry

The proteins were identified by MALDI-MS and MSMS on an AB3700 (Applied Biosystems) instrument. Tryptic in gel proteolysis was done after standard protocols (Shevchenko, A. et al., Anal. Chem. 68, 850-858, 1996). Peptides were spotted on steal targets with the dried droplet method using alpha-cyano-4-hydroxycinnamic acid (Sigma) as matrix (Shevchenko, A. et al., supra). Obtained MS and MS/MS spectra were analysed by GPS explorer software suite (Applied Biosystems).

Kinase Activity Assays (Autophosphorylation Assay)

For kinase assays (autophoshorylation assays), Strep/Flag-tagged full-length wild-type LRRK2 or LRRK2-I2020T variant were transiently expressed in HEK293 cells (4x14 cm culture dishes per construct, 2×14 cm dishes for the vector control). After cell lysis and removal of the nuclei, the purification of LRRK2 variants was done by immunoprecipitation with anti-Flag M2 agarose. The resin was washed 3× in lysis buffer. The tagged proteins were not eluted, since the kinase assays were directly performed on the resin. Each sample was divided in 4 aliquots and stored in TBS+10% glycerol at −80° C. until use.

For the kinase assay, one aliquot of each condition (wild-type LRRK2 and LRRK2-I2020T) was divided into three sub-aliquots (1/2, 1/3, 1/6). Each sub-aliquot, as well as one aliquot of the vector control was incubated with 50 µM ATP, 0.3 µCi [$\gamma$-$^{32}$P] ATP in 30 µl assay buffer (25 mM Tris-HCl pH 7.5, 5 mM β-glycerophosphate, 2 mM DTT, 0.1 mM orthovanadate; 10 mM MgCl$_2$; Cell Signaling) for 1 h at 30° C. Reaction was stopped with Laemmli buffer. Protein samples were resolved by SDS-PAGE and transferred onto Hybond-P PVDF membranes (GE Healthcare). Imaging was done on a phosphoimager system (BioRad). Equal loading was ensured by Western blotting analyses (anti-Flag M2).

Immunofluorescence

HEK293 cells were grown on glass coverslips prior to transfection with GFP-tagged wild-type LRRK2. To avoid cell detachment, coverslips were pre-treated with poly-D-lysine (Sigma) and laminin (Sigma). 48 h post-transfection cells were fixed for 15 min with 4% paraformaldehyde at RT.

Fixed cells were permeabilised with PBS containing 0.1% Triton-X 100 for 5 min, blocked with PBS containing 0.1% Tween-20 and 1% BSA and incubated 3 h at RT with primary antibodies in blocking solution [mouse anti-58K Golgi, 1:100 (Abcam); mouse anti-PDI (protein disulfide isomerase), 1:100 (Abcam); rabbit anti-PMP70 (70 kD peroxisomal membrane protein), 1:200; mouse anti-TOM20 (translocase outer mitochondrial membrane protein), 1:500 (BD); mouse anti-β-Tubulin, 1:500 (Sigma); mouse anti-Vimentin, 1:200 (Sigma)]. Coverslips were rinsed six times with PBS and labelled for 1 h with alexa 568-conjugated goat anti-mouse, goat anti-rabbit IgG (Invitrogen) or Phalloidin-TRITC (1:10, 000, Sigma). For nuclear staining the solution also contained 1 µg/ml 4,6-diamnodiphenyl-2-phenylindole (DAPI, Sigma). Coverslips were washed six times with PBS, mounted with FluorSave (Calbiochem) and evaluated by fluorescence microscopy using a Zeiss Apotome equipped with Cy3, FITC and Dapi optical filter sets. The obtained images provide an axial resolution comparable to confocal microscopy (Garini, Y. et al., Curr. Opin. Biotechnol., 16, 3-12, 2005).

Results

KASPP/LRRK2 is a Membrane-Associated 280 kD Protein

For functional and biochemical studies, KASPP/LRRK2 was cloned from human cDNA and generated a series of constructs for the expression of Hemagglutinin (HA), Strep/Flag and green fluorescent protein (GFP)-tagged LRRK2 fusion proteins (FIG. 12A). HEK293 cells that were transiently transfected with c-terminal Strep/Flag-tagged wild-type human KASPP/LRRK2, express a ~280 kD protein recognised by anti-Flag antibody (FIG. 12B). The observed molecular weight corresponds to that expected for KASPP/LRRK2. An additional weaker signal could be also detected in some cases at ~180 kD that is most likely an N-terminal degradation product of KASPP/LRRK2.

In order to determine the subcellular localisation of KASPP/LRRK2, two approaches were used: subcellular fractionation and fluorescence microscopy. For detection of the subcellular distribution of KASPP/LRRK2 in vitro, transfected cells were fractionated by differential centrifugation. The distribution of subcellular organelles in the obtained fractions was then analysed by antibodies specific for mitochondria (TOM20), cytoskeleton (β-tubulin), peroxisomes (PMP70), microsomes (BiP/GRP78, Sec61α) and soluble cytosolic proteins (p50$^{cdc37}$). LRRK2 was found only in membranous fractions (both 10K and 160K pellets), i.e., fractions enriched in mitochondria (10K pellet) and microsomal membranes (160K pellet) but was absent from the cytosol (FIG. 13A).

In order to investigate whether KASPP/LRRK2 is a membrane-associated or an integral membrane protein, the 160K pellet was treated with sodium carbonate, pH 11.5 (Fujiki, Y. et al., J. Cell Biol., 93, 97-102, 1982). KASPP/LRRK2, together with other known membrane-associated proteins, the luminal ER marker BiP/GRP78 (78 kD glucose regulated protein) and peripheral cytosolic ER-associated marker VCP (valosin-containing protein), was extracted from microsomal membranes, whereas the integral membrane protein Sec61α was recovered in the membrane pellet (FIG. 13B). This provides evidence for KASPP/LRRK2 being a membrane-associated protein rather than integrated into membranes.

Additionally, HEK293 cells that expressed recombinantly Strep/Flag-tagged KASPP/LRRK2 kinase-domain were subjected to subcellular fractionation. In contrast to full-length KASPP/LRRK2, the kinase-domain construct was found in the cytosol, whereas little or no fusion-protein was detected in the particulate fractions (both, 10K and 160K pellet, FIG. 13A). Thus, the kinase-domain is not implicated in the association of KASPP/LRRK2 to membranous structures.

LRRK2 Co-Localises with Discrete Cytoplasmic Structures

Immunofluorescence microscopy was used to determine the subcellular localisation of GFP-tagged KASPP/LRRK2 transiently expressed in HEK293 cells. After fixation, cells were permeabilised and co-immunolabelled with antibodies specific for distinct subcellular structures. In HEK293 cells, GFP-tagged KASPP/LRRK2 demonstrated a cytoplasmic distribution (FIG. 314 column 2). Partial co-localization was observed with inner cellular structures, i.e., mitochondria (TOM20), ER (PDI) and Golgi (58K Golgi). In contrast, no overlap was observed with peroxisomes (PMP70). No co-localization was found with the actin cytoskeleton (Phalloidin-Tritc) and intermediate filaments (Vimentin). However, the strongest co-localisation was an overlap with β-tubulin, suggesting an interaction between KASPP/LRRK2 and the microtubular cytoskeleton. Thus, KASPP/LRRK2 is a cytoplasmic protein associated with a subset of inner cellular membranes, i.e., mitochondria, ER and Golgi, and with the microtubular cytoskeleton.

Autophosphorylation Levels Between I2020T Mutant and Wildtype KASPP/LRRK2

Kinase-domain signatures can be easily detected by bioinformatical tools. Nevertheless, it is necessary to verify the kinase activity of KASPP/LRRK2 by biochemical assays. Furthermore, a comparison of wildtype and mutated KASPP/LRRK2 will contribute to the understanding of the mutation's nature, whether it is a gain- or loss of function mutation.

The wildtype full length protein vs. the I2020T mutant variant was tested for its ability for auto-phosphorylation. No significant differences in the autophosphorylation levels have been observed between the I2020T variant and the wild-type (FIG. 8). This confirms that both, KASPP/LRRK2 and the disease-associated mutation I2020T in the kinase domain of KASPP/LRRK2, possess kinase activity. Quantification of autophosphorylation rates revealed an increase in activity of the I2020T mutant compared to wild-type KASPP/LRRK2 of about 30-50%. This finding may be the basis for the development of an appropriate screening assay for modulating compounds, in particular inhibitors, of the increased kinase activity of the I2020T mutant, as e.g. further described herein.

KASPP/LRRK2 Homodimerization

The kinase domain of LRRK2 is predicted to belong to the class of MAPKKK. A characteristic of such kinases is the formation of dimers. Moreover, for Raf-1 and MLK-3 (mixed lineage kinase 3), one of the closest relatives of LRRK2 in vertebrates, homo-dimerisation is required for activity.

In a first approach, KASPP/LRRK2 was tested for its ability to interact with itself by co-precipitation experiments. Therefore, tandem Flag-tagged KASPP/LRRK2 baits were co-expressed with HA-tagged full length KASPP/LRRK2. As shown in FIG. 9a, the full length KASPP/LRRK2 bait could pull out HA-KASPP/LRRK2 whereas a bait-protein containing only the kinase domain showed no interaction with full length KASPP/LRRK2. Thus, KASPP/LRRK2 interacts with itself indicating formation of homodimers or oligomers of higher order.

In a second approach, differently-tagged KASPP/LRRK2 proteins and co-transfected HEK293 cells were utilized with two constructs for expression of HA and the Strep/Flag-tagged KASPP/LRRK2 fusion proteins, with the intention that a certain fraction of cells expressing two different KASPP/LRRK2 fusion proteins would to address the question of dimerisation by co-precipitation experiments. In addition to the full-length LRRK2 protein, a Strep/Flag-tagged version of the kinase domain only was used (FIG. 12). A comparison of purifications with all three tags showed the best results for streptactin, which almost completely precipitates the tagged proteins. Therefore, streptactin was used for precipitation of KASPP/LRRK2 fusion proteins from solubilised cells co-expressing HA and Strep/Flag-tagged KASPP/LRRK2. As shown in FIG. 15A (lower part) by an anti-Flag antibody, both, the full-length and the KASPP/LRRK2 kinase domain baits were precipitated with the same efficiency. Analysis of the precipitated proteins with the anti-HA antibody showed that only the full-length KASPP/LRRK2 bait could pull out HA-tagged KASPP/LRRK2, whereas the kinase domain did not display any interaction with full-length KASPP/LRRK2 (FIG. 15A, upper left panel). Thus, only full-length KASPP/LRRK2 interacts with itself forming homodimers or oligomers of higher order.

KASPP/LRRK2 Interaction with HSP90 and its Co-chaperone p50$^{cdc37}$

To identify proteins which interact with the KASPP/LRRK2 kinase domain tandem affinity purification experiments were performed with a tag system. The purified protein complexes were subjected to SDS page (FIG. 9b). The interacting proteins were identified using mass spectrometry. As shown in FIG. 10b the isolated kinase domain of KASPP/LRRK2 is associated with HSP90 and its co-chaperone p50$^{cdc37}$. The full-length KASPP/LRRK2, however, binds to HSP90 and p50$^{cdc37}$ to a very low extend. The interaction with the HSP90/p50$^{cdc37}$ chaperone-system is shown for several kinases, including the MAPKKK Raf-1 and MLK-3. In both instances, they do not serve as substrates but associate as chaperones participating in maintenance of proper folding of the kinase. This experiment is a further evidence that KASPP/LRRK2 possesses kinase activity and is active in transfected cells.

KASPP/LRRK2 Association with Microsomal Membranes

Information of the localization of KASPP/LRRK2 will help to understand its in vivo function. Using fluorescence microscopy experiments with a c-terminal GFP tagged construct it was shown that KASPP/LRRK2 is cytoplasmic distributed in HEK293 and COST cells (FIG. 10). By immuno co-staining there was no clear co localisation observed with any cellular structure like cytoskeleton or organelles. However, by co-staining with TOM20 and TIM23 partial overlap with mitochondria was obtained.

To further analyze the subcellular localization of this protein, a cell fractionation was performed (FIG. 11a). Surprisingly, no KASPP/LRRK2 was found in the cytosol. However, high amounts of KASPP/LRRK2 were found in the analyzed membranous fractions (both 10K and 160K pellets), i.e. fractions enriched with mitochondria (10K-pellet) and microsomal membranes (160 k pellet).

In order to test if KASPP/LRRK2 is an integral membrane or a membrane-associated protein, carbonate extraction of the microsomal membrane fraction (160K pellet) was applied. Since KASPP/LRRK2 could be extracted with carbonate (FIG. 11b) it is a membrane-associated protein rather than being integrated into the membrane. Thus, KASPP/LRRK2 is a protein with cytoplasmic but not cytosolic distribution and demonstrates strong association to membranes.

GENERATION OF MONOCLONAL ANTIBODIES AGAINST KASPP/LRRK2

General

The immunization, generation of hybridoma clones and ELISA for positive clones against peptide #2025 used for the immunization were carried out according to standard protocols. The antibody producing clones were tested for sensitivity and specificity against KASPP/LRRK2. Peptide #2025 with the amino acid sequence "CRMGIKTSEG TPG-FRAPEVA RGNVIYNQQA D" (SEQ ID NO:3) represents the kinase domain of KASPP/LRRK2 (amino acids Nos. 2025-2055). This particular peptide was chosen because the homology of the sequences between mouse and human is 100%.

Test Conditions for Sensitivity and Specificity of the Generated Antibodies

A lysate of HEK293 cells overexpressing recombinant KASPP/LRRK2 and a control lysate of HEK 293 cells transfected with an empty vector were separated in a PAGE gels (8%). The probe was applied in a broad slot over the whole gel. After electrophoretic separation the separated lysates were transferred on PVDF membranes (western blot procedure). After the transfer the membranes were first blocked with blocking buffer (5% low-fat milk powder, BioRad, in TBS-Tween 20) for 1 h with the effect that unspecific adsorption of the antibodies to the membrane was avoided. Thereafter the blots were incubated with the positively tested hybridoma supernatants for 3 h (ELISA for testing the affinity to the peptide). The incubation was carried out in a multiscreen chamber (BioRad). The chamber allows the incubation of a blot with different primary antibodies. The membranes were taken form the chambers for washing (4×5 min in TBST buffer). Then. the incubation was carried out with a HRP (horse reddish peroxidase) coupled secondary antibody (anti rat IgG) for 1 h. After the incubation the blots were washed with TBST (4 ×10 min). The detection of the antibody reaction was done with the help of chemolumineszenz (ECL+, GE Healthcare) and exposition of a film (hyperfilm, GE Healthcare).

Result

The results of the above described Western blots are shown in FIG. 16. Clone 3G6 (No. 10) and 4B7 (No. 15) (peptide #2025) produced a specific signal. A signal was specific if (a) it appeared at the position of the correct molecular weight (280 kD) and (b) it appeared stronger or only for the lysate of the KASSP/LRRK2 overexpressing cells.

TABLE 1

| Gene Symbol | Accession Nr. |
| --- | --- |
| PKP2 | NM_001005242 |
| ALG10 | NM_032834 |
| CPNE8 | NM_153634 |
| KIF21A | NM_017641 |
| ABCD2 | NM_005164 |
| FLJ40126 | NM_173599 |
| SLC2A13 | NM_052885 |
| KASPP/LRRK2 | |
| MUC19 | AY236870 |
| CNTN1 | NM_001843 |
| PDZRN4 | NM_013377 |
| LOC283464 | BC039145 |
| YAF2 | NM_005748 |
| MADP-1 | NM_033114 |
| PPHLN1 | NM_201438 |
| PRICKLE1 | NM_153026 |
| ADAMTS20 | NM_025003 |
| DKFZp434G1415 | NM_031292 |
| IRAK4 | NM_016123 |
| PTK9 | NM_002822 |
| DKFZp434K2435 | NM_032256 |
| NELL2 | NM_006159 |
| PLEKHA9 | NM_015899 |
| DKFZp451M105 | AL832340 |
| FLJ14711 | AK027617 |
| FLJ22820 | AK026473 |
| SLC38A1 | NM_030674 |
| SLC38A2 | NM_018976 |
| SLC38A4 | NM_018018 |

TABLE 2

| Location | Forward | Reverse |
| --- | --- | --- |
| D12s2194 | F_GAGGACTATGATTGCCATGG | R_AGGGCATACAAAATGTCCCT |
| D12s1048 | F_GGTCTGCTTAGGTCCCTTTT | R_AAGGAACCAAGGAGTGGAAG |
| Intragenic_1 | F_TTCAGATGTTTGGGGCAAGT | R_CATGAAGACTGTGAATGGTTTG |
| Intragenic_2 | F_CCAGACAGAAGTCTGAAGGACA | R_TCCAAAACAGACAAGAGGTTGA |
| Intragenic_3 | F_ATGAAGCCTTGGCTCTTCAA | R_TCCCAATTCAAAATTTTAGTGC |

TABLE 3

| Variant | Exon | PD Families (n = 55) | Idiopathic PD (n = 337) | Controls (n = 1200) | Family |
| --- | --- | --- | --- | --- | --- |
| R793M; 2378G>T | 19 | 2 | 1 | 1 | DE041 T11239 |
| Q930R; 2789A>G | 21 | 1 | 0 | 0 | DE022 |
| S1096C; 3287C>G | 24 | 1 | 0 | 0 | famE |
| L1114L; 3342A>G | 24 | 1 | 0 | 0 | DE038 T11288 |
| S1228T; 3683G>C | 27 | 1 | 0 | 0 | DE031 |
| G2019S; 6055G>A | 41 | 0 | 1 | 0 | Hernandez DG et al. (2005) |
| I2020T; 6059T>C | 41 | 1 | 0 | 0 | DE032 T10738 |

TABLE 4

| | Family/Patient | | | | | | |
|---|---|---|---|---|---|---|---|
| | T11239 | DE041/ II-1//II-2 | DE022/ III-5// III-6//III-7 | Fam. E | T11288/II-5 | DE031/III-1//III-2 | T10738/II-2 |
| Mutation | R793M | R793M | Q930R | S1096C | 3342A > G | S1228T | I2020T |
| Age at onset (y) | 42 uncle: 79 | 55//70 | 68//58//47 | | 77 | 49//49 father: 62 granny: 68 | 57 father: 59 |
| Disease duration | 25~ | 14~//10~ | 8~//19//30 | | 4~ | 8~//12~ | 3~ |
| Initial symtom | B/RT | PT//RT | B, RT//B// B, RT | | B | RT//B, RT | B, RT |
| Response to L-dopa | + | +//+ | +//+//+ | + | + | +//+ | + |
| Bradykinesia | + | +//+ | +//+//+ | | + | +//+ | + |
| Rigidity | + | +//+ | +//+//+ | | + | +//+ | + |
| Resting Tremor | + | −//+ | +//+//+ | | − | +//+ | + |
| Postural instability | + | +//+ | −//+//+ | | + | −//− | − |
| Sleeping disturbances | + | +//− | +//+//+ | | + | −//+ | + |
| Long-term complications | + | +//+ | +//+//+ | | − | +//+ | − |
| Hallucinations | + | −//− | −//−//+ | | + | −//− | − |
| Additional findings | Tongue dystonia | − | | | Dementia L-dopa hypersensitivity | | |
| Sniffing test | 2/8 | nd | nd | nd | 7/8 | 5/8//5/8 | 7/8 |
| Electro-neurography | na | nd | nd | nd | na | na//na | Na |
| Electro-myography | na | nd | nd | nd | na | na//na | Na |
| Magnet evoked potentials | na | nd | nd | nd | na | na//na | Na |
| TCS (r; l) | 0.21; 0.24 | nd | nd | nd | 0.24; 0.19 | 0.23; 0.24// 0.22; 0.24 | 0.16; 0.17 |
| MRI | nd, because of electrodes | nd | nd | nd | global atrophy, microangiopathy | slightly increased atrophy in both, slight microangiopathie in III-2 | Slight frontotemporally enhanced atrophy |

TABLE 5

| | Family/Patient | | | | |
|---|---|---|---|---|---|
| | T11239 | T11288/II-5 | DE031/III-1// | DE031/III-2 | T10738/II-2 |
| Mutation | R793M | 3342A > G | | S1228T | I2020T |
| LPS-K/SPM (IQ) | /90↓ | 75↓↓/ | 111↑/ | 117↑/ | 120↑/ |
| Tower of London (PR) | xx | — | 6↓↓ | 27↓ | xx |
| CWIT (T-Value INT) | — | (63) | 37 | 41 | 41 |
| CERAD 1 (Verbal Fluency) | — | 6 | 20~ | 31↑ | 36↑ |
| CERAD 2 (Boston Naming Test) | — | 12 | 14~ | 15~ | 14- |
| CERAD 3 (MMSE) | 22 | 24 | 30~ | 30~ | 29~ |
| CERAD 4 (Word List Memory) | — | 10 | 19~ | 22~ | 29↑ |
| CERAD 5 (Constructional Praxis) | — | 7 | 10~ | 10~ | 11~ |
| CERAD 6.1 (Word List Recall) | — | 1 | 7~ | 7~ | 10↑ |
| CERAD 7.1 (Word List Recognition) | — | 10 | 9 | 10 | 10 |
| CERAD 8 (Recall of Constructional Praxis) | — | 2 | 10~ | 13↑ | 12↑ |
| D2-Test (Concentration) | — | — | 38 | 46 | 46 |
| BDI | 23↑ | 11 | 3 | 9 | 7.5 |
| PDQ-39 (PDSI) | 40.4 | 25.6 | 8.8 | 18.6 | 23.6 |

SEQUENCE LISTING

<160> NUMBER OF SEQ ID NOS: 54

<210> SEQ ID NO 1
<211> LENGTH: 9104
<212> TYPE: DNA
<213> ORGANISM: Homo sapiens
<220> FEATURE:

<221> NAME/KEY: exon
<222> LOCATION: (1)..(7584)

<400> SEQUENCE: 1

```
atg gct agt ggc agc tgt cag ggg tgc gaa gag gac gag gaa act ctg      48
Met Ala Ser Gly Ser Cys Gln Gly Cys Glu Glu Asp Glu Glu Thr Leu
1               5                   10                  15 aag aag ttg ata gtc agg ctg aac aat gtc cag gaa gga aaa cag ata      96
Lys Lys Leu Ile Val Arg Leu Asn Asn Val Gln Glu Gly Lys Gln Ile
                20                  25                  30 gaa acg ctg gtc caa atc ctg gag gat ctg ctg gtg ttc acg tac tcc     144
Glu Thr Leu Val Gln Ile Leu Glu Asp Leu Leu Val Phe Thr Tyr Ser
            35                  40                  45 gag cgc gcc tcc aag tta ttt caa ggc aaa aat atc cat gtg cct ctg     192
Glu Arg Ala Ser Lys Leu Phe Gln Gly Lys Asn Ile His Val Pro Leu
        50                  55                  60 ttg atc gtc ttg gac tcc tat atg aga gtc gcg agt gtg cag cag gtg     240
Leu Ile Val Leu Asp Ser Tyr Met Arg Val Ala Ser Val Gln Gln Val
65                  70                  75                  80 ggt tgg tca ctt ctg tgc aaa tta ata gaa gtc tgt cca ggt aca atg     288
Gly Trp Ser Leu Leu Cys Lys Leu Ile Glu Val Cys Pro Gly Thr Met
                85                  90                  95 caa agc tta atg gga ccc cag gat gtt gga aat gat tgg gaa gtc ctt     336
Gln Ser Leu Met Gly Pro Gln Asp Val Gly Asn Asp Trp Glu Val Leu
                100                 105                 110 ggt gtt cac caa ttg att ctt aaa atg cta aca gtt cat aat gcc agt     384
Gly Val His Gln Leu Ile Leu Lys Met Leu Thr Val His Asn Ala Ser
            115                 120                 125 gta aac ttg tca gtg att gga ctg aag acc tta gat ctc ctc cta act     432
Val Asn Leu Ser Val Ile Gly Leu Lys Thr Leu Asp Leu Leu Leu Thr
        130                 135                 140 tca ggt aaa atc acc ttg ctg ata ttg gat gaa gaa agt gat att ttc     480
Ser Gly Lys Ile Thr Leu Leu Ile Leu Asp Glu Glu Ser Asp Ile Phe
145                 150                 155                 160 atg tta att ttt gat gcc atg cac tca ttt cca gcc aat gat gaa gtc     528
Met Leu Ile Phe Asp Ala Met His Ser Phe Pro Ala Asn Asp Glu Val
                165                 170                 175 cag aaa ctt gga tgc aaa gct tta cat gtg ctg ttt gag aga gtc tca     576
Gln Lys Leu Gly Cys Lys Ala Leu His Val Leu Phe Glu Arg Val Ser
            180                 185                 190 gag gag caa ctg act gaa ttt gtt gag aac aaa gat tat atg ata ttg     624
Glu Glu Gln Leu Thr Glu Phe Val Glu Asn Lys Asp Tyr Met Ile Leu
        195                 200                 205 tta agt gcg tca aca aat ttt aaa gat gaa gag gaa att gtg ctt cat     672
Leu Ser Ala Ser Thr Asn Phe Lys Asp Glu Glu Glu Ile Val Leu His
        210                 215                 220 gtg ctg cat tgt tta cat tcc cta gcg att cct tgc aat aat gtg gaa     720
Val Leu His Cys Leu His Ser Leu Ala Ile Pro Cys Asn Asn Val Glu
225                 230                 235                 240 gtc ctc atg agt ggc aat gtc agg tgt tat aat att gtg gtg gaa gct     768
Val Leu Met Ser Gly Asn Val Arg Cys Tyr Asn Ile Val Val Glu Ala
                245                 250                 255 atg aaa gca ttc cct atg agt gaa aga att caa gaa gtg agt tgc tgt     816
Met Lys Ala Phe Pro Met Ser Glu Arg Ile Gln Glu Val Ser Cys Cys
            260                 265                 270 ttg ctc cat agg ctt aca tta ggt aat ttt tca aat atc ctg gta tta     864
Leu Leu His Arg Leu Thr Leu Gly Asn Phe Phe Asn Ile Leu Val Leu
        275                 280                 285 aac gaa gtc cat gag ttt gtg gtg aaa gct gtg cag cag tac cca gag     912
Asn Glu Val His Glu Phe Val Val Lys Ala Val Gln Gln Tyr Pro Glu
        290                 295                 300
```

```
aat gca gca ttg cag atc tca gcg ctc agc tgt ttg gcc ctc ctc act      960
Asn Ala Ala Leu Gln Ile Ser Ala Leu Ser Cys Leu Ala Leu Leu Thr
305                 310                 315                 320 gag act att ttc tta aat caa gat tta gag gaa aag aat gag aat caa     1008
Glu Thr Ile Phe Leu Asn Gln Asp Leu Glu Glu Lys Asn Glu Asn Gln
                325                 330                 335 gag aat gat gat gag ggg gaa gaa gat aaa ttg ttt tgg ctg gaa gcc     1056
Glu Asn Asp Asp Glu Gly Glu Glu Asp Lys Leu Phe Trp Leu Glu Ala
            340                 345                 350 tgt tac aaa gca tta acg tgg cat aga aag aac aag cac gtg cag gag     1104
Cys Tyr Lys Ala Leu Thr Trp His Arg Lys Asn Lys His Val Gln Glu
        355                 360                 365 gcc gca tgc tgg gca cta aat aat ctc ctt atg tac caa aac agt tta     1152
Ala Ala Cys Trp Ala Leu Asn Asn Leu Leu Met Tyr Gln Asn Ser Leu
    370                 375                 380 cat gag aag att gga gat gaa gat ggc cat ttc cca gct cat agg gaa     1200
His Glu Lys Ile Gly Asp Glu Asp Gly His Phe Pro Ala His Arg Glu
385                 390                 395                 400 gtg atg ctc tcc atg ctg atg cat tct tca aag gaa gtt ttc cag         1248
Val Met Leu Ser Met Leu Met His Ser Ser Lys Glu Val Phe Gln
                405                 410                 415 gca tct gcg aat gca ttg tca act ctc tta gaa caa aat gtt aat ttc     1296
Ala Ser Ala Asn Ala Leu Ser Thr Leu Leu Glu Gln Asn Val Asn Phe
            420                 425                 430 aga aaa ata ctg tta tca aaa gga ata cac ctg aat gtt ttg gag tta     1344
Arg Lys Ile Leu Leu Ser Lys Gly Ile His Leu Asn Val Leu Glu Leu
        435                 440                 445 atg cag aag cat ata cat tct cct gaa gtg gct gaa agt ggc tgt aaa     1392
Met Gln Lys His Ile His Ser Pro Glu Val Ala Glu Ser Gly Cys Lys
    450                 455                 460 atg cta aat cat ctt ttt gaa gga agc aac act tcc ctg gat ata atg     1440
Met Leu Asn His Leu Phe Glu Gly Ser Asn Thr Ser Leu Asp Ile Met
465                 470                 475                 480 gca gca gtg gtc ccc aaa ata cta aca gtt atg aaa cgt cat gag aca     1488
Ala Ala Val Val Pro Lys Ile Leu Thr Val Met Lys Arg His Glu Thr
                485                 490                 495 tca tta cca gtg cag ctg gag gcg ctt cga gct att tta cat ttt ata     1536
Ser Leu Pro Val Gln Leu Glu Ala Leu Arg Ala Ile Leu His Phe Ile
            500                 505                 510 gtg cct ggc atg cca gaa gaa tcc agg gag gat aca gaa ttt cat cat     1584
Val Pro Gly Met Pro Glu Glu Ser Arg Glu Asp Thr Glu Phe His His
        515                 520                 525 aag cta aat atg gtt aaa aaa cag tgt ttc aag aat gat att cac aaa     1632
Lys Leu Asn Met Val Lys Lys Gln Cys Phe Lys Asn Asp Ile His Lys
    530                 535                 540 ctg gtc cta gca gct ttg aac agg ttc att gga aat cct ggg att cag     1680
Leu Val Leu Ala Ala Leu Asn Arg Phe Ile Gly Asn Pro Gly Ile Gln
545                 550                 555                 560 aaa tgt gga tta aaa gta att tct tct att gta cat ttt cct gat gca     1728
Lys Cys Gly Leu Lys Val Ile Ser Ser Ile Val His Phe Pro Asp Ala
                565                 570                 575 tta gag atg tta tcc ctg gaa ggt gct atg gat tca gtg ctt cac aca     1776
Leu Glu Met Leu Ser Leu Glu Gly Ala Met Asp Ser Val Leu His Thr
            580                 585                 590 ctg cag atg tat cca gat gac caa gaa att cag tgt ctg ggt tta agt     1824
Leu Gln Met Tyr Pro Asp Asp Gln Glu Ile Gln Cys Leu Gly Leu Ser
        595                 600                 605 ctt ata gga tac ttg att aca aag aag aat gtg ttc ata gga act gga     1872
Leu Ile Gly Tyr Leu Ile Thr Lys Lys Asn Val Phe Ile Gly Thr Gly
    610                 615                 620
```

```
cat ctg ctg gca aaa att ctg gtt tcc agc tta tac cga ttt aag gat    1920
His Leu Leu Ala Lys Ile Leu Val Ser Ser Leu Tyr Arg Phe Lys Asp
625                 630                 635                 640 gtt gct gaa ata cag act aaa gga ttt cag aca atc tta gca atc ctc    1968
Val Ala Glu Ile Gln Thr Lys Gly Phe Gln Thr Ile Leu Ala Ile Leu
                645                 650                 655 aaa ttg tca gca tct ttt tct aag ctg ctg gtg cat cat tca ttt gac    2016
Lys Leu Ser Ala Ser Phe Ser Lys Leu Leu Val His His Ser Phe Asp
            660                 665                 670 tta gta ata ttc cat caa atg tct tcc aat atc atg gaa caa aag gat    2064
Leu Val Ile Phe His Gln Met Ser Ser Asn Ile Met Glu Gln Lys Asp
        675                 680                 685 caa cag ttt cta aac ctc tgt tgc aag tgt ttt gca aaa gta gct atg    2112
Gln Gln Phe Leu Asn Leu Cys Cys Lys Cys Phe Ala Lys Val Ala Met
690                 695                 700 gat gat tac tta aaa aat gtg atg cta gag aga gcg tgt gat cag aat    2160
Asp Asp Tyr Leu Lys Asn Val Met Leu Glu Arg Ala Cys Asp Gln Asn
705                 710                 715                 720 aac agc atc atg gtt gaa tgc ttg ctt cta ttg gga gca gat gcc aat    2208
Asn Ser Ile Met Val Glu Cys Leu Leu Leu Leu Gly Ala Asp Ala Asn
                725                 730                 735 caa gca aag gag gga tct tct tta att tgt cag gta tgt gag aaa gag    2256
Gln Ala Lys Glu Gly Ser Ser Leu Ile Cys Gln Val Cys Glu Lys Glu
            740                 745                 750 agc agt ccc aaa ttg gtg gaa ctc tta ctg aat agt gga tct cgt gaa    2304
Ser Ser Pro Lys Leu Val Glu Leu Leu Leu Asn Ser Gly Ser Arg Glu
        755                 760                 765 caa gat gta cga aaa gcg ttg acg ata agc att ggg aaa ggt gac agc    2352
Gln Asp Val Arg Lys Ala Leu Thr Ile Ser Ile Gly Lys Gly Asp Ser
770                 775                 780 cag atc atc agc ttg ctc tta agg agg ctg gcc ctg gat gtg gcc aac    2400
Gln Ile Ile Ser Leu Leu Leu Arg Arg Leu Ala Leu Asp Val Ala Asn
785                 790                 795                 800 aat agc att tgc ctt gga gga ttt tgt ata gga aaa gtt gaa cct tct    2448
Asn Ser Ile Cys Leu Gly Gly Phe Cys Ile Gly Lys Val Glu Pro Ser
                805                 810                 815 tgg ctt ggt cct tta ttt cca gat aag act tct aat tta agg aaa caa    2496
Trp Leu Gly Pro Leu Phe Pro Asp Lys Thr Ser Asn Leu Arg Lys Gln
            820                 825                 830 aca aat ata gca tct aca cta gca aga atg gtg atc aga tat cag atg    2544
Thr Asn Ile Ala Ser Thr Leu Ala Arg Met Val Ile Arg Tyr Gln Met
        835                 840                 845 aaa agt gct gtg gaa gaa gga aca gcc tca ggc agc gat gga aat ttt    2592
Lys Ser Ala Val Glu Glu Gly Thr Ala Ser Gly Ser Asp Gly Asn Phe
850                 855                 860 tct gaa gat gtg ctg tct aaa ttt gat gaa tgg acc ttt att cct gac    2640
Ser Glu Asp Val Leu Ser Lys Phe Asp Glu Trp Thr Phe Ile Pro Asp
865                 870                 875                 880 tct tct atg gac agt gtg ttt gct caa agt gat gac ctg gat agt gaa    2688
Ser Ser Met Asp Ser Val Phe Ala Gln Ser Asp Asp Leu Asp Ser Glu
                885                 890                 895 gga agt gaa ggc tca ttt ctt gtg aaa aag aaa tct aat tca att agt    2736
Gly Ser Glu Gly Ser Phe Leu Val Lys Lys Lys Ser Asn Ser Ile Ser
            900                 905                 910 gta gga gaa ttt tac cga gat gcc gta tta cag cgt tgc tca cca aat    2784
Val Gly Glu Phe Tyr Arg Asp Ala Val Leu Gln Arg Cys Ser Pro Asn
        915                 920                 925 ttg caa aga cat tcc aat tcc ttg ggg ccc att ttt gat cat gaa gat    2832
Leu Gln Arg His Ser Asn Ser Leu Gly Pro Ile Phe Asp His Glu Asp
930                 935                 940
```

```
tta ctg aag cga aaa aga aaa ata tta tct tca gat gat tca ctc agg      2880
Leu Leu Lys Arg Lys Arg Lys Ile Leu Ser Ser Asp Asp Ser Leu Arg
945                 950                 955                 960 tca tca aaa ctt caa tcc cat atg agg cat tca gac agc att tct tct      2928
Ser Ser Lys Leu Gln Ser His Met Arg His Ser Asp Ser Ile Ser Ser
                965                 970                 975 ctg gct tct gag aga gaa tat att aca tca cta gac ctt tca gca aat      2976
Leu Ala Ser Glu Arg Glu Tyr Ile Thr Ser Leu Asp Leu Ser Ala Asn
            980                 985                 990 gaa cta aga gat att gat gcc cta agc cag aaa tgc tgt ata agt gtt      3024
Glu Leu Arg Asp Ile Asp Ala Leu Ser Gln Lys Cys Cys Ile Ser Val
        995                 1000                1005 cat ttg gag cat ctt gaa aag ctg gag ctt cac cag aat gca ctc          3069
His Leu Glu His Leu Glu Lys Leu Glu Leu His Gln Asn Ala Leu
    1010                1015                1020 acg agc ttt cca caa cag cta tgt gaa act ctg aag agt ttg aca          3114
Thr Ser Phe Pro Gln Gln Leu Cys Glu Thr Leu Lys Ser Leu Thr
1025                1030                1035 cat ttg gac ttg cac agt aat aaa ttt aca tca ttt cct tct tat          3159
His Leu Asp Leu His Ser Asn Lys Phe Thr Ser Phe Pro Ser Tyr
    1040                1045                1050 ttg ttg aaa atg agt tgt att gct aat ctt gat gtc tct cga aat          3204
Leu Leu Lys Met Ser Cys Ile Ala Asn Leu Asp Val Ser Arg Asn
1055                1060                1065 gac att gga ccc tca gtg gtt tta gat cct aca gtg aaa tgt cca          3249
Asp Ile Gly Pro Ser Val Val Leu Asp Pro Thr Val Lys Cys Pro
    1070                1075                1080 act ctg aaa cag ttt aac ctg tca tat aac cag ctg tct ttt gta          3294
Thr Leu Lys Gln Phe Asn Leu Ser Tyr Asn Gln Leu Ser Phe Val
1085                1090                1095 cct gag aac ctc act gat gtg gta gag aaa ctg gag cag ctc att          3339
Pro Glu Asn Leu Thr Asp Val Val Glu Lys Leu Glu Gln Leu Ile
    1100                1105                1110 tta gaa gga aat aaa ata tca ggg ata tgc tcc ccc ttg aga ctg          3384
Leu Glu Gly Asn Lys Ile Ser Gly Ile Cys Ser Pro Leu Arg Leu
1115                1120                1125 aag gaa ctg aag att tta aac ctt agt aag aac cac att tca tcc          3429
Lys Glu Leu Lys Ile Leu Asn Leu Ser Lys Asn His Ile Ser Ser
    1130                1135                1140 cta tca gag aac ttt ctt gag gct tgt cct aaa gtg gag agt ttc          3474
Leu Ser Glu Asn Phe Leu Glu Ala Cys Pro Lys Val Glu Ser Phe
1145                1150                1155 agt gcc aga atg aat ttt ctt gct gct atg cct ttc ttg cct cct          3519
Ser Ala Arg Met Asn Phe Leu Ala Ala Met Pro Phe Leu Pro Pro
    1160                1165                1170 tct atg aca atc cta aaa tta tct cag aac aaa ttt tcc tgt att          3564
Ser Met Thr Ile Leu Lys Leu Ser Gln Asn Lys Phe Ser Cys Ile
1175                1180                1185 cca gaa gca att tta aat ctt cca cac ttg cgg tct tta gat atg          3609
Pro Glu Ala Ile Leu Asn Leu Pro His Leu Arg Ser Leu Asp Met
    1190                1195                1200 agc agc aat gat att cag tac cta cca ggt ccc gca cac tgg aaa          3654
Ser Ser Asn Asp Ile Gln Tyr Leu Pro Gly Pro Ala His Trp Lys
1205                1210                1215 tct ttg aac tta agg gaa ctc tta ttt agc cat aat cag atc agc          3699
Ser Leu Asn Leu Arg Glu Leu Leu Phe Ser His Asn Gln Ile Ser
    1220                1225                1230 atc ttg gac ttg agt gaa aaa gca tat tta tgg tct aga gta gag          3744
Ile Leu Asp Leu Ser Glu Lys Ala Tyr Leu Trp Ser Arg Val Glu
1235                1240                1245
```

| | | | | | | | | | | | |
|---|---|---|---|---|---|---|---|---|---|---|---|
| aaa | ctg | cat | ctt | tct | cac | aat | aaa | ctg | aaa | gag | att | cct | cct | gag | 3789 |
| Lys | Leu | His | Leu | Ser | His | Asn | Lys | Leu | Lys | Glu | Ile | Pro | Pro | Glu | |
| | 1250 | | | | 1255 | | | | 1260 | | | | | | |

| att | ggc | tgt | ctt | gaa | aat | ctg | aca | tct | ctg | gat | gtc | agt | tac | aac | 3834 |
| Ile | Gly | Cys | Leu | Glu | Asn | Leu | Thr | Ser | Leu | Asp | Val | Ser | Tyr | Asn | |
| 1265 | | | | | 1270 | | | | 1275 | | | | | | |

| ttg | gaa | cta | aga | tcc | ttt | ccc | aat | gaa | atg | ggg | aaa | tta | agc | aaa | 3879 |
| Leu | Glu | Leu | Arg | Ser | Phe | Pro | Asn | Glu | Met | Gly | Lys | Leu | Ser | Lys | |
| | 1280 | | | | 1285 | | | | 1290 | | | | | | |

| ata | tgg | gat | ctt | cct | ttg | gat | gaa | ctg | cat | ctt | aac | ttt | gat | ttt | 3924 |
| Ile | Trp | Asp | Leu | Pro | Leu | Asp | Glu | Leu | His | Leu | Asn | Phe | Asp | Phe | |
| 1295 | | | | | 1300 | | | | 1305 | | | | | | |

| aaa | cat | ata | gga | tgt | aaa | gcc | aaa | gac | atc | ata | agg | ttt | ctt | caa | 3969 |
| Lys | His | Ile | Gly | Cys | Lys | Ala | Lys | Asp | Ile | Ile | Arg | Phe | Leu | Gln | |
| | 1310 | | | | 1315 | | | | 1320 | | | | | | |

| cag | cga | tta | aaa | aag | gct | gtg | cct | tat | aac | cga | atg | aaa | ctt | atg | 4014 |
| Gln | Arg | Leu | Lys | Lys | Ala | Val | Pro | Tyr | Asn | Arg | Met | Lys | Leu | Met | |
| 1325 | | | | | 1330 | | | | 1335 | | | | | | |

| att | gtg | gga | aat | act | ggg | agt | ggt | aaa | acc | acc | tta | ttg | cag | caa | 4059 |
| Ile | Val | Gly | Asn | Thr | Gly | Ser | Gly | Lys | Thr | Thr | Leu | Leu | Gln | Gln | |
| | 1340 | | | | 1345 | | | | 1350 | | | | | | |

| tta | atg | aaa | acc | aag | aaa | tca | gat | ctt | gga | atg | caa | agt | gcc | aca | 4104 |
| Leu | Met | Lys | Thr | Lys | Lys | Ser | Asp | Leu | Gly | Met | Gln | Ser | Ala | Thr | |
| 1355 | | | | | 1360 | | | | 1365 | | | | | | |

| gtt | ggc | ata | gat | gtg | aaa | gac | tgg | cct | atc | caa | ata | aga | gac | aaa | 4149 |
| Val | Gly | Ile | Asp | Val | Lys | Asp | Trp | Pro | Ile | Gln | Ile | Arg | Asp | Lys | |
| | 1370 | | | | 1375 | | | | 1380 | | | | | | |

| aga | aag | aga | gat | ctc | gtc | cta | aat | gtg | tgg | gat | ttt | gca | ggt | cgt | 4194 |
| Arg | Lys | Arg | Asp | Leu | Val | Leu | Asn | Val | Trp | Asp | Phe | Ala | Gly | Arg | |
| 1385 | | | | | 1390 | | | | 1395 | | | | | | |

| gag | gaa | ttc | tat | agt | act | cat | ccc | cat | ttt | atg | acg | cag | cga | gca | 4239 |
| Glu | Glu | Phe | Tyr | Ser | Thr | His | Pro | His | Phe | Met | Thr | Gln | Arg | Ala | |
| | 1400 | | | | 1405 | | | | 1410 | | | | | | |

| ttg | tac | ctt | gct | gtc | tat | gac | ctc | agc | aag | gga | cag | gct | gaa | gtt | 4284 |
| Leu | Tyr | Leu | Ala | Val | Tyr | Asp | Leu | Ser | Lys | Gly | Gln | Ala | Glu | Val | |
| 1415 | | | | | 1420 | | | | 1425 | | | | | | |

| gat | gcc | atg | aag | cct | tgg | ctc | ttc | aat | ata | aag | gct | cgc | gct | tct | 4329 |
| Asp | Ala | Met | Lys | Pro | Trp | Leu | Phe | Asn | Ile | Lys | Ala | Arg | Ala | Ser | |
| | 1430 | | | | 1435 | | | | 1440 | | | | | | |

| tct | tcc | cct | gtg | att | ctc | gtt | ggc | aca | cat | ttg | gat | gtt | tct | gat | 4374 |
| Ser | Ser | Pro | Val | Ile | Leu | Val | Gly | Thr | His | Leu | Asp | Val | Ser | Asp | |
| 1445 | | | | | 1450 | | | | 1455 | | | | | | |

| gag | aag | caa | cgc | aaa | gcc | tgc | atg | agt | aaa | atc | acc | aag | gaa | ctc | 4419 |
| Glu | Lys | Gln | Arg | Lys | Ala | Cys | Met | Ser | Lys | Ile | Thr | Lys | Glu | Leu | |
| | 1460 | | | | 1465 | | | | 1470 | | | | | | |

| ctg | aat | aag | cga | ggg | ttc | cct | gcc | ata | cga | gat | tac | cac | ttt | gtg | 4464 |
| Leu | Asn | Lys | Arg | Gly | Phe | Pro | Ala | Ile | Arg | Asp | Tyr | His | Phe | Val | |
| 1475 | | | | | 1480 | | | | 1485 | | | | | | |

| aat | gcc | acc | gag | gaa | tct | gat | gct | ttg | gca | aaa | ctt | cgg | aaa | acc | 4509 |
| Asn | Ala | Thr | Glu | Glu | Ser | Asp | Ala | Leu | Ala | Lys | Leu | Arg | Lys | Thr | |
| | 1490 | | | | 1495 | | | | 1500 | | | | | | |

| atc | ata | aac | gag | agc | ctt | aat | ttc | aag | atc | cga | gat | cag | ctt | gtt | 4554 |
| Ile | Ile | Asn | Glu | Ser | Leu | Asn | Phe | Lys | Ile | Arg | Asp | Gln | Leu | Val | |
| 1505 | | | | | 1510 | | | | 1515 | | | | | | |

| gtt | gga | cag | ctg | att | cca | gac | tgc | tat | gta | gaa | ctt | gaa | aaa | atc | 4599 |
| Val | Gly | Gln | Leu | Ile | Pro | Asp | Cys | Tyr | Val | Glu | Leu | Glu | Lys | Ile | |
| | 1520 | | | | 1525 | | | | 1530 | | | | | | |

| att | tta | tcg | gag | cgt | aaa | aat | gtg | cca | att | gaa | ttt | ccc | gta | att | 4644 |
| Ile | Leu | Ser | Glu | Arg | Lys | Asn | Val | Pro | Ile | Glu | Phe | Pro | Val | Ile | |
| 1535 | | | | | 1540 | | | | 1545 | | | | | | |

-continued

| | | |
|---|---|---|
| gac cgg aaa cga tta tta caa cta gtg aga gaa aat cag ctg cag<br>Asp Arg Lys Arg Leu Leu Gln Leu Val Arg Glu Asn Gln Leu Gln<br>　　　1550　　　　　　　　1555　　　　　　　　1560 | | 4689 |
| tta gat gaa aat gag ctt cct cac gca gtt cac ttt cta aat gaa<br>Leu Asp Glu Asn Glu Leu Pro His Ala Val His Phe Leu Asn Glu<br>1565　　　　　　　　1570　　　　　　　　1575 | | 4734 |
| tca gga gtc ctt ctt cat ttt caa gac cca gca ctg cag tta agt<br>Ser Gly Val Leu Leu His Phe Gln Asp Pro Ala Leu Gln Leu Ser<br>　　1580　　　　　　　　1585　　　　　　　　1590 | | 4779 |
| gac ttg tac ttt gtg gaa ccc aag tgg ctt tgt aaa atc atg gca<br>Asp Leu Tyr Phe Val Glu Pro Lys Trp Leu Cys Lys Ile Met Ala<br>　　　1595　　　　　　　　1600　　　　　　　　1605 | | 4824 |
| cag att ttg aca gtg aaa gtg gaa ggt tgt cca aaa cac cct aag<br>Gln Ile Leu Thr Val Lys Val Glu Gly Cys Pro Lys His Pro Lys<br>　　　　1610　　　　　　　　1615　　　　　　　　1620 | | 4869 |
| ggc att att tcg cgt aga gat gtg gaa aaa ttt ctt tca aaa aaa<br>Gly Ile Ile Ser Arg Arg Asp Val Glu Lys Phe Leu Ser Lys Lys<br>1625　　　　　　　　1630　　　　　　　　1635 | | 4914 |
| agg aaa ttt cca aag aac tac atg tca cag tat ttt aag ctc cta<br>Arg Lys Phe Pro Lys Asn Tyr Met Ser Gln Tyr Phe Lys Leu Leu<br>　　1640　　　　　　　　1645　　　　　　　　1650 | | 4959 |
| gaa aaa ttc cag att gct ttg cca ata gga gaa gaa tat ttg ctg<br>Glu Lys Phe Gln Ile Ala Leu Pro Ile Gly Glu Glu Tyr Leu Leu<br>　　　1655　　　　　　　　1660　　　　　　　　1665 | | 5004 |
| gtt cca agc agt ttg tct gac cac agg cct gtg ata gag ctt ccc<br>Val Pro Ser Ser Leu Ser Asp His Arg Pro Val Ile Glu Leu Pro<br>　　　　1670　　　　　　　　1675　　　　　　　　1680 | | 5049 |
| cat tgt gag aac tct gaa att atc atc cga cta tat gaa atg cct<br>His Cys Glu Asn Ser Glu Ile Ile Ile Arg Leu Tyr Glu Met Pro<br>1685　　　　　　　　1690　　　　　　　　1695 | | 5094 |
| tat ttt cca atg gga ttt tgg tca aga tta atc aat cga tta ctt<br>Tyr Phe Pro Met Gly Phe Trp Ser Arg Leu Ile Asn Arg Leu Leu<br>　　1700　　　　　　　　1705　　　　　　　　1710 | | 5139 |
| gag att tca cct tac atg ctt tca ggg aga gaa cga gca ctt cgc<br>Glu Ile Ser Pro Tyr Met Leu Ser Gly Arg Glu Arg Ala Leu Arg<br>　　　1715　　　　　　　　1720　　　　　　　　1725 | | 5184 |
| cca aac aga atg tat tgg cga caa ggc att tac tta aat tgg tct<br>Pro Asn Arg Met Tyr Trp Arg Gln Gly Ile Tyr Leu Asn Trp Ser<br>　　　　1730　　　　　　　　1735　　　　　　　　1740 | | 5229 |
| cct gaa gct tat tgt ctg gta gga tct gaa gtc tta gac aat cat<br>Pro Glu Ala Tyr Cys Leu Val Gly Ser Glu Val Leu Asp Asn His<br>1745　　　　　　　　1750　　　　　　　　1755 | | 5274 |
| cca gag agt ttc tta aaa att aca gtt cct tct tgt aga aaa ggc<br>Pro Glu Ser Phe Leu Lys Ile Thr Val Pro Ser Cys Arg Lys Gly<br>　　1760　　　　　　　　1765　　　　　　　　1770 | | 5319 |
| tgt att ctt ttg ggc caa gtt gtg gac cac att gat tct ctc atg<br>Cys Ile Leu Leu Gly Gln Val Val Asp His Ile Asp Ser Leu Met<br>　　　1775　　　　　　　　1780　　　　　　　　1785 | | 5364 |
| gaa gaa tgg ttt cct ggg ttg ctg gag att gat att tgt ggt gaa<br>Glu Glu Trp Phe Pro Gly Leu Leu Glu Ile Asp Ile Cys Gly Glu<br>　　　　1790　　　　　　　　1795　　　　　　　　1800 | | 5409 |
| gga gaa act ctg ttg aag aaa tgg gca tta tat agt ttt aat gat<br>Gly Glu Thr Leu Leu Lys Lys Trp Ala Leu Tyr Ser Phe Asn Asp<br>1805　　　　　　　　1810　　　　　　　　1815 | | 5454 |
| ggt gaa gaa cat caa aaa atc tta ctt gat gac ttg atg aag aaa<br>Gly Glu Glu His Gln Lys Ile Leu Leu Asp Asp Leu Met Lys Lys<br>　　1820　　　　　　　　1825　　　　　　　　1830 | | 5499 |
| gca gag gaa gga gat ctc tta gta aat cca gat caa cca agg ctc<br>Ala Glu Glu Gly Asp Leu Leu Val Asn Pro Asp Gln Pro Arg Leu<br>　　　1835　　　　　　　　1840　　　　　　　　1845 | | 5544 |

```
                                                    -continued acc att cca ata tct cag att gcc cct gac ttg att ttg gct gac       5589
Thr Ile Pro Ile Ser Gln Ile Ala Pro Asp Leu Ile Leu Ala Asp
1850            1855                1860 ctg cct aga aat att atg ttg aat aat gat gag ttg gaa ttt gaa       5634
Leu Pro Arg Asn Ile Met Leu Asn Asn Asp Glu Leu Glu Phe Glu
    1865            1870                1875 caa gct cca gag ttt ctc cta ggt gat ggc agt ttt gga tca gtt       5679
Gln Ala Pro Glu Phe Leu Leu Gly Asp Gly Ser Phe Gly Ser Val
1880            1885                1890 tac cga gca gcc tat gaa gga gaa gaa gtg gct gtg aag att ttc       5724
Tyr Arg Ala Ala Tyr Glu Gly Glu Glu Val Ala Val Lys Ile Phe
    1895            1900                1905 aat aaa cat aca tca ctc agg ctg tta aga caa gag ctt gtg gtg       5769
Asn Lys His Thr Ser Leu Arg Leu Leu Arg Gln Glu Leu Val Val
1910            1915                1920 ctt tgc cac ctc cac cac ccc agt ttg ata tct ttg ctg gca gct       5814
Leu Cys His Leu His His Pro Ser Leu Ile Ser Leu Leu Ala Ala
    1925            1930                1935 ggg att cgt ccc cgg atg ttg gtg atg gag tta gcc tcc aag ggt       5859
Gly Ile Arg Pro Arg Met Leu Val Met Glu Leu Ala Ser Lys Gly
1940            1945                1950 tcc ttg gat cgc ctg ctt cag cag gac aaa gcc agc ctc act aga       5904
Ser Leu Asp Arg Leu Leu Gln Gln Asp Lys Ala Ser Leu Thr Arg
    1955            1960                1965 acc cta cag cac agg att gca ctc cac gta gct gat ggt ttg aga       5949
Thr Leu Gln His Arg Ile Ala Leu His Val Ala Asp Gly Leu Arg
1970            1975                1980 tac ctc cac tca gcc atg att ata tac cga gac ctg aaa ccc cac       5994
Tyr Leu His Ser Ala Met Ile Ile Tyr Arg Asp Leu Lys Pro His
    1985            1990                1995 aat gtg ctg ctt ttc aca ctg tat ccc aat gct gcc atc att gca       6039
Asn Val Leu Leu Phe Thr Leu Tyr Pro Asn Ala Ala Ile Ile Ala
2000            2005                2010 aag att gct gac tac ggc att gct cag tac tgc tgt aga atg ggg       6084
Lys Ile Ala Asp Tyr Gly Ile Ala Gln Tyr Cys Cys Arg Met Gly
    2015            2020                2025 ata aaa aca tca gag ggc aca cca ggg ttt cgt gca cct gaa gtt       6129
Ile Lys Thr Ser Glu Gly Thr Pro Gly Phe Arg Ala Pro Glu Val
2030            2035                2040 gcc aga gga aat gtc att tat aac caa cag gct gat gtt tat tca       6174
Ala Arg Gly Asn Val Ile Tyr Asn Gln Gln Ala Asp Val Tyr Ser
    2045            2050                2055 ttt ggt tta cta ctc tat gac att ttg aca act gga ggt aga ata       6219
Phe Gly Leu Leu Leu Tyr Asp Ile Leu Thr Thr Gly Gly Arg Ile
2060            2065                2070 gta gag ggt ttg aag ttt cca aat gag ttt gat gaa tta gaa ata       6264
Val Glu Gly Leu Lys Phe Pro Asn Glu Phe Asp Glu Leu Glu Ile
    2075            2080                2085 caa gga aaa tta cct gat cca gtt aaa gaa tat ggt tgt gcc cca       6309
Gln Gly Lys Leu Pro Asp Pro Val Lys Glu Tyr Gly Cys Ala Pro
2090            2095                2100 tgg cct atg gtt gag aaa tta att aaa cag tgt ttg aaa gaa aat       6354
Trp Pro Met Val Glu Lys Leu Ile Lys Gln Cys Leu Lys Glu Asn
    2105            2110                2115 cct caa gaa agg cct act tct gcc cag gtc ttt gac att ttg aat       6399
Pro Gln Glu Arg Pro Thr Ser Ala Gln Val Phe Asp Ile Leu Asn
2120            2125                2130 tca gct gaa tta gtc tgt ctg acg aga cgc att tta tta cct aaa       6444
Ser Ala Glu Leu Val Cys Leu Thr Arg Arg Ile Leu Leu Pro Lys
    2135            2140                2145
```

| | | | | | | | | | | | | | | |
|---|---|---|---|---|---|---|---|---|---|---|---|---|---|---|
| aac | gta | att | gtt | gaa | tgc | atg | gtt | gct | aca | cat | cac | aac | agc | agg | 6489 |
| Asn | Val | Ile | Val | Glu | Cys | Met | Val | Ala | Thr | His | His | Asn | Ser | Arg | |
| | 2150 | | | | 2155 | | | | 2160 | | | | | | |
| aat | gca | agc | att | tgg | ctg | ggc | tgt | ggg | cac | acc | gac | aga | gga | cag | 6534 |
| Asn | Ala | Ser | Ile | Trp | Leu | Gly | Cys | Gly | His | Thr | Asp | Arg | Gly | Gln | |
| | 2165 | | | | 2170 | | | | 2175 | | | | | | |
| ctc | tca | ttt | ctt | gac | tta | aat | act | gaa | gga | tac | act | tct | gag | gaa | 6579 |
| Leu | Ser | Phe | Leu | Asp | Leu | Asn | Thr | Glu | Gly | Tyr | Thr | Ser | Glu | Glu | |
| | 2180 | | | | 2185 | | | | 2190 | | | | | | |
| gtt | gct | gat | agt | aga | ata | ttg | tgc | tta | gcc | ttg | gtg | cat | ctt | cct | 6624 |
| Val | Ala | Asp | Ser | Arg | Ile | Leu | Cys | Leu | Ala | Leu | Val | His | Leu | Pro | |
| | 2195 | | | | 2200 | | | | 2205 | | | | | | |
| gtt | gaa | aag | gaa | agc | tgg | att | gtg | tct | ggg | aca | cag | tct | ggt | act | 6669 |
| Val | Glu | Lys | Glu | Ser | Trp | Ile | Val | Ser | Gly | Thr | Gln | Ser | Gly | Thr | |
| | 2210 | | | | 2215 | | | | 2220 | | | | | | |
| ctc | ctg | gtc | atc | aat | acc | gaa | gat | ggg | aaa | aag | aga | cat | acc | cta | 6714 |
| Leu | Leu | Val | Ile | Asn | Thr | Glu | Asp | Gly | Lys | Lys | Arg | His | Thr | Leu | |
| | 2225 | | | | 2230 | | | | 2235 | | | | | | |
| gaa | aag | atg | act | gat | tct | gtc | act | tgt | ttg | tat | tgc | aat | tcc | ttt | 6759 |
| Glu | Lys | Met | Thr | Asp | Ser | Val | Thr | Cys | Leu | Tyr | Cys | Asn | Ser | Phe | |
| | 2240 | | | | 2245 | | | | 2250 | | | | | | |
| tcc | aag | caa | agc | aaa | caa | aaa | aat | ttt | ctt | ttg | gtt | gga | acc | gct | 6804 |
| Ser | Lys | Gln | Ser | Lys | Gln | Lys | Asn | Phe | Leu | Leu | Val | Gly | Thr | Ala | |
| | 2255 | | | | 2260 | | | | 2265 | | | | | | |
| gat | ggc | aag | tta | gca | att | ttt | gaa | gat | aag | act | gtt | aag | ctt | aaa | 6849 |
| Asp | Gly | Lys | Leu | Ala | Ile | Phe | Glu | Asp | Lys | Thr | Val | Lys | Leu | Lys | |
| | 2270 | | | | 2275 | | | | 2280 | | | | | | |
| gga | gct | gct | cct | ttg | aag | ata | cta | aat | ata | gga | aat | gtc | agt | act | 6894 |
| Gly | Ala | Ala | Pro | Leu | Lys | Ile | Leu | Asn | Ile | Gly | Asn | Val | Ser | Thr | |
| | 2285 | | | | 2290 | | | | 2295 | | | | | | |
| cca | ttg | atg | tgt | ttg | agt | gaa | tcc | aca | aat | tca | acg | gaa | aga | aat | 6939 |
| Pro | Leu | Met | Cys | Leu | Ser | Glu | Ser | Thr | Asn | Ser | Thr | Glu | Arg | Asn | |
| | 2300 | | | | 2305 | | | | 2310 | | | | | | |
| gta | atg | tgg | gga | gga | tgt | ggc | aca | aag | att | ttc | tcc | ttt | tct | aat | 6984 |
| Val | Met | Trp | Gly | Gly | Cys | Gly | Thr | Lys | Ile | Phe | Ser | Phe | Ser | Asn | |
| | 2315 | | | | 2320 | | | | 2325 | | | | | | |
| gat | ttc | acc | att | cag | aaa | ctc | att | gag | aca | aga | aca | agc | caa | ctg | 7029 |
| Asp | Phe | Thr | Ile | Gln | Lys | Leu | Ile | Glu | Thr | Arg | Thr | Ser | Gln | Leu | |
| | 2330 | | | | 2335 | | | | 2340 | | | | | | |
| ttt | tct | tat | gca | gct | ttc | agt | gat | tcc | aac | atc | ata | aca | gtg | gtg | 7074 |
| Phe | Ser | Tyr | Ala | Ala | Phe | Ser | Asp | Ser | Asn | Ile | Ile | Thr | Val | Val | |
| | 2345 | | | | 2350 | | | | 2355 | | | | | | |
| gta | gac | act | gct | ctc | tat | att | gct | aag | caa | aat | agc | cct | gtt | gtg | 7119 |
| Val | Asp | Thr | Ala | Leu | Tyr | Ile | Ala | Lys | Gln | Asn | Ser | Pro | Val | Val | |
| | 2360 | | | | 2365 | | | | 2370 | | | | | | |
| gaa | gtg | tgg | gat | aag | aaa | act | gaa | aaa | ctc | tgt | gga | cta | ata | gac | 7164 |
| Glu | Val | Trp | Asp | Lys | Lys | Thr | Glu | Lys | Leu | Cys | Gly | Leu | Ile | Asp | |
| | 2375 | | | | 2380 | | | | 2385 | | | | | | |
| tgc | gtg | cac | ttt | tta | agg | gag | gta | atg | gta | aaa | gaa | aac | aag | gaa | 7209 |
| Cys | Val | His | Phe | Leu | Arg | Glu | Val | Met | Val | Lys | Glu | Asn | Lys | Glu | |
| | 2390 | | | | 2395 | | | | 2400 | | | | | | |
| tca | aaa | cac | aaa | atg | tct | tat | tct | ggg | aga | gtg | aaa | acc | ctc | tgc | 7254 |
| Ser | Lys | His | Lys | Met | Ser | Tyr | Ser | Gly | Arg | Val | Lys | Thr | Leu | Cys | |
| | 2405 | | | | 2410 | | | | 2415 | | | | | | |
| ctt | cag | aag | aac | act | gct | ctt | tgg | ata | gga | act | gga | gga | ggc | cat | 7299 |
| Leu | Gln | Lys | Asn | Thr | Ala | Leu | Trp | Ile | Gly | Thr | Gly | Gly | Gly | His | |
| | 2420 | | | | 2425 | | | | 2430 | | | | | | |
| att | tta | ctc | ctg | gat | ctt | tca | act | cgt | cga | ctt | ata | cgt | gta | att | 7344 |
| Ile | Leu | Leu | Leu | Asp | Leu | Ser | Thr | Arg | Arg | Leu | Ile | Arg | Val | Ile | |
| | 2435 | | | | 2440 | | | | 2445 | | | | | | |

| | | | | | | | | | | | | | |
|---|---|---|---|---|---|---|---|---|---|---|---|---|---|
| tac | aac | ttt | tgt | aat | tcg | gtc | aga | gtc | atg | atg | aca | gca cag cta | 7389 |
| Tyr | Asn | Phe | Cys | Asn | Ser | Val | Arg | Val | Met | Met | Thr | Ala Gln Leu | |
| | 2450 | | | | 2455 | | | | 2460 | | | | |
| gga | agc | ctt | aaa | aat | gtc | atg | ctg | gta | ttg | ggc | tac | aac cgg aaa | 7434 |
| Gly | Ser | Leu | Lys | Asn | Val | Met | Leu | Val | Leu | Gly | Tyr | Asn Arg Lys | |
| | 2465 | | | | 2470 | | | | 2475 | | | | |
| aat | act | gaa | ggt | aca | caa | aag | cag | aaa | gag | ata | caa | tct tgc ttg | 7479 |
| Asn | Thr | Glu | Gly | Thr | Gln | Lys | Gln | Lys | Glu | Ile | Gln | Ser Cys Leu | |
| | 2480 | | | | 2485 | | | | 2490 | | | | |
| acc | gtt | tgg | gac | atc | aat | ctt | cca | cat | gaa | gtg | caa | aat tta gaa | 7524 |
| Thr | Val | Trp | Asp | Ile | Asn | Leu | Pro | His | Glu | Val | Gln | Asn Leu Glu | |
| | 2495 | | | | 2500 | | | | 2505 | | | | |
| aaa | cac | att | gaa | gtg | aga | aaa | gaa | tta | gct | gaa | aaa | atg aga cga | 7569 |
| Lys | His | Ile | Glu | Val | Arg | Lys | Glu | Leu | Ala | Glu | Lys | Met Arg Arg | |
| | 2510 | | | | 2515 | | | | 2520 | | | | |
| aca | tct | gtt | gag | taa | gagagaaata | | ggaattgtct | | ttggatagga | | aaattattct | | 7624 |
| Thr | Ser | Val | Glu | | | | | | | | | | |
| | 2525 | | | | | | | | | | | | |

| | | | | |
|---|---|---|---|---|
| ctcctcttgt | aaatatttat | tttaaaaatg | ttcacatgga | aagggtactc acatttttg | 7684 |
| aaatagctcg | tgtgtatgaa | ggaatgttat | tatttttaat | ttaaatatat gtaaaaatac | 7744 |
| ttaccagtaa | atgtgtattt | taagaactta | tttaaaacac | aatgttatat ttcttataaa | 7804 |
| taccagttac | tttcgttcat | taattaatga | aaataaatct | gtgaagtacc taatttaagt | 7864 |
| actcatacta | aaatttataa | ggccgataat | ttttgtttt | cttgtctgta atggaggtaa | 7924 |
| actttatttt | aaattctgtg | cttaagacag | gactattgct | tgtcgatttt tctagaaatc | 7984 |
| tgcacggtat | aatgaaaata | ttaagacagt | ttcccatgta | atgtattcct tcttagattg | 8044 |
| catcgaaatg | cactatcata | tatgcttgta | aatattcaaa | tgaatttgca ctaataaagt | 8104 |
| cctttgttgg | tatgtgaatt | ctctttgttg | ctgttgcaaa | cagtgcatct tacacaactt | 8164 |
| cactcaattc | aaaagaaaac | tccattaaaa | gtactaatga | aaaaacatga catactgtca | 8224 |
| aagtcctcat | atctaggaaa | gacacagaaa | ctctctttgt | cacagaaact ctctgtgtct | 8284 |
| ttcctagaca | taatagagtt | gtttttcaac | tctatgtttg | aatgtggata ccctgaattt | 8344 |
| tgtataatta | gtgtaaatac | agtgttcagt | ccttcaagtg | atattttat tttttttattc | 8404 |
| ataccactag | ctacttgttt | tctaatctgc | ttcattctaa | tgcttatatt catcttttcc | 8464 |
| ctaaatttgt | gatgctgcag | atcctacatc | attcagatag | aaacctttt ttttttcaga | 8524 |
| attatagaat | tccacagctc | ctaccaagac | catgaggata | aatatctaac acttttcagt | 8584 |
| tgctgaagga | gaaaggagct | ttagttatga | tggataaaaa | tatctgccac cctaggcttc | 8644 |
| caaattatac | ttaaattgtt | tacatagctt | accacaatag | gagtatcagg gccaaatacc | 8704 |
| tatgtaataa | tttgaggtca | tttctgcttt | aggaaaagta | ctttcggtaa attctttggc | 8764 |
| cctgaccagt | attcattatt | tcagataatt | ccctgtgata | ggacaactag tacatttaat | 8824 |
| attctcagaa | cttatggcat | tttactatgt | gaaaacttta | aatttattta tattaagggt | 8884 |
| aatcaaattc | ttaaagatga | aagatttttct | gtatttaaaa | ggaagctatg ctttaacttg | 8944 |
| ttatgtaatt | aacaaaaaaa | tcatatataa | tagagctctt | tgttccagtg ttatctcttt | 9004 |
| cattgttact | ttgtatttgc | aatttttttt | accaaagaca | aattaaaaaa atgaatacca | 9064 |
| tatttaaatg | gaataataaa | ggttttttaa | aaactttaaa | | 9104 |

<210> SEQ ID NO 2
<211> LENGTH: 9104
<212> TYPE: DNA
<213> ORGANISM: Homo sapiens -continued

```
<220> FEATURE:
<221> NAME/KEY: exon
<222> LOCATION: (1)..(7584)

<400> SEQUENCE: 2 atg gct agt ggc agc tgt cag ggg tgc gaa gag gac gag gaa act ctg      48
Met Ala Ser Gly Ser Cys Gln Gly Cys Glu Glu Asp Glu Glu Thr Leu
1               5                   10                  15 aag aag ttg ata gtc agg ctg aac aat gtc cag gaa gga aaa cag ata      96
Lys Lys Leu Ile Val Arg Leu Asn Asn Val Gln Glu Gly Lys Gln Ile
            20                  25                  30 gaa acg ctg gtc caa atc ctg gag gat ctg ctg gtg ttc acg tac tcc     144
Glu Thr Leu Val Gln Ile Leu Glu Asp Leu Leu Val Phe Thr Tyr Ser
        35                  40                  45 gag cac gcc tcc aag tta ttt caa ggc aaa aat atc cat gtg cct ctg     192
Glu His Ala Ser Lys Leu Phe Gln Gly Lys Asn Ile His Val Pro Leu
    50                  55                  60 ttg atc gtc ttg gac tcc tat atg aga gtc gcg agt gtg cag cag gtg     240
Leu Ile Val Leu Asp Ser Tyr Met Arg Val Ala Ser Val Gln Gln Val
65                  70                  75                  80 ggt tgg tca ctt ctg tgc aaa tta ata gaa gtc tgt cca ggt aca atg     288
Gly Trp Ser Leu Leu Cys Lys Leu Ile Glu Val Cys Pro Gly Thr Met
                85                  90                  95 caa agc tta atg gga ccc cag gat gtt gga aat gat tgg gaa gtc ctt     336
Gln Ser Leu Met Gly Pro Gln Asp Val Gly Asn Asp Trp Glu Val Leu
            100                 105                 110 ggt gtt cac caa ttg att ctt aaa atg cta aca gtt cat aat gcc agt     384
Gly Val His Gln Leu Ile Leu Lys Met Leu Thr Val His Asn Ala Ser
        115                 120                 125 gta aac ttg tca gtg att gga ctg aag acc tta gat ctc ctc cta act     432
Val Asn Leu Ser Val Ile Gly Leu Lys Thr Leu Asp Leu Leu Leu Thr
    130                 135                 140 tca ggt aaa atc acc ttg ctg ata ctg gat gaa gaa agt gat att ttc     480
Ser Gly Lys Ile Thr Leu Leu Ile Leu Asp Glu Glu Ser Asp Ile Phe
145                 150                 155                 160 atg tta att ttt gat gcc atg cac tca ttt cca gcc aat gat gaa gtc     528
Met Leu Ile Phe Asp Ala Met His Ser Phe Pro Ala Asn Asp Glu Val
                165                 170                 175 cag aaa ctt gga tgc aaa gct tta cat gtg ctg ttt gag aga gtc tca     576
Gln Lys Leu Gly Cys Lys Ala Leu His Val Leu Phe Glu Arg Val Ser
            180                 185                 190 gag gag caa ctg act gaa ttt gtt gag aac aaa gat tat atg ata ttg     624
Glu Glu Gln Leu Thr Glu Phe Val Glu Asn Lys Asp Tyr Met Ile Leu
        195                 200                 205 tta agt gcg tca aca aat ttt aaa gat gaa gag gaa att gtg ctt cat     672
Leu Ser Ala Ser Thr Asn Phe Lys Asp Glu Glu Glu Ile Val Leu His
    210                 215                 220 gtg ctg cat tgt tta cat tcc cta gcg att cct tgc aat aat gtg gaa     720
Val Leu His Cys Leu His Ser Leu Ala Ile Pro Cys Asn Asn Val Glu
225                 230                 235                 240 gtc ctc atg agt ggc aat gtc agg tgt tat aat att gtg gtg gaa gct     768
Val Leu Met Ser Gly Asn Val Arg Cys Tyr Asn Ile Val Val Glu Ala
                245                 250                 255 atg aaa gca ttc cct atg agt gaa aga att caa gaa gtg agt tgc tgt     816
Met Lys Ala Phe Pro Met Ser Glu Arg Ile Gln Glu Val Ser Cys Cys
            260                 265                 270 ttg ctc cat agg ctt aca tta ggt aat ttt ttc aat atc ctg gta tta     864
Leu Leu His Arg Leu Thr Leu Gly Asn Phe Phe Asn Ile Leu Val Leu
        275                 280                 285 aac gaa gtc cat gag ttt gtg gtg aaa gct gtg cag cag tac cca gag     912
Asn Glu Val His Glu Phe Val Val Lys Ala Val Gln Gln Tyr Pro Glu
```

```
                   290                  295                  300
aat gca gca ttg cag atc tca gcg ctc agc tgt ttg gcc ctc ctc act        960
Asn Ala Ala Leu Gln Ile Ser Ala Leu Ser Cys Leu Ala Leu Leu Thr
305                 310                  315                 320 gag act att ttc tta aat caa gat tta gag gaa aag aat gag aat caa       1008
Glu Thr Ile Phe Leu Asn Gln Asp Leu Glu Glu Lys Asn Glu Asn Gln
                325                  330                  335 gag aat gat gat gag ggg gaa gaa gat aaa ttg ttt tgg ctg gaa gcc       1056
Glu Asn Asp Asp Glu Gly Glu Glu Asp Lys Leu Phe Trp Leu Glu Ala
                340                  345                  350 tgt tac aaa gca tta acg tgg cat aga aag aac aag cac gtg cag gag       1104
Cys Tyr Lys Ala Leu Thr Trp His Arg Lys Asn Lys His Val Gln Glu
                355                  360                  365 gcc gca tgc tgg gca cta aat aat ctc ctt atg tac caa aac agt tta       1152
Ala Ala Cys Trp Ala Leu Asn Asn Leu Leu Met Tyr Gln Asn Ser Leu
                370                  375                  380 cat gag aag att gga gat gaa gat ggc cat ttc cca gct cat agg gaa       1200
His Glu Lys Ile Gly Asp Glu Asp Gly His Phe Pro Ala His Arg Glu
385                 390                  395                 400 gtg atg ctc tcc atg ctg atg cat tct tca tca aag gaa gtt ttc cag       1248
Val Met Leu Ser Met Leu Met His Ser Ser Ser Lys Glu Val Phe Gln
                405                  410                  415 gca tct gcg aat gca ttg tca act ctc tta gaa caa aat gtt aat ttc       1296
Ala Ser Ala Asn Ala Leu Ser Thr Leu Leu Glu Gln Asn Val Asn Phe
                420                  425                  430 aga aaa ata ctg tta tca aaa gga ata cac ctg aat gtt ttg gag tta       1344
Arg Lys Ile Leu Leu Ser Lys Gly Ile His Leu Asn Val Leu Glu Leu
                435                  440                  445 atg cag aag cat ata cat tct cct gaa gtg gct gaa agt ggc tgt aaa       1392
Met Gln Lys His Ile His Ser Pro Glu Val Ala Glu Ser Gly Cys Lys
                450                  455                  460 atg cta aat cat ctt ttt gaa gga agc aac act tcc ctg gat ata atg       1440
Met Leu Asn His Leu Phe Glu Gly Ser Asn Thr Ser Leu Asp Ile Met
465                 470                  475                 480 gca gca gtg gtc ccc aaa ata cta aca gtt atg aaa cgt cat gag aca       1488
Ala Ala Val Val Pro Lys Ile Leu Thr Val Met Lys Arg His Glu Thr
                485                  490                  495 tca tta cca gtg cag ctg gag gcg ctt cga gct att tta cat ttt ata       1536
Ser Leu Pro Val Gln Leu Glu Ala Leu Arg Ala Ile Leu His Phe Ile
                500                  505                  510 gtg cct ggc atg cca gaa gaa tcc agg gag gat aca gaa ttt cat cat       1584
Val Pro Gly Met Pro Glu Glu Ser Arg Glu Asp Thr Glu Phe His His
                515                  520                  525 aag cta aat atg gtt aaa aaa cag tgt ttc aag aat gat att cac aaa       1632
Lys Leu Asn Met Val Lys Lys Gln Cys Phe Lys Asn Asp Ile His Lys
                530                  535                  540 ctg gtc cta gca gct ttg aac agg ttc att gga aat cct ggg att cag       1680
Leu Val Leu Ala Ala Leu Asn Arg Phe Ile Gly Asn Pro Gly Ile Gln
545                 550                  555                 560 aaa tgt gga tta aaa gta att tct tct att gta cat ttt cct gat gca       1728
Lys Cys Gly Leu Lys Val Ile Ser Ser Ile Val His Phe Pro Asp Ala
                565                  570                  575 tta gag atg tta tcc ctg gaa ggt gct atg gat tca gtg ctt cac aca       1776
Leu Glu Met Leu Ser Leu Glu Gly Ala Met Asp Ser Val Leu His Thr
                580                  585                  590 ctg cag atg tat cca gat gac caa gaa att cag tgt ctg ggt tta agt       1824
Leu Gln Met Tyr Pro Asp Asp Gln Glu Ile Gln Cys Leu Gly Leu Ser
                595                  600                  605 ctt ata gga tac ttg att aca aag aag aat gtg ttc ata gga act gga       1872
Leu Ile Gly Tyr Leu Ile Thr Lys Lys Asn Val Phe Ile Gly Thr Gly
```

```
                                                                 -continued
         610                615                620
cat ctg ctg gca aaa att ctg gtt tcc agc tta tac cga ttt aag gat   1920
His Leu Leu Ala Lys Ile Leu Val Ser Ser Leu Tyr Arg Phe Lys Asp
625                 630                 635                 640 gtt gct gaa ata cag act aaa gga ttt cag aca atc tta gca atc ctc   1968
Val Ala Glu Ile Gln Thr Lys Gly Phe Gln Thr Ile Leu Ala Ile Leu
                    645                 650                 655 aaa ttg tca gca tct ttt tct aag ctg ctg gtg cat cat tca ttt gac   2016
Lys Leu Ser Ala Ser Phe Ser Lys Leu Leu Val His His Ser Phe Asp
                660                 665                 670 tta gta ata ttc cat caa atg tct tcc aat atc atg gaa caa aag gat   2064
Leu Val Ile Phe His Gln Met Ser Ser Asn Ile Met Glu Gln Lys Asp
            675                 680                 685 caa cag ttt cta aac ctc tgt tgc aag tgt ttt gca aaa gta gct atg   2112
Gln Gln Phe Leu Asn Leu Cys Cys Lys Cys Phe Ala Lys Val Ala Met
        690                 695                 700 gat gat tac tta aaa aat gtg atg cta gag aga gcg tgt gat cag aat   2160
Asp Asp Tyr Leu Lys Asn Val Met Leu Glu Arg Ala Cys Asp Gln Asn
705                 710                 715                 720 aac agc atc atg gtt gaa tgc ttg ctt cta ttg gga gca gat gcc aat   2208
Asn Ser Ile Met Val Glu Cys Leu Leu Leu Leu Gly Ala Asp Ala Asn
                    725                 730                 735 caa gca aag gag gga tct tct tta att tgt cag gta tgt gag aaa gag   2256
Gln Ala Lys Glu Gly Ser Ser Leu Ile Cys Gln Val Cys Glu Lys Glu
                740                 745                 750 agc agt ccc aaa ttg gtg gaa ctc tta ctg aat agt gga tct cgt gaa   2304
Ser Ser Pro Lys Leu Val Glu Leu Leu Leu Asn Ser Gly Ser Arg Glu
            755                 760                 765 caa gat gta cga aaa gcg ttg acg ata agc att ggg aaa ggt gac agc   2352
Gln Asp Val Arg Lys Ala Leu Thr Ile Ser Ile Gly Lys Gly Asp Ser
        770                 775                 780 cag atc atc agc ttg ctc tta agg agg ctg gcc ctg gat gtg gcc aac   2400
Gln Ile Ile Ser Leu Leu Leu Arg Arg Leu Ala Leu Asp Val Ala Asn
785                 790                 795                 800 aat agc att tgc ctt gga gga ttt tgt ata gga aaa gtt gaa cct tct   2448
Asn Ser Ile Cys Leu Gly Gly Phe Cys Ile Gly Lys Val Glu Pro Ser
                    805                 810                 815 tgg ctt ggt cct tta ttt cca gat aag act tct aat tta agg aaa caa   2496
Trp Leu Gly Pro Leu Phe Pro Asp Lys Thr Ser Asn Leu Arg Lys Gln
                820                 825                 830 aca aat ata gca tct aca cta gca aga atg gtg atc aga tat cag atg   2544
Thr Asn Ile Ala Ser Thr Leu Ala Arg Met Val Ile Arg Tyr Gln Met
            835                 840                 845 aaa agt gct gtg gaa gaa gga aca gcc tca ggc agc gat gga aat ttt   2592
Lys Ser Ala Val Glu Glu Gly Thr Ala Ser Gly Ser Asp Gly Asn Phe
        850                 855                 860 tct gaa gat gtg ctg tct aaa ttt gat gaa tgg acc ttt att cct gac   2640
Ser Glu Asp Val Leu Ser Lys Phe Asp Glu Trp Thr Phe Ile Pro Asp
865                 870                 875                 880 tct tct atg gac agt gtg ttt gct caa agt gat gac ctg gat agt gaa   2688
Ser Ser Met Asp Ser Val Phe Ala Gln Ser Asp Asp Leu Asp Ser Glu
                    885                 890                 895 gga agt gaa ggc tca ttt ctt gtg aaa aag aaa tct aat tca att agt   2736
Gly Ser Glu Gly Ser Phe Leu Val Lys Lys Lys Ser Asn Ser Ile Ser
                900                 905                 910 gta gga gaa ttt tac cga gat gcc gta tta cag cgt tgc tca cca aat   2784
Val Gly Glu Phe Tyr Arg Asp Ala Val Leu Gln Arg Cys Ser Pro Asn
            915                 920                 925 ttg caa aga cat tcc aat tcc ttg ggg ccc att ttt gat cat gaa gat   2832
Leu Gln Arg His Ser Asn Ser Leu Gly Pro Ile Phe Asp His Glu Asp
```

|     |     |     |     |     |     |     |     |     |     |     |     |     |     |     |     |
|---|---|---|---|---|---|---|---|---|---|---|---|---|---|---|---|
| | | 930 | | | | 935 | | | | 940 | | | | | |
| tta | ctg | aag | cga | aaa | aga | aaa | ata | cta | tct | tca | gat | gat | tca | ctc | agg | 2880 |
| Leu | Leu | Lys | Arg | Lys | Arg | Lys | Ile | Leu | Ser | Ser | Asp | Asp | Ser | Leu | Arg |
| 945 | | | | 950 | | | | 955 | | | | 960 | | | |
| tca | tca | aaa | ctt | caa | tcc | cat | atg | agg | cat | tca | gac | agc | att | tct | tct | 2928 |
| Ser | Ser | Lys | Leu | Gln | Ser | His | Met | Arg | His | Ser | Asp | Ser | Ile | Ser | Ser |
| | | | | 965 | | | | 970 | | | | 975 | | | |
| ctg | gct | tct | gag | aga | gaa | tat | att | aca | tca | cta | gac | ctt | tca | gca | aat | 2976 |
| Leu | Ala | Ser | Glu | Arg | Glu | Tyr | Ile | Thr | Ser | Leu | Asp | Leu | Ser | Ala | Asn |
| | | | 980 | | | | 985 | | | | 990 | | | | |
| gaa | cta | aga | gat | att | gat | gcc | cta | agc | cag | aaa | tgc | tgt | ata | agt | gtt | 3024 |
| Glu | Leu | Arg | Asp | Ile | Asp | Ala | Leu | Ser | Gln | Lys | Cys | Cys | Ile | Ser | Val |
| | | 995 | | | | 1000 | | | | 1005 | | | | | |
| cat | ttg | gag | cat | ctt | gaa | aag | ctg | gag | ctt | cac | cag | aat | gca | ctc | | 3069 |
| His | Leu | Glu | His | Leu | Glu | Lys | Leu | Glu | Leu | His | Gln | Asn | Ala | Leu | |
| | 1010 | | | | 1015 | | | | 1020 | | | | | | |
| acg | agc | ttt | cca | caa | cag | cta | tgt | gaa | act | ctg | aag | agt | ttg | aca | | 3114 |
| Thr | Ser | Phe | Pro | Gln | Gln | Leu | Cys | Glu | Thr | Leu | Lys | Ser | Leu | Thr | |
| 1025 | | | | 1030 | | | | 1035 | | | | | | | |
| cat | ttg | gac | ttg | cac | agt | aat | aaa | ttt | aca | tca | ttt | cct | tct | tat | | 3159 |
| His | Leu | Asp | Leu | His | Ser | Asn | Lys | Phe | Thr | Ser | Phe | Pro | Ser | Tyr | |
| 1040 | | | | 1045 | | | | 1050 | | | | | | | |
| ttg | ttg | aaa | atg | agt | tgt | att | gct | aat | ctt | gat | gtc | tct | cga | aat | | 3204 |
| Leu | Leu | Lys | Met | Ser | Cys | Ile | Ala | Asn | Leu | Asp | Val | Ser | Arg | Asn |
| 1055 | | | | 1060 | | | | 1065 | | | | | | | |
| gac | att | gga | ccc | tca | gtg | gtt | tta | gat | cct | aca | gtg | aaa | tgt | cca | | 3249 |
| Asp | Ile | Gly | Pro | Ser | Val | Val | Leu | Asp | Pro | Thr | Val | Lys | Cys | Pro |
| 1070 | | | | 1075 | | | | 1080 | | | | | | | |
| act | ctg | aaa | cag | ttt | aac | ctg | tca | tat | aac | cag | ctg | tct | ttt | gta | | 3294 |
| Thr | Leu | Lys | Gln | Phe | Asn | Leu | Ser | Tyr | Asn | Gln | Leu | Ser | Phe | Val |
| 1085 | | | | 1090 | | | | 1095 | | | | | | | |
| cct | gag | aac | ctc | act | gat | gtg | gta | gag | aaa | ctg | gag | cag | ctc | att | | 3339 |
| Pro | Glu | Asn | Leu | Thr | Asp | Val | Val | Glu | Lys | Leu | Glu | Gln | Leu | Ile |
| | 1100 | | | | 1105 | | | | 1110 | | | | | | |
| tta | gaa | gga | aat | aaa | ata | tca | ggg | ata | tgc | tcc | ccc | ttg | aga | ctg | | 3384 |
| Leu | Glu | Gly | Asn | Lys | Ile | Ser | Gly | Ile | Cys | Ser | Pro | Leu | Arg | Leu |
| 1115 | | | | 1120 | | | | 1125 | | | | | | | |
| aag | gaa | ctg | aag | att | tta | aac | ctt | agt | aag | aac | cac | att | tca | tcc | | 3429 |
| Lys | Glu | Leu | Lys | Ile | Leu | Asn | Leu | Ser | Lys | Asn | His | Ile | Ser | Ser |
| 1130 | | | | 1135 | | | | 1140 | | | | | | | |
| cta | tca | gag | aac | ttt | ctt | gag | gct | tgt | cct | aaa | gtg | gag | agt | ttc | | 3474 |
| Leu | Ser | Glu | Asn | Phe | Leu | Glu | Ala | Cys | Pro | Lys | Val | Glu | Ser | Phe |
| 1145 | | | | 1150 | | | | 1155 | | | | | | | |
| agt | gcc | aga | atg | aat | ttt | ctt | gct | gct | atg | cct | ttg | cct | cct | | | 3519 |
| Ser | Ala | Arg | Met | Asn | Phe | Leu | Ala | Ala | Met | Pro | Phe | Leu | Pro | Pro |
| 1160 | | | | 1165 | | | | 1170 | | | | | | | |
| tct | atg | aca | atc | cta | aaa | tta | tct | cag | aac | aaa | ttt | tcc | tgt | att | | 3564 |
| Ser | Met | Thr | Ile | Leu | Lys | Leu | Ser | Gln | Asn | Lys | Phe | Ser | Cys | Ile |
| 1175 | | | | 1180 | | | | 1185 | | | | | | | |
| cca | gaa | gca | att | tta | aat | ctt | cca | cac | ttg | cgg | tct | tta | gat | atg | | 3609 |
| Pro | Glu | Ala | Ile | Leu | Asn | Leu | Pro | His | Leu | Arg | Ser | Leu | Asp | Met |
| | 1190 | | | | 1195 | | | | 1200 | | | | | | |
| agc | agc | aat | gat | att | cag | tac | cta | cca | ggt | ccc | gca | cac | tgg | aaa | | 3654 |
| Ser | Ser | Asn | Asp | Ile | Gln | Tyr | Leu | Pro | Gly | Pro | Ala | His | Trp | Lys |
| 1205 | | | | 1210 | | | | 1215 | | | | | | | |
| tct | ttg | aac | tta | agg | gaa | ctc | tta | ttt | agc | cat | aat | cag | atc | agc | | 3699 |
| Ser | Leu | Asn | Leu | Arg | Glu | Leu | Leu | Phe | Ser | His | Asn | Gln | Ile | Ser |
| 1220 | | | | 1225 | | | | 1230 | | | | | | | |
| atc | ttg | gac | ttg | agt | gaa | aaa | gca | tat | tta | tgg | tct | aga | gta | gag | | 3744 |
| Ile | Leu | Asp | Leu | Ser | Glu | Lys | Ala | Tyr | Leu | Trp | Ser | Arg | Val | Glu |

```
                    1235                  1240                  1245
aaa ctg cat ctt tct cac aat aaa ctg aaa gag att cct cct gag    3789
Lys Leu His Leu Ser His Asn Lys Leu Lys Glu Ile Pro Pro Glu
1250                  1255                  1260 att ggc tgt ctt gaa aat ctg aca tct ctg gat gtc agt tac aac    3834
Ile Gly Cys Leu Glu Asn Leu Thr Ser Leu Asp Val Ser Tyr Asn
1265                  1270                  1275 ttg gaa cta aga tcc ttt ccc aat gaa atg ggg aaa tta agc aaa    3879
Leu Glu Leu Arg Ser Phe Pro Asn Glu Met Gly Lys Leu Ser Lys
1280                  1285                  1290 ata tgg gat ctt cct ttg gat gaa ctg cat ctt aac ttt gat ttt    3924
Ile Trp Asp Leu Pro Leu Asp Glu Leu His Leu Asn Phe Asp Phe
1295                  1300                  1305 aaa cat ata gga tgt aaa gcc aaa gac atc ata agg ttt ctt caa    3969
Lys His Ile Gly Cys Lys Ala Lys Asp Ile Ile Arg Phe Leu Gln
1310                  1315                  1320 cag cga tta aaa aag gct gtg cct tat aac cga atg aaa ctt atg    4014
Gln Arg Leu Lys Lys Ala Val Pro Tyr Asn Arg Met Lys Leu Met
1325                  1330                  1335 att gtg gga aat act ggg agt ggt aaa acc acc tta ttg cag caa    4059
Ile Val Gly Asn Thr Gly Ser Gly Lys Thr Thr Leu Leu Gln Gln
1340                  1345                  1350 tta atg aaa acc aag aaa tca gat ctt gga atg caa agt gcc aca    4104
Leu Met Lys Thr Lys Lys Ser Asp Leu Gly Met Gln Ser Ala Thr
1355                  1360                  1365 gtt ggc ata gat gtg aaa gac tgg cct atc caa ata aga gac aaa    4149
Val Gly Ile Asp Val Lys Asp Trp Pro Ile Gln Ile Arg Asp Lys
1370                  1375                  1380 aga aag aga gat ctc gtc cta aat gtg tgg gat ttt gca ggt cgt    4194
Arg Lys Arg Asp Leu Val Leu Asn Val Trp Asp Phe Ala Gly Arg
1385                  1390                  1395 gag gaa ttc tat agt act cat ccc cat ttt atg acg cag cga gca    4239
Glu Glu Phe Tyr Ser Thr His Pro His Phe Met Thr Gln Arg Ala
1400                  1405                  1410 ttg tac ctt gct gtc tat gac ctc agc aag gga cag gct gaa gtt    4284
Leu Tyr Leu Ala Val Tyr Asp Leu Ser Lys Gly Gln Ala Glu Val
1415                  1420                  1425 gat gcc atg aag cct tgg ctc ttc aat ata aag gct cgc gct tct    4329
Asp Ala Met Lys Pro Trp Leu Phe Asn Ile Lys Ala Arg Ala Ser
1430                  1435                  1440 tct tcc cct gtg att ctc gtt ggc aca cat ttg gat gtt tct gat    4374
Ser Ser Pro Val Ile Leu Val Gly Thr His Leu Asp Val Ser Asp
1445                  1450                  1455 gag aag caa cgc aaa gcc tgc atg agt aaa atc acc aag gaa ctc    4419
Glu Lys Gln Arg Lys Ala Cys Met Ser Lys Ile Thr Lys Glu Leu
1460                  1465                  1470 ctg aat aag cga ggg ttc cct gcc ata cga gat tac cac ttt gtg    4464
Leu Asn Lys Arg Gly Phe Pro Ala Ile Arg Asp Tyr His Phe Val
1475                  1480                  1485 aat gcc acc gag gaa tct gat gct ttg gca aaa ctt cgg aaa acc    4509
Asn Ala Thr Glu Glu Ser Asp Ala Leu Ala Lys Leu Arg Lys Thr
1490                  1495                  1500 atc ata aac gag agc ctt aat ttc aag atc cga gat cag ctt gtt    4554
Ile Ile Asn Glu Ser Leu Asn Phe Lys Ile Arg Asp Gln Leu Val
1505                  1510                  1515 gtt gga cag ctg att cca gac tgc tat gta gaa ctt gaa aaa atc    4599
Val Gly Gln Leu Ile Pro Asp Cys Tyr Val Glu Leu Glu Lys Ile
1520                  1525                  1530 att tta tcg gag cgt aaa aat gtg cca att gaa ttt ccc gta att    4644
Ile Leu Ser Glu Arg Lys Asn Val Pro Ile Glu Phe Pro Val Ile
```

```
                1535                1540                1545 gac cgg aaa cga tta tta caa cta gtg aga gaa aat cag ctg cag        4689
Asp Arg Lys Arg Leu Leu Gln Leu Val Arg Glu Asn Gln Leu Gln
1550                1555                1560 tta gat gaa aat gag ctt cct cac gca gtt cac ttt cta aat gaa        4734
Leu Asp Glu Asn Glu Leu Pro His Ala Val His Phe Leu Asn Glu
1565                1570                1575 tca gga gtc ctt ctt cat ttt caa gac cca gca ctg cag tta agt        4779
Ser Gly Val Leu Leu His Phe Gln Asp Pro Ala Leu Gln Leu Ser
1580                1585                1590 gac ttg tac ttt gtg gaa ccc aag tgg ctt tgt aaa atc atg gca        4824
Asp Leu Tyr Phe Val Glu Pro Lys Trp Leu Cys Lys Ile Met Ala
1595                1600                1605 cag att ttg aca gtg aaa gtg gaa ggt tgt cca aaa cac cct aag        4869
Gln Ile Leu Thr Val Lys Val Glu Gly Cys Pro Lys His Pro Lys
1610                1615                1620 ggc att att tcg cgt aga gat gtg gaa aaa ttt ctt tca aaa aaa        4914
Gly Ile Ile Ser Arg Arg Asp Val Glu Lys Phe Leu Ser Lys Lys
1625                1630                1635 agg aaa ttt cca aag aac tac atg tca cag tat ttt aag ctc cta        4959
Arg Lys Phe Pro Lys Asn Tyr Met Ser Gln Tyr Phe Lys Leu Leu
1640                1645                1650 gaa aaa ttc cag att gct ttg cca ata gga gaa gaa tat ttg ctg        5004
Glu Lys Phe Gln Ile Ala Leu Pro Ile Gly Glu Glu Tyr Leu Leu
1655                1660                1665 gtt cca agc agt ttg tct gac cac agg cct gtg ata gag ctt ccc        5049
Val Pro Ser Ser Leu Ser Asp His Arg Pro Val Ile Glu Leu Pro
1670                1675                1680 cat tgt gag aac tct gaa att atc atc cga cta tat gaa atg cct        5094
His Cys Glu Asn Ser Glu Ile Ile Ile Arg Leu Tyr Glu Met Pro
1685                1690                1695 tat ttt cca atg gga ttt tgg tca aga tta atc aat cga tta ctt        5139
Tyr Phe Pro Met Gly Phe Trp Ser Arg Leu Ile Asn Arg Leu Leu
1700                1705                1710 gag att tca cct tac atg ctt tca ggg aga gaa cga gca ctt cgc        5184
Glu Ile Ser Pro Tyr Met Leu Ser Gly Arg Glu Arg Ala Leu Arg
1715                1720                1725 cca aac aga atg tat tgg cga caa ggc att tac tta aat tgg tct        5229
Pro Asn Arg Met Tyr Trp Arg Gln Gly Ile Tyr Leu Asn Trp Ser
1730                1735                1740 cct gaa gct tat tgt ctg gta gga tct gaa gtc tta gac aat cat        5274
Pro Glu Ala Tyr Cys Leu Val Gly Ser Glu Val Leu Asp Asn His
1745                1750                1755 cca gag agt ttc tta aaa att aca gtt cct tct tgt aga aaa ggc        5319
Pro Glu Ser Phe Leu Lys Ile Thr Val Pro Ser Cys Arg Lys Gly
1760                1765                1770 tgt att ctt ttg ggc caa gtt gtg gac cac att gat tct ctc atg        5364
Cys Ile Leu Leu Gly Gln Val Val Asp His Ile Asp Ser Leu Met
1775                1780                1785 gaa gaa tgg ttt cct ggg ttg ctg gag att gat att tgt ggt gaa        5409
Glu Glu Trp Phe Pro Gly Leu Leu Glu Ile Asp Ile Cys Gly Glu
1790                1795                1800 gga gaa act ctg ttg aag aaa tgg gca tta tat agt ttt aat gat        5454
Gly Glu Thr Leu Leu Lys Lys Trp Ala Leu Tyr Ser Phe Asn Asp
1805                1810                1815 ggc gaa gaa cat caa aaa atc tta ctt gat gac ttg atg aag aaa        5499
Gly Glu Glu His Gln Lys Ile Leu Leu Asp Asp Leu Met Lys Lys
1820                1825                1830 gca gag gaa gga gat ctc tta gta aat cca gat caa cca agg ctc        5544
Ala Glu Glu Gly Asp Leu Leu Val Asn Pro Asp Gln Pro Arg Leu
```

-continued

|  |  |  |  |
|---|---|---|---|
| 1835 | 1840 | 1845 | |
| acc att cca ata tct cag att gcc cct gac ttg att ttg gct gac<br>Thr Ile Pro Ile Ser Gln Ile Ala Pro Asp Leu Ile Leu Ala Asp<br>1850       1855            1860 | | | 5589 |
| ctg cct aga aat att atg ttg aat aat gat gag ttg gaa ttt gaa<br>Leu Pro Arg Asn Ile Met Leu Asn Asn Asp Glu Leu Glu Phe Glu<br>1865       1870            1875 | | | 5634 |
| caa gct cca gag ttt ctc cta ggt gat ggc agt ttt gga tca gtt<br>Gln Ala Pro Glu Phe Leu Leu Gly Asp Gly Ser Phe Gly Ser Val<br>1880       1885            1890 | | | 5679 |
| tac cga gca gcc tat gaa gga gaa gaa gtg gct gtg aag att ttt<br>Tyr Arg Ala Ala Tyr Glu Gly Glu Glu Val Ala Val Lys Ile Phe<br>1895       1900            1905 | | | 5724 |
| aat aaa cat aca tca ctc agg ctg tta aga caa gag ctt gtg gtg<br>Asn Lys His Thr Ser Leu Arg Leu Leu Arg Gln Glu Leu Val Val<br>1910       1915            1920 | | | 5769 |
| ctt tgc cac ctc cac cac ccc agt ttg ata tct ttg ctg gca gct<br>Leu Cys His Leu His His Pro Ser Leu Ile Ser Leu Leu Ala Ala<br>1925       1930            1935 | | | 5814 |
| ggg att cgt ccc cgg atg ttg gtg atg gag tta gcc tcc aag ggt<br>Gly Ile Arg Pro Arg Met Leu Val Met Glu Leu Ala Ser Lys Gly<br>1940       1945            1950 | | | 5859 |
| tcc ttg gat cgc ctg ctt cag cag gac aaa gcc agc ctc act aga<br>Ser Leu Asp Arg Leu Leu Gln Gln Asp Lys Ala Ser Leu Thr Arg<br>1955       1960            1965 | | | 5904 |
| acc cta cag cac agg att gca ctc cac gta gct gat ggt ttg aga<br>Thr Leu Gln His Arg Ile Ala Leu His Val Ala Asp Gly Leu Arg<br>1970       1975            1980 | | | 5949 |
| tac ctc cac tca gcc atg att ata tac cga gac ctg aaa ccc cac<br>Tyr Leu His Ser Ala Met Ile Ile Tyr Arg Asp Leu Lys Pro His<br>1985       1990            1995 | | | 5994 |
| aat gtg ctg ctt ttc aca ctg tat ccc aat gct gcc atc att gca<br>Asn Val Leu Leu Phe Thr Leu Tyr Pro Asn Ala Ala Ile Ile Ala<br>2000       2005            2010 | | | 6039 |
| aag att gct gac tac ggc att gct cag tac tgc tgt aga atg ggg<br>Lys Ile Ala Asp Tyr Gly Ile Ala Gln Tyr Cys Cys Arg Met Gly<br>2015       2020            2025 | | | 6084 |
| ata aaa aca tca gag ggc aca cca ggg ttt cgt gca cct gaa gtt<br>Ile Lys Thr Ser Glu Gly Thr Pro Gly Phe Arg Ala Pro Glu Val<br>2030       2035            2040 | | | 6129 |
| gcc aga gga aat gtc att tat aac caa cag gct gat gtt tat tca<br>Ala Arg Gly Asn Val Ile Tyr Asn Gln Gln Ala Asp Val Tyr Ser<br>2045       2050            2055 | | | 6174 |
| ttt ggt tta cta ctc tat gac att ttg aca act gga ggt aga ata<br>Phe Gly Leu Leu Leu Tyr Asp Ile Leu Thr Thr Gly Gly Arg Ile<br>2060       2065            2070 | | | 6219 |
| gta gag ggt ttg aag ttt cca aat gag ttt gat gaa tta gaa ata<br>Val Glu Gly Leu Lys Phe Pro Asn Glu Phe Asp Glu Leu Glu Ile<br>2075       2080            2085 | | | 6264 |
| caa gga aaa tta cct gat cca gtt aaa gaa tat ggt tgt gcc cca<br>Gln Gly Lys Leu Pro Asp Pro Val Lys Glu Tyr Gly Cys Ala Pro<br>2090       2095            2100 | | | 6309 |
| tgg cct atg gtt gag aaa tta att aaa cag tgt ttg aaa gaa aat<br>Trp Pro Met Val Glu Lys Leu Ile Lys Gln Cys Leu Lys Glu Asn<br>2105       2110            2115 | | | 6354 |
| cct caa gaa agg cct act tct gcc cag gtc ttt gac att ttg aat<br>Pro Gln Glu Arg Pro Thr Ser Ala Gln Val Phe Asp Ile Leu Asn<br>2120       2125            2130 | | | 6399 |
| tca gct gaa tta gtc tgt ctg acg aga cgc att tta tta cct aaa<br>Ser Ala Glu Leu Val Cys Leu Thr Arg Arg Ile Leu Leu Pro Lys | | | 6444 |

|       |       |       |       |       |       |       |       |       |       |       |       |       |       |       |      |
|-------|-------|-------|-------|-------|-------|-------|-------|-------|-------|-------|-------|-------|-------|-------|------|
|       |       | 2135  |       |       |       |       | 2140  |       |       |       |       | 2145  |       |       |      |
| aac   | gta   | att   | gtt   | gaa   | tgc   | atg   | gtt   | gct   | aca   | cat   | cac   | aac   | agc   | agg   | 6489 |
| Asn   | Val   | Ile   | Val   | Glu   | Cys   | Met   | Val   | Ala   | Thr   | His   | His   | Asn   | Ser   | Arg   |      |
|       |       | 2150  |       |       |       |       | 2155  |       |       |       |       | 2160  |       |       |      |
| aat   | gca   | agc   | att   | tgg   | ctg   | ggc   | tgt   | ggg   | cac   | acc   | gac   | aga   | gga   | cag   | 6534 |
| Asn   | Ala   | Ser   | Ile   | Trp   | Leu   | Gly   | Cys   | Gly   | His   | Thr   | Asp   | Arg   | Gly   | Gln   |      |
|       |       | 2165  |       |       |       |       | 2170  |       |       |       |       | 2175  |       |       |      |
| ctc   | tca   | ttt   | ctt   | gac   | tta   | aat   | act   | gaa   | gga   | tac   | act   | tct   | gag   | gaa   | 6579 |
| Leu   | Ser   | Phe   | Leu   | Asp   | Leu   | Asn   | Thr   | Glu   | Gly   | Tyr   | Thr   | Ser   | Glu   | Glu   |      |
|       |       | 2180  |       |       |       |       | 2185  |       |       |       |       | 2190  |       |       |      |
| gtt   | gct   | gat   | agt   | aga   | ata   | ttg   | tgc   | tta   | gcc   | ttg   | gtg   | cat   | ctt   | cct   | 6624 |
| Val   | Ala   | Asp   | Ser   | Arg   | Ile   | Leu   | Cys   | Leu   | Ala   | Leu   | Val   | His   | Leu   | Pro   |      |
|       |       | 2195  |       |       |       |       | 2200  |       |       |       |       | 2205  |       |       |      |
| gtt   | gaa   | aag   | gaa   | agc   | tgg   | att   | gtg   | tct   | ggg   | aca   | cag   | tct   | ggt   | act   | 6669 |
| Val   | Glu   | Lys   | Glu   | Ser   | Trp   | Ile   | Val   | Ser   | Gly   | Thr   | Gln   | Ser   | Gly   | Thr   |      |
|       |       | 2210  |       |       |       |       | 2215  |       |       |       |       | 2220  |       |       |      |
| ctc   | ctg   | gtc   | atc   | aat   | acc   | gaa   | gat   | ggg   | aaa   | aag   | aga   | cat   | acc   | cta   | 6714 |
| Leu   | Leu   | Val   | Ile   | Asn   | Thr   | Glu   | Asp   | Gly   | Lys   | Lys   | Arg   | His   | Thr   | Leu   |      |
|       |       | 2225  |       |       |       |       | 2230  |       |       |       |       | 2235  |       |       |      |
| gaa   | aag   | atg   | act   | gat   | tct   | gtc   | act   | tgt   | ttg   | tat   | tgc   | aat   | tcc   | ttt   | 6759 |
| Glu   | Lys   | Met   | Thr   | Asp   | Ser   | Val   | Thr   | Cys   | Leu   | Tyr   | Cys   | Asn   | Ser   | Phe   |      |
|       |       | 2240  |       |       |       |       | 2245  |       |       |       |       | 2250  |       |       |      |
| tcc   | aag   | caa   | agc   | aaa   | caa   | aaa   | aat   | ttt   | ctt   | ttg   | gtt   | gga   | acc   | gct   | 6804 |
| Ser   | Lys   | Gln   | Ser   | Lys   | Gln   | Lys   | Asn   | Phe   | Leu   | Leu   | Val   | Gly   | Thr   | Ala   |      |
|       |       | 2255  |       |       |       |       | 2260  |       |       |       |       | 2265  |       |       |      |
| gat   | ggc   | aag   | tta   | gca   | att   | ttt   | gaa   | gat   | aag   | act   | gtt   | aag   | ctt   | aaa   | 6849 |
| Asp   | Gly   | Lys   | Leu   | Ala   | Ile   | Phe   | Glu   | Asp   | Lys   | Thr   | Val   | Lys   | Leu   | Lys   |      |
|       |       | 2270  |       |       |       |       | 2275  |       |       |       |       | 2280  |       |       |      |
| gga   | gct   | gct   | cct   | ttg   | aag   | ata   | cta   | aat   | ata   | gga   | aat   | gtc   | agt   | act   | 6894 |
| Gly   | Ala   | Ala   | Pro   | Leu   | Lys   | Ile   | Leu   | Asn   | Ile   | Gly   | Asn   | Val   | Ser   | Thr   |      |
|       |       | 2285  |       |       |       |       | 2290  |       |       |       |       | 2295  |       |       |      |
| cca   | ttg   | atg   | tgt   | ttg   | agt   | gaa   | tcc   | aca   | aat   | tca   | acg   | gaa   | aga   | aat   | 6939 |
| Pro   | Leu   | Met   | Cys   | Leu   | Ser   | Glu   | Ser   | Thr   | Asn   | Ser   | Thr   | Glu   | Arg   | Asn   |      |
|       |       | 2300  |       |       |       |       | 2305  |       |       |       |       | 2310  |       |       |      |
| gta   | atg   | tgg   | gga   | gga   | tgt   | ggc   | aca   | aag   | att   | ttc   | tcc   | ttt   | tct   | aat   | 6984 |
| Val   | Met   | Trp   | Gly   | Gly   | Cys   | Gly   | Thr   | Lys   | Ile   | Phe   | Ser   | Phe   | Ser   | Asn   |      |
|       |       | 2315  |       |       |       |       | 2320  |       |       |       |       | 2325  |       |       |      |
| gat   | ttc   | acc   | att   | cag   | aaa   | ctc   | att   | gag   | aca   | aga   | aca   | agc   | caa   | ctg   | 7029 |
| Asp   | Phe   | Thr   | Ile   | Gln   | Lys   | Leu   | Ile   | Glu   | Thr   | Arg   | Thr   | Ser   | Gln   | Leu   |      |
|       |       | 2330  |       |       |       |       | 2335  |       |       |       |       | 2340  |       |       |      |
| ttt   | tct   | tat   | gca   | gct   | ttc   | agt   | gat   | tcc   | aac   | atc   | ata   | aca   | gtg   | gtg   | 7074 |
| Phe   | Ser   | Tyr   | Ala   | Ala   | Phe   | Ser   | Asp   | Ser   | Asn   | Ile   | Ile   | Thr   | Val   | Val   |      |
|       |       | 2345  |       |       |       |       | 2350  |       |       |       |       | 2355  |       |       |      |
| gta   | gac   | act   | gct   | ctc   | tat   | att   | gct   | aag   | caa   | aat   | agc   | cct   | gtt   | gtg   | 7119 |
| Val   | Asp   | Thr   | Ala   | Leu   | Tyr   | Ile   | Ala   | Lys   | Gln   | Asn   | Ser   | Pro   | Val   | Val   |      |
|       |       | 2360  |       |       |       |       | 2365  |       |       |       |       | 2370  |       |       |      |
| gaa   | gtg   | tgg   | gat   | aag   | aaa   | act   | gaa   | aaa   | ctc   | tgt   | gga   | cta   | ata   | gac   | 7164 |
| Glu   | Val   | Trp   | Asp   | Lys   | Lys   | Thr   | Glu   | Lys   | Leu   | Cys   | Gly   | Leu   | Ile   | Asp   |      |
|       |       | 2375  |       |       |       |       | 2380  |       |       |       |       | 2385  |       |       |      |
| tgc   | gtg   | cac   | ttt   | tta   | agg   | gag   | gta   | atg   | gta   | aaa   | gaa   | aac   | aag   | gaa   | 7209 |
| Cys   | Val   | His   | Phe   | Leu   | Arg   | Glu   | Val   | Met   | Val   | Lys   | Glu   | Asn   | Lys   | Glu   |      |
|       |       | 2390  |       |       |       |       | 2395  |       |       |       |       | 2400  |       |       |      |
| tca   | aaa   | cac   | aaa   | atg   | tct   | tat   | tct   | ggg   | aga   | gtg   | aaa   | acc   | ctc   | tgc   | 7254 |
| Ser   | Lys   | His   | Lys   | Met   | Ser   | Tyr   | Ser   | Gly   | Arg   | Val   | Lys   | Thr   | Leu   | Cys   |      |
|       |       | 2405  |       |       |       |       | 2410  |       |       |       |       | 2415  |       |       |      |
| ctt   | cag   | aag   | aac   | act   | gct   | ctt   | tgg   | ata   | gga   | act   | gga   | gga   | ggc   | cat   | 7299 |
| Leu   | Gln   | Lys   | Asn   | Thr   | Ala   | Leu   | Trp   | Ile   | Gly   | Thr   | Gly   | Gly   | Gly   | His   |      |
|       |       | 2420  |       |       |       |       | 2425  |       |       |       |       | 2430  |       |       |      |
| att   | tta   | ctc   | ctg   | gat   | ctt   | tca   | act   | cgt   | cga   | ctt   | ata   | cgt   | gta   | att   | 7344 |
| Ile   | Leu   | Leu   | Leu   | Asp   | Leu   | Ser   | Thr   | Arg   | Arg   | Leu   | Ile   | Arg   | Val   | Ile   |      |

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     | 2435 |    |     |     | 2440 |    |     |     | 2445 |    |     |     |      |
| tac | aac | ttt | tgt | aat | tcg | gtc | aga | gtc | atg | atg | aca | gca | cag | cta | 7389 |
| Tyr | Asn | Phe | Cys | Asn | Ser | Val | Arg | Val | Met | Met | Thr | Ala | Gln | Leu |      |
|     |     |     | 2450 |    |     |     | 2455 |    |     |     | 2460 |    |     |     |      |
| gga | agc | ctt | aaa | aat | gtc | atg | ctg | gta | ttg | ggc | tac | aac | cgg | aaa | 7434 |
| Gly | Ser | Leu | Lys | Asn | Val | Met | Leu | Val | Leu | Gly | Tyr | Asn | Arg | Lys |      |
|     |     |     | 2465 |    |     |     | 2470 |    |     |     | 2475 |    |     |     |      |
| aat | act | gaa | ggt | aca | caa | aag | cag | aaa | gag | ata | caa | tct | tgc | ttg | 7479 |
| Asn | Thr | Glu | Gly | Thr | Gln | Lys | Gln | Lys | Glu | Ile | Gln | Ser | Cys | Leu |      |
|     |     |     | 2480 |    |     |     | 2485 |    |     |     | 2490 |    |     |     |      |
| acc | gtt | tgg | gac | atc | aat | ctt | cca | cat | gaa | gtg | caa | aat | tta | gaa | 7524 |
| Thr | Val | Trp | Asp | Ile | Asn | Leu | Pro | His | Glu | Val | Gln | Asn | Leu | Glu |      |
|     |     |     | 2495 |    |     |     | 2500 |    |     |     | 2505 |    |     |     |      |
| aaa | cac | att | gaa | gtg | aga | aaa | gaa | tta | gct | gaa | aaa | atg | aga | cga | 7569 |
| Lys | His | Ile | Glu | Val | Arg | Lys | Glu | Leu | Ala | Glu | Lys | Met | Arg | Arg |      |
|     |     |     | 2510 |    |     |     | 2515 |    |     |     | 2520 |    |     |     |      |
| aca | tct | gtt | gag | taa | gagagaaata | | ggaattgtct | | ttggatagga | | aaattattct | | | | 7624 |
| Thr | Ser | Val | Glu |     |     |     |     |     |     |     |     |     |     |     |      |
|     |     |     | 2525 |    |     |     |     |     |     |     |     |     |     |     |      |

```
ctcctcttgt aaatatttat tttaaaaatg ttcacatgga aagggtactc acattttttg    7684
aaatagctcg tgtgtatgaa ggaatgttat tatttttaat ttaaatatat gtaaaaatac    7744
ttaccagtaa atgtgtattt taaagaacta tttaaaacac aatgttatat ttcttataaa    7804
taccagttac tttcgttcat taattaatga aaataaatct gtgaagtacc taatttaagt    7864
actcatacta aaatttataa ggccgataat ttttgtttt cttgtctgta atggaggtaa     7924
actttatttt aaattctgtg cttaagacag gactattgct tgtcgatttt tctagaaatc    7984
tgcacggtat aatgaaaata ttaagacagt ttcccatgta atgtattcct tcttagattg    8044
catcgaaatg cactatcata tatgcttgta aatattcaaa tgaatttgca ctaataaagt    8104
cctttgttgg tatgtgaatt ctctttgttg ctgttgcaaa cagtgcatct tacacaactt    8164
cactcaattc aaaagaaaac tccattaaaa gtactaatga aaaaacatga catactgtca    8224
aagtcctcat atctaggaaa gacacagaaa ctctctttgt cacagaaact ctctgtgtct    8284
ttcctagaca taatagagtt gttttcaac tctatgtttg aatgtggata ccctgaattt     8344
tgtataatta gtgtaaatac agtgttcagt ccttcaagtg atattttat ttttttattc     8404
ataccactag ctacttgttt tctaatctgc ttcattctaa tgcttatatt catcttttcc    8464
ctaaatttgt gatgctgcag atcctacatc attcagatag aaacctttt tttttttcaga   8524
attatagaat tccacagctc ctaccaagac catgaggata aatatctaac acttttcagt    8584
tgctgaagga gaaaggagct ttagttatga tggataaaaa tatctgccac cctaggcttc    8644
caaattatac ttaaattgtt tacatagctt accacaatag gagtatcagg gccaaatacc    8704
tatgtaataa tttgaggtca tttctgcttt aggaaaagta ctttcggtaa attctttggc    8764
cctgaccagt attcattatt tcagataatt ccctgtgata ggacaactag tacatttaat    8824
attctcagaa cttatggcat tttactatgt gaaaacttta aatttattta tattaagggt    8884
aatcaaattc ttaaagatga aagattttct gtatttaaa ggaagctatg ctttaacttg     8944
ttatgtaatt aacaaaaaaa tcatatataa tagagctctt tgttccagtg ttatctcttt    9004
cattgttact ttgtatttgc aattttttt accaaagaca aattaaaaaa atgaatacca     9064
tatttaaatg gaataataaa ggttttttaa aaactttaaa                          9104
```

<210> SEQ ID NO 3
<211> LENGTH: 31
<212> TYPE: PRT

-continued

<213> ORGANISM: Homo sapiens

<400> SEQUENCE: 3

```
Cys Arg Met Gly Ile Lys Thr Ser Glu Gly Thr Pro Gly Phe Arg Ala
1               5                   10                  15
Pro Glu Val Ala Arg Gly Asn Val Ile Tyr Asn Gln Gln Ala Asp
            20                  25                  30
```

<210> SEQ ID NO 4
<211> LENGTH: 6
<212> TYPE: PRT
<213> ORGANISM: Homo sapiens

<400> SEQUENCE: 4

```
Leu Ser Ala Leu Thr Asn
1               5
```

<210> SEQ ID NO 5
<211> LENGTH: 18
<212> TYPE: DNA
<213> ORGANISM: Homo sapiens

<400> SEQUENCE: 5
ttaagtgcgt taacaaat                                                 18

<210> SEQ ID NO 6
<211> LENGTH: 6
<212> TYPE: PRT
<213> ORGANISM: Homo sapiens

<400> SEQUENCE: 6

```
Arg Glu Val Thr Val Lys
1               5
```

<210> SEQ ID NO 7
<211> LENGTH: 18
<212> TYPE: DNA
<213> ORGANISM: Homo sapiens

<400> SEQUENCE: 7
agggaggtaa cggtaaaa                                                 18

<210> SEQ ID NO 8
<211> LENGTH: 2527
<212> TYPE: PRT
<213> ORGANISM: Homo sapiens

<400> SEQUENCE: 8

```
Met Ala Ser Gly Ser Cys Gln Gly Cys Glu Glu Asp Glu Glu Thr Leu
1               5                   10                  15
Lys Lys Leu Ile Val Arg Leu Asn Asn Val Gln Glu Gly Lys Gln Ile
            20                  25                  30
Glu Thr Leu Val Gln Ile Leu Glu Asp Leu Leu Val Phe Thr Tyr Ser
        35                  40                  45
Glu Arg Ala Ser Lys Leu Phe Gln Gly Lys Asn Ile His Val Pro Leu
    50                  55                  60
Leu Ile Val Leu Asp Ser Tyr Met Arg Val Ala Ser Val Gln Gln Val
65                  70                  75                  80
Gly Trp Ser Leu Leu Cys Lys Leu Ile Glu Val Cys Pro Gly Thr Met
                85                  90                  95
Gln Ser Leu Met Gly Pro Gln Asp Val Gly Asn Asp Trp Glu Val Leu
            100                 105                 110
```

-continued

```
Gly Val His Gln Leu Ile Leu Lys Met Leu Thr Val His Asn Ala Ser
            115                 120                 125
Val Asn Leu Ser Val Ile Gly Leu Lys Thr Leu Asp Leu Leu Leu Thr
130                 135                 140
Ser Gly Lys Ile Thr Leu Leu Ile Leu Asp Glu Glu Ser Asp Ile Phe
145                 150                 155                 160
Met Leu Ile Phe Asp Ala Met His Ser Phe Pro Ala Asn Asp Glu Val
                165                 170                 175
Gln Lys Leu Gly Cys Lys Ala Leu His Val Leu Phe Glu Arg Val Ser
            180                 185                 190
Glu Glu Gln Leu Thr Glu Phe Val Glu Asn Lys Asp Tyr Met Ile Leu
        195                 200                 205
Leu Ser Ala Ser Thr Asn Phe Lys Asp Glu Glu Ile Val Leu His
    210                 215                 220
Val Leu His Cys Leu His Ser Leu Ala Ile Pro Cys Asn Asn Val Glu
225                 230                 235                 240
Val Leu Met Ser Gly Asn Val Arg Cys Tyr Asn Ile Val Val Glu Ala
                245                 250                 255
Met Lys Ala Phe Pro Met Ser Glu Arg Ile Gln Glu Val Ser Cys Cys
            260                 265                 270
Leu Leu His Arg Leu Thr Leu Gly Asn Phe Phe Asn Ile Leu Val Leu
        275                 280                 285
Asn Glu Val His Glu Phe Val Val Lys Ala Val Gln Gln Tyr Pro Glu
    290                 295                 300
Asn Ala Ala Leu Gln Ile Ser Ala Leu Ser Cys Leu Ala Leu Leu Thr
305                 310                 315                 320
Glu Thr Ile Phe Leu Asn Gln Asp Leu Glu Glu Lys Asn Glu Asn Gln
                325                 330                 335
Glu Asn Asp Asp Glu Gly Glu Glu Asp Lys Leu Phe Trp Leu Glu Ala
            340                 345                 350
Cys Tyr Lys Ala Leu Thr Trp His Arg Lys Asn Lys His Val Gln Glu
        355                 360                 365
Ala Ala Cys Trp Ala Leu Asn Asn Leu Leu Met Tyr Gln Asn Ser Leu
    370                 375                 380
His Glu Lys Ile Gly Asp Glu Asp Gly His Phe Pro Ala His Arg Glu
385                 390                 395                 400
Val Met Leu Ser Met Leu Met His Ser Ser Lys Glu Val Phe Gln
                405                 410                 415
Ala Ser Ala Asn Ala Leu Ser Thr Leu Leu Glu Gln Asn Val Asn Phe
            420                 425                 430
Arg Lys Ile Leu Leu Ser Lys Gly Ile His Leu Asn Val Leu Glu Leu
        435                 440                 445
Met Gln Lys His Ile His Ser Pro Glu Val Ala Glu Ser Gly Cys Lys
    450                 455                 460
Met Leu Asn His Leu Phe Glu Gly Ser Asn Thr Ser Leu Asp Ile Met
465                 470                 475                 480
Ala Ala Val Val Pro Lys Ile Leu Thr Val Met Lys Arg His Glu Thr
                485                 490                 495
Ser Leu Pro Val Gln Leu Glu Ala Leu Arg Ala Ile Leu His Phe Ile
            500                 505                 510
Val Pro Gly Met Pro Glu Glu Ser Arg Glu Asp Thr Glu Phe His His
        515                 520                 525
Lys Leu Asn Met Val Lys Lys Gln Cys Phe Lys Asn Asp Ile His Lys
```

```
                530                 535                 540
Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
                580                 585                 590

Leu Gln Met Tyr Pro Asp Asp Gln Glu Ile Gln Cys Leu Gly Leu Ser
                595                 600                 605

Leu Ile Gly Tyr Leu Ile Thr Lys Lys Asn Val Phe Ile Gly Thr Gly
                610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
                660                 665                 670

Leu Val Ile Phe His Gln Met Ser Ser Asn Ile Met Glu Gln Lys Asp
                675                 680                 685

Gln Gln Phe Leu Asn Leu Cys Cys Lys Cys Phe Ala Lys Val Ala Met
                690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
                740                 745                 750

Ser Ser Pro Lys Leu Val Glu Leu Leu Leu Asn Ser Gly Ser Arg Glu
                755                 760                 765

Gln Asp Val Arg Lys Ala Leu Thr Ile Ser Ile Gly Lys Gly Asp Ser
                770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
                820                 825                 830

Thr Asn Ile Ala Ser Thr Leu Ala Arg Met Val Ile Arg Tyr Gln Met
                835                 840                 845

Lys Ser Ala Val Glu Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Lys Ser Asn Ser Ile Ser
                900                 905                 910

Val Gly Glu Phe Tyr Arg Asp Ala Val Leu Gln Arg Cys Ser Pro Asn
                915                 920                 925

Leu Gln Arg His Ser Asn Ser Leu Gly Pro Ile Phe Asp His Glu Asp
                930                 935                 940

Leu Leu Lys Arg Lys Arg Lys Ile Leu Ser Ser Asp Asp Ser Leu Arg
945                 950                 955                 960
```

-continued

Ser Ser Lys Leu Gln Ser His Met Arg His Ser Asp Ser Ile Ser Ser
        965                 970                 975

Leu Ala Ser Glu Arg Glu Tyr Ile Thr Ser Leu Asp Leu Ser Ala Asn
        980                 985                 990

Glu Leu Arg Asp Ile Asp Ala Leu Ser Gln Lys Cys Cys Ile Ser Val
        995                 1000                1005

His Leu Glu His Leu Glu Lys Leu Glu Leu His Gln Asn Ala Leu
    1010            1015            1020

Thr Ser Phe Pro Gln Gln Leu Cys Glu Thr Leu Lys Ser Leu Thr
    1025            1030            1035

His Leu Asp Leu His Ser Asn Lys Phe Thr Ser Phe Pro Ser Tyr
    1040            1045            1050

Leu Leu Lys Met Ser Cys Ile Ala Asn Leu Asp Val Ser Arg Asn
    1055            1060            1065

Asp Ile Gly Pro Ser Val Val Leu Asp Pro Thr Val Lys Cys Pro
    1070            1075            1080

Thr Leu Lys Gln Phe Asn Leu Ser Tyr Asn Gln Leu Ser Phe Val
    1085            1090            1095

Pro Glu Asn Leu Thr Asp Val Val Glu Lys Leu Glu Gln Leu Ile
    1100            1105            1110

Leu Glu Gly Asn Lys Ile Ser Gly Ile Cys Ser Pro Leu Arg Leu
    1115            1120            1125

Lys Glu Leu Lys Ile Leu Asn Leu Ser Lys Asn His Ile Ser Ser
    1130            1135            1140

Leu Ser Glu Asn Phe Leu Glu Ala Cys Pro Lys Val Glu Ser Phe
    1145            1150            1155

Ser Ala Arg Met Asn Phe Leu Ala Ala Met Pro Phe Leu Pro Pro
    1160            1165            1170

Ser Met Thr Ile Leu Lys Leu Ser Gln Asn Lys Phe Ser Cys Ile
    1175            1180            1185

Pro Glu Ala Ile Leu Asn Leu Pro His Leu Arg Ser Leu Asp Met
    1190            1195            1200

Ser Ser Asn Asp Ile Gln Tyr Leu Pro Gly Pro Ala His Trp Lys
    1205            1210            1215

Ser Leu Asn Leu Arg Glu Leu Leu Phe Ser His Asn Gln Ile Ser
    1220            1225            1230

Ile Leu Asp Leu Ser Glu Lys Ala Tyr Leu Trp Ser Arg Val Glu
    1235            1240            1245

Lys Leu His Leu Ser His Asn Lys Leu Lys Glu Ile Pro Pro Glu
    1250            1255            1260

Ile Gly Cys Leu Glu Asn Leu Thr Ser Leu Asp Val Ser Tyr Asn
    1265            1270            1275

Leu Glu Leu Arg Ser Phe Pro Asn Glu Met Gly Lys Leu Ser Lys
    1280            1285            1290

Ile Trp Asp Leu Pro Leu Asp Glu Leu His Leu Asn Phe Asp Phe
    1295            1300            1305

Lys His Ile Gly Cys Lys Ala Lys Asp Ile Ile Arg Phe Leu Gln
    1310            1315            1320

Gln Arg Leu Lys Lys Ala Val Pro Tyr Asn Arg Met Lys Leu Met
    1325            1330            1335

Ile Val Gly Asn Thr Gly Ser Gly Lys Thr Thr Leu Leu Gln Gln
    1340            1345            1350

Leu Met Lys Thr Lys Lys Ser Asp Leu Gly Met Gln Ser Ala Thr
    1355            1360            1365

```
Val Gly Ile Asp Val Lys Asp Trp Pro Ile Gln Ile Arg Asp Lys
    1370            1375                1380

Arg Lys Arg Asp Leu Val Leu Asn Val Trp Asp Phe Ala Gly Arg
    1385            1390                1395

Glu Glu Phe Tyr Ser Thr His Pro His Phe Met Thr Gln Arg Ala
    1400            1405                1410

Leu Tyr Leu Ala Val Tyr Asp Leu Ser Lys Gly Gln Ala Glu Val
    1415            1420                1425

Asp Ala Met Lys Pro Trp Leu Phe Asn Ile Lys Ala Arg Ala Ser
    1430            1435                1440

Ser Ser Pro Val Ile Leu Val Gly Thr His Leu Asp Val Ser Asp
    1445            1450                1455

Glu Lys Gln Arg Lys Ala Cys Met Ser Lys Ile Thr Lys Glu Leu
    1460            1465                1470

Leu Asn Lys Arg Gly Phe Pro Ala Ile Arg Asp Tyr His Phe Val
    1475            1480                1485

Asn Ala Thr Glu Glu Ser Asp Ala Leu Ala Lys Leu Arg Lys Thr
    1490            1495                1500

Ile Ile Asn Glu Ser Leu Asn Phe Lys Ile Arg Asp Gln Leu Val
    1505            1510                1515

Val Gly Gln Leu Ile Pro Asp Cys Tyr Val Glu Leu Glu Lys Ile
    1520            1525                1530

Ile Leu Ser Glu Arg Lys Asn Val Pro Ile Glu Phe Pro Val Ile
    1535            1540                1545

Asp Arg Lys Arg Leu Leu Gln Leu Val Arg Glu Asn Gln Leu Gln
    1550            1555                1560

Leu Asp Glu Asn Glu Leu Pro His Ala Val His Phe Leu Asn Glu
    1565            1570                1575

Ser Gly Val Leu Leu His Phe Gln Asp Pro Ala Leu Gln Leu Ser
    1580            1585                1590

Asp Leu Tyr Phe Val Glu Pro Lys Trp Leu Cys Lys Ile Met Ala
    1595            1600                1605

Gln Ile Leu Thr Val Lys Val Glu Gly Cys Pro Lys His Pro Lys
    1610            1615                1620

Gly Ile Ile Ser Arg Arg Asp Val Glu Lys Phe Leu Ser Lys Lys
    1625            1630                1635

Arg Lys Phe Pro Lys Asn Tyr Met Ser Gln Tyr Phe Lys Leu Leu
    1640            1645                1650

Glu Lys Phe Gln Ile Ala Leu Pro Ile Gly Glu Glu Tyr Leu Leu
    1655            1660                1665

Val Pro Ser Ser Leu Ser Asp His Arg Pro Val Ile Glu Leu Pro
    1670            1675                1680

His Cys Glu Asn Ser Glu Ile Ile Ile Arg Leu Tyr Glu Met Pro
    1685            1690                1695

Tyr Phe Pro Met Gly Phe Trp Ser Arg Leu Ile Asn Arg Leu Leu
    1700            1705                1710

Glu Ile Ser Pro Tyr Met Leu Ser Gly Arg Glu Arg Ala Leu Arg
    1715            1720                1725

Pro Asn Arg Met Tyr Trp Arg Gln Gly Ile Tyr Leu Asn Trp Ser
    1730            1735                1740

Pro Glu Ala Tyr Cys Leu Val Gly Ser Glu Val Leu Asp Asn His
    1745            1750                1755

Pro Glu Ser Phe Leu Lys Ile Thr Val Pro Ser Cys Arg Lys Gly
```

-continued

```
                1760                1765                1770

Cys Ile Leu Leu Gly Gln Val Val Asp His Ile Asp Ser Leu Met
    1775                1780                1785

Glu Glu Trp Phe Pro Gly Leu Leu Glu Ile Asp Ile Cys Gly Glu
    1790                1795                1800

Gly Glu Thr Leu Leu Lys Lys Trp Ala Leu Tyr Ser Phe Asn Asp
    1805                1810                1815

Gly Glu Glu His Gln Lys Ile Leu Leu Asp Asp Leu Met Lys Lys
    1820                1825                1830

Ala Glu Glu Gly Asp Leu Leu Val Asn Pro Asp Gln Pro Arg Leu
    1835                1840                1845

Thr Ile Pro Ile Ser Gln Ile Ala Pro Asp Leu Ile Leu Ala Asp
    1850                1855                1860

Leu Pro Arg Asn Ile Met Leu Asn Asn Asp Glu Leu Glu Phe Glu
    1865                1870                1875

Gln Ala Pro Glu Phe Leu Leu Gly Asp Gly Ser Phe Gly Ser Val
    1880                1885                1890

Tyr Arg Ala Ala Tyr Glu Gly Glu Glu Val Ala Val Lys Ile Phe
    1895                1900                1905

Asn Lys His Thr Ser Leu Arg Leu Leu Arg Gln Glu Leu Val Val
    1910                1915                1920

Leu Cys His Leu His His Pro Ser Leu Ile Ser Leu Leu Ala Ala
    1925                1930                1935

Gly Ile Arg Pro Arg Met Leu Val Met Glu Leu Ala Ser Lys Gly
    1940                1945                1950

Ser Leu Asp Arg Leu Leu Gln Gln Asp Lys Ala Ser Leu Thr Arg
    1955                1960                1965

Thr Leu Gln His Arg Ile Ala Leu His Val Ala Asp Gly Leu Arg
    1970                1975                1980

Tyr Leu His Ser Ala Met Ile Ile Tyr Arg Asp Leu Lys Pro His
    1985                1990                1995

Asn Val Leu Leu Phe Thr Leu Tyr Pro Asn Ala Ala Ile Ile Ala
    2000                2005                2010

Lys Ile Ala Asp Tyr Gly Ile Ala Gln Tyr Cys Cys Arg Met Gly
    2015                2020                2025

Ile Lys Thr Ser Glu Gly Thr Pro Gly Phe Arg Ala Pro Glu Val
    2030                2035                2040

Ala Arg Gly Asn Val Ile Tyr Asn Gln Gln Ala Asp Val Tyr Ser
    2045                2050                2055

Phe Gly Leu Leu Leu Tyr Asp Ile Leu Thr Thr Gly Gly Arg Ile
    2060                2065                2070

Val Glu Gly Leu Lys Phe Pro Asn Glu Phe Asp Glu Leu Glu Ile
    2075                2080                2085

Gln Gly Lys Leu Pro Asp Pro Val Lys Glu Tyr Gly Cys Ala Pro
    2090                2095                2100

Trp Pro Met Val Glu Lys Leu Ile Lys Gln Cys Leu Lys Glu Asn
    2105                2110                2115

Pro Gln Glu Arg Pro Thr Ser Ala Gln Val Phe Asp Ile Leu Asn
    2120                2125                2130

Ser Ala Glu Leu Val Cys Leu Thr Arg Arg Ile Leu Leu Pro Lys
    2135                2140                2145

Asn Val Ile Val Glu Cys Met Val Ala Thr His His Asn Ser Arg
    2150                2155                2160
```

```
Asn Ala Ser Ile Trp Leu Gly Cys Gly His Thr Asp Arg Gly Gln
2165                2170                    2175

Leu Ser Phe Leu Asp Leu Asn Thr Glu Gly Tyr Thr Ser Glu Glu
2180                2185                    2190

Val Ala Asp Ser Arg Ile Leu Cys Leu Ala Leu Val His Leu Pro
2195                2200                    2205

Val Glu Lys Glu Ser Trp Ile Val Ser Gly Thr Gln Ser Gly Thr
2210                2215                    2220

Leu Leu Val Ile Asn Thr Glu Asp Gly Lys Lys Arg His Thr Leu
2225                2230                    2235

Glu Lys Met Thr Asp Ser Val Thr Cys Leu Tyr Cys Asn Ser Phe
2240                2245                    2250

Ser Lys Gln Ser Lys Gln Lys Asn Phe Leu Leu Val Gly Thr Ala
2255                2260                    2265

Asp Gly Lys Leu Ala Ile Phe Glu Asp Lys Thr Val Lys Leu Lys
2270                2275                    2280

Gly Ala Ala Pro Leu Lys Ile Leu Asn Ile Gly Asn Val Ser Thr
2285                2290                    2295

Pro Leu Met Cys Leu Ser Glu Ser Thr Asn Ser Thr Glu Arg Asn
2300                2305                    2310

Val Met Trp Gly Gly Cys Gly Thr Lys Ile Phe Ser Phe Ser Asn
2315                2320                    2325

Asp Phe Thr Ile Gln Lys Leu Ile Glu Thr Arg Thr Ser Gln Leu
2330                2335                    2340

Phe Ser Tyr Ala Ala Phe Ser Asp Ser Asn Ile Ile Thr Val Val
2345                2350                    2355

Val Asp Thr Ala Leu Tyr Ile Ala Lys Gln Asn Ser Pro Val Val
2360                2365                    2370

Glu Val Trp Asp Lys Lys Thr Glu Lys Leu Cys Gly Leu Ile Asp
2375                2380                    2385

Cys Val His Phe Leu Arg Glu Val Met Val Lys Glu Asn Lys Glu
2390                2395                    2400

Ser Lys His Lys Met Ser Tyr Ser Gly Arg Val Lys Thr Leu Cys
2405                2410                    2415

Leu Gln Lys Asn Thr Ala Leu Trp Ile Gly Thr Gly Gly Gly His
2420                2425                    2430

Ile Leu Leu Leu Asp Leu Ser Thr Arg Arg Leu Ile Arg Val Ile
2435                2440                    2445

Tyr Asn Phe Cys Asn Ser Val Arg Val Met Met Thr Ala Gln Leu
2450                2455                    2460

Gly Ser Leu Lys Asn Val Met Leu Val Leu Gly Tyr Asn Arg Lys
2465                2470                    2475

Asn Thr Glu Gly Thr Gln Lys Gln Lys Glu Ile Gln Ser Cys Leu
2480                2485                    2490

Thr Val Trp Asp Ile Asn Leu Pro His Glu Val Gln Asn Leu Glu
2495                2500                    2505

Lys His Ile Glu Val Arg Lys Glu Leu Ala Glu Lys Met Arg Arg
2510                2515                    2520

Thr Ser Val Glu
2525
```

<210> SEQ ID NO 9
<211> LENGTH: 2527
<212> TYPE: PRT
<213> ORGANISM: Homo sapiens

<400> SEQUENCE: 9

```
Met Ala Ser Gly Ser Cys Gln Gly Cys Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
            35                  40                  45

Glu His Ala Ser Lys Leu Phe Gln Gly Lys Asn Ile His Val Pro Leu
        50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
            115                 120                 125

Val Asn Leu Ser Val Ile Gly Leu Lys Thr Leu Asp Leu Leu Leu Thr
130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
            195                 200                 205

Leu Ser Ala Ser Thr Asn Phe Lys Asp Glu Glu Ile Val Leu His
210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
            275                 280                 285

Asn Glu Val His Glu Phe Val Val Lys Ala Val Gln Gln Tyr Pro Glu
290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
            340                 345                 350

Cys Tyr Lys Ala Leu Thr Trp His Arg Lys Asn Lys His Val Gln Glu
            355                 360                 365

Ala Ala Cys Trp Ala Leu Asn Asn Leu Leu Met Tyr Gln Asn Ser Leu
370                 375                 380

His Glu Lys Ile Gly Asp Glu Asp Gly His Phe Pro Ala His Arg Glu
385                 390                 395                 400

Val Met Leu Ser Met Leu Met His Ser Ser Ser Lys Glu Val Phe Gln
                405                 410                 415
```

```
Ala Ser Ala Asn Ala Leu Ser Thr Leu Leu Glu Gln Asn Val Asn Phe
            420                 425                 430

Arg Lys Ile Leu Leu Ser Lys Gly Ile His Leu Asn Val Leu Glu Leu
        435                 440                 445

Met Gln Lys His Ile His Ser Pro Glu Val Ala Glu Ser Gly Cys Lys
    450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
        515                 520                 525

Lys Leu Asn Met Val Lys Lys Gln Cys Phe Lys Asn Asp Ile His Lys
    530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
    610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
        675                 680                 685

Gln Gln Phe Leu Asn Leu Cys Cys Lys Cys Phe Ala Lys Val Ala Met
    690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Asn Ser Gly Ser Arg Glu
        755                 760                 765

Gln Asp Val Arg Lys Ala Leu Thr Ile Ser Ile Gly Lys Gly Asp Ser
    770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
```

-continued

```
                835                 840                 845
Lys Ser Ala Val Glu Glu Gly Thr Ala Ser Gly Ser Asp Gly Asn Phe
            850                 855                 860
Ser Glu Asp Val Leu Ser Lys Phe Asp Glu Trp Thr Phe Ile Pro Asp
865                 870                 875                 880
Ser Ser Met Asp Ser Val Phe Ala Gln Ser Asp Asp Leu Asp Ser Glu
                885                 890                 895
Gly Ser Glu Gly Ser Phe Leu Val Lys Lys Ser Asn Ser Ile Ser
            900                 905                 910
Val Gly Glu Phe Tyr Arg Asp Ala Val Leu Gln Arg Cys Ser Pro Asn
            915                 920                 925
Leu Gln Arg His Ser Asn Ser Leu Gly Pro Ile Phe Asp His Glu Asp
            930                 935                 940
Leu Leu Lys Arg Lys Arg Lys Ile Leu Ser Ser Asp Asp Ser Leu Arg
945                 950                 955                 960
Ser Ser Lys Leu Gln Ser His Met Arg His Ser Asp Ser Ile Ser Ser
                965                 970                 975
Leu Ala Ser Glu Arg Glu Tyr Ile Thr Ser Leu Asp Leu Ser Ala Asn
            980                 985                 990
Glu Leu Arg Asp Ile Asp Ala Leu Ser Gln Lys Cys Cys Ile Ser Val
            995                 1000                1005
His Leu Glu His Leu Glu Lys Leu Glu Leu His Gln Asn Ala Leu
        1010                1015                1020
Thr Ser Phe Pro Gln Gln Leu Cys Glu Thr Leu Lys Ser Leu Thr
        1025                1030                1035
His Leu Asp Leu His Ser Asn Lys Phe Thr Ser Phe Pro Ser Tyr
        1040                1045                1050
Leu Leu Lys Met Ser Cys Ile Ala Asn Leu Asp Val Ser Arg Asn
        1055                1060                1065
Asp Ile Gly Pro Ser Val Val Leu Asp Pro Thr Val Lys Cys Pro
        1070                1075                1080
Thr Leu Lys Gln Phe Asn Leu Ser Tyr Asn Gln Leu Ser Phe Val
        1085                1090                1095
Pro Glu Asn Leu Thr Asp Val Val Glu Lys Leu Glu Gln Leu Ile
        1100                1105                1110
Leu Glu Gly Asn Lys Ile Ser Gly Ile Cys Ser Pro Leu Arg Leu
        1115                1120                1125
Lys Glu Leu Lys Ile Leu Asn Leu Ser Lys Asn His Ile Ser Ser
        1130                1135                1140
Leu Ser Glu Asn Phe Leu Glu Ala Cys Pro Lys Val Glu Ser Phe
        1145                1150                1155
Ser Ala Arg Met Asn Phe Leu Ala Ala Met Pro Phe Leu Pro Pro
        1160                1165                1170
Ser Met Thr Ile Leu Lys Leu Ser Gln Asn Lys Phe Ser Cys Ile
        1175                1180                1185
Pro Glu Ala Ile Leu Asn Leu Pro His Leu Arg Ser Leu Asp Met
        1190                1195                1200
Ser Ser Asn Asp Ile Gln Tyr Leu Pro Gly Pro Ala His Trp Lys
        1205                1210                1215
Ser Leu Asn Leu Arg Glu Leu Leu Phe Ser His Asn Gln Ile Ser
        1220                1225                1230
Ile Leu Asp Leu Ser Glu Lys Ala Tyr Leu Trp Ser Arg Val Glu
        1235                1240                1245
```

```
Lys Leu His Leu Ser His Asn Lys Leu Lys Glu Ile Pro Pro Glu
1250                1255                1260

Ile Gly Cys Leu Glu Asn Leu Thr Ser Leu Asp Val Ser Tyr Asn
1265                1270                1275

Leu Glu Leu Arg Ser Phe Pro Asn Glu Met Gly Lys Leu Ser Lys
1280                1285                1290

Ile Trp Asp Leu Pro Leu Asp Glu Leu His Leu Asn Phe Asp Phe
1295                1300                1305

Lys His Ile Gly Cys Lys Ala Lys Asp Ile Ile Arg Phe Leu Gln
1310                1315                1320

Gln Arg Leu Lys Lys Ala Val Pro Tyr Asn Arg Met Lys Leu Met
1325                1330                1335

Ile Val Gly Asn Thr Gly Ser Gly Lys Thr Thr Leu Leu Gln Gln
1340                1345                1350

Leu Met Lys Thr Lys Lys Ser Asp Leu Gly Met Gln Ser Ala Thr
1355                1360                1365

Val Gly Ile Asp Val Lys Asp Trp Pro Ile Gln Ile Arg Asp Lys
1370                1375                1380

Arg Lys Arg Asp Leu Val Leu Asn Val Trp Asp Phe Ala Gly Arg
1385                1390                1395

Glu Glu Phe Tyr Ser Thr His Pro His Phe Met Thr Gln Arg Ala
1400                1405                1410

Leu Tyr Leu Ala Val Tyr Asp Leu Ser Lys Gly Gln Ala Glu Val
1415                1420                1425

Asp Ala Met Lys Pro Trp Leu Phe Asn Ile Lys Ala Arg Ala Ser
1430                1435                1440

Ser Ser Pro Val Ile Leu Val Gly Thr His Leu Asp Val Ser Asp
1445                1450                1455

Glu Lys Gln Arg Lys Ala Cys Met Ser Lys Ile Thr Lys Glu Leu
1460                1465                1470

Leu Asn Lys Arg Gly Phe Pro Ala Ile Arg Asp Tyr His Phe Val
1475                1480                1485

Asn Ala Thr Glu Glu Ser Asp Ala Leu Ala Lys Leu Arg Lys Thr
1490                1495                1500

Ile Ile Asn Glu Ser Leu Asn Phe Lys Ile Arg Asp Gln Leu Val
1505                1510                1515

Val Gly Gln Leu Ile Pro Asp Cys Tyr Val Glu Leu Glu Lys Ile
1520                1525                1530

Ile Leu Ser Glu Arg Lys Asn Val Pro Ile Glu Phe Pro Val Ile
1535                1540                1545

Asp Arg Lys Arg Leu Leu Gln Leu Val Arg Glu Asn Gln Leu Gln
1550                1555                1560

Leu Asp Glu Asn Glu Leu Pro His Ala Val His Phe Leu Asn Glu
1565                1570                1575

Ser Gly Val Leu Leu His Phe Gln Asp Pro Ala Leu Gln Leu Ser
1580                1585                1590

Asp Leu Tyr Phe Val Glu Pro Lys Trp Leu Cys Lys Ile Met Ala
1595                1600                1605

Gln Ile Leu Thr Val Lys Val Glu Gly Cys Pro Lys His Pro Lys
1610                1615                1620

Gly Ile Ile Ser Arg Arg Asp Val Glu Lys Phe Leu Ser Lys Lys
1625                1630                1635

Arg Lys Phe Pro Lys Asn Tyr Met Ser Gln Tyr Phe Lys Leu Leu
1640                1645                1650
```

-continued

```
Glu Lys Phe Gln Ile Ala Leu Pro Ile Gly Glu Tyr Leu Leu
    1655                1660            1665

Val Pro Ser Ser Leu Ser Asp His Arg Pro Val Ile Glu Leu Pro
    1670                1675            1680

His Cys Glu Asn Ser Glu Ile Ile Ile Arg Leu Tyr Glu Met Pro
    1685                1690            1695

Tyr Phe Pro Met Gly Phe Trp Ser Arg Leu Ile Asn Arg Leu Leu
    1700                1705            1710

Glu Ile Ser Pro Tyr Met Leu Ser Gly Arg Glu Arg Ala Leu Arg
    1715                1720            1725

Pro Asn Arg Met Tyr Trp Arg Gln Gly Ile Tyr Leu Asn Trp Ser
    1730                1735            1740

Pro Glu Ala Tyr Cys Leu Val Gly Ser Glu Val Leu Asp Asn His
    1745                1750            1755

Pro Glu Ser Phe Leu Lys Ile Thr Val Pro Ser Cys Arg Lys Gly
    1760                1765            1770

Cys Ile Leu Leu Gly Gln Val Val Asp His Ile Asp Ser Leu Met
    1775                1780            1785

Glu Glu Trp Phe Pro Gly Leu Leu Glu Ile Asp Ile Cys Gly Glu
    1790                1795            1800

Gly Glu Thr Leu Leu Lys Lys Trp Ala Leu Tyr Ser Phe Asn Asp
    1805                1810            1815

Gly Glu Glu His Gln Lys Ile Leu Leu Asp Asp Leu Met Lys Lys
    1820                1825            1830

Ala Glu Glu Gly Asp Leu Leu Val Asn Pro Asp Gln Pro Arg Leu
    1835                1840            1845

Thr Ile Pro Ile Ser Gln Ile Ala Pro Asp Leu Ile Leu Ala Asp
    1850                1855            1860

Leu Pro Arg Asn Ile Met Leu Asn Asn Asp Glu Leu Glu Phe Glu
    1865                1870            1875

Gln Ala Pro Glu Phe Leu Leu Gly Asp Gly Ser Phe Gly Ser Val
    1880                1885            1890

Tyr Arg Ala Ala Tyr Glu Gly Glu Glu Val Ala Val Lys Ile Phe
    1895                1900            1905

Asn Lys His Thr Ser Leu Arg Leu Leu Arg Gln Glu Leu Val Val
    1910                1915            1920

Leu Cys His Leu His His Pro Ser Leu Ile Ser Leu Leu Ala Ala
    1925                1930            1935

Gly Ile Arg Pro Arg Met Leu Val Met Glu Leu Ala Ser Lys Gly
    1940                1945            1950

Ser Leu Asp Arg Leu Leu Gln Gln Asp Lys Ala Ser Leu Thr Arg
    1955                1960            1965

Thr Leu Gln His Arg Ile Ala Leu His Val Ala Asp Gly Leu Arg
    1970                1975            1980

Tyr Leu His Ser Ala Met Ile Ile Tyr Arg Asp Leu Lys Pro His
    1985                1990            1995

Asn Val Leu Leu Phe Thr Leu Tyr Pro Asn Ala Ala Ile Ile Ala
    2000                2005            2010

Lys Ile Ala Asp Tyr Gly Ile Ala Gln Tyr Cys Cys Arg Met Gly
    2015                2020            2025

Ile Lys Thr Ser Glu Gly Thr Pro Gly Phe Arg Ala Pro Glu Val
    2030                2035            2040

Ala Arg Gly Asn Val Ile Tyr Asn Gln Gln Ala Asp Val Tyr Ser
```

```
                    2045              2050              2055
Phe Gly Leu Leu Leu Tyr Asp Ile Leu Thr Thr Gly Gly Arg Ile
        2060              2065              2070
Val Glu Gly Leu Lys Phe Pro Asn Glu Phe Asp Glu Leu Glu Ile
        2075              2080              2085
Gln Gly Lys Leu Pro Asp Pro Val Lys Glu Tyr Gly Cys Ala Pro
        2090              2095              2100
Trp Pro Met Val Glu Lys Leu Ile Lys Gln Cys Leu Lys Glu Asn
        2105              2110              2115
Pro Gln Glu Arg Pro Thr Ser Ala Gln Val Phe Asp Ile Leu Asn
        2120              2125              2130
Ser Ala Glu Leu Val Cys Leu Thr Arg Arg Ile Leu Leu Pro Lys
        2135              2140              2145
Asn Val Ile Val Glu Cys Met Val Ala Thr His His Asn Ser Arg
        2150              2155              2160
Asn Ala Ser Ile Trp Leu Gly Cys Gly His Thr Asp Arg Gly Gln
        2165              2170              2175
Leu Ser Phe Leu Asp Leu Asn Thr Glu Gly Tyr Thr Ser Glu Glu
        2180              2185              2190
Val Ala Asp Ser Arg Ile Leu Cys Leu Ala Leu Val His Leu Pro
        2195              2200              2205
Val Glu Lys Glu Ser Trp Ile Val Ser Gly Thr Gln Ser Gly Thr
        2210              2215              2220
Leu Leu Val Ile Asn Thr Glu Asp Gly Lys Lys Arg His Thr Leu
        2225              2230              2235
Glu Lys Met Thr Asp Ser Val Thr Cys Leu Tyr Cys Asn Ser Phe
        2240              2245              2250
Ser Lys Gln Ser Lys Gln Lys Asn Phe Leu Leu Val Gly Thr Ala
        2255              2260              2265
Asp Gly Lys Leu Ala Ile Phe Glu Asp Lys Thr Val Lys Leu Lys
        2270              2275              2280
Gly Ala Ala Pro Leu Lys Ile Leu Asn Ile Gly Asn Val Ser Thr
        2285              2290              2295
Pro Leu Met Cys Leu Ser Glu Ser Thr Asn Ser Thr Glu Arg Asn
        2300              2305              2310
Val Met Trp Gly Gly Cys Gly Thr Lys Ile Phe Ser Phe Ser Asn
        2315              2320              2325
Asp Phe Thr Ile Gln Lys Leu Ile Glu Thr Arg Thr Ser Gln Leu
        2330              2335              2340
Phe Ser Tyr Ala Ala Phe Ser Asp Ser Asn Ile Ile Thr Val Val
        2345              2350              2355
Val Asp Thr Ala Leu Tyr Ile Ala Lys Gln Asn Ser Pro Val Val
        2360              2365              2370
Glu Val Trp Asp Lys Lys Thr Glu Lys Leu Cys Gly Leu Ile Asp
        2375              2380              2385
Cys Val His Phe Leu Arg Glu Val Met Val Lys Glu Asn Lys Glu
        2390              2395              2400
Ser Lys His Lys Met Ser Tyr Ser Gly Arg Val Lys Thr Leu Cys
        2405              2410              2415
Leu Gln Lys Asn Thr Ala Leu Trp Ile Gly Thr Gly Gly Gly His
        2420              2425              2430
Ile Leu Leu Leu Asp Leu Ser Thr Arg Arg Leu Ile Arg Val Ile
        2435              2440              2445
```

-continued

Tyr Asn Phe Cys Asn Ser Val Arg Val Met Met Thr Ala Gln Leu
2450                2455                2460

Gly Ser Leu Lys Asn Val Met Leu Val Leu Gly Tyr Asn Arg Lys
    2465                2470                2475

Asn Thr Glu Gly Thr Gln Lys Gln Lys Glu Ile Gln Ser Cys Leu
        2480                2485                2490

Thr Val Trp Asp Ile Asn Leu Pro His Glu Val Gln Asn Leu Glu
    2495                2500                2505

Lys His Ile Glu Val Arg Lys Glu Leu Ala Glu Lys Met Arg Arg
        2510                2515                2520

Thr Ser Val Glu
    2525

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
gaggactatg attgccatgg                                         20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
agggcataca aaatgtccct                                         20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
ggtctgctta ggtccctttt                                         20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
aaggaaccaa ggagtggaag                                         20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
ttcagatgtt tggggcaagt                                         20

<210> SEQ ID NO 15

```
<211> LENGTH: 22
<212> TYPE: DNA
<213> ORGANISM: Artificial Sequence
<220> FEATURE:
<223> OTHER INFORMATION: Synthetic Construct

<400> SEQUENCE: 15
catgaagact gtgaatggtt tg                                              22

<210> SEQ ID NO 16
<211> LENGTH: 22
<212> TYPE: DNA
<213> ORGANISM: Artificial Sequence
<220> FEATURE:
<223> OTHER INFORMATION: Synthetic Construct

<400> SEQUENCE: 16
ccagacagaa gtctgaagga ca                                              22

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
tccaaaacag acaagaggtt ga                                              22

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
atgaagcctt ggctcttcaa                                                 20

<210> SEQ ID NO 19
<211> LENGTH: 22
<212> TYPE: DNA
<213> ORGANISM: Artificial Sequence
<220> FEATURE:
<223> OTHER INFORMATION: Synthetic Construct

<400> SEQUENCE: 19
tcccaattca aaattttagt gc                                              22

<210> SEQ ID NO 20
<211> LENGTH: 7584
<212> TYPE: DNA
<213> ORGANISM: Homo sapiens

<400> SEQUENCE: 20
atggctagtg gcagctgtca ggggtgcgaa gaggacgagg aaactctgaa gaagttgata     60
gtcaggctga caatgtcca ggaaggaaaa cagatagaaa cgctggtcca atcctggag      120 gatctgctgg tgttcacgta ctccgagcgc gcctccaagt tatttcaagg caaaaatatc    180
catgtgcctc tgttgatcgt cttggactcc tatatgagag tcgcgagtgt gcagcaggtg    240
ggttggtcac ttctgtgcaa attaatagaa gtctgtccag gtacaatgca aagcttaatg    300
ggaccccagg atgttggaaa tgattgggaa gtccttggtg ttcaccaatt gattcttaaa    360
atgctaacag ttcataatgc cagtgtaaac ttgtcagtga ttggactgaa gaccttagat    420
```

```
ctcctcctaa cttcaggtaa aatcaccttg ctgatattgg atgaagaaag tgatatttc     480
atgttaattt ttgatgccat gcactcattt ccagccaatg atgaagtcca gaaacttgga    540
tgcaaagctt tacatgtgct gtttgagaga gtctcagagg agcaactgac tgaatttgtt    600
gagaacaaag attatatgat attgttaagt gcgtcaacaa attttaaaga tgaagaggaa    660
attgtgcttc atgtgctgca ttgtttacat tccctagcga ttccttgcaa taatgtggaa    720
gtcctcatga gtggcaatgt caggtgttat aatattgtgg tggaagctat gaaagcattc    780
cctatgagtg aaagaattca agaagtgagt tgctgtttgc tccataggct tacattaggt    840
aatttttca atatcctggt attaaacgaa gtccatgagt ttgtggtgaa agctgtgcag     900
cagtacccag agaatgcagc attgcagatc tcagcgctca gctgtttggc cctcctcact    960
gagactattt tcttaaatca agatttagag gaaaagaatg agaatcaaga gaatgatgat   1020
gaggggaag aagataaatt gttttggctg gaagcctgtt acaaagcatt aacgtggcat    1080
agaaagaaca agcacgtgca ggaggccgca tgctgggcac taaataatct ccttatgtac   1140
caaaacagtt tacatgagaa gattggagat gaagatggcc atttcccagc tcatagggaa   1200
gtgatgctct ccatgctgat gcattcttca tcaaaggaag ttttccaggc atctgcgaat   1260
gcattgtcaa ctctcttaga acaaaatgtt aatttcagaa aaatactgtt atcaaaagga   1320
atacacctga atgttttgga gttaatgcag aagcatatac attctcctga agtggctgaa   1380
agtggctgta aaatgctaaa tcatcttttt gaaggaagca cacttccct ggatataatg    1440
gcagcagtgg tccccaaaat actaacagtt atgaaacgtc atgagacatc attaccagtg   1500
cagctggagg cgcttcgagc tatttttacat tttatagtgc ctggcatgcc agaagaatcc   1560
agggaggata cagaatttca tcataagcta aatatggtta aaaaacagtg tttcaagaat   1620
gatattcaca aactggtcct agcagctttg aacaggttca ttggaaatcc tgggattcag   1680
aaatgtggat taaaagtaat ttcttctatt gtacattttc ctgatgcatt agagatgtta   1740
tccctggaag gtgctatgga ttcagtgctt cacacactgc agatgtatcc agatgaccaa   1800
gaaattcagt gtctgggttt aagtcttata ggatacttga ttacaaagaa gaatgtgttc   1860
ataggaactg gacatctgct ggcaaaaatt ctggttccca gcttataccg atttaaggat   1920
gttgctgaaa tacagactaa aggatttcag acaatcttag caatcctcaa attgtcagca   1980
tctttttcta gctgctggt gcatcattca tttgacttag taatattcca tcaaatgtct   2040
tccaatatca tggaacaaaa ggatcaacag tttctaaacc tctgttgcaa gtgttttgca   2100
aaagtagcta tggatgatta cttaaaaaat gtgatgctag agagcgtg tgatcagaat    2160
aacagcatca tggttgaatg cttgcttcta ttgggagcag atgccaatca agcaaggag    2220
ggatcttctt taatttgtca ggtatgtgag aaagagagca gtcccaaatt ggtggaactc   2280
ttactgaata gtggatctcg tgaacaagat gtacgaaag cgttgacgat aagcattggg   2340
aaaggtgaca gccagatcat cagcttgctc ttaaggaggc tggccctgga tgtggccaac   2400
aatagcattt gccttggagg attttgtata ggaaaagttg aaccttcttg gcttggtcct   2460
ttatttccag ataagacttc taatttaagg aaacaaacaa atatagcatc tacactagca   2520
agaatggtga tcagatatca gatgaaaagt gctgtggaag aaggaacagc ctcaggcagc   2580
gatgaaaatt tttctgaaga tgtgctgtct aaatttgatg aatggacctt tattcctgac   2640
tcttctatgg acagtgtgtt tgctcaaagt gatgacctgg atagtgaagg aagtgaaggc   2700
tcatttcttg tgaaaaagaa atctaattca attagtgtag gagaattta ccgagatgcc     2760
gtattacagc gttgctcacc aaatttgcaa agacattcca attccttggg gcccattttt   2820
```

```
gatcatgaag atttactgaa gcgaaaaaga aaatattat cttcagatga ttcactcagg    2880
tcatcaaaac ttcaatccca tatgaggcat tcagacagca tttcttctct ggcttctgag    2940
agagaatata ttacatcact agacctttca gcaaatgaac taagagatat tgatgccta     3000 agccagaaat gctgtataag tgttcatttg gagcatcttg aaaagctgga gcttcaccag    3060
aatgcactca cgagctttcc acaacagcta tgtgaaactc tgaagagttt gacacatttg    3120
gacttgcaca gtaataaatt tacatcattt ccttcttatt tgttgaaaat gagttgtatt    3180
gctaatcttg atgtctctcg aaatgacatt ggaccctcag tggttttaga tcctacagtg    3240
aaatgtccaa ctctgaaaca gtttaacctg tcatataacc agctgtcttt tgtacctgag    3300
aacctcactg atgtggtaga gaaactggag cagctcattt tagaaggaaa taaaatatca    3360
gggatatgct cccccttgag actgaaggaa ctgaagattt taaaccttag taagaaccac    3420
atttcatccc tatcagagaa cttcttgag gcttgtccta aagtggagag tttcagtgcc     3480
agaatgaatt tcttgctgc tatgcctttc ttgcctcctt ctatgacaat cctaaaatta     3540
tctcagaaca aattttcctg tattccagaa gcaattttaa atcttccaca cttgcggtct    3600
ttagatatga gcagcaatga tattcagtac ctaccaggtc ccgcacactg gaaatctttg    3660
aacttaaggg aactcttatt tagccataat cagatcagca tcttggactt gagtgaaaaa    3720
gcatatttat ggtctagagt agagaaactg catctttctc acaataaact gaaagagatt    3780
cctcctgaga ttggctgtct tgaaaatctg acatctctgg atgtcagtta caacttggaa    3840
ctaagatcct ttcccaatga aatggggaaa ttaagcaaaa tatgggatct tcctttggat    3900
gaactgcatc ttaactttga ttttaaacat ataggatgta agccaaaga catcataagg      3960 tttcttcaac agcgattaaa aaaggctgtg ccttataacc gaatgaaact tatgattgtg    4020
ggaaatactg ggagtggtaa aaccacctta ttgcagcaat taatgaaaac caagaaatca    4080
gatcttggaa tgcaaagtgc cacagttggc atagatgtga aagactggcc tatccaaata    4140
agagacaaaa gaaagagaga tctcgtccta aatgtgtggg attttgcagg tcgtgaggaa    4200
ttctatagta ctcatcccca ttttatgacg cagcgagcat tgtaccttgc tgtctatgac    4260
ctcagcaagg gacaggctga agttgatgcc atgaagcctt ggctcttcaa tataaaggct    4320
cgcgcttctt cttcccctgt gattctcgtt ggcacacatt tggatgtttc tgatgagaag    4380
caacgcaaag cctgcatgag taaaatcacc aaggaactcc tgaataagcg agggttccct    4440
gccatacgag attaccactt tgtgaatgcc accgaggaat ctgatgcttt ggcaaaactt    4500
cggaaaacca tcataaacga gagccttaat ttcaagatcc gagatcagct tgttgttgga    4560
cagctgattc cagactgcta tgtagaactt gaaaaaatca ttttatcgga gcgtaaaaat    4620
gtgccaattg aatttcccgt aattgaccgg aaacgattat tacaactagt gagagaaaat    4680
cagctgcagt tagatgaaaa tgagcttcct cacgcagttc actttctaaa tgaatcagga    4740
gtccttcttc attttcaaga cccagcactg cagttaagtg acttgtactt tgtggaaccc    4800
aagtggcttt gtaaaatcat ggcacagatt ttgacagtga agtggaagg ttgtccaaaa     4860 caccctaagg gcattatttc gcgtagagat gtggaaaaat ttctttcaaa aaaaaggaaa    4920
tttccaaaga actacatgtc acagtatttt aagctcctag aaaaattcca gattgctttg    4980
ccaataggaa agaatatttt gctggttcca agcagtttgt ctgaccacag gcctgtgata    5040
gagcttcccc attgtgagaa ctctgaaatt atcatccgac tatatgaaat gccttatttt    5100
ccaatgggat tttggtcaag attaatcaat cgattacttg agatttcacc ttacatgctt    5160
tcagggagag aacgagcact tcgcccaaac agaatgtatt ggcgacaagg catttactta    5220
```

| | |
|---|---|
| aattggtctc ctgaagctta ttgtctggta ggatctgaag tcttagacaa tcatccagag | 5280 |
| agtttcttaa aaattacagt tccttcttgt agaaaaggct gtattctttt gggccaagtt | 5340 |
| gtggaccaca ttgattctct catggaagaa tggtttcctg ggttgctgga gattgatatt | 5400 |
| tgtggtgaag gagaaactct gttgaagaaa tgggcattat atagttttaa tgatggtgaa | 5460 |
| gaacatcaaa aaatcttact tgatgacttg atgaagaaag cagaggaagg agatctctta | 5520 |
| gtaaatccag atcaaccaag gctcaccatt ccaatatctc agattgcccc tgacttgatt | 5580 |
| ttggctgacc tgcctagaaa tattatgttg aataatgatg agttggaatt tgaacaagct | 5640 |
| ccagagtttc tcctaggtga tggcagtttt ggatcagttt accgagcagc ctatgaagga | 5700 |
| gaagaagtgg ctgtgaagat ttttaataaa catacatcac tcaggctgtt aagacaagag | 5760 |
| cttgtggtgc tttgccacct ccaccacccc agtttgatat ctttgctggc agctgggatt | 5820 |
| cgtccccgga tgttggtgat ggagttagcc tccaagggtt ccttggatcg cctgcttcag | 5880 |
| caggacaaag ccagcctcac tagaacccta cagcacagga ttgcactcca cgtagctgat | 5940 |
| ggtttgagat acctccactc agccatgatt atataccgag acctgaaacc ccacaatgtg | 6000 |
| ctgctttttca cactgtatcc caatgctgcc atcattgcaa agattgctga ctacggcatt | 6060 |
| gctcagtact gctgtagaat ggggataaaa acatcagagg gcacaccagg gtttcgtgca | 6120 |
| cctgaagttg ccagaggaaa tgtcatttat aaccaacagg ctgatgttta ttcatttggt | 6180 |
| ttactactct atgacatttt gacaactgga ggtagaatag tagagggttt gaagtttcca | 6240 |
| aatgagtttg atgaattaga aatacaagga aaattacctg atccagttaa agaatatggt | 6300 |
| tgtgccccat ggcctatggt tgagaaatta attaaacagt gtttgaaaga aaatcctcaa | 6360 |
| gaaaggccta cttctgccca ggtctttgac attttgaatt cagctgaatt agtctgtctg | 6420 |
| acgagacgca ttttattacc taaaaacgta attgttgaat gcatggttgc tacacatcac | 6480 |
| aacagcagga atgcaagcat ttggctgggc tgtgggcaca ccgacagagg acagctctca | 6540 |
| tttcttgact aaatactga aggatacact tctgaggaag ttgctgatag tagaatattg | 6600 |
| tgcttagcct tggtgcatct tcctgttgaa aaggaaagct ggattgtgtc tgggacacag | 6660 |
| tctggtactc tcctggtcat caataccgaa gatgggaaaa agagacatac cctagaaaag | 6720 |
| atgactgatt ctgtcacttg tttgtattgc aattcctttt ccaagcaaag caaacaaaaa | 6780 |
| aattttcttt tggttggaac cgctgatggc aagttagcaa ttttttgaaga taagactgtt | 6840 |
| aagcttaaag gagctgctcc tttgaagata ctaaatatag gaaatgtcag tactccattg | 6900 |
| atgtgtttga gtgaatccac aaattcaacg gaaagaaatg taatgtgggg aggatgtggc | 6960 |
| acaaagattt tctccttttc taatgatttc accattcaga aactcattga dacaagaaca | 7020 |
| agccaactgt tttcttatgc agctttcagt gattccaaca tcataacagt ggtggtagac | 7080 |
| actgctctct atattgctaa gcaaaatagc cctgttgtgg aagtgtggga taagaaaact | 7140 |
| gaaaaactct gtggactaat agactgcgtg cacttttaa gggaggtaat ggtaaaagaa | 7200 |
| aacaaggaat caaaacacaa aatgtcttat tctgggagag tgaaaccct ctgccttcag | 7260 |
| aagaacactg ctctttggat aggaactgga ggaggccata ttttactcct ggatctttca | 7320 |
| actcgtcgac ttatacgtgt aatttacaac ttttgtaatt cggtcagagt catgatgaca | 7380 |
| gcacagctag gaagcttaa aaatgtcatg ctggtattgg gctacaaccg gaaaaatact | 7440 |
| gaaggtacac aaaagcagaa agagatacaa tcttgcttga ccgtttggga catcaatctt | 7500 |
| ccacatgaag tgcaaaattt agaaaaacac attgaagtga gaaagaatt agctgaaaaa | 7560 |
| atgagacgaa catctgttga gtaa | 7584 |

```
<210> SEQ ID NO 21
<211> LENGTH: 7
<212> TYPE: PRT
<213> ORGANISM: Homo sapiens

<400> SEQUENCE: 21

Ile Ser Gly Ile Cys Ser Pro
1               5

<210> SEQ ID NO 22
<211> LENGTH: 7
<212> TYPE: PRT
<213> ORGANISM: Mus musculus

<400> SEQUENCE: 22

Ile Ser Gly Ile Cys Ser Pro
1               5

<210> SEQ ID NO 23
<211> LENGTH: 7
<212> TYPE: PRT
<213> ORGANISM: Fugu rubripes

<400> SEQUENCE: 23

Ile Ala Glu Leu Cys Val Pro
1               5

<210> SEQ ID NO 24
<211> LENGTH: 5
<212> TYPE: PRT
<213> ORGANISM: Drosophila melanogaster

<400> SEQUENCE: 24

Ile Ser Cys Trp Pro
1               5

<210> SEQ ID NO 25
<211> LENGTH: 7
<212> TYPE: PRT
<213> ORGANISM: Homo sapiens

<400> SEQUENCE: 25

Ile Lys Ala Arg Ala Ser Ser
1               5

<210> SEQ ID NO 26
<211> LENGTH: 7
<212> TYPE: PRT
<213> ORGANISM: Mus musculus

<400> SEQUENCE: 26

Ile Lys Ala Arg Ala Ser Ser
1               5

<210> SEQ ID NO 27
<211> LENGTH: 7
<212> TYPE: PRT
<213> ORGANISM: Fugu rubripes

<400> SEQUENCE: 27

Ile Lys Ala Val Ala Pro Leu
1               5

<210> SEQ ID NO 28
<211> LENGTH: 7
```

```
<212> TYPE: PRT
<213> ORGANISM: Caenorhabditis elegans

<400> SEQUENCE: 28

Ile His Ala Arg Ala Pro Asn
1               5

<210> SEQ ID NO 29
<211> LENGTH: 7
<212> TYPE: PRT
<213> ORGANISM: Drosophila melanogaster

<400> SEQUENCE: 29

Ile Gln Ala Arg Ala Pro Asn
1               5

<210> SEQ ID NO 30
<211> LENGTH: 7
<212> TYPE: PRT
<213> ORGANISM: Homo sapiens

<400> SEQUENCE: 30

Glu Met Pro Tyr Phe Pro Met
1               5

<210> SEQ ID NO 31
<211> LENGTH: 7
<212> TYPE: PRT
<213> ORGANISM: Mus musculus

<400> SEQUENCE: 31

Glu Met Pro Tyr Phe Pro Met
1               5

<210> SEQ ID NO 32
<211> LENGTH: 7
<212> TYPE: PRT
<213> ORGANISM: Fugu rubripes

<400> SEQUENCE: 32

Glu Met Pro Tyr Phe Pro Met
1               5

<210> SEQ ID NO 33
<211> LENGTH: 7
<212> TYPE: PRT
<213> ORGANISM: Caenorhabditis elegans

<400> SEQUENCE: 33

Ala Leu Ala Tyr Ile Pro Ser
1               5

<210> SEQ ID NO 34
<211> LENGTH: 7
<212> TYPE: PRT
<213> ORGANISM: Drosophila melanogaster

<400> SEQUENCE: 34

Leu Met Thr Tyr Phe Pro Ser
1               5

<210> SEQ ID NO 35
<211> LENGTH: 7
<212> TYPE: PRT
<213> ORGANISM: Homo sapiens
```

```
<400> SEQUENCE: 35

Asp Tyr Gly Ile Ala Gln Tyr
1               5

<210> SEQ ID NO 36
<211> LENGTH: 7
<212> TYPE: PRT
<213> ORGANISM: Mus musculus

<400> SEQUENCE: 36

Asp Tyr Gly Ile Ala Gln Tyr
1               5

<210> SEQ ID NO 37
<211> LENGTH: 6
<212> TYPE: PRT
<213> ORGANISM: Fugu rubripes

<400> SEQUENCE: 37

Tyr Gly Ile Ala Gln His
1               5

<210> SEQ ID NO 38
<211> LENGTH: 7
<212> TYPE: PRT
<213> ORGANISM: Caenorhabditis elegans

<400> SEQUENCE: 38

Asp Tyr Gly Ile Ser Arg Ser
1               5

<210> SEQ ID NO 39
<211> LENGTH: 7
<212> TYPE: PRT
<213> ORGANISM: Drosophila melanogaster

<400> SEQUENCE: 39

Asp Tyr Gly Ile Ser Arg Gln
1               5

<210> SEQ ID NO 40
<211> LENGTH: 10
<212> TYPE: PRT
<213> ORGANISM: Homo sapiens

<400> SEQUENCE: 40

Asn Ile Lys Ala Arg Ala Ser Ser Ser Pro
1               5                   10

<210> SEQ ID NO 41
<211> LENGTH: 10
<212> TYPE: PRT
<213> ORGANISM: Mus musculus

<400> SEQUENCE: 41

Asn Ile Lys Ala Arg Ala Ser Ser Ser Pro
1               5                   10

<210> SEQ ID NO 42
<211> LENGTH: 10
<212> TYPE: PRT
<213> ORGANISM: Rattus norvegicus

<400> SEQUENCE: 42

Asn Ile Lys Ala Arg Ala Ser Ser Ser Pro
```

```
1               5                   10
```

<210> SEQ ID NO 43
<211> LENGTH: 10
<212> TYPE: PRT
<213> ORGANISM: Caenorhabditis elegans

<400> SEQUENCE: 43

```
Asn Ile His Ala Arg Ala Pro Asn Ser Thr
1               5                   10
```

<210> SEQ ID NO 44
<211> LENGTH: 10
<212> TYPE: PRT
<213> ORGANISM: Drosophila melanogaster

<400> SEQUENCE: 44

```
Asn Ile Gln Ala Arg Ala Pro Asn Ser Pro
1               5                   10
```

<210> SEQ ID NO 45
<211> LENGTH: 10
<212> TYPE: PRT
<213> ORGANISM: Homo sapiens

<400> SEQUENCE: 45

```
Arg Leu Tyr Glu Met Pro Tyr Phe Pro Met
1               5                   10
```

<210> SEQ ID NO 46
<211> LENGTH: 10
<212> TYPE: PRT
<213> ORGANISM: Mus musculus

<400> SEQUENCE: 46

```
Arg Leu Tyr Glu Met Pro Tyr Phe Pro Met
1               5                   10
```

<210> SEQ ID NO 47
<211> LENGTH: 10
<212> TYPE: PRT
<213> ORGANISM: Rattus norvegicus

<400> SEQUENCE: 47

```
Arg Leu Tyr Glu Met Pro Tyr Phe Pro Met
1               5                   10
```

<210> SEQ ID NO 48
<211> LENGTH: 10
<212> TYPE: PRT
<213> ORGANISM: Caenorhabditis elegans

<400> SEQUENCE: 48

```
Arg Ile Tyr Ala Leu Ala Tyr Ile Pro Ser
1               5                   10
```

<210> SEQ ID NO 49
<211> LENGTH: 10
<212> TYPE: PRT
<213> ORGANISM: Drosophila melanogaster

<400> SEQUENCE: 49

```
Arg Ile Leu Leu Met Thr Tyr Phe Pro Ser
1               5                   10
```

-continued

```
<210> SEQ ID NO 50
<211> LENGTH: 10
<212> TYPE: PRT
<213> ORGANISM: Homo sapiens

<400> SEQUENCE: 50

Ala Asp Tyr Gly Ile Ala Gln Tyr Cys Cys
1               5                   10

<210> SEQ ID NO 51
<211> LENGTH: 10
<212> TYPE: PRT
<213> ORGANISM: Mus musculus

<400> SEQUENCE: 51

Ala Asp Tyr Gly Ile Ala Gln Tyr Cys Cys
1               5                   10

<210> SEQ ID NO 52
<211> LENGTH: 10
<212> TYPE: PRT
<213> ORGANISM: Rattus norvegicus

<400> SEQUENCE: 52

Ala Asp Tyr Gly Ile Ala Gln Tyr Cys Cys
1               5                   10

<210> SEQ ID NO 53
<211> LENGTH: 10
<212> TYPE: PRT
<213> ORGANISM: Caenorhabditis elegans

<400> SEQUENCE: 53

Gly Asp Tyr Gly Ile Ser Arg Ser Val Leu
1               5                   10

<210> SEQ ID NO 54
<211> LENGTH: 10
<212> TYPE: PRT
<213> ORGANISM: Drosophila melanogaster

<400> SEQUENCE: 54

Ala Asp Tyr Gly Ile Ser Arg Gln Thr Ala
1               5                   10
```

The invention claimed is:

1. A method of detecting a mutation at position 4321 in the nucleic acid molecule of SEQ ID NO: 1 or 2 in a sample, the method comprising:
   (a) contacting a sample with a probe consisting of 10 to 50 nucleotides for the detection of said mutation, wherein said probe hybridizes under high stringency conditions to any of the polynucleotide sequences (i), (ii), (iii), (iv), or (v):
      (i) a polynucleotide sequence selected from nucleotides 1 to 9104 of SEQ ID NO: 1 or 2;
      (ii) a polynucleotide sequence selected from nucleotides 1 to 7584 of SEQ ID NO: 1 or 2;
      (iii) a polynucleotide sequence selected from nucleotides 1 to 7581 of SEQ ID NO: 1 or 2;
      (iv) a polynucleotide sequence selected from a nucleotide sequence coding for the protein sequence of SEQ ID NO:8 or 9 or for the protein sequence of SEQ ID NO:8 or 9 containing at least one of the mutations depicted in SEQ ID NO: 1 or 2; or
      (v) a polynucleotide sequence selected from a nucleotide sequence complementary to any of the nucleotide sequences of (i), (ii), (iii), or (iv):
         wherein the polynucleotide sequence codes for the protein sequence of SEQ ID NO. 8 or 9 containing a mutation at position 1441, and wherein said high stringency conditions comprise hybridization at 68° C. in a solution comprising 50% formamide, 5×SSC (Sodium and sodium Citrate buffer) or 5× SSPE (Sodium, Sodium Phosphate, and EDTA buffer at pH 7.7), 5× Denhardt's solution, 1% Sodium Dodecyl Sulfate (SDS), and 100 μg/ml denatured salmon sperm DNA, followed by washing at 68° C. in a buffer comprising 0.2 SSC and 0.1% SDS, and
   (b) detecting the presence of the mutation in the nucleic acid of the sample.

2. The method of claim 1, wherein the sample is selected from
   (a) a biopsy from human tissue or cells; or
   (b) RNA or DNA from a biopsy from human tissue or cells.

3. The method of claim 1, wherein the detecting of the mutation comprises Southern blot hybridization, Northern blot hybridization, PCR, RT-PCR, real-time RT-PCR or automated sequencing.

4. The method of claim 1, wherein the detecting of the mutation comprises radiography, fluorescence, chemiluminescence, or any combination thereof.

5. The method of claim 1, wherein the method is carried out on an array.

6. The method of claim 1, wherein the method is carried out in a robotics system.

7. The method of claim 1, wherein the method is carried out using microfluidics.

8. The method of claim 1, wherein said probe consists of 10 to 35 nucleotides.

9. The method of claim 1, wherein said probe consists of 20 to 35 nucleotides.

10. The method of claim 2, wherein said sample is from the brain.

11. The method of claim 10, wherein said sample is from putamen or substantia nigra.

12. The method of claim 2, wherein said sample is from heart, lung, or blood lymphocytes.

13. The method of claim 2, wherein said RNA or DNA is from the brain.

14. The method of claim 13, wherein said RNA or DNA is from putamen or substantia nigra.

15. The method of claim 2, wherein said RNA or DNA is from heart, lung, or blood lymphocytes.

16. The method of claim 1, wherein said method is diagnostic of a neurodegenerative disorder selected from the group consistent of Parkinson disease (PD), sporadic PD, Alzheimer disease (AD), amyotrophic lateral sclerosis (ALS), synucleinopathy, and tauopathy.

\* \* \* \* \*

UNITED STATES PATENT AND TRADEMARK OFFICE
CERTIFICATE OF CORRECTION

PATENT NO. : 8,409,809 B2
APPLICATION NO. : 13/219131
DATED : April 2, 2013
INVENTOR(S) : Meitinger et al.

It is certified that error appears in the above-identified patent and that said Letters Patent is hereby corrected as shown below:

In the Specification

Column 1, Line 20-21 should read

"Statement as to Federally Sponsored Research

This invention was made with government support under NS040256 awarded by the National Institute of Health. The government has certain rights in the invention."

Signed and Sealed this
Third Day of September, 2013

Teresa Stanek Rea
*Acting Director of the United States Patent and Trademark Office*